US00RE49967E

(19) United States
(12) Reissued Patent
Schiff et al.

(10) Patent Number: US RE49,967 E
(45) Date of Reissued Patent: May 14, 2024

(54) COMBINATIONS AND METHODS FOR SUBCUTANEOUS ADMINISTRATION OF IMMUNE GLOBULIN AND HYALURONIDASE

(71) Applicant: Takeda Pharmaceutical Company Limited, Osaka (JP)

(72) Inventors: Richard Schiff, Eastsound, WA (US); Heinz Leibl, Pechtoldsdorf (AT)

(73) Assignee: Takeda Pharmaceutical Company Limited, Osaka (JP)

(21) Appl. No.: 17/332,776

(22) Filed: May 27, 2021

Related U.S. Patent Documents

Reissue of:
(64) Patent No.: 10,301,376
Issued: May 28, 2019
Appl. No.: 12/381,844
Filed: Mar. 16, 2009

U.S. Applications:
(60) Provisional application No. 61/069,841, filed on Mar. 17, 2008.

(51) Int. Cl.

| | |
|---|---|
| ***C07K 16/06*** | (2006.01) |
| ***A61K 39/395*** | (2006.01) |
| ***C12N 9/26*** | (2006.01) |
| *A61K 38/00* | (2006.01) |
| *A61K 39/00* | (2006.01) |

(52) U.S. Cl.
CPC ..... *C07K 16/06* (2013.01); *A61K 39/39516* (2013.01); *C12N 9/2408* (2013.01); *A61K 38/00* (2013.01); *A61K 2039/505* (2013.01); *A61K 2039/54* (2013.01); *A61K 2039/545* (2013.01); *C07K 2317/21* (2013.01); *Y02A 50/30* (2018.01)

(58) Field of Classification Search
CPC ..... C07K 16/06; A61K 39/395; C12N 9/26
See application file for complete search history.

(56) References Cited

U.S. PATENT DOCUMENTS

| | | | | |
|---|---|---|---|---|
| 3,710,795 | A | 1/1973 | Higuchi et al. | 424/424 |
| 3,869,436 | A | 3/1975 | Falksveden et al. | 260/112 |
| 3,966,906 | A | 6/1976 | Schultze et al. | 424/177.1 |
| 4,093,606 | A | 6/1978 | Coval | 530/390.5 |
| 4,124,576 | A | 11/1978 | Coval | 530/390.5 |
| 4,126,605 | A | 11/1978 | Schneider et al. | 530/390.5 |
| 4,165,370 | A | 8/1979 | Coval | 424/177.1 |
| 4,186,192 | A | 1/1980 | Lundblad et al. | 424/177.1 |
| 4,362,661 | A | 12/1982 | Ono et al. | 424/177.1 |
| 4,374,763 | A | 2/1983 | Takagai | 530/390.5 |
| 4,396,608 | A | 8/1983 | Tenold | 424/177.1 |
| 4,439,421 | A | 3/1984 | Hooper et al. | 424/177.1 |
| 4,499,073 | A | 2/1985 | Tenold | 424/159.1 |
| 4,597,966 | A | 7/1986 | Zolton et al. | 424/141.1 |
| 4,952,496 | A | 8/1990 | Studier et al. | 435/91.41 |
| 5,033,252 | A | 7/1991 | Carter | 53/425 |
| 5,052,558 | A | 10/1991 | Carter | 206/439 |
| 5,122,373 | A | 6/1992 | Eibl et al. | 424/171.1 |
| 5,177,194 | A | 1/1993 | Sarno et al. | 530/390.1 |
| 5,180,810 | A | 1/1993 | Gomi et al. | 530/350 |
| 5,323,907 | A | 6/1994 | Kalvelage | 206/531 |
| 5,608,038 | A | 3/1997 | Eibl et al. | 530/387.1 |
| 5,665,069 | A | 9/1997 | Cumer et al. | 604/116 |
| 5,721,348 | A | 2/1998 | Primakoff et al. | 536/22.1 |
| 5,747,027 | A | 5/1998 | Stern et al. | 424/94.62 |
| 5,827,721 | A | 10/1998 | Stern et al. | 435/201 |
| 5,854,046 | A | 12/1998 | Au-Young et al. | 435/201 |
| 5,871,736 | A | 2/1999 | Bruegger et al. | 424/177.1 |
| 5,945,098 | A | 8/1999 | Sarno et al. | 424/85.5 |
| 5,958,750 | A | 9/1999 | Au-Young et al. | 435/201 |
| 6,057,110 | A | 5/2000 | Au-Young et al. | 435/6 |
| 6,069,236 | A | 5/2000 | Burnouf-Radosevich et al. | 530/416 |
| 6,103,525 | A | 8/2000 | Stern et al. | 435/326 |
| 6,123,938 | A | 9/2000 | Stern et al. | 424/94.62 |
| 6,193,963 | B1 | 2/2001 | Stern et al. | 424/94.6 |
| 6,552,170 | B1 | 4/2003 | Thompson et al. | 530/351 |
| 6,682,904 | B1 | 1/2004 | Frost | 435/18 |
| 6,828,431 | B1 | 12/2004 | Frudakis et al. | 536/23.1 |
| 6,875,848 | B2 | 4/2005 | Ristol Debart et al. | 530/390.1 |
| 7,105,330 | B2 | 9/2006 | Stern et al. | 435/200 |

(Continued)

FOREIGN PATENT DOCUMENTS

| | | |
|---|---|---|
| CH | 684 164 | 7/1994 |
| EP | 0246579 | 11/1987 |

(Continued)

OTHER PUBLICATIONS

Teschner et al. A new liquid, intravenous immunglobulin product (IGIV 10%) highly purified by a state-of-the-art process. Vox Sanguinis. 92(1): 42-55, Jan. 2007.*

Gardulf et al., J. Clin. Immunol. 26(2):177-185, Mar. 2006.*

Gammagard S/D, 1994.*

Gammagard Liquid, 2005.*

Mouthon et al., "Intravenous immunoglobulins in autoimmune- or parovirus B19-mediated pure red cell aplasia," Autoimmunity Reviews 4(5):264-269 (2005).

Greenway, "The Next Chapter Begins: Creating Value Through Growth," Presented at the JMP Securities 2015 Life Sciences Conference, Jun. 24, 2015, 24 pages.

(Continued)

*Primary Examiner* — Sharon L Turner
(74) *Attorney, Agent, or Firm* — MORGAN, LEWIS & BOCKIUS LLP

(57) ABSTRACT

Provided are combinations, compositions and kits containing a immune globulin (IG) composition and a soluble hyaluronidase composition formulated for subcutaneous administration. Such products can be used in methods of treating IG-treatable diseases or conditions. Also provided are methods for subcutaneous administration of immune globulin whereby the dosing regimen is substantially the same as for intravenous administration of the same dosage for treatment of the same IG-treatable disease or condition.

78 Claims, No Drawings

Specification includes a Sequence Listing.

(56) References Cited

U.S. PATENT DOCUMENTS

| | | | | |
|---|---|---|---|---|
| 7,148,201 | B2 | 12/2006 | Stern et al. | 514/44 |
| 7,309,810 | B2 | 12/2007 | Takai et al. | 800/3 |
| 7,368,108 | B2 | 5/2008 | DeFrees et al. | 424/94.5 |
| 7,544,499 | B2 | 6/2009 | Frost et al. | 435/200 |
| 7,718,428 | B2 | 5/2010 | Frost et al. | 435/375 |
| 7,767,429 | B2 | 8/2010 | Bookbinder et al. | 435/201 |
| 7,781,397 | B2 | 8/2010 | Stern et al. | 514/2 |
| 7,829,081 | B2 | 11/2010 | Bookbinder et al. | 424/94.62 |
| 7,846,431 | B2 | 12/2010 | Bookbinder et al. | 424/94.62 |
| 7,871,607 | B2 | 1/2011 | Bookbinder et al. | 424/94.62 |
| 8,105,586 | B2 | 1/2012 | Bookbinder et al. | 424/94.3 |
| 8,187,855 | B2 | 5/2012 | Baker et al. | 435/201 |
| 8,257,699 | B2 | 9/2012 | Bookbinder et al. | 424/94.62 |
| 8,450,470 | B2 | 5/2013 | Bookbinder et al. | 536/23.2 |
| 8,765,685 | B2 | 7/2014 | Bookbinder et al. | 514/20.9 |
| 2003/0170243 | A1 | 9/2003 | Stern et al. | 424/146.1 |
| 2003/0212021 | A1 | 11/2003 | Frost et al. | 514/44 R |
| 2004/0096921 | A1 | 5/2004 | Stern et al. | 435/7.92 |
| 2004/0268425 | A1 | 12/2004 | Bookbinder et al. | 800/18 |
| 2005/0053598 | A1 | 3/2005 | Burke et al. | 424/133.1 |
| 2005/0260186 | A1 | 11/2005 | Bookbinder et al. | 424/94.61 |
| 2005/0287134 | A1 | 12/2005 | Klein | 424/94.61 |
| 2006/0104968 | A1 | 5/2006 | Bookbinder et al. | C12N 9/2474 435/200 |
| 2006/0247201 | A1 | 11/2006 | Frost et al. | 514/44 R |
| 2007/0134228 | A1 | 6/2007 | Stern et al. | 424/94.61 |
| 2007/0148156 | A1 | 6/2007 | Frost et al. | 424/94.61 |
| 2008/0171014 | A1 | 7/2008 | Wu et al. | 530/387.9 |
| 2009/0123367 | A1 | 5/2009 | Bookbinder et al. | C12N 9/2408 424/85.7 |
| 2009/0181013 | A1 | 7/2009 | Bookbinder et al. | 424/130.1 |
| 2009/0181032 | A1 | 7/2009 | Bookbinder et al. | 424/141.1 |
| 2009/0214505 | A1 | 8/2009 | Bookbinder et al. | 424/94.1 |
| 2009/0215722 | A1 | 8/2009 | Frost et al. | 514/59 |
| 2009/0253175 | A1 | 10/2009 | Bookbinder et al. | 435/69.1 |
| 2009/0304665 | A1 | 12/2009 | Frost et al. | 424/94.5 |
| 2009/0311237 | A1 | 12/2009 | Frost | 424/94.62 |
| 2010/0003238 | A1 | 1/2010 | Frost et al. | 424/94.62 |
| 2010/0143457 | A1 | 6/2010 | Wei et al. | 424/450 |
| 2010/0172892 | A1 | 7/2010 | Uvarkina et al. | 424/94.62 |
| 2010/0184845 | A1 | 7/2010 | Frost et al. | 514/44 R |
| 2010/0196423 | A1 | 8/2010 | Bookbinder et al. | 424/247.1 |
| 2010/0211015 | A1 | 8/2010 | Bookbinder et al. | 604/187 |
| 2010/0330071 | A1 | 12/2010 | Teschner et al. | 530/412 |
| 2011/0008309 | A1 | 1/2011 | Bookbinder et al. | 424/94.3 |
| 2011/0053247 | A1 | 3/2011 | Baker et al. | 435/201 |
| 2011/0066111 | A1 | 3/2011 | Teschner et al. | 604/187 |
| 2011/0152359 | A1 | 6/2011 | Bookbinder et al. | 435/200 |
| 2011/0212074 | A1 | 9/2011 | Frost et al. | 424/85.1 |
| 2011/0293598 | A1 | 12/2011 | Bruckschwaiger et al. | 424/530 |
| 2011/0293638 | A1 | 12/2011 | Bruckschwaiger et al. | 424/140.1 |
| 2012/0020951 | A1 | 1/2012 | Shepard et al. | 424/130.1 |
| 2012/0076772 | A1 | 3/2012 | Butterweck et al. | 424/133.1 |
| 2012/0076779 | A1 | 3/2012 | Butterweck et al. | 424/130.1 |
| 2012/0093770 | A1 | 4/2012 | Bookbinder et al. | 424/94.62 |
| 2012/0148555 | A1 | 6/2012 | Bookbinder et al. | 435/200 |
| 2012/0171153 | A1 | 7/2012 | Frost et al. | 424/94.62 |
| 2012/0196348 | A1 | 8/2012 | Baker et al. | 424/94.62 |

FOREIGN PATENT DOCUMENTS

| | | | | |
|---|---|---|---|---|
| EP | 0278422 | | 8/1988 | |
| EP | 0440483 | | 8/1991 | |
| EP | 0661060 | | 12/1994 | |
| JP | 54020124 | | 2/1979 | |
| JP | 57031623 | | 2/1982 | |
| JP | 57128635 | | 8/1982 | |
| JP | 6-503721 | | 4/1994 | |
| JP | H10-265407 | A | 10/1998 | |
| JP | 4346934 | | 12/2002 | |
| WO | WO 92/010569 | | 6/1992 | |
| WO | WO 94/29334 | | 12/1994 | |
| WO | WO 96/031596 | | 10/1996 | |
| WO | WO 99/029841 | | 10/1996 | |
| WO | WO 98/016655 | | 4/1998 | |
| WO | WO 1998/042376 | | 10/1998 | |
| WO | WO 2003/099862 | | 12/2003 | |
| WO | WO 04/056312 | | 7/2004 | |
| WO | WO 04/058147 | | 7/2004 | |
| WO | WO 04/078140 | | 9/2004 | |
| WO | WO 05/049078 | | 6/2005 | |
| WO | WO 06/091871 | | 8/2006 | |
| WO | WO-2006091871 | A1 * | 8/2006 | A61K 35/768 |
| WO | WO 2007/028196 | | 3/2007 | |
| WO | WO 2009/111066 | | 9/2009 | |
| WO | WO 2009/111083 | | 9/2009 | |
| WO | WO 2009/117085 | | 9/2009 | |
| WO | WO-2009111066 | A1 * | 9/2009 | C12N 9/2408 |
| WO | WO 2009/128917 | | 10/2009 | |
| WO | WO 2009/128918 | | 10/2009 | |
| WO | WO 09/134380 | | 11/2009 | |
| WO | WO 2010/138736 | | 2/2010 | |
| WO | WO 2010/077297 | | 7/2010 | |
| WO | WO 2011/034604 | | 3/2011 | |

OTHER PUBLICATIONS

News Release, Halozyme Therapeutics, Inc., "Halozyme Reports Second Quarter 2016 Financial Results," Published Aug. 9, 2016 [online], Retrieved from: <URL:prnewswire.com/news-releases/halozyme-reports-second-quarter-2016-financial-results-300311374.html [retrieved on Aug. 31, 2016], 10 pages.

Response, filed Nov. 30, 2016, to Office Action, issued Aug. 29, 2016, in connection with Argentinian Patent Application No. P090100943 [English instructions and document as filed in Spanish], 25 pages.

Communication under Rule 97(1) Decision to Grant, issued Apr. 6, 2017, in connection with European Patent Application No. 09721669.1, 3 pages.

Examiner's Report, issued Mar. 31, 2017, in connection with Canadian Patent Application No. 2,714,708, 3 pages.

Office Action, issued Jul. 18, 2017, in connection with Vietnamese Patent Application No. 1-2010-02743 [English translation and original document in Vietnamese], 2 pages.

Response, filed Oct. 4, 2017, to Office Action, issued Jun. 30, 2017, in connection with Argentinian Patent Application No. P090100943 [English instructions and document as-filed in Spanish], 68 pages.

Response, filed Sep. 27, 2017, to Examiner's Report, issued Mar. 31, 2017, in connection with Canadian Patent Application No. 2,714,708 [Response as-filed and cited references], 43 pages.

Response, filed Sep. 8, 2017, to Office Action, issued Jul. 27, 2017, in connection with Chilean Patent Application No. 633-2009 [English instructions and document as filed in Spanish], 35 pages.

Response, filed Sep. 18, 2017, to Office Action, issued Jul. 18, 2017, in connection with Vietnamese Patent Application No. 1-2010-02743 [English instructions and document as filed in Vietnamese], 4 pages.

Notice of Allowance, issued Nov. 20, 2017 and received on Nov. 26, 2017, in connection with corresponding Chilean Patent Application No. 633-2009 [English reporting letter with Original document in Spanish], 5 pages.

Notice of Grant, dated Oct. 9, 2017 and received on Nov. 15, 2017, issued in connection with corresponding Indonesian Patent Application No. 201003534, 2 pages.

"Immunoglobulin-Overview" retrieved from <URL:webmd.com/cancer/tc/immune-globulin-overview[retrieved on Apr. 12, 2017], 4 pages.

News Release, "Enhaze draws BMS and Roche money; Halozyme could receive $2B+," Published Sep. 14, 2017 [online] Retrieved from:<URL: bioworld.com/content/enhanze-draws-bms-and-roche-money-halozyme-could-receive-2b [retrieved on Sep. 18, 2017], 2 pages.

Notice of Allowance, issued Nov. 20, 2017, in connection with Chilean Patent Application No. 633-2009 [English translation and original document in Spanish], 10 pages.

(56) References Cited

OTHER PUBLICATIONS

Examination Report/ Hearing Notice, dated Dec. 14, 2017, in connection with Indian Patent Application No. 7321/DELNP/2010, 3 pages.
Response, filed Aug. 9, 2018, to Office Action, issued May 23, 2018, in connection with Argentinian Patent Application No. P090100943 [English instructions and document as-filed in Spanish], 72 pages.
Letter/Written Disclosure of the Supplemental Information Disclosure Statement for the above-referenced application, filed herewith Dec. 13, 2018, 3 pages.
Written Opinion, issued Jul. 1, 2016, in connection with Singapore Patent Application No. 10201503296Q, 7 pages.
Halozyme Therapeutics, Analyst and Investor Meeting presentations "Matrix Therapeutics for Life" presentations including Lim, J., "Introduction and strategy overview, Roche program update," Gustafson, K., "Strategic deployment of cash," Wasserman, R., "HyQ treatment of primary immunodeficiency patients," Muchmore, D., "Ultrafast insulin-clinical results and ongoing trials," Cefalu, W., "Unmet needs in diabetes management," Little, R., Market overview-ultrafast insulin and SC immunoglobin and Frost, G., "PEGPH20 and HTI-501 status report," Presented 10.15.10 in New York, NY. (124 pages).
Lee et al."Subcutaneous immunoglobulin administration using recombinant human hyaluronidase: a novel approach for the treatment of peripheral neuropathies in children," abstract for the xIth world congress of ICNC Cairo May 2-7, 2010. Retrieved from the Internet:<URL: icnc2010.org/index.php?option=com_content&view=article&id=163&Itemid=9, [retrieved on Jul. 12, 2010] [1 page].
International Prelimnary Report on Patentability issued Jun. 8, 2010, in connection with corresponding International Patent Application No. PCT/US2009/001670.
News Release, "Halozyme Therapeutics Announces Implementation of Development Focused Strategy," Oct. 11, 2010, San Diego, CA, Retrieved from the Internet: phx.corporate-ir.net/phoenix.zhtml?c=175436&p=irol-newsArticle&ID=1481205&highlight=, (accessed Nov. 19, 2010; 3 pages).
News Release, Halozyme Therapeutics Inc., "Halozyme Therapeutics Reports 2008 Second Quarter Financial Results" Aug. 8, 2008, retrieved from the Internet:<URL: sec.gov/Archives/edgar/data/1159036/000129993308003838/exhibit1.htm, [retrieved on Mar. 31, 2010] [5 pages].
Reipert et al., "Fc function of a new intravenous immunoglobulin product:IGIV 10% triple virally inactivated solution," Vox Sang 91(3)256-263 (2006).
Baxter Health Care Corporation, Gammagard Liquid (Immune Globulin Intravenous (Human) 10%] product literature, found at: www.baxter.com/products/biopharmaceuticals/downloads/gamliquid_PI.pdf, published Apr. 2005, 4 pages.
Leibl et al. "Efficacy and Safety of a New Intravenous Immunoglobulin in Adult Subjects with Chronic Idiopathic Thrombocytopenia Purpura," Blood (ASH Annual Meeting Abstracts) 2005 106:Abstract 3984, 2 pages (2005).
Leesch et al., "30-Day Pharmacokinetic Evaluation of IV versus Subcutaneous Administration of Immunoglobulin with and without Recombinant Human Hyaluronidase in Dogs," Journal of Allergy and Clinical Immunology 123(2):Suppl. S, p. s10 (2009) and 65th annual meeting of the american academy of allergy asthma and immunology; washington DC, Mar. 13-17, 2009.
Melamed et al., "Recombinant Human Hyaluronidase Facilitates Dispersion of Subcutaneously Administered Gammagard Liquid and Enables Administration of a Full Monthly Dose in a Single Site to Patients with Immunodeficiency Diseases," J Allergy Clin Immunol. 121(2):Suppl.1, page S83 (2008) [1 page].
News Release, Halozyme Therapeutics Inc., Q1 2008 Earnings Call Transcript found at: http://seekingalpha.com/article/76655-halozyme-therapeutics-inc-q1-2008-earnings-call-transcript [accessed on Jun. 25, 09] [14 pages].
News Release, Halozyme Therapeutics Inc., Q3 2009 Earnings Call Transcript found at: http://seekingalpha.com/article/171883-halozyme-therapeutics-inc-q3-2009-earnings-call-transcript?page=-1 [accessed on Nov. 6, 2009] [11 pages].
International Search Report, issued Aug. 31, 2009, in connection with corresponding International Patent Application No. PCT/US2009/001670.
Letter/Written Disclosure of the Supplemental Information Disclosure Statement for the above- referenced application, dated Dec. 17, 2013, 2 pages.
Ko et al., "Clinical Review Memorandum: BLA STN 125105/708, Baxter's Immune Globulin Infusion (Human) 10%, 10, 25, 50, 100, 200 and 300 mL Solutions for Subcutaneous Administration," Prepared Feb. 21, 2010. Retrieved from the Internet at http://www.google.com/url?sa=t&rct=j&q=&esrc=s&frm=1&source=web&cd=3&ved=0CDMQFjAC&url=http%3A%2F%2Fwww.fda.gov%2Fdownloads%2FBiologicsBloodVaccines%2FBloodBloodProducts%2FApprovedProducts%2FLicensedProductsBLAs%2FFractionatedPlasmaProducts%2FUCM275415.pdf&ei=jD-vUov9D8LX2AXNmICYCQ&usg=AFQjCNG5hbn36PZ5ifK_5xhiBdqQmSFwIQ [Retrieved on Dec. 16, 2013], 39 pages.
Lloyd, J., "Gammagard therapy offers hope for Alzheimer's patients, " USA Today. Published on Jan. 17, 2012 [Retrieved on Dec. 17, 2012] Retrieved from the Internet: URL:usatoday30.usatoday.com/news/health/story/2012-07-16/alzheimers-treatment-gammagard/56270084/1 [6 pages].
Halozyme Therapeutics Investor Presentation, "Halozyme Therapeutics, Inc.: Thinking outside the cell," Presented on Oct. 2, 2012 [online] [retrieved on Oct. 11, 2012] Retrieved from:<URL:sec.gov/Archives/edgar/data/1159036/000119312512412748/d419091dex991.htm [82 pages].
News Release, "Baxter Receives Marketing Authorization for HyQvia in European Union," May 21, 2013 [online][retrieved on Dec. 16, 2013], Retrieved from: <URL: halozyme.com/Investors/News-Releases/News-Release-Details/2013/Baxter-Receives-Marketing-Authorization-for-HyQvia-in-European-Union/default.aspx, 4 pages.
News Release, "Baxter Submits Amended BLA to U.S. FDA for HyQvia for Primary Immunodeficiency," Dec. 2, 2013 [online] [retrieved on Dec. 16, 2013], Retrieved from: <URL: halozyme.com/Investors/News-Releases/News-Release-Details/2013/Baxter-Submits-Amended-BLA-to-US-FDA-for-HyQvia-for-Primary-Immunodeficiency/default.aspx, 3 page.
Transcript, "Halozyme Therapeutics's CEO hosts analyst/investor day conference call (Transcript)," Published on Oct. 2, 2012 [online] [retrieved on Oct. 25, 2012] Retrieved from:<URL:seekingalpha.com/article/901141-halozy me-therapeutics-s-ceo-hosts-analyst-investor-day-conference-call-transcript?part=single, 49 pages.
Response to Examiner's Report, issued Oct. 5, 2011, in connection with corresponding Australian Patent Application No. 2009226141, 29 pages.
Response, dated Aug. 7, 2013, to Office Action, issued Feb. 7, 2013, in connection with corresponding Canadian Patent Application No. 2,714,708, 27 pages.
Instructions for response to Office Action, issued Jul. 4, 2012, in connection with corresponding Chinese Patent Application No. 200980109505.9, 19 pages.
Instructions, dated Sep. 25, 2013, for response to Office Action, issued May 15, 2013, in connection with corresponding Chinese Patent Application No. 200980109505.9, 17 pages.
Final Rejection, received Sep. 4, 2013, in connection with corresponding Colombian Patent Application No. 10.111.104, 4 pages.
Instructions, dated Sep. 11, 2013, for response to Final Rejection, received Sep. 4, 2013, in connection with corresponding Colombian Patent Application No. 10.111.104, 16 pages.
Response to Examination Report, dated Nov. 22, 2012, in connection with corresponding European Patent Application No. 09721669.1, 26 pages.
Instructions, dated Sep. 25, 2013, for response to Office Action, issued Apr. 2, 2013, in connection with corresponding Japanese Patent Application No. 2011-500795, 16 pages.
Official Action, dated Oct. 4, 2013, in connection with corresponding Mexican Patent Application No. MX/a/2010/009478, 4 pages.

(56) References Cited

OTHER PUBLICATIONS

Instructions, dated Sep. 24, 2013, for response to Office Action, issued Mar. 29, 2013, in connection with corresponding Taiwan Patent Application No. 098108166, 22 pages.
Response to Written Opinion, dated Oct. 13, 2011, in connection with related International Patent Application No. PCT/US2010/002545, 24 pages.
Baxter Healthcare Corporation, "Study to determine the dose of recombinant human hyaluronidase needed to infuse a dose of IGIV subcutaneously," found at: http://clinicaltrials.gov/ct2/show/NCT00782106 [accessed on May 13, 2009] [3 pages].
Bernoist, C. and P. Chambon, "In vivo sequence requirements of the SV40 early promotor region," Nature 290:304-310 (1981).
Bianchi et al., "Synthetic depsipeptide substrates for the assay of human hepatitis C virus protease," Anal. Biochem. 237:239-244 (1996).
Bookbinder et al., "Biochemical Characterization of Recombinant Human PH20 (SPAM1) Hyaluronidase," Hyaluronan (ISHAS) 2007, Charleston, SC, 1 page.
Conserved domain search from U.S. Appl. No. 10/795,095 of Seq Id No. 6, Primakoff et al. U.S. Pat. No. 5,721,348, performed on the NCBI website on Aug. 5, 2008.
Danilkovitch-Miagkova, et al., "Hyaluronidase 2 negatively regulates RON receptor tyrosine kinase and mediates transformation of epithelial cells by jaagsiekte sheep retrovirus," Proc Natl Acad Sci USA. 100(8):4580-4585 (2003).
Frost et al., "HYALILUCA-1, a candidate tumor suppressor gene on chromosome 3p21.3, is inactivated in head and neck squamous cell carcinomas by aberrant splicing of pre-mRNA," Oncogene (19):870-877 (2000).
Frost, G., "Recombinant human hyaluronidase (rHuPH20): an enabling platform for subcutaneous drug and fluid administration," Expert Opin. Drug. Deliv. 4:427-440 (2007).
Godeau et al., "Intravenous immunoglobulin for adults with autoimmune thrombocytopeni purpura: results of a randomized trial comparing 0.5 and 1 g/kg b.w.," Br J Haematol 107(4):716-719 (1999).
Godeau et al., "Treatment of adult chronic autoimmune thrombocytopenia purpura with repeated high-dose intravenous immunoglobulin," Blood 82(5):1415-1421 (1993).
Gribskov, M. and R. Burgess, "Sigma factors from *E. coli*, B. subtilis, phage SP01, and phage T4 are homologous proteins," Nucl. Acids Res. 14:6745-6763 (1986).
Hammer et al., "Diversity of alpha-fetoprotein gene expression in mice is generated by a combination of separate enhancer elements," Science 235:53-58 (1987).
News Release, Halozyme Therapeutics Inc., "Data Presented at AAAAI Reinforce Baxter's Commitment to Making Gammagard Liquid Therapy More Convenient" Deerfield I1, Mar. 16, 2009, http://www.businesswire.com/portal/site/google/?ndmViewId=newsview&newsId=20090316005731&newsLang=en [16 pages].
News Release, Halozyme Therapeutics Inc., "Halozyme Therapeutics Announces Roche Begins Phase 1 Clinical Trial and Selects Fourth Exclusive Biologic Target," San Diego, CA, Dec. 8, 2008, http://phx.corporate-ir.net/phoenix.zhtml?c=175436&p=irol-newsArticle_Print&ID=1233454&highlight= (accessed Jan. 6, 09), 2 pages.
News Release, Halozyme Therapeutics Inc., "Halozyme Therapeutics Releases Results of Enhanze Technology Clinical Trial to Improve the Subcutaneous Absorption of a Large Protein Molecule Therapeutic," San Diego, CA, Jan. 22, 2007, http://phx.corporate-ir.net/phoenix.zhtml?c=175436&p-irol-newsArticle_Print&ID=952285&highlight= (accessed Jan. 6, 2009), 3 pages.
News Release, Halozyme Therapeutics Inc., "Halozyme Therapeutics Files NDA for Enhanze SC," San Diego, CA, Mar. 28, 2005, http://phx.corporate-ir.net/phoenix.zhtml?c=175436&p=irol-newsArticle_Print&ID=689194&highlight= (accessed Jan. 6, 2009), 2 pages.
News Release, Halozyme Therapeutics Inc., "Phase III Trial Begins for Gammagard Liquid Plus rHuPH20 in Primary Immunodeficiency Patients," San Diego, CA, Jan. 5, 2009, http://phx.corporate-ir.net/phoenix.zhtml?c=175436&p=irol-newsArticle_Print&ID=1240232&highlight= (accessed Jan. 6, 2009), 3 pages.
News Release, Halozyme Therapeutics Inc., Q4 2008 Earnings Call Transcript found at: http://seekingalpha.com/article/125929-balozyme-therapeutics-inc-q4-2008-earnings-call-transcript [accessed on May 13, 2009] [12 pages].
Oyaizu et al., "(NZW x BXSB)F1 mouse. A new animal model of idiopathic thrombocytopeni purpura," J Exp Med 2017-2022 (1988).
Pinkstaff et al., "Evaluation of the Compatibility and Pharmacokinetics of Co-formulated Biologics with Recombinant Human Hyaluronidase: Dose Response," American Association of Pharmaceutical Scientists Conference, Jun. 2006, San Antonio, TX, 2 pages.
Schiff et al., "Alterations in the half-life and clearance of IgG during therapy with intravenous gamma-globulin in 16 patients with severe primary humoral immunodeficiency," J. Clin. Immunol. 6:256-264 (1986).
Steinkuhler et al., "Product inhibition of the hepatitis C virus NS3 protease," Biochem. 37:8899-8905 (1998).
Zalipsky, S and C Lee, "Poly(ethy lene glycol) Chemistry: Biotechnical and Biomedical Applications," J. Hams, ed., Plenum: NY, Chapter 21, pp. 341-370 (1992).
Leesch et al., "30-day pharmacokinetic evaluation of IV versus subcutaneous administration of immunoglobulin with and without recombinant human hyaluronidase in dogs," J Allergy and Clin Immunol 123(2, Suppl. S):S10 (2009), Abstract, 1 page.
Skoda-Smith et al., "Subcutaneous immunoglobulin replacement therapy in the treatment of patients with primary immunodeficiency disease," Ther Clin Risk Manag 6:1-10 (2010).
News Release, "Baxter presents data from interim analyses of phase III clinical trial of HyQ at European Society for Immunodeficiencies meeting," Published on Oct. 6, 2010 [online] [retrieved on Jan. 25, 2012] Retrieved from:<URL:baxter.com/press_room/press_releases/2010/10_06_10_hyq.html [5 pages].
Office Action, issued Feb. 17, 2011, in connection with related U.S. Appl. No. 12/378,969, 12 pages.
Response of Aug. 17, 2011 to Office Action, issued Feb. 17, 2011, in connection with related U.S. Appl. No. 12/378,969, 16 pages.
Examiner's Report, issued Oct. 5, 2011, in connection with corresponding Australian Patent Application No. 2009226141, 2 pages.
Search Report and Written Opinion, issued Dec. 2, 2011 (received Jan. 19, 2012), in connection with Singapore Patent Application No. 201005998-8, 15 pages.
Arming et al., "In vitro mutagenesis of PH-20 hyaluronidase from human sperm," Eur J Biochem 247(3):810-814 (1997).
Response, filed Feb. 10, 2016, to Examiner's Report, issued Aug. 10, 2015, in connection with Canadian Patent Application No. 2,714,708, 57 pages.
Notification of Reexamination, issued Mar. 7, 2016, in connection with Chinese Patent Application No. 200980109505.9 [English Translation and original document in Chinese], 14 pages.
Response, filed Dec. 29, 2015, to Examination Report, issued Oct. 21, 2015, in connection with European Patent Application No. 09721669.1, 8 pages.
Communication under Rule 71(3) Intention to Grant, issued Mar. 16, 2016, in connection with European Patent Application No. 09721669.1, 5 pages.
Response, filed Mar. 21, 2016, to Examination Report, issued Apr. 30, 2015, in connection with Indian Patent Application No. 7321/DELNP/2010, 47 pages.
Response, filed Sep. 28, 2015, to Office Action, issued Jun. 30, 2105, in connection with Japanese Patent Application No. 2014-192938 [English language instructions and document as filed in Japanese], 18 pages.
Office Action, issued Dec. 22, 2015, in connection with Japanese Patent Application No. 2014-192938 [English translation and original document in Japanese], 3 pages.
Response, filed Jan. 21, 2016, to Office Action, issued Dec. 22, 2105, in connection with Japanese Patent Application No. 2014-192938 [English language instructions and document as filed in Japanese], 34 pages.

(56) References Cited

OTHER PUBLICATIONS

Letter, dated Feb. 17, 2016, reporting Decision to Grant, issued Feb. 16, 2016, in connection with Japanese Patent Application No. 2014-192938 [English letter and original document in Japanese], 4 pages.
Response, filed May 29, 2015, to Official Action, issued Jan. 28, 2015, in connection with Mexican Patent Application No. MX/a/2010/009478 [English language instructions and document as filed in Spanish], 35 pages.
Response, filed Feb. 2, 2016, to Office Action, issued Sep. 17, 2015, in connection with Mexican Patent Application No. MX/a/2010/009478 [English language instructions and document as filed in Spanish], 31 pages.
Response, filed Nov. 24, 2015, to Office Action, issued Jul. 27, 2015, in connection with Vietnamese Patent Application No. 1-2010-02743 [English instructions and document as filed in Vietnamese], 6 pages.
Letter, dated Mar. 31, 2016, reporting Decision to Grant, issued Mar. 23, 2016, in connection with Eurasian Patent Application No. 201200490 [English letter and document as issued in Russian], 9 pages.
Notice of Grant, issued Aug. 10, 2015, in connection with Mexican Patent Application No. MX/a/2012/003282 [Letter Reporting Notice of Allowance and Letters Patent], 3 pages.
Baxter BioScience, Briefing Book: Blood Products Advisory Committee Meeting. "HyQvia: Immune Globulin Infusion 10% (Human) with Recombinant Human Hyaluronidase," Published Jul. 31, 2014. Available on-line at <URL:google.com/url?sa=t&rct=j&q=&esrc=s&frm=1&source=web&cd=3&ved=0CCwQFjAC&url=http%3A%2F%2Fwww.fda.gov%2Fdownloads%2FAdvisoryCommittees%2FCommitteesMeetingMaterials%2FBloodVaccinesandOtherBiologics%2FBloodProductsAdvisoryCommittee%2FUCM407013.pdf&ei=zTFBVJXELfOHsQSX14DICQ&usg=AFQjCNFmAm634vKiaGB5cLM-mvOEMFGu-w, 204 pages.
"PEGPH20: The Science & The Strategy," presented at J. P. Morgan Healthcare Conference on Jan. 7, 2015. Presentation. 81 pages.
News Release, Halozyme Therapeutics, Inc., "Halozyme announces Roche marketing authorization for MabThera SC for patients with common forms of non-hodgkin lymphoma in European Union," Published Mar. 28, 2014 [online], Retrieved from: <URL:halozyme.com/Investors/News-Releases/News-Release-Details/2014/Halozyme-Announces-Roche-Marketing-Authorization-For-MabThera-SC-For-Patients-With-Common-Forms-Of-Non-Hodgkin-Lymphoma-In-European-Union/default.aspx [retrieved on Mar. 31, 2014] 3 pages.
Instructions, dated Jan. 25, 2014, for Response, filed Jan. 28, 2014, to Office Action, issued Oct. 15, 2013, in connection with Chilean Patent Application No. 633-2009, 20 pages [English language instructions and document, as filed, in Spanish].
Instructions, dated Jun. 1, 2014, for request for reexamination in Response, filed Jun. 5, 2014, to Office Action, issued Feb. 18, 2014, in connection with Chinese Patent Application No. 200980109505.9), 32 pages [English language instructions and document, as filed, in Chinese].
Final Office Action, issued May 20, 2014, in connection with Japanese Patent Application No. 2011-500795, 5 pages [English language translation, original document in Japanese and cited reference D1: Melamed et al., J Allergy and Clin Immunol 121(2, suppl.):S83 (2008)].
Instructions, dated Sep. 18, 2014, for Response, filed Sep. 22, 2014, to Final Office Action, issued May 20, 2014, in connection with Japanese Patent Application No. 2011-500795, 17 pages [English language instructions and document, as filed, in Japanese].
Pre-appeal Examination Report, issued Jan. 7, 2015, in connection with Japanese Patent Application No. 2011-500795, 3 pages [English language translation and cited reference D1: Melamed et al., J Allergy and Clin Immunol 121(2, suppl.):S83 (2008)].
Instructions, dated Jan. 16, 2014, for response, filed Jan. 20, 2014, to Official Action, received Oct. 4, 2013, in connection with Mexican Patent Application No. MX/a/2010/009478, 25 pages [English language instructions and document, as filed, in Spanish].
Official Action, issued May 9, 2014, in connection with Mexican Patent Application No. MX/a/2010/009478, 4 pages [English language translation and original document in Spanish].
Instructions, dated Jan. 14, 2015 and Jan. 23, 2015, for Response, filed Jan. 28, 2015, to Office Action, issued Oct. 17, 2014, in connection with Taiwanese Patent Application No. 098108166, 61 pages [English language instructions and document, as filed, in Chinese].
Letter/Written Disclosure of the Supplemental Information Disclosure Statement for the above-referenced application, dated Sep. 11, 2012, 2 pages.
Wasserman et al., Pharmacokinetic (PK) of human immuneglobulin 10% (IgG) administered intraveneously (IGIV), subcutaneously (IGSC) or facilitated subcutaneously with recombinant human hyaluronidase hyaluronidase (IGHy) in a subset of patients with primary immunodeficiency (PI) Presented May 18, 2012 at the Clinical Immunology Society Annual Meeting: Primary Immune Deficiency Disease North American Conference May 17-20, 2012, Chicago, IL. Abstract, 1 page.
Wasserman et al., "Tolerability and efficacy of facilitated—subcutaneous infusion of immuneglobulin (HUMAN) 10% and recombinant human hyaluronidase (IGHy) in patients with primary immunodeficiency (PI)," Presented May 18, 2012 at the Clinical Immunolgy Society Annual Meeting: Primary Immune Deficiency Disease North American Conference, Chicago, IL. Abstract, 2 pages.
News Release, Baxter International Inc., "Baxter and Halozyme Provide Update on HyQ Biologics License Application," Published on Apr. 16, 12 [online] [retrieved on Jul. 27, 2012] Retrieved from: <URL:finance.yahoo.com/news/baxter-halozyme-hyq-biologics-license-120000974.html [2 pages].
Response to Written Opinion, dated Aug. 31, 2009, in connection with International Application No. PCT/US2009/001670 (3058PC), 32 pages.
English translation of Examiniation Report dated Apr. 24, 2012 in connection with Taiwanese Patent Application No. 098108166 (3058TW), 5 pages.
Response to Search Report and Written Opinion, dated Dec. 2, 2011, in connection with Singapore Patent Application No. 201005998-8 (3058SG), 9 pages.
Bee et al., "Effects of rHuPH20 on SC Administration of 10% and 20% IgG in Yucatan Mini Pigs" AAAAI Feb. 26-Mar. 2, 2010, New Orleans [2 pages].
Gellene, D., "San Diego's Halozyme Injects New Life into Old Drugs" Feb. 28, 2010, retrieved from: http://www.signonsandiego.com/news/2010/feb/28/wwwxconomycom60025/, on Apr. 26, 2010 [3 pages].
Jefferies 2010 Global life science conference call, Jun. 8, 2010, wsw.com/webcast/jeff46/hzym (transcript) [7 pages].
Haller, M., "Enzyme-facilitated Parenteral Drug Transport." Strategic Research Institute's 10th Anniversary Drug Delivery Technology and Deal-making Summit, 2005 New Brunswick, NJ [24 pages].
Halozyme Therapeutics, Analyst and Investor Meeting presentations including by Lim, J., "Introduction and strategic review," Little, R., "Leveraging the technology across multiple partners," Frost, G., "Discovery and early development pipeline update," and D. Muchmore, "Ultrafast insulin-PH20 program-where we are going." Presented 10.15.09 in New York. (88 pages).
Halozyme Therapeutics, "Securities and Exchange Commission Form 10K," Mar. 12, 2010 [121 pages].
Halozyme Therapeutics, "Securities and Exchange Commission Form 10Q," Nov. 6, 2009 [45 pages].
Halozyme Therapeutics, "Securities and Exchange Commission Form 10Q," Aug. 7, 2009 [45 pages].
Halozyme Therapeutics, "Securities and Exchange Commission Form 10-KSB," Mar. 24, 2006 [50 pages].
Halozyme Therapeutics, "Securities and Exchange Commission Form 10K," Mar. 2007 [108 pages].
Halozyme Therapeutics, "Securities and Exchange Commission Form SB-2," Mar. 23, 2004, 102 pages.
Halozyme Therapeutics, "Securities and Exchange Commission Amendment No. 1 to Form SB- 2," Jun. 21, 2004, 108 pages.

(56) References Cited

OTHER PUBLICATIONS

Halozyme Therapeutics, "Securities and Exchange Commission Form 10-QSB," Nov. 12, 2004, 34 pages.
Halozyme Therapeutics, "Securities and Exchange Commission Form S-3," Nov. 12, 2004, 30 pages.
ICSI Cumulase, "Human hyaluronidase for human oocytes" Medicult Product information Jun. 16, 2009, 2 pages [accessed on Mar. 30, 2010].
New Release, Halozyme Therapeutics Reports Fourth Quarter and Year End 2008 Financial Results, Mar. 13, 2009, retrieved from: www.sec.gov/Archives/edgar/data/1159036/000129993309001189/exhibit1.htm [retrieved on Mar. 30, 2010].
News Release, Halozyme Therapeutics Inc., "Halozyme Therapeutics and Baxter Healthcare Corporation Sign Exclusive Sales and Marketing Agreement for Halozyme's Investigational Therapeutic, Enhanze SC," Aug. 16, 2004, retrieved from the Internet:<URL: sec.gov/Archives/edgar/data/1159036/000095013704006885/a01296exv99w1.txt, [retrieved on Mar. 29, 2010] [2 pages].
Stern, R., "Devising a pathway for hyaluronan catabolism are we there yet?" Glycobiology 13:105R-115R (2003).
Varga et al., "Efficacy and safety of IGIV, 10% TVR solution, a new intravenous immunoglobulin, in adult subjects with chronic idiopathic thrombocytopenia purpura" Transf Med Hemother 33:509-514 (2006).
Misbah et al., "Subcutaneous immunoglobin: opportunities and outlook," J Trans1 Immunol 158 (Suppl. 1):51-59 (2009) and available on-line Oct. 30, 2009.
Fernandes, P. and J. Lundblad, "Preparation of a stable intravenous gamma-globulin: process design and scale-up," Vox Sang. 39:101-112 (1980).
Planitzer et al., "Neutralization of different echovirus serotypes by individual lots of intravenous immunoglobulin," J Med Virol 83(2):305-310 (2011).
Wang, Y. and M. Hanson, "Parenteral formulations of proteins and peptides: Stability and stabilizers," J. of Parenteral Science & Technology 42(supp):S4-S26 (1988).
Melamed et al. (The Journal of Allergy and Clinical Immunology 121(2), supplement 1: S83, Feb. 2008).*
ZLB Behring LLC (Immune Globulin Subcutaneous (Human), Vivaglobin®, pp. 1-14, Jan. 2006).*
Office Action, dated Mar. 5, 2012 in connection with corresponding Chilean Patent Application No. 541-2009, 3 pages.
International Preliminary Report on Patentability, dated Mar. 2, 2012, in connection with international Application No. PCT/US2010/002545, 26 pages.
Letter/Written Disclosure of the Supplemental Information Disclosure Statement for the above-referenced applicatoin, dated Dec. 17, 2013, 2 pages.
Ko et al., "Clinical Review Memorandum: BLA STN 125105/708, Baxter's Immune Globulin Infusion (Human) 10%, 10, 25, 50, 100, 200 and 300 mL Solutions for Subcutaneous Administration," Prepared Feb. 21, 2010. Retrieved from the Internet at http://www.google.com/url?sa=t&rct=j&q=&esrc=s&frm=1&source=web&cd=3&ved=0CDMQFjAC&url=http%3A%2F%2Fwww.fda.gov%2Fdownloads%2FBiologicsBloodVaccines%2FBloodBloodProducts%2FApprovedProducts%2FLicensedProductsBLAs%2FFractionatedPlasmaProducts%2FUCM275415.pdf&ei=jD-vU0v9D8LX2AXNmICYCQ&usg=AFQjCNG5hbn36PZ5ifK_5xhiBdqQmSFwIQ [Retrieved on Dec. 16, 2013], 39 pages.
Lloyd, J., "Gammagard therapy offers hope for Alzheimer's patients," USA Today. Published on Jul. 17, 2012 [Retrieved on Dec. 17, 2012] Retrieved from the Internet: URL:usatoday30,usatoday.com/news/health/story/2012-07-16/alzheimers-treatment-gammagard/56270084/1 [6 pages].
Pollack, A., "Small Trial Hints Drug Can Slow Alzheimer's," New York Times. Published Jul. 17, 2012 [online][Accessed Dec. 17, 2012] Retrieved from the Internet: URL: www.nytimes.com/2012/07/18/business/study-shows-drug-may-help-alzheimers-patients.html?_r=0 [3 pages].
Frost, G. I., "Halozyme Therapeutics, Inc. Thinking outside the cell," presented at J. P. Morgan Healthcare Conference on Jan. 10, 2013. Presentation, 23 pages.
Stein et al., "Pharmacokinetics (PK) of Human Immunoglobulin 10% (IgG) Administered Intravenously (IGIV), Subcutaneously (IGSC) or Facilitated Subcutaneously with Recombinant Human Hyaluronidase (IGHy) in a Subset of Patients with Primary Immunodeficiency Disease (PIDD)," J Allergy Clinl Immunol. 129(2):AB14. Presented Mar. 3, 2012 at AAAAI Annual Meeting, Orlando, FL. Abstract #55.
Stein et al., "Pharmacokinetics (PK) of Human Immunoglobulin 10% (IgG) Administered Intravenously (IGIV), Subcutaneously (IGSC) or Facilitated Subcutaneously with Recombinant Human Hyaluronidase (IGHy) in a Subset of Patients with Primary Immunodeficiency Disease (PIDD)," Presented Mar. 3, 2012 at AAAAI Annual Meeting, Orlando, FL, Poster #55, 1 page.
Wasserman et al., "Tolerability and Efficacy of Facilitated-Subcutaneous Infusion of Immune Globulin (Human), 10% and Recombinant Human Hyaluronidase (IGHy) in a Subset of Study Patients With Primary Immunodeficiency Disease (PIDD)," J Allergy Clinl Immunol. 129(2):AB15. Presented Mar. 3, 2012 at the American College of Allergy, Asthma, & Immunology Meeting, Orlando, FL. Abstract #56, 1 page.
Wasserman et al., "Tolerability and Efficacy of Facilitated- Subcutaneous Infusion of Immune Globulin (Human), 10% and Recombinant Human Hyaluronidase (IGHy) in a Subset of Study Patients With Primary Immunodeficiency Disease (PIDD)" Presented Mar. 3, 2012 at the American College of Allergy, Asthma, & Immunology Meeting, Orlando, FL, Poster #56, 1 page.
Halozyme Therapeutics Investor Presentation, "Halozyme Therapeutics, Inc.: Thinking outside the cell," Presented on Oct. 2, 2012 [online][retrieved on Oct. 11, 2012] Retrieved from:<URL:sec.gov/Archives/edgar/data/1159036/000119312512412748/d419091dex991.htm [82 pages].
News Release, Halozyme Therapeutics, Inc., "Halozyme Confirms Baxter Has Received a Complete Response Letter For HyQ BLA," Published Aug. 1, 2012 [online][retrieved on Dec 17, 2012]Retrieved from: <URL:halozyme.com/Investors/News-Releases/News-Release-Details/2012/Halozyme-Confirms-Baxter-Has-Received-A-Complete-Response-Letter-For-HyQ-BLA1130436/default.aspx, 3 page.
News Release, "Baxter And Halozyme Announce Positive Opinion For HyQvia For Treatment Of Primary And Secondary Immunodeficiencies In The European Union," published Mar. 22, 2013 [online][Retrieved on Dec. 16, 2013], Retrieved from: <URL:halozyme.com/Investors/News-Releases/News-Release-Details/2013/Baxter-And-Halozyme-Announce-Positive-Opinion-For-HyQvia-For-Treatment-Of-Primary-And-Secondary-Immunodeficiencies-In-The-European-Union/defaultaspx, 3 pages.
News Release, "Baxter Receives Marketing Authorization for HyQvia in European Union," May 21, 2013 [online][retrieved on Dec. 16, 2013], Retrieved from: <URL: halozyme,com/Investors/News-Releases/News-Release-Details/2013/Baxter-Receives-Marketing-Authorization-for-HyQvia-in-European-Union/defaultraspx, 4 pages.
News Release, "Baxter Submits Amended BLA to U.S. FDA for HyQvia for Primary Immunodeficiency," Dec. 2, 2013 [online][retrieved on Dec. 16, 2013], Retrieved from: <URL: halozyme.com/Investors/News-Releases/News-Release-Details/2013/Baxter-Submjts-Amended-BLA-t0-US-FDA-for-HyQvia-for-Prunary-Immunodeficiency/defaulti.aspx, 3 page.
News Release, "Baxter presents long-term data on HyQ during AAAAI annual meeting," Published on Mar, 2, 2012 [online][retrieved on Nov. 6, 2012] Retrieved from:<URL:http://www.baxter.com/press_room/press_releases/2012/03_02_12_hyq.html, 2 pages.
News Release, "Halozyme Announced Roche Filed A Marketing Authorization Application For Subcutaneous MabThera,"Published Dec. 8, 2012 [online][Retrieved Jan. 3, 2013] Retrieved from the Internet: URL:http://halozyme.com/Investors/News-Releases/News-Release-Details/2012/Halozyme-Announced-Roche-Filed-A-Marketing-Authorization-Application-For-Subcutaneous-MabThera1132247/default.aspx, 2 pages.
Transcript, "Halozyme Therapeutics's CEO hosts analyst/investor day conference call (Transcript)," Published on Oct. 2, 2012 [online][retrieved on Oct. 25, 2012] Retrieved from: <URL:

(56) References Cited

OTHER PUBLICATIONS seekingalpha.com/article/901141-halozyme-therapeutlcs-s-ceo-hosts-analyst-investor-day-conference-call-transcript?part=single, 49 pages.
News Release, "Halozyme Therapeutics to present at the 31st Annual J.P. Morgan Healthcare Conference,"Published Jan, 3, 2013 [online][Retrieved Jan. 17, 2013]Retrieved from:<URL:halozyme.com/Investors/News-Releases/News-Release-Details/2013/Halozyme-Therapeutics-to-Present-at-the-31st-Annual-JP-Morgan-Healthcare-Conference1132508/default.aspx, 2 pages.
Response to Examiner's Report, dated Oct. 5, 2011, in connection with corresponding Australian Patent Application No. 2009226141, 29 pages.
Response, dated Aug. 7,2013, to Office Action, dated Feb. 7, 2013, in connection with corresponding Canadian Patent Application No. 2,714,708, 27 pages.
Instructions, dated Jul. 11, 2013, for Response to Office Action, received Feb. 13, 2013, in connection with corresponding Chilean Patent Application No. 633-2009, 23 pages.
Office Action, dated Oct. 15, 2013, in connection with corresponding Chilean Patent Application No. 633-2009 [English translation together with Original in the Spanish language] 13 pages.
Instructions for response to Office Action, dated Jul. 4, 2012, in connection with corresponding Chinese Patent Application No. 200980109505.9, 19 pages.
Instructions, dated Sep. 25, 2013, for response to Office Action, dated May 15, 2013, in connection with corresponding Chinese Patent Application No. 200980109505.9, 17 pages.
Instructions, dated Apr. 2, 2013, for response to Office Action, received Feb. 25, 2013, in connection with corresponding Colombian Patent Application No. 10.111.104, 19 pages.
Final Rejection, received Sep. 4, 2013, in connection with corresponding Colombian Patent Application No. 10.111.104, 4 pages.
Instructions, dated Sep. 11, 2013, for response to Final Rejection, received Sep. 4, 2013, in connection with corresponding Colombian Patent Application No. 10.111.104, 16 pages.
Response to Examination Report, dated Nov. 22, 2012, in connection with corresponding European Patent Application No. 09721669.1 (3058EP), 26 pages.
Instructions, dated Sep. 25, 2013, for response to Office Action, dated Apr. 2, 2013, in connection with corresponding Japanese Patent Application No. 2011-500795, 16 pages.
Official Action, received Oct. 4, 2013, in connection with corresponding Mexican Patent Application No. MX/a/2010/009478, 4 pages.
Response, dated Jun. 25, 2013, to Written Opinion, dated Jan. 25, 2013, in connection with corresponding Singapore Patent Application No. 201005998-8, 10 pages.
Instructions for response to Examination Report, dated Apr. 24, 2012, in connection with corresponding Taiwanese Patent Application No. 098108166, 26 pages.
Instructions, dated Sep. 24, 2013, for response to Office Action, dated Mar. 29, 2013, in connection with corresponding Taiwan Patent Application No. 098108166, 22 pages.
Search and Examination Report, dated May 7, 2013, in connection with related Singapore Patent Application No. 201202729-8, 11 pages.
Letter/Written Disclosure of the Supplemental Information Disclosure Statement for the above-referenced application, filed Aug. 20, 2014, 2 pages.
Examiner's Report, dated Jul, 22, 2014, in connection with Canadian Patent Application No. 2,714,708, 4 pages.
Letter/Written Disclosure of the Supplemental Information Disclosure Statement for the above-referenced application, dated May 16, 2014, 2 pages.
Office Action, dated Feb. 18, 2014 (received Mar. 7, 2014), in connection with corresponding Chinese Patent Application No. 2009801095059 [English Translation], 6 pages.
Communication, dated Mar. 31, 2014, providing English translation of Resolution 13045, dated Feb. 28, 2014, in connection with corresponding Colombian Patent Application No. 10.111.104, 5 pages.
Letter/Written Disclosure of the Supplemental Information Disclosure Statement for the above-referenced application, filed herewith Nov. 10, 2015, 2 pages.
Office Action, dated Sep. 17, 2015, in connection with Mexican Patent Application No. MX/a/2010/009478, 5 pages [English language translation, original document in Spanish].
Examination Report, dated Oct. 21, 2015, in connection with European Patent Application No. 09721669.1, 4 pages.
Letter/Written Disclosure of the Supplemental Information Disclosure Statement for the above-referenced application, filed herewith Aug. 12, 2015, 3 pages.
Office Action, dated Jun. 30, 2015, in connection with Japanese Patent Application No. 2014-192938 [English translation and original document in Japanese], 6 pages.
Letter, dated Aug. 5, 2015, reporting Certificate of Grant, published Jul. 1, 2015, in connection with Taiwan Patent Application No. 098108166 [English letter and Certificate of Grant], 5 pages.
Letter/Written Disclosure ofthe Supplemental Information Disclosure Statement for the above-referenced application, filed herewith Jun. 30, 2015, 3 pages.
Examination Report, dated Apr. 30, 2015 and received Jun. 4, 2015, in connection with Indian Patent Application No. 7321/DELNP/2010, 5 pages.
Allen et al., "Recombinant Human Hyaluronidase-Enabled Subcutaneous Pediatric Rehydration." Pediatrics 124(5):e858-e867 (2009) found at: http://pediatrics.aappublications.org/cgi/content/abstract/124/5/e858.
Form 10-Q for Halozyme Therapeutics dated May 8, 2009, retrieved from: http://biz.yahoo.com/e/090508/halo10-q.html [retrieved on Nov. 25, 2009] [6 pages].
Frost G., "Subcutaneous Strategies for Monoclonal Antibody Delivery." IBC Life Sciences Antibodies and Beyond Antibodies: Optimizing Antibody Leads and Exploring Next Generation Scaffolds for Protein Therapeutics, Coronado CA, 2006 [20 pages].
Haller, M., "Enzyme-facilitated Parenteral Drug Transport. Strategic Research Institute's 10$^{th}$ Anniversary Drug Delivery Technology and Deal-making Sununit," 2005 New Brunswick, NJ [24 pages].
Haller et al., "Revolutionizing Drug Dispersion with Enhanze Technology." American Association of Pharmaceutical Scientists Annual Meeting, Nov. 6-10, 2005 poster, Nashville, TN, poster, 1 page.
Halozyme Therapeutics, Analyst and Investor Meeting presentations including by Lim, J., "Introduction and strategic review," Little, R., "Leveraging the technology across multiple partners,"Frost, G., "Discovery and early development pipeline update," and D. Muchmore, "Ultrafast insulin-PH20 program-where we are going. "Presented Oct. 15, 2009 in New York. (88 pages).
Halozyme Therapeutics, "Securities and Exchange Comission Form 10K," Mar. 12, 2010 [121 pages].
Halozyme Therapeutics, "Securities and Exchange Comission Form 10Q," Nov. 6, 2009 [45 pages].
Halozyme Therapeutics, "Securities and Exchange Comission Form 10Q," Aug. 7, 2009 [45 pages].
Halozyme Therapeutics, "Halozyme Therapeutic, Inc. Prospectus Supplement," Jun. 23, 2009 [85 pages].
Halozyme Therapeutics, "Securities and Exchange Commission Form 10K," Mar. 13, 2009 [122 pages].
Halozyme Therapeutics, "Securities and Exchange Commission Form 10-KSB," Mar. 11, 2005 [45 pages].
Halozyme Therapeutics, "Securities and Exchange Comission Form 10-KSB," Mar. 24, 2006 [50 pages].
Halozyme Therapeutics, "Securities and Exchange Comission Form 10K," Mar. 2007 [108 pages].
Halozyme Therapeutics, "Securities and Exchange Comission Form SB-2," Mar. 23, 2004, 102 pages.
Halozyme Therapeutics, "Securities and Exchange Comission Amendment No. 1 to Form SB-2," Jun. 21, 2004, 108 pages.
Halozyme Therapeutics, "Securities and Exchange Comission Form 10-QSB," Nov. 12, 2004, 34 pages.

(56) References Cited

OTHER PUBLICATIONS

Halozyme Therapeutics, "Securities and Exchange Comission Form S-3," Nov. 12, 2004, 30 pages.
Halozyme Therapeutics, "Exclusive Distribution Agreement," Aug. 13, 2004, 13 pages.
Halozyme Therapeutics, "Non-Exclusive Distribution Agreement," Jan. 30, 2004, 19 pages.
Halozyme Therapeutics, "Non-Exclusive Distribution Agreement," Feb. 9, 2004, 21 pages.
Halozyme Therapeutics, "Non-Exclusive Distribution Agreement," Apr. 13, 2004, 22 pages.
ICSI Cumulase, "Human hyaluronidase for hlunan oocytes" Medicult Product information Jun. 16, 2009, 2 pages [accessed on Mar. 30, 2010].
Jefferies Investor Presentation "Matrix Therapies for Life" New York, Jun. 17, 2009 [30 pages].
Lim et al "Matrix Therapies for life" 28th Annual JP Morgan Healthcare Conference San Francisco Jan. 13, 2010, 42 pages.
Meyer et al., "The soluble hyaluronidase from bull testes is a fragment of the membrane-bound PH-20 enzyme," FEBS Letters 413(2):385-388 (1997).
Modena et al., "Hyaluronidase-injectable microparticles intended for the treatment of extravasation," J. Microencapsulation, 15(1):85-92 (1998).
New Release, Halozyme Therapeutics Reports Fourth Quarter and Year End 2008 Financial Results, Mar. 13, 2009, retrieved from: www.sec.gov/Archives/edgar/data/1159036/000129993309001189/exhibitl.htm [retrieved on Mar. 30, 2010].
News Release, Halozyme Therapeutics Inc., "Halozyme Therapeutics Reports Second Quarter 2009 Financial Results" Aug. 7, 2009, retrieved from the Internet:<URL: www.sec.gov/Archives/edgar/data/1159036/000129993309003275/exhibit1.htm, [retrieved on Mar. 30, 2010] [5 pages].
News Release, Halozyme Therapeutics Inc., "Halozyme Therapeutics and Baxter Healthcare Corporation Sign Exclusive Sales and Marketing Agreement for Halozyme's Investigational Therapeutic, Enhanze SC," Aug, 16, 2004, retrieved from the Internet:<URL: sec.gov/Archives/edgar/data/1159036/000095013704006885/a01296exv99wl.txt, [retrieved on Mar. 29, 2010] [2 pages].
Schiff, R., "Half-life and clearance of pH 6.8 and pH 4.25 immunoglobulin G intravenous preparations in patients with primary disorders of humoral immunity" Rev Infect Dis, Jul.-Aug. ;8(4)S449- 56 (1986).
Schiff, R, "Individualizing the dose of intravenous immune serum globulin for therapy of patients with primary humoral immunodeficiency" Vox Sang 49(1):15-24 (1985).
Schiff et al., "Use of a new chemically modified intravenous IgG preparation in severe primary humoral immunodeficiency: clinical efficacy and attempts to individualize dosage" Clin Immunol Immunopathol 31(1):13-23 (1984).
Stem, R., "Devising a pathway for hyaluronan catabolism: are we there yet?" Glycobiology 13:105R-115R (2003).
Varga et al., "Efficacy and safety of IGIV, 10% TVR solution, a new intravenous immunoglobulin, in adult subjects with chronic idiopathic thrombocytopenic purpura" Transf Med Hemother 33:509-514 (2006).
Yocum et al., "Phase IV study of the PK, safety and tolerability of HUMIRA administered with escalating doses ofrecombinant human hyaluronidase (rHuPH20); an Enhanze Technology Study with a Large Protein Molecule Therapeutic" Controlled Release Society Conference. Long Beach, CA, Jul. 9, 2007 [20 pages].
Letter/Written Disclosure of the Supplemental Information Disclosure Statement for the above-referenced application, mailed the same day herewith. 2 pages.
Notice of Acceptance, dated Jul. 12, 2013, in connection with corresponding Australian Patent Application No. 2009226141, 3 pages.
Letter/Written Disclosure of the Supplemental Information Disclosure Statement for the above-referenced application, filed herewith Sep. 22, 2015, 3 pages.
Examiner's Report, dated Aug. 10, 2015, in connection with Canadian Patent Application No. 2,714,708, 8 pages.
Office Action, dated Jul. 27, 2015, in connection with Vietnamese Patent Application No. 1-2010-02743 [English translation and original document in Chinese], 2 pages.
Angelborg et al., "The HYAL 1LuCA1 Gene Is Inactivated In Breast Carcinomas By Hypermethylation/Chromatin condensation And Mediates Tumor Suppression In Vivo," Am Assoc Cancer Res 2002, 2 pages.
Baxter Health Care Corporation (R. Schiff, MD), "Gammagard Liquid and rHuPH20 in PID," found at: www.clinicaltrials.gov/ct2/show/NCT00814320, last updated Oct. 27, 2009, 5 pages.
Baxter Health Care Corporation, Ganunagard Liquid (Immune Globulin Intravenous (Human) 10%] product literature, found at:www.baxter.com/products/biopharmaceuticals/downloads/gamliquid_PI.pdf, published Apr. 2005, 4 pages.
Bee et al., "Recombinant human PH20 is well tolerated at higher intravenous and subcutaneous doses in cynomolgus monkeys," EUFEPS 2008, Munich, Germany, 3 pages.
Björkander et al.,"Prospective open-label study of pharmacokinetics, efficacy and safety of a new 10% liquid intravenous immunoglobulin in patients with hypo- or agammaglobulinemia," Vox Sanguinis 90(4):286-293 (2006).
Bookbinder et al., "Biochemical Characterization of Recombinant Human PH20 (SPAM1) Hyaluronidase," Hyaluronan (ISHAS) 2007, Charleston, SC, 2 pages.
Bookbinder et al., "Enhancing drug transport through temporary matrix depolymerization," Keystone Symposia 2005, 13 pages.
Bookbinder et al., "EnhanzeTM Technology for Antibody Dispersion," Strategic Research Institute Antibody World Summit, 2005, Jersey City, NJ [41 pages].
Favre et al, "Hyaluronidase enhances recombinant adeno-associated virus (rAAV)—mediated gene transfer in the rat skeletal muscle," Gene Ther 7(16):1417-1420 (2000).
Federal Register Sep. 23, 1970 (35 FR 14800); Wydase NDA 6-343, (40 pages).
Few, B., "Hyaluronidase for treating intravenous extravasations," MCN Amer. J. Matern. Child Nurs. 12(1):23 (1987).
Frost et al.. "Punctuated Equilibrium: The Evolution of Recombinant Human Hyaluronidase," Ophthalmic Anesthesia Society, 2006, Chicago, IL, 36 pages.
Greenbaum, "Early Experience with Hylenex-assisted Parabulbar Anesthesia," Annual Meeting of the Ophthalmic Anesthesia Society in Chicago, IL. Sep. 2007, 2 pages.
Haller et al,, "Enhanze Technology—A Revolution in Drug Dispersion," Biotechnology Industry Organization (BIO) Annual Meeting, 2005, Philadelphia, PA [4 pages].
Haller, M., "Focus on Enhanced and Innovative Recombinant Human Enzymes," Japanese Export Trade Organization, Sep. 2004, Chicago, IL. (16 pages).
Hofer et al., "Human Recombinant Hyaluronidase Increases the Convection of Molecules up to 0.2 μm in Athymic Nude Mice," J. Am. Assoc, Lab. Animal Sci, 45:120 abstract P97 (2006). 2 pages.
Jiang et al., "Reduction of ischemic stroke mortality with chronic intravenous recombinant human hyaluronidase (rHuPH20): effects of pharmacokinetic optimization," American Neurological Association Annual Meeting, 2005, San Diego, CA, 6 pages.
Keller et al., "Pharmacokinetic, Pharmacodynamic and Toxicologic Effects of a Recombinant Human Hyaluronidase (rHuPH20) in Rodent and Non-Human Primate models," Hyaluronan (ISHAS) 2007, Charleston, SC, 2 pages.
Kundu et al., "Dispersion of the Cumulus Matrix with a Highly Purified Recombinant Human Hyaluronidase (rHuPH20)," Hyaluronan Meeting, 2003, Cleveland, OH. 2 pages.
Leibl et al. "Efficacy and Safety of a New Intravenous Immunoglobulin in Adult Subjects with Chronic Idiopathic Thrombocytopenic Purpura," Blood (ASH Annual Meeting Abstracts) 2005 106:Abstract 3984. 2 pages (2005).
Leibl et al., "Multiple infusions of human intravenous immunoglobulin in chimpanzees do not lead to immune elimination," Clin. Exp. Immunol. 81:454-458 (1990).
Leesch et al., "30-Day Pharmacokinetic Evaluation of IV versus Subcutaneous Administration of Immunoglobulin with and without

(56) References Cited

OTHER PUBLICATIONS

Recombinant Human Hyaluronidase in Dogs," Journal of Allergy and Clinical Immunology 123(2):Supp1. S, p. s10 (2009) and 65th annual meeting of the american academy of allergy asthma and immunology; washington DC, Mar. 13-17, 2009.
Melamed et al., "Recombinant Human Hyaluronidase Facilitates Dispersion of Subcutaneously Administered Gammagard Liquid and Enables Administration ofa Full Monthly Dose in a Single Site to Patients with Immunodeficiency Diseases," J Allergy Clin Immunol. 121(2):Suppl.1, p. S83 (2008) [1 page].
Melamed et al., "Recombinant Human Hyaluronidase Facilitates Dispersion of Subcutaneously Administered Gammagard Liquid and Enables Administration of a Full Monthly Dose in a Single Site to Patients with Immunodeficiency Diseases," Am Acad Allergy Asthma Immunol; Philadelphia, PA., Mar. 16, 2008, [6 pages].
Menzel, E. and C. Farr, "Hyaluronidase and its substrate hyaluronan: biochemistry, biological activities and therapeutic uses," Cancer Lett. 131:3-11 (2003).
News Release, Halozyme Therapeutics Inc., Q1 2008 Earnings Call Transcript found at: http://seekingalpha.com/article/76655-halozyme-therapeutics-inc-q1-2008-earnings-call-transcript [accessed on Jun. 25, 2009] [14 pages].
News Release, Halozyme Therapeutics Inc., Q3 2009 Earnings Call Transcript found at: http://seeldngalpha.com/article/171883-halozyme-therapeutics-inc-q3-2009-earnings-call-transcript?page=-1 [accessed on Nov. 6, 2009] [11 pages].
News Release, Halozyme Therapeutics Inc., Q3 2008 Earnings Call Transcript found at: http://seekingalpha.com/article/106797-halozyme-therapeutics-inc-q3-2008-earnings-call-transcript?page=-1 [accessed on Nov. 6, 2009] [9 pages].
Pinkstaff et al., "Evaluation of the Compatibility and Pharmacokinetics of Co-formulated Biologics with Recombinant Human Hyaluronidase: Dose Response," American Association of Pharmaceutical Scientists Conference, Jun. 2006, San Antonio, TX [3 pages].
Pinkstaff et al., "Recombinant Human Hyaluronidase for Drug and Fluid Dispersion," American Association of Pharmaceutical Scientists Annual Meeting, Nov. 2006, Boston, MA [3 pages].
Pinkstaff et al., "Recombinant Human Hyaluronidase for Use with Therapeutic Antibodies," Controlled Release Society Conference, Vienna, Austria, 2006 [2 pages].
Rousell et al., "Prospective Study on the Hepatitis Safety of Intravenous Immunoglobulin, pH 4.25," Vox Sang. 60(2):65-68 (1991).
Schiff et al., "Multicenter Crossover Comparison of the Safety and Efficacy of Intraglobin-F with Gamimune-N, Sandoglobulin and Gammagard in Patients with Primary Immunodeficiency Diseases" Journal of Clinical Immunology 17(1):21-28 (1997).
Weksler et al., "Drug-Ranging Study of Intravenous Immunoglobulin in Patients with Alzheimer's Disease," Abstracts: Pharmacological Treatments Suppl 1:S94-S95 (2005).
Wilson, M., "Enhanze Technology—An Enzymatic Drug Delivery System (DDS)," Japanese Export Trade Organization, 2005, Santa Clara, CA, 22 pages.
Berger et al., "Immunoglobulin replacement therapy by slow subcutaneous infusion," Ann Intern Med 93:55-56 (1980).
Berger, M., "Subcutaneous immunoglobulin therapy in primary immunodeficiencies,"Clin Immuno 112:1-7 (2004).
Gardulf et al., "Safety of rapic subcutaneous gammaglobulin by rapid infusion in patients with primary antibody deficiency," Immunodeficiency 4:81-84 (1993).
Gardulf et al., "Subcutaneous immunoglobulin replacement in patients with primary antibody deficiencies:safety and costs," Lancet 345:365-369 (1995).
Grunebaum et al., "Novel aspects of hypogammaglobulinemic states: subcutaneous immunoglobulin treatment," Isr. Med. Assoc J 4:288-289 (2002).
Halozyme Therapeutics, "Securities and Exchange Commission Form 10Q," Aug. 6, 2010 [41 pages].
Halozyme Therapeutics, "Securities and Exchange Commission Form 10Q," Nov. 5, 2010 [45 pages].
News Release, "Halozyme Therapeutics Announces Implementation of Development Focused Strategy," Oct. 11, 2010, San Diego, CA, Retrieved from the Internet: phx.corporate-ir.net/phoenix.zhtml?c=175436&p=ir0l-newsArticle&ID=1481205&highlight=, (accessed Nov. 19, 2010; 3 pages).
News Release, "Halozyme Therapeutics Awarded Four Qualifying Therapeutic Discovery Project Grants," Nov. 4, 2010, San Diego, CA, Retrieved from the Internet: phx.corporate-ir.net/phoenix.zhtml?c=175436&p=irol-newsArticle&ID=1491739&highlight=, (accessed Nov. 19, 2010; 2 pages).
News Release, "Halozyme Therapeutics Inc., Second Quarter 2010 Financial Results Conference Call Transcript," Moderator: Uhl, R., Aug. 6. 2010, (accessed Sep. 3, 2010; 16 pages).
News Release, "KIOVIG, Baxter's New IVIG Product Received Unanimous Positive Opinion in Europe as Replacement Therapy for Immunodeficiencies and for Immunomodulation in ImmuneMediated Diseases," Nov. 22, 2005, Retrieved from the Internet: <URL: baxter.com/press_room/press_releases/2005/11-23-05-kiovig.html, (accessed Oct. 20, 2010; 4 pages).
News Release, Halozyme Therapeutics Inc., "Halozyme Therapeutics Reports 2008 Second Quarter Financial Results"Aug. 8, 2008, retrieved from the Internet:<URL: sec.gov/Archives/edgar/data/1159036/000129993308003838/exhibit.htm, [retrieved on Mar. 31, 2010] [5 pages].
Poelsler et al., "A new liquid intravenous inmmunoglobulin with three dedicated virus reduction steps: virus and prion reduction capacity," Vox Sang 94(3):184-192 (2007).
Reipeit et al., "Fc function of a new intravenous immunoglobulin product:IGIV 10% triple virally inactivated solution," Vox Sang 91(3)256-263 (2006).
Roord et al., "Home treatment in patients with antibody deficiency by slow subcutaneous infusion of gammaglobulin," Lancet 1(8273):689-690 (1982).
Stiehm et al. "Slow subcutaneous human intravenous immunoglobulin in the treatment of antibody immunodeficiency: Use of an old method with a new product," J Allergy Clin Immunol 101:848-849 (1998).
Welch, M. and E. Stiehm, "Slow subcutaneous immunoglobulin therapy in a patient with reactions to intramuscular immunoglobulin," J Clin Immunol 3(3):285-286 (1983).
Halozyme Therapeutics, Analyst and Investor Meeting presentations "Matrix Therapeutics for Life" presentations including Lim, J., "Introduction and strategy overview, Roche program update," Gustafson, K., "Strategic deployment of cash," Wasserman, R., "HyQ treatment of primary immunodeficiency patients," Muchmore, D., "Ultrafast insulin-clinical results and ongoing trials,"Cefalu, W., "Unmet needs in diabetes management," Little, R., Market overview-ultrafast insulin and SC immunoglobin and Frost, G., "PEGPH20 and HTI-501 status report," Presented Oct. 15, 2010 in New York, NY. (124 pages).
Lee et al "Subcutaneous immunoglobulin administration using recombinant human hyaluronidase: a novel approach for the treatment of peripheral neuropathies in children," abstract for the xIth world congress of ICNC Cairo May 2-7, 2010. Retrieved from the Intenet:<URL: icnc2010.org/index.php?option=com_content&view=article&id=163&Itemid=9, [retrieved on Jul. 12, 2010] [1 page].
McCoy et al. "Pharmacokinetics of 10% Immunoglobulin Administered Intravenously or Subcutaneously Alone of Following Recombinant Human Hyaluronidase in Subjects with PID," Retrieved from the Internet<URL: baxter.com/downloads/press_room/press_releases/2010/BAXTER_HyQ_PK_ESID_10_2010.PDF, [retrieved on Oct. 29, 2010] [1 page].
News Release, Halozyme Therapeutics Inc., "First Quarter 2010 Financial Results Conference Call," May 7, 2010. Retrieved from the Internet<URL: phx.corporate-ir.net/phoenix.zhtml?c:175436&p=irol-newsArticle_print&ID=142401, [retrieved on Jun. 1, 2010] [4 pages].
News Release, "Halozyme Therapeutics Inc., Second Quarter 2010 Financial Results Conference Call Transcript," Aug. 6, 2010, 16 pages.

(56) References Cited

OTHER PUBLICATIONS

News Release, "Baxter Presents Data from Interim Analyses of Phase III Clinical Trial of HyQ at European Society for Immunodeficiencies Meeting" Oct. 6, 2010, Retrieved from the Internet:<URL: finance.yahoo.com/news/Baxter-Presents-Data-from-bw-3233016796.html?x=0, [retrieved on Oct. 6, 2010] [3 pages].
International Prelimnary Report on Patentability dated Jun. 8, 2010, in connection with corresponding International Patent Application No. PCT/US2009/001670.
Adams et al., "The c-myc oncogene driven by immunoglobulin enhancers induces lymphoid malignancy in transgenic mice," Nature 318:533-538 (1985).
Afify et al., "Purification and characterization of human serum hyaluronidases," Arch. Biochem. Biophys. 305:434-441 (1993).
Alexander et al., "Expression of the c-myc oncogene under control of an immunoglobulin enhancer in E mu-myc transgenic mice," Mol. Cell Biol. 7:1436-1444 (1987).
Angelborg et al., "The HYAL1LuCA1 Gene Is Inactivated In Breast Carcinomas By Hypermethylation/Chromatin condensation And Mediates Tumor Suppression In Vivo," Am Assoc Cancer Res 2002, 1 page.
Ansel, Introduction to Pharmaceutical Dosage Forms, Fourth Edition, 126 (1985).
Atschul, S., "Basic local alignment search tool," J Molec Biol 215(3):403-410 (1990).
Baxter Healthcare Corporation, "Study to determine the dose of recombinant human hyaluronidase needed to infuse a dose of IGIV subcutaneously," found at: http://clinicaltrials.gov/ct2/showiNCT00782106 [accessed on May 13, 2009] [3 pages].
Bee et al., "Recombinant human PH20 is well tolerated at higher intravenous and subcutaneous doses in cynomolgus monkeys," EUFEPS 2008, Munich, Germany, 1 page.
Benhar et al., "Pseudomonas exotoxin A mutants. Replacement of surface-exposed residues in domain III with cysteine residues that can be modified with polyethylene glycol in a site-specific manner," J. Biol. Chem. 269:13398-14404 (1994).
Bernoist, C. and P, Chaanon, "In vivo sequence requirements of the SV40 early promotor region," Nature 290:304-310 (1981).
Bianchi et al., "Synthetic depsipeptide substrates for the assay of hmnan hepatitis C virus protease," Anal. Biochem. 237:239-244 (1996).
BioWorld Today, "Clinic roundup," BioWorld Today 20(2):5 (2009).
Bookbinder et al., "A recombinant human enzyme for enhanced interstitial transport of therapeutics," J Control Release. 114(2):230-241 (2006) Epub Jun. 7, 2006.
Bookbinder et al., "Biochemical Characterization of Recombinant Human PH20 (SPAMl) Hyaluronidase,"Hyaluronan (ISHAS) 2007, Charleston, SC, 1 page.
Bookbinder et al., "Enhancing Drug Transport Through Temporary Matrix Depolymerization," Keystone Symposia 2005, 1 page.
Bookbinder et al., "EnhanzeTM Technology for Antibody Dispersion," Strategic Research Institute Antibody World Summit, 2005, Jersey City, NJ, 1 page.
Bookbinder et al., "Evaluation of the compatibility and pharmacokinetics of co-formulated biologics with recombinant human hyaluronidase: Dose Response," American Association of Pharmaceutical Scientists Conference, Nov. 2006, 2 pages.
Bordier, C., "Phase separation of integral membrane proteins in Triton X-114 solution," J. Biol. Chem. 256:1604-1607 (1981).
Bouffard et al., "An in vitro assay for hepatitis C virus NS3 serine proteinase," Virology 209:52-59 (1995).
Brinster et al., "Regulation of metallothionein-thymidine kinase fusion plasmids injected into mouse eggs," Nature 296:39-42 (1982).
Brumeanu et al., "Derivatization with monomethoxypolyethylene glycol of Igs expressing viral epitopes obviates adjuvant requirements," J Immunol. 154:3088-3095 (1995).
Buckley, R. and R. Schiff, "The use ofintravenous immune globulin in immunodeficiency diseases," N Engl J Med. 325(2):110-117 (1991).
Byerley et al., "'Cutting out the bull'. Recombinant human hyaluronidase: Moving to an animal-free system," Association of Clinical Embryologists, 2006, Dublin, Ireland. Abstract published in Human Fertility 9(2): 110 (2006).
Caliceti, P. and F. Veronese, "Pharmacokinetic and biodistribution properties of poly(ethylene glycol)-protein conjugates," Adv. Drug Deliv. Rev. 55(10):1261-1277 (2003).
Carrillo et al., "The multiple-sequence alignment problem in biology," SIAM J Applied Math 481:1073-1082 (1988).
Chapel et al. "Randomised trial of intravenous immunoglobulin as prophylaxis against infection in plateau-phase multiple myeloma. The UK Group for Immunoglobulin Replacement Therapy in Multiple Myeloma," Lancet 343:1059-1063 (1994).
Cheng et al., "PEGylated adenoviruses for gene delivery to the intestinal epithelium by the oral route," Pharm. Res. 20(9):1444-1451 (2003).
Cherr et al., "The dual functions of GPI-anchored PH-20: hyaluronidase and intracellular signaling," Matrix Biol., 20:515-525 (2001).
Cherr et al., "The PH-20 protein in cynomolgus macaque spermatozoa: identification of two different forms exhibiting hyaluronidase activity," Dev. Biol., 175:142-153, 1996.
Cho et al., "Construction of hepatitis C-SIN virus recombinants with replicative dependency on hepatitis C virus serine protease activity." J. Virol. Meth. 65:201-207 (1997).
Christadoss et al., "Animal models of myasthenia gravis," Clin Immunol. 94:75-87 (2000).
Church et al., "Efficacy, safety and tolerability of a new 10% liquid intravenous immune globulin [IGIV 10%] in patients with primary immunodeficiency," US-PID-IGIV 10%—Study Group10. J Clin Immunol. 26(4):388-395 (2006).
Cohn et al., "Preparation and Properties of Serum and Plasma Proteins. IV. A System for the Separation into Fractions of the Protein and Lipoprotein Components of Biological Tissues and Fluids[1,a,b,c,d]," J. Am. Chem. Soc. 68:459-475 (1946).
Conserved domain search from U.S. Appl. No. 10/795,095 of SEQ ID No. 6, Primakotf et al. U.S. Pat. No. 5,721,348, performed on the NCBI website on Aug. 5, 2008.
Csoka et al., "Hyaluronidases in tissue invasion," FEBS Lett., 417:307-310 (1997).
Csoka et al., "Hyaluronidases in tissue invasion," Invasion Metastasis 17:297-311 (1997).
Csoka et al, "The six hyaluronidase-like genes in the human and mouse genomes," Matrix Biol. 20:499-508 (2001).
Czitrom et al., "The function of antigen-presenting cells in mice with severe combined immunodeficiency," J Immunol 134:2276-2280 (1985).
D'Souza et al., "In vitro cleavage of hepatitis C virus polyprotein substrates by purified recombinant NS3 protease," J Gen. Virol. 76:1729-1736 (1995).
Dalakas et al., "A controlled study of intravenous immunoglobulin combined with prednisone in the treatment of IBM," Neurology 56(3):323-327 (2001).
Dalakas et al., "A controlled trial of high-dose intravenous immune globulin infusions as treatment for dermatomyositis," N Engl J Med 329(27):1993-2000 (1993).
Dalakas et al., "High-dose intravenous immune globulin for stiff person syndrome," N Engl J Med 345(26):1870-1876 (2001).
Dalakas, M., "The use of intravenous immunoglobulin in the treatment of autoimmune neuromuscular diseases: evidence-based indications and safety profile," Pharmacol Ther 102(3):177-193 (2004).
Danilkovitch-Miagkova, et al., "Hyalluonidase 2 negatively regulates RON receptor tyrosine kinase and mediates transformation of epithelial cells by jaagsiekte sheep retrovirus," Proc Natl Acad Sci USA. 100(8):4580-4585 (2003).
Deboer et al., "The tac promoter: a functional hybrid derived from the trp and lac promoters." Proc. Natl, Acad, Sci, USA 80:21-25 (1983).
Delpech et al., "Enzyme-linked hyaluronectin: a unique reagent for hyaluronan assay and tissue location and for hyaluronidase activity detection." Anal. Biochem. 229:35-41 (1995).
Derwent patent abstract citing JP 4346934 published Dec. 2, 2002, for: "Liq. Compsn. For intravenous injection for infectious disease

(56) References Cited

OTHER PUBLICATIONS treatment-comprises chemically unmodified mol. Type gamma globulin with low conductivity and contains no sorbitol." Inventor: Kamimura et al. Dialog File No. 351. Accession No. 6231217 [2 pages].
Derwent patent abstract citing JP 54020124 published Feb. 15, 1979, for: "Intraveneously injectable gamma-globulin compsn. Prodn. by addn. of amino acids, sugars and neutral salts as dissociation agents." Inventor: Funakoshi et al. Dialog File No. 351. Accession No. 1699807 [2 pages].
Derwent patent abstract citing JP 57128635 published Aug. 10. 1982, for: "Gamma-globulin prepn. For intravenous injection contains sodium chloride and L-arginine or L-lysine," Inventor: Matsuo et al. Dialog File No. 351. Accession No. 2496703 [2 pages].
Devereux et al, "A comprehensive set of sequence analysis programs for the VAX." Nucleic Acids Research 12:387-395 (1984).
Dodel et al., "Intravenous immunoglobulins containing antibodies against beta-amyloid for the treatment of Alzheimer's disease," J Neurol Neurosurg. Psychiatry 75:1472-1474 (2004).
Ellmeier et al., "Severe B cell deficiency in mice lacking the tec kinase family members Tec and Btk," J Exp Med. 192:1611-1624 (2000).
Evison et al., "Improvement in ICSI Survival and Fertilisation rates with the use of Cumulase, Recombinant Hyaluronidase (Rochford Medical)," 5th Biennial Joint Meeting of the UK Fertility Societies Association of Clinical Embryologists, British Fertility Society, Society for Reproduction & Fertility, Apr. 2007, York, England, Abstract p. 22.
Felix et al., "Pegylated peptides. IV. Enhanced biological activity of site-directed pegylated GRF analogs," Int. J. Peptide Res. 46:253-264 (1995).
Filocamo et al., "Chimeric Sindbis Viruses dependent on the NS3 protease of hepatitis C virus," J Virology 71:1417-1427 (1997).
Frost et al., "HYAL1LUCA-1, a candidate tumor suppressor gene on chromosome 3p21.3, is inactivated in head and neck squamous cell carcinomas by aberrant splicing of pre-mRNA," Oncogene (19):870-877 (2000).
Frost et al., "Punctuated Equilibrium: The Evolution of Recombinant Human Hyaluronidase," Ophthalmic Anesthesia Society, 2006, Chicago, IL, 1 page.
Frost et al., "Purification, cloning, and expression of human plasma hyaluronidase," Biochem Biophys Res Commun. 236(1):10-15 (1997).
Frost et al., "Subcutaneous Strategies for Monoclonal Antibody Delivery," Drug Delivery 2007: Where Science and Business Meet, 2007, San Diego, CA, 1 page.
Frost, G. and R. Stern, "A microtiter-based assay for hyaluronidase activity not requiring specialized reagents," Anal.Biochem. 251:263-269 (1997).
Frost, G., "Recombinant human hyaluronidase (rHuPHZO): an enabling platform for subcutaneous drug and fluid administration," Expert Opin. Drug. Deliv. 4:427-440 (2007).
Gardner et al., "The complete nucleotide sequence of an infectious clone of cauliflower mosaic virus by M13mp7 shotgun sequencing," Nucleic Acids Res, 9:2871-2888 (1981).
Gardulf et al., "Home treatment of hypogammaglobulinaemia with subcutaneous gammaglobulin by rapid infusion," Lancet 338:162-166 (1991).
Gardulf et al., "Lifelong treatment with gammaglobulin for primary antibody deficiencies: the patients' experiences of subcutaneous self-infusions and home therapy," J Adv. Nurs. 21:917-927 (1995).
Gardulf et al., "Rapid subcutaneous IgG replacement therapy is effective and safe in children and adults with primary immunodeficiencies—a prospective, multi-national study," J Clin. Immunol. 26:177-185 (2006).
Gardulf et al., "The life situations of patients with primary antibody deficiency untreated or treated with subcutaneous gammaglobulin infusions," Clin. Exp. Immunol. 92:200-204 (1993).
Gardulf, A. and U. Nicolay, "Replacement IgG therapy and self-therapy at home improve the health-related quality of life in patients with primary antibody deficiencies," Curr. Opin, Allergy Clin. Immunol., 6: 434-442 (2006).
Gilbert, W. and L. Villa-Komaroff, "Useful Proteins from Recombinant Bacteria," Scientific American 242:79-94 (1980).
Gmachl et al., "The human sperm protein PH-20 has hyaluronidase activity," FEBS 336(3):545-548 (1993).
Godeau et al., "Intravenous immunoglobulin for adults with autoimmune thrombocytopenic purpura: results of a randomized trial comparing 0.5 and 1 g/kg b.w.," Br J Haematol 107(4):716-719 (1999).
Godeau et al., "Treatment of adult chronic autoimmune thrombocytopenic purpura with repeated high-dose intravenous immunoglobulin." Blood 82(5): 1415-1421 (1993).
Greenbaum, "Early Experience with Hylenex-assisted Parabulbar Anesthesia." Annual Meeting of the Ophthalmic Anesthesia Society in Chicago, IL. Sep. 2007, 1 page.
Gribskov, M. and R. Burgess, "Sigma factors from *E. coli, B. sublilis*. phage SP01, and phage T4 are homologous proteins" Nucl. Acids Res. 14:6745-6763 (1986).
Griffiths et al., "Crossover study of immunoglobulin replacement therapy in patients with low-grade B-cell tumors," Blood 73:366-368 (1989).
Grosschedl et al., "Introduction of a mu immunoglobulin gene into the mouse germ line: specific expression in lymphoid cells and synthesis of functional antibody," Cell 38:647-658 (1984).
Guo et al., "Protein tolerance to random amino acid change," Proc. Nat'l. Acad. Sci. USA 101:9205-9210 (2004).
Gustafson et al., "Rapid subcutaneous immunoglobulin administration every second week results in high and stable serum immunoglobulin G levels in patients with primary antibody deficiencies," Immunol. 152(2):274-279 (2008).
Hahm et al., "Generation of a novel poliovirus with a requirement of hepatitis C virus protease NS3 activity," Virology 226:318-326 (1996).
Haller et al., "Enhanze Technology—A Revolution in Drug Dispersion," Biotechnology Industry Organization (BIO) Annual Meeting, 2005, Philadelphia, PA, 3 pages.
Haller et al., "Escaping the Interstitial Matrix With Enzyme-Mediated Drug Delivery," Drug Delivery Technology, 5(5):1-6, 2005.
Haller et al., "Recombinant Human Hyaluronidase for the Interstitial Transport of Therapeutics," American Association of Pharmaceutical Scientists Conference, Jun. 2006, San Antonio, TX, 2 pages.
Haller et al., "Recombinant Human Hyaluronidase for the Interstitial Transport of Therapeutics," Controlled Release Society Conference, Vienna, Austria, 2006, 2 pages.
Haller et al., "The Effects of Recombinant Human Hyaluronidase on Drug Dispersion," American Association of Pharmaceutical Scientists Annual Meeting, 2005, Nashville, TN, 3 pages.
Haller, "Converting Intravenous Dosing to Subcutaneous Dosing with Recombinant Human Hyaluronidase," Pharmaceut Tech. Oct. 2007 Newsletter, 14 pgs.
Haller, "Enhanze Technology—An Enzymatic Drug Delivery System (DDS)," Japanese Export Trade Organization, 2005, Santa Clara, CA, 2 pages.
Haller, "Halozyme's Enhanze Technology for the Enhanced Dispersion of Co-Injected Pharmaceuticals," Japanese Export Trade Organization, Sep. 2004, Chicago, IL, 2 pages.
Halozyme Therapeutics Investor Presentation, "Company Overview," May 15, 2008. [15 pages].
Halozyme Therapeutics Investor Presentation, "Company Overview," Feb. 12, 2008. [37 pages].
Halozyme Therapeutics Investor Presentation, "Company Overview," Feb. 22, 2007. [25 pages].
Halozyme Therapeutics Investor Presentation, "Company Overview," Jun. 28, 2006. [28 pages].
Halozyme Therapeutics Investor Presentation, "Company Overview," Feb. 1, 2006. [34 pages].
Halozyme Therapeutics Investor Presentation, "Company Overview," Nov. 29, 2005. [34 pages].

(56) References Cited

OTHER PUBLICATIONS

Halozyme Therapeutics Investor Presentation, "Focus on enhanced and innovative recombinant human enzymes," Jan. 28, 2005. [28 pages].
Halozyme Therapeutics Investor Presentation. "Focus on enhanced and innovative recombinant human enzymes." Mar, 12, 2004, [32 pages].
Hamatake et al., "Establishment of an in vitro assay to characterize hepatitis C virus NS3-4A protease trans-processing activity," Intervirology 39:249-258 (1996).
Hammer et al., "Diversity of alpha-fetoprotein gene expression in mice is generated by a combination of separate enhancer elements," 235:53-58 (1987).
Hanahan, D, "Heritable formation of pancreatic beta-cell tumours in transgenic mice expressing recombinant insulin/simian virus 40 oncogenes," Nature (3)15:115-122 (1985).
Hansen, R. and J. Balthasar, "Effects of intravenous immunoglobulin on platelet count and antiplatelet antibody disposition in a rat model of immune thrombocytopenia," Blood 100:2087-2093 (2002).
Herrera-Estrella et al., "Exp[ression of chimaeric genes transferred into plant cells using a ti-plasmid-derived vector,"Nature 303:209-213 (1984).
Herrera-Estrella et al., "Light-inducible and chloroplast-associated expression of a chimaeric gene introduced into Nicotiana tabacum using a Ti plasmid vector," Nature 310(5973):115-120 (1984).
Hiemstra et al., "Comparison of antibody activity against various microorganisms in intravenous immunoglobulin preparations determined by ELISA and opsonic assay," J Lab Clin Med 123:241-246 (1994).
Hofer, "Human Recombinant Hyaluronidase Increases the Convection of Molecules up to 0.2 μm in Athymic Nude Mice," American Association for Laboratory Animal Science, 2006, Salt Lake City, UT. Abstract published in J. Am. Assoc. Lab. Animal Sci., 45:120, 2006, abstract p. 97.
Hunnicut et al., "Structural relationship of sperm soluble hyaluronidase to the sperm membrane protein PH-20," Biol Reprod. 54(6):1343-1349 (1996).
Ito et al., "Cultivation of hepatitis C virus in primary hepatocyte culture from patients with chronic hepatitis C results in release of high titre infectious virus," J. Gen. Virol., 77:1043-1054 (1996).
IUPAC, "IUPAC-IUB Commission on Biochemical Nomenclature. A one-letter notation for amino acid sequences. Tentative rules," J. Biol. Chem. 243:3557-3559 (1968).
IUPAC-IUB, "Abbreviated nomenclature of synthetic poypeptidespolymerized amino acids-revised recommendations," Commission on Biochemical Nomenclature, Biochemistry 11:1726-1731 (1972).
Jay et al., "Construction ofa general vector for efficient expression of mammalian proteins in bacteria: use of a synthetic ribosome binding site," Proc. Natl. Acad. Sci, USA 78:5543-5548 (1981).
Jiang et al, "Effects of Recombinant Human PH20 (rHuPH20) on Interstitial Matrices: Creating a Favorable Environment for The Delivery of Cytostatic Agents," American Association for Cancer Research Annual Meeting, 2005, Anaheim, CA, 1 page.
Keller et al., "Pharmacokinetic, Pharmacodynamic and Toxicologic Effects of a Recombinant Human Hyaluronidase (rHuPH20) in Rodent and Non-Human Primate models," Hyaluronan (ISHAS) 2007, Charleston, SC, 1 page.
Kelsey et al., "Species- and tissue-specific expression of human alpha 1-antitrypsin in transgenic mice," Genes And Devel. 1:161-171 (1987).
Kim et al., "An autoimmune animal model of the Lambert-Eaton syndrome," Annals NY Acad Sci 841:670-676 (1998).
Kollias et al., "Regulated expression of human a gamma-, beta-, and hybrid gamma beta-globin genes in transgenic mice: manipulation of the developmental expression patterns," Cell 46:89-94 (1986).
Kriel et al., "Hyaluronidases—a group of neglected enzymes," Protein Science 4:1666-1669 (1995).
Kummer et al., "Expression of human recombinant granzyme A zymogen and its activation by the cysteine proteinase cathepsin C," J Biol. Chem. 271:9281-9286 (1996).
Kundu et al., "Dispersion of the Cumulus Matrix with a Highly Purified Recombinant Human Hyaluronidase (rHuPH20)," Hyaluronan Meeting, 2003, Cleveland, OH. [1 page].
Lalancette et al, "Characterization of an 80-kilodalton bull sperm protein identified as PH-20," Biol Reprod. 65(2):628-636 (2001).
Lathrop et al., "cDNA cloning reveals the molecular structure of a sperm surface protein, PH-20, involved in sperm-egg adhesion and the wide distribution of its gene among mammals," J Cell Biol. 111(6 Pt 2):2939-2949 (1990).
Leder et al., "Consequences of widespread deregulation of the c-myc gene in transgenic mice: multiple neoplasms and normal development," Cell 45:485-495 (1986).
Li et al., "Irradiation-induced expression ofhyaluronan (HA) synthase 2 and hyaluronidase 2 genes in rat lung tissue accompanies active turnover of HA and induction of types I and III collagen gene expression," Am. J. Respir. Cell Mol. Biol. 23:411-418 (2000).
Lin et al., "Molecular cloning of the human and monkey sperm surface protein PH-20," Proc. Natl. Acad. Sci. USA 90:10071-10075 (1993).
Lu, Y. and A. Felix, "Pegylated peptides I: Solid-phase synthesis of N alpha-pegylated peptides using Fmoc strategy," Peptide Res 6:140-146 (1993).
Lu, Y. and A. Felix, "Pegylated peptides. II. Solid-phase synthesis of amino-, carboxy- and side-chain pegylated peptides," Int. J. Peptide Protein Res. 43: 127-138 (1994).
Macdonald, R., "Expression of the pancreatic elastase I gene in transgenic mice," Hepatology 7:42S-51S (1987).
Magram et al., "Developmental regulation of a cloned adult beta-globin gene in transgenic mice," Nature 315(6017):338-340 (1985).
Mammalian Gene Collection (MGC) Program Team, "Generation and initial analysis of more than 15,000 full-length human and mouse cDNA sequences," Proc. Natl. Acad. Sci. USA 99:16899-16903 (2002).
Mason et al., "The hypogonadal mouse: reproductive functions restored by gene therapy," Science 234:1372-1378 (1986).
Melamed et al., "Recombinant human hyaluronidase facilitates dispersion of subcutaneously administered gammagard liquid and enables administration of a full monthly dose in a single site to patients with immunodeficiency diseases," Am Acad Allergy Asthma Immunol Poster 2008 Philadelphia, PA, and Abstract #3204, 2 pages. (2008).
Mizutani et al., "Characterization of hepatitis C virus replication in cloned cells obtained from a human T-cell leukemia virus type 1-infected cell line, MT-2," J. Virol. 70:7219-7223 (1996).
Mizutani et al., "Inhibition of hepatitis C virus replication by antisense oligonucleotide in culture cells,"Biochem. Biophys. Res. Commun., 212:906-911 (1995).
Mizutani et al., "Long-term human T-cell culture system supporting hepatitis C virus replication," Biochem. Biophys. Res. Commun. 227:822-826 (1996).
Molineux, G., "Pegylation: engineering improved biopharmaceuticals for oncology," Pharmacotherapy 23 (8 Pt 2):3S-8S (2003).
Nagy et al., "Prospective, randomized study on bovine and recombinant human (Cumulase®) Hyaluronidases," American Society of Reproductive Medicine, 2006, New Orleans, LA, 06-A-886-ASRM. [2 pages].
Needleman, S. and C. Wunsch "A general method applicable to the search for similarities in the amino acid sequence of two proteins," J Mol Biol. 48:443-453 (1970).
News Release, Halozyme Therapeutics Inc., "Baxter Presents Latest Clinical Trial Results of Gammagard Liquid Administered Subcutaneously," Philadelphia, PA, Mar, 16, 2008, http://phx.corporate-ir.net/phoenix.zhtml?c=175436&p=irol-newsArticle_Print&ID=1120341&highlight=(accessed Jan. 6, 2009), 4 pages.
News Release, Halozyme Therapeutics Inc., "Data Presented at AAAAI Reinforce Baxter's Commitment to Making Gammagard Liquid Therapy More Convenient" Deerfield Il, Mar. 16, 2009, http://www.businesswire.com/portal/site/google/?ndmViewId=news_view&newsId=20090316005731&newsLang=en. [16 pages].

(56) References Cited

OTHER PUBLICATIONS

News Release, Halozyme Therapeutics Inc., "Halozyme and Baxter Announce Availability of Hylenex for Subcutaneous Delivery of Medications and Fluids," San Diego, CA, Jun. 27, 2006, http://phx.corporate-ir.net/phoenix.zhtml?c=175436&p=irol-newsArticle_Print&ID=876530&highlight=(accessed Jan, 6, 2009), 3 pages.
News Release, Halozyme Therapeutics Inc., "Halozyme Therapeutics Announces Roche Begins Phase I Clinical Trial and Selects Fourth Exclusive Biologic Target," San Diego, CA, Dec. 8, 2008, http://phx.corporate-ir.net/phoenix.zhtml?c=175436&p=irol-newsArticle_Print&ID=1233454&highlight= (accessed Jan. 6, 2009), 2 pages.
News Release, Halozyme Therapeutics Inc., "Halozyme Therapeutics Releases Results of Enhanze Technology Clinical Trial to Improve the Subcutaneous Absorption of a Large Protein Molecule Therapeutic," San Diego, CA, Jan. 22, 2007, http://phx.corporate-ir.net/phoenix.zhtml?c=l75436&p=irol-newsArticle_Print&ID=952285&highlight= (accessed Jan, 6, 2009), 3 pages.
News Release, Halozyme Therapeutics Inc., "Halozyme Therapeutics Completes Enrollment of Enhanze Technology Clinical Trial to Improve the Subcutaneous Absorption of a Large Protein Molecule Therapeutic," San Diego, CA, Nov. 27, 2006, http://phx.corporate-ir.net/phoenix.zhtml?c=175436&p=irol-newsArticle_Print&ID=935824&highlight= (accessed Jan, 6, 2009), 2 pages.
News Release, Halozyme Therapeutics Inc., "Halozyme Therapeutics Initiates First Enhanze Technology Clinical Trial to Improve the Subcutaneous Absorption of a Large Molecule Protein Therapeutic," San Diego, CA, Aug. 8, 2006, http://phx.corporate-ir.net/phoenix.zhtml?c=175436&p=irol-newsArticle_Print&ID=893361&highlight= (accessed Jan. 6, 2009), 2 pages.
News Release, Halozyme Therapeutics Inc., "Halozyme Therapeutics and Baxter Release Results From the INFUSE-LR Study," San Diego, CA, and Deerfield, IL, Feb. 8, 2006, http://phx.corporate-ir.net/phoenix.zhtml?c=175436&p=irol-newsArticle_Print&ID=814561&highlight= (accessed Jan. 6, 2009), 4 pages.
News Release, Halozyme Therapeutics Inc., "Halozyme Therapeutics Completes Enrollment of INFUSE-LR, a Hylenex Clinical Trial of Subcutaneous Hydration," San Diego, CA, Jan. 24, 2006, http://phx.corporate-ir.net/phoenix.zhtml?c=175436&p=irol-newsArticle_Print&ID=807598&highlight= (accessed Jan. 6, 2009), 2 pages.
News Release, Halozyme Therapeutics Inc., "Halozyme Therapeutics Initiates Hylenex Clinical Trial of Subcutaneous Hydration," San Diego, CA, Dec. 15, 2005, http://phx.corporate-ir.net/phoenix.zhtml?c=175436&p=irol-newsArticle_Print&ID=796125&highlight= (accessed Jan. 6, 2009), 2 pages.
News Release, Halozyme Therapeutics Inc., "Halozyme Therapeutics and Baxter Healthcare Corporation Announce FDA Approval of Hylenex," San Diego, CA, and Deerfield, IL, Dec. 5, 2005, http://phx.corporate-ir.net/phoenix.zhtml?c=175436&p=irol-newsArticle_Print&ID=792608&highlight= (accessed Jan. 6, 2009), 3 pages.
News Release, Halozyme Therapeutics Inc., "Halozyme Therapeutics Announces FDA Acceptance of Hylenex NDA,"San Diego, CA, May 26, 2005, http://phx.corporate-ir.net/phoenix.zhtml?c=175436&p=irol-newsArticle_Print&ID=714327&highlight= (accessed Jan. 6, 2009), 2 pages.
News Release, Halozyme Therapeutics Inc., "Halozyme Therapeutics Files NDA for Enhanze SC," San Diego, CA, Mar. 28, 2005, http://phx.corporate-ir.net/phoenixi.zhtml?c=175436&p=irol-newsArticle_Print&ID=689194&highlight= (accessed Jan. 6, 2009), 2 pages.
News Release, Halozyme Therapeutics Inc., "Phase III Trial Begins for Gammagard Liquid Plus rHuPHZO in Primary Immunodeficiency Patients," San Diego, CA, Jan. 5, 2009, hup://phx.corporate-innet/phoenix.zhtml?c=175436&p=irol-newsArticle_Print&ID=1240232&highlight= (accessed Jan. 6, 2009), 3 pages.
News Release, Halozyme Therapeutics Inc., Q4 2008 Earnings Call Transcript found at: http://seekingalpha.com/article/125929-halozyme-therapeutics-inc-q4-2008-earnings-call-transcript [accessed on May 13, 2009] [12 pages].
News Release, Halozyme Therapeutics Inc. Q4 2007 Earnings Call Transcript found at: http://seekingalpha.com/article/68609-halozyme-therapeutics-q4-2007-earnings-call-transcript [accessed on Jun. 24, 2009] [12 pages].
Ochs et al., "Safety and efficacy of self-administered subcutaneous immunoglobulin in patients with primary immunodeficiency diseases," J Clin. Immunol. 26:265-273 (2006).
Ohno, N., Models of Kawasaki disease, Drug Discovery Today: Disease Models 3(1):83-89 (2006).
Oncley, M. and M. Melin, "The separation of the antibodies, isoagglutinins, prothrombin, plasminogen and betal-lipoprotein into subfractions of human plasma," J Am. Chem. Soc. 71:541-550 (1949).
Ornitz et al., "Elastase I promoter directs expression of human growth hormone and SV40 T antigen genes to pancreatic acinar cells in transgenic mice," Cold Spring Harbor Symp. Quant. Biol. 50:399-409 (1986).
Oyaizu et al, "(NZW x BXSB)F1 mouse. A new animal model of idiopathic thrombocytopenic purpura," J Exp Med 2017-2022 (1988).
Pearson, W. and D. Lipman "Improved tools for biological sequence comparison," Proc. Natl. Acad. Sci, USA 851:2444-2448 (1988).
Pham et al., "Large-scale transient transfection of serum-free suspension-growing HEK293 EBNA1 cells: peptone additives improve cell growth and transfection efficiency," Biotechnology and Bioengineering 84:332-342 (2003).
Pinkert et al., "An albumin enhancer located 10 kb upstream functions along with its promoter to direct efficient, liver-specific expression in transgenic mice," Genes and Devel. 1:268-276 (1987).
Pinkstaff et al., "Evaluation of the Companbllity and Pharmacokinetics of Co-formulated Biologics with Recombinant Human Hyaluronidase: Dose Response," American Association of Pharmaceutical Scientists Conference, Jun. 2006, San Antonio, TX, 2 pages.
Pinkstaff et al., "Recombinant Human Hyaluronidase for Drug and Fluid Dispersion," American Association of Pharmaceutical Scientists Annual Meeting, Nov. 2006, Boston, MA, 2 pages.
Pinkstaff et al., "Recombinant Human Hyaluronidase for Use with Therapeutic Antibodies," Controlled Release Society Conference, Vienna, Austria, 2006, 1 page.
Pirrello et al., "Initial experiences with subcutaneous recombinant human hyaluronidase," J Palliat Med. 10(4):861-864 (2007).
Polson et al., "The Fractionation of protein mixtures by linear polymers of high molecular weight," Biochim. Biophys. Acta. 82:463-475 (1964).
Readhead et al., "Expression of a myelin basic protein gene in transgenic shiverer mice: correction of the dysmyelinating phenotype," Cell 48:703-712 (1987).
Relkin et al., "18-Month study of intravenous immunoglobulin for treatment of mild Alzheimer disease," Neurobiol Aging (2008). [9 pages].
Schiff et al., "Alterations in the half-life and clearance of IgG during therapy with intravenous gamma-globulin in 16 patients with severe primary humoral immunodefciency," J. Clin. Immunol. 6:256-264 (1986).
Schwartz and Dayhoff, eds., Atlas of Protein Science and Structure, National Biomedical Research Foundation, pp. 353-358 (1979).
Sequence alignments from U.S. Appl. No. 10/795,095 search of SEQ ID No. 1 in the Issued Patents database, performed on Sep. 25, 2007.
Shani, M., "Tissue-specific expression of rat myosin light-chain," Nature 314:283-286 (1985).
Shapiro et al., "Intravenous gamma globulin inhibits the production of matrix metalloproteinase-9 in macrophages," Cancer 95:2032-2037 (2002).
Shekhar et al., "The matrix reloaded: halozyme's recombinant enzyme helps injected drugs spread faster," Chem. Biol. 14:603-604 (2007).
Shimizu, Y. and H. Yoshikura, "Multicycle infection of hepatitis C virus in cell culture and inhibition by alpha and beta interferons," J. Virol. 68:8406-8408 (1994).
Smith, T. and M. Waterman, "Comparison of biosequences," Advances in Applied Mathematics 2:482-489 (1981).

(56) References Cited

OTHER PUBLICATIONS

Solomon, B., "Intravenous immunoglobulin and Alzheimer's disease immunotherapy," Curr. Opin. Mol. Ther. 9:79-85 (2007).
Sommer et al., "Paraneoplastic stiff-person syndrome: passive transfer to rats by means of IgG antibodies to amphiphysin," Lancet 365:1406-1411 (2005).
Steinlcuhler et al., "Product inhibition of the hepatitis C virus NS3 protease," Biochem. 37:8899-8905 (1998).
Strongwater et al., "A murine model of polymyositis induced by coxsackievirus B1 (Tucson strain)," Arthritis Rheum. 27:433-442 (1984).
Sudo et al., "Establishment of an in vitro assay system for screening hepatitis C virus protease inhibitors using high performance liquid chromatography," Antiviral Res. 32:9-18 (1996).
Supersaxo et al,"Effect of molecular weight on the lymphatic absorption of water-soluble compounds following subcutaneous administration," Pharm. Res, 7:167-169 (1990).
Swift et al., "Tissue-specific expression of the rat pancreatic elastase I gene in transgenic mice," Cell 38:639-646 (1984).
Takahashi et al., "A fluorimetric Morgan-Elson assay method for hyaluronidase activity," Anal. Biochem. 322:257-263 (2003).
Takeshita et al., "An enzyme-linked immunosorbent assay for detecting proteolytic activity of hepatitis C virus proteinase," Anal. Biochem. 247:242-246 (1997).
Taliani et al., "A continous assay of hepatitis C Virus protease based on resonance energy transfer depsipeptide substrates," Anal. Biochem. 240:60-67 (1996).
Thomas et al., "Assessing the Role of Human Recombinant Hyaluronidase in Gravity-Driven Subcutaneous Hydration: The INFUSE-LR Study," J Palliat Med. 10:1312-1320 (2007).
Trebst et al., "Expression of chemokine receptors on peripheral blood mononuclear cells of patients with immune-mediated neuropathies treated with intravenous immunoglobins," Eur J Neurology 13:1359-1363 (2006).
van Schaik et al., "Intravenous immunoglobulin for chronic inflammatory demyelinating polyradicloneuropathy: a systematic review," Lancet Neurol. 1:497-498 (2002).
Varnell et al., "Effect of Recombinant Human Hyaluronidase on Intraocular Pressure in Rabbits Following Injection of Viscoelastic Substances," Association for Research in Vision and Ophthalmology Annual Meeting, 2005 Fort Lauderdale, FL, 2 pages.
Wagner et al., "Nucleotide sequence of the thymidine kinase gene of herpes simplex virus type 1," Proc. Natl. Acad. Sci. USA 78:1441-1445 (1981).
Walter et al., "High-dose immunoglobulin therapy in sporadic inclusion body myositis: a double-blind, placebo-controlled study," J Neurol 247(1):22-28 (2000).
Wei et al., "Structure function analysis of the human hyaluronidase enzymes," American Society for Matrix Biology Biennial Meeting, San Diego, CA, Dec. 5, 2008, B4. [2 pages].
Yamamoto et al., "Identification of a functional promoter in the long terminal repeat of Rous sarcoma virus," Cell 22:787-797 (1980).
Yocum et al., "Assessment and Implication of the Allergic Sensitivity to a Single Dose of Recombinant Human Hyaluronidase Injection: A Double-Blind Placebo-Controlled Clinical Trial," J Infus Nursing. 30:293-299 (2007).
Zalipsky, S and C Lee, "Poly(ethyl ene glycol) Chemistry: Biotechnical and Biomedical Applications," J. Hams, ed., Plenmn: NY, Chapter 21, pp. 341-370 (1992).
Letter/Written Disclosure of the Supplemental Information Disclosure Statement for the above-referenced application, mailed on the same date herewith, 2 pages.
Office Action, dated Apr, 2, 2013, in connection with corresponding Japanese Patent Application No. 2011-500795 [English Translation], 3 pages.
Examination Report, dated Mar. 29, 2013, in connection with corresponding Taiwan Patent Application No. 098108166 [English Translation], 8 pages.
Notice of Allowance, dated Apr. 17, 2013, in connection with corresponding Korean Patent Application No. 10-2010-7023180 [English Translation], 1 page.
Letter/Written Disclosure of the Supplemental Information Disclosure Statement for the above-referenced application, filed herewith Apr. 27, 2015, 2 pages.
Baxter BioScience, Briefng Book: Blood Products Advisory Committee Meeting. "HyQvia: Immune Globulin Infusion 10% (Human) with Recombinant Human Hyaluronidase," Published Jul. 31, 2014. Available on-line at <URL:google.com/url?sa=t&rct=j&cr&esrc=s&frm=1&source=web&cd=3&Ved=0CCwQFjAC&url=http%3A%2F%2Fwww.fda.gov%2Fdownloads%2FAdvisoryCommittees%2FCommitteesMeetingMaterials%2FBloodVacc-inesandOtherBiologics%2FBloodProductsAdvisoryCommittee%2FUCM407013.pdf&ei=zTFBVJXELfOHsQSX14DICQ&usg=AFQjCNFmAm634vKiaGB5cLM-mvOEMEGu-w, 204 pages.
Osgood et al., "Pegylated recombinant human hyaluronidase PH20 (PEGPH20) enhances cetuximab efficacy in BxPC-3/HAS3 human pancreatic cancer xenografts," AACR Annual Meeting Apr. 5-9, 2014. San Diego, CA Abstract #3646, Available on-line Mar. 2014 [Retrieved from the internet Mar. 18, 2014], 1 page.
"PEGPH2O: The Science & The Strategy," presented at J. P. Morgan Healthcare Conference on Jan. 7, 2015. Presentation. 81 pages.
News Release, "FDA advisory committee panel provides favorable recommendation on Baxter's HyQvia for primary immunodeficiency," published Jul. 31, 2014 [retrieved on Sep. 2, 2014] Retrieved from:<URL:online.wsj.com/article/PR-CO-20140731-915905.html#printMode [2 pages].
News Release, "Baxter launches HYQVIA in the United States for adult Patients with primary immunodeficiency," Published Oct. 20, 2014 [online] [retrieved on Nov. 11, 2014] Retrieved from:<URL:http://www.halozyme.com/Investors/News-Releases/News-Release-Details/2014/Baxter-Launches-HYQVIA-in-the-United-States-for-Adult-Patients-with-Primary-Immunodeficiency/default.aspx [4 pages].
News release, Halozyme Therapeutics, Inc., "Halozyme announces preclinical data presentations at the Association Of Cancer Research Annual Meeting," Published on Apr. 8, 2014 [on line][retrieved on Apr. 14, 2014] Retrieved from: <URL:halozyme.com/Investors/News-Releases/News-Release-Details/2014/Halozyme-Announces-Preclinical-Data-Presentations-At-The-Association-Of-Cancer-Research-Annual-Meeting/default.aspx [3 pages].
News Release, Halozyme Therapeutics, Inc, "Halozyme announces Roche marketing authorization for MabThera SC for patients with common forms of non-hodgkin lymphoma in European Union," Published Mar. 28, 2014 [online], Retrieved from: <URL:halozyme.com/Investors/News-Releases/News-Release-Details/2014/Halozyme-Announces-Roche-Marketing-Authorization-For-MabThera-SC-For-Patients-With-Cornmon-Forms-Of-Non-Hodgkin-Lymphoma-In-European-Union/default.aspx [retrieved on Mar. 31, 2014] 3 pages.
News release, Halozyme Therapeutics, Inc., "Halozyme therapeutics reports selection of first product candidate under Janssen Collaboration," Published on Mar. 10, 2015 [online][retrieved on Mar. 10, 2015] Retrieved from:<URL:halozyme.com/Investors/News-Releases/News-Release-Details/2015/Halozyme-Therapeutics-Reports-Selection-Of-First-Product-Candidate-Under-Janssen-Collaboration/default.aspx [3 pages].
Response, dated Jan. 12, 2012, to Written Opinion, dated Oct. 13, 2011, in connection with International Patent Application No. PCT/US2010/002545, 24 pages.
Office Action, dated Jun. 4, 2014, in connection with U.S. Appl. No. 12/807,991, 7 pages.
Response, filed Sep. 4, 2014, to Office Action, dated Jun. 4, 2014, in connection with U.S. Appl. No. 12/807,991, 23 pages.
Office Action, dated Oct. 16, 2014, in connection with U.S. Appl. No. 12/807,991, 7 pages.
Response, filed Jan. 16, 2015, to Office Action, dated Oct. 16, 2014, in connection with U.S. Appl. No. 12,807,991, 22 pages.
Response, filed Jan. 22, 2015, to Examiner's Report, dated Jul. 22, 2014, in connection with Canadian Patent Application No. 2,714,708, 27 pages.
Instructions, dated Jan. 25, 2014, for Response, filed Jan. 28, 2014, to Office Action, dated Oct. 15, 2013, in connection with Chilean

(56) References Cited

OTHER PUBLICATIONS

Patent Application No. 633-2009, 20 pages [English language instructions and document, as filed, in Spanish].
Instructions, dated Jun. 1, 2014, for request for reexamination in Response, filed Jun. 5, 2014, to Office Action, dated Feb. 18, 2014, in connection with Chinese Patent Application No, 200980109505.9), 32 pages [English language instructions and document, as filed, in Chinese].
Examination Report, dated Sep. 10, 2014, in connection with European Patent Application No, 09721669.1, 8 pages [Examination Report and cited reference D1-Melamed et al., J Allergy and Clin Immunol 121(2, suppl.):S83 (2008)].
Response, filed Mar. 5, 2015, to Examination Report, dated Sep. 10, 2014, in connection with European Patent Application No. 09721669.1, 18 pages.
Final Office Action, dated May 20, 2014, in connection with Japanese Patent Application No. 2011-500795, 5 pages [English language translation, original document in Japanese and cited reference D1: Melamed et al., J Allergy and Clin Immunol 121(2, suppl.):583 (2008)].
Instructions, dated Sep. 18, 2014, for Response, filed Sep. 22, 2014, to Final Office Action, dated May 20. 2014, in connection with Japanese Patent Application No. 2011-500795, 17 pages [English language instructions and document, as filed, in Japanese].
Pre-appeal Examination Report, dated Jan. 7, 2015, in connection with Japanese Patent Application No. 2011-500795, 3 pages [English language translation and cited reference D1: Melamed et al., J Allergy and Clin Immunol 121(2, suppl.):583 (2008)].
Instructions, dated Nov. 7, 2014, for filing Appeal Brief and Appeal Brief, as filed Nov. 13, 2014, in connection with Japanese Patent Application No. 2011-500795, 26 pages [English language instructions and document, as filed, in Japanese].
Instructions, dated Jan. 16, 2014, for response, filed Jan. 20, 2014, to Official Action, in connection with Mexican Patent Application No. MX/a/2010/009478, 25 pages [English language instructions and document, as filed, in Spanish].
Offcial Action, dated May 9, 2014, in connection with Mexican Patent Application No. MX/a/2010/009478, 4 pages [English language translation and original document in Spanish].
Instructions, dated Sep. 15, 2014 for response, filed Sep. 19, 2014, to Official Action, dated May 9, 2014, in connection with Mexican Patent Application No, MX/a/2010/009478, 71 pages [English language instructions and document, as filed, in Spanish].
Official Action, dated Jan, 28, 2015, in connection with Mexican Patent Application No. MX/a/2010/009478, 6 pages [English language translation, original document in Spanish, and cited reference D1: Melamed et al., J Allergy and Clin Immunol 121(2, suppl.):S83 (2008)].
Instructions, dated Jan. 14, 2015 and Jan. 23, 2015, for Response, filed Jan. 28, 2015, to Office Action, dated Oct. 17, 2014, in connection with Taiwanese Patent Application No. 098108166, 61 pages [English language instructions and document, as filed, in Chinese].
Office Action, dated Oct, 17, 2014, in connection with corresponding Taiwanese Patent Application No. 098108166, 17 pages [English language translation, original document in Chinese, and cited reference: Melamed et al., J Allergy and Clin Immunol 121(2, suppl.):S83 (2008)].
Examination Report, dated Jan. 6, 2015 (received Feb, 24, 2015), in connection with Singaporean Patent Application No. 201005998-8 (3058SG), 14 pages [cited reference D1: Melamed et al., J Allergy and Clin Immunol 121(2, suppl.):S83 (2008)].
Office Action, dated May 15, 2013 (received Jun. 9, 2013), in connection with corresponding Chinese Patent Application No. 200980109505.9 [English Translation], 6 pages.
Barandun et al., "Intravenous administration of human gammaglobulin," Vox Sang, 7:157-174 (1962).
Berger, M., "Principles ofand advances in immunoglobulin replacement therapy for primary immunodeficiency," Immunol. Allergy Clin. North Am. 28(2):413-438 (2003).
Fernandes, P, and J. Lundblad, "Preparation ofa stable intavenous gamma-globulin: process design and scale-up," Vox Sang. 39:101-112 (1980).
Hamamoto et al., "A novel method for removal of human immunodeficiency virus: filtration with polymeric membranes," Vox Sang. 56:230-236 (1989).
Koblet et al., "Turnover of standard-gammaglobulin, pH-4-Gammaglobulin and pepsin desaggregated Gammaglobulin and clinical implications," Vox Sang. 13(1):93-102 (1967).
Louie et al., "Inactivation of Hepatitis C Virus in low pH intravenous immunoglobulin," Biologicals 22:13-19 (1994).
Marcus, D., "A study ofthe mechanism of the anticomplementary activity of gamma-globulin," J. Immunol. 84:273-284 (1960).
Mayer, M., "Quantitative C' fixation analysis, complement and complement fixation," in Experimental Immunochemistry Eds, Kabat, E. and M. Meyer, Thomas, Springfield, II., pp. 214-216 and pp. 227-228 (1961).
News Release: Baxter International Inc., "Baxter presents latest clinical trial results of Gammagard Liquid administered subcutaneously," Rx Times, published Mar. 16, 2008, Retrieved from the Internet:<URL: rxtimes.com/baxter-presents-latest-clinical-trial-results-of-gammagard-liquid-administered-subcutaneously/, Retrieved on Jun. 7, 2011, 18 pages.
Pearlman, R. and T. Nguyen, "Analysis of protein drugs," in Peptide and Protein Drug Delivery Ed, Lee, V., Peptide and Protein Drug Delivery, Marcel Dekker:New York, N.Y., pp. 247-301 (1991).
Planitzer et al., "Neutralization of different echovims serotypes by individual lots of intravenous immunoglobulin," J Med Virol 83(2):305-310 (2011).
Wang, Y. and M. Hanson, "Parenteral formulations of proteins and peptides: Stability and stabalizers," J. of Parenteral Science & Technology 42(supp):S4-S26 (1988).
Wasserman et al.. "Efficacy, Safety, and Pharmacokinetics of a 10% Liquid Immune Globulin Preparation (Gammagard Liquid, 10%) Administered Subcutaneously in Subjects with Primary Immunodeficiency Disease," J Clin Immunol., Epub ahead of print, 9 pages (2011).
Williams, R., "The effects of continuous local injection of hyaluronidase on skin and subcutaneous tissue in rats." Anat. Rec. 122:349-361 (1955).
Halozyme Therapeutics, Securities and Exchange Commission form 10K, Mar. 11, 2011, 124 pages.
Halozyme Therapeutics, Securities and Exchange Commission Form 8-K. Jan. 10, 2011, 43 pages.
Misbah et al., "Subcutaneous immunoglobin: opportunities and outlook." J Transl Immunol 158 (Suppl. 1):51-59 (2009) and available on-line Oct. 30, 2009.
News Release, "Halzoyme Therapeutics Reports Third Quarter 2010 Financial Results." San Diego, CA Nov. 5, 2010, Retrieved from the Internet:<URL: phx.corporate-ir.net/phoenix.zhtml?c=175436&p=irol-newsArticle&ID=1492590&highlight=, Retrieved on Jun. 7, 2011, 5 pages.
News Release, Halozyme Therapeutics Inc., "Fourth Quarter and Full Year 2010 Conference Call Transcript," published Mar, 11, 2011, Retrieved from the Internet<URL: phx.corporate-ir.net/External.File?item=UGFyZW50SUQ9NDE5MjUyfENoaWxkSUQ9NDMyNDcwfFR5cGU9MQ==&t=1, Retrieved on Apr. 7, 2011, 18 pages.
Bookbinder et al, "Evaluation of the compatibility and pharmacokinetics of co-formulated biologics with recombinant human hyaluronidase: Dose Response," American Association of Pharmaceutical Scientists Conference, Nov. 2006, Abstract, 2 pages.
Pinkstaff et al., "Evaluation ofthe compatibility and pharmacokinetics of co-formulated biologics with recombinant human hyaluronidase: Dose Response," American Association of Pharmaceutical Scientists Conference, Nov. 2006, Poster, 1 page.
Haller et al., "Revolutionizing Drug Dispersion with Enhanze Technology," American Association of Pharmaceutical Scientists Annual Meeting, Nov. 6-10, 2005, Nashville, TN, Abstract, 3 pages.
Haller et al., "Revolutionizing Drug Dispersion with Enhanze Technology," American Association of Pharmaceutical Scientists Annual Meeting, Nov, 6-10, 2005, Nashville, TN, Poster, 1 page.
Halozyme Therapeutics, J.P. Morgan 29th Annual Healthcare Conference Presentation, Jan. 12, 2011, 35 pages.

(56) References Cited

OTHER PUBLICATIONS

Halozyme Therapeutics, "Matrix therapies for life," Presented at Canaccord Cardiovascular, Diabetes & Obesity Conference, Dec. 8, 2010, 38 pages.
Yang, T., "An alternative approach for delivering high dose biologics subcutaneously," presented at PEP Talk, presented Jan. 11, 2011, Presentation, 28 pages.
Office Action, dated Jan. 15. 2013 (received Feb. 13, 2013), in connection with corresponding Chilean Patent Application No. 633-2009 [English Translation together with Original in the Spanish language], 16 pages.
Office Action, received Feb. 25, 2013, in connection with corresponding Colombian Patent Application No. 10.111.104 [English Translation and Original in the Spanish language], 10 pages.
Office Action, dated Feb. 7, 2013 (received Mar. 4, 2013), in connection with Corresponding Canadian Patent Application No. 2,714,708, 3 pages.
Written Opinion, dated Jan. 25, 2013 (received Mar. 7, 2013), in connection with corresponding Singapore Patent Application No. 201005998-8, 8 pages.
Letter/Written Disclosure of the Information Disclosure Statement for the above-referenced application, dated Feb. 17, 2012, 2 pages.
Derwent English language patent abstract for CH 684 164 (Item AF). Inventor: Friedli et al., Publication Date: Jul. 29, 1994, Dialog File No. 351, Accession No. 6846186, 1 page.
Leesch et al., "30-day pharmacokinetic evaluation of IV versus subcutaneous administration of inuriunoglobulin with and without recombinant human hyaluronidase in dogs," J Allergy and Clin Immunol 123(2, Suppl. S):S10 (2009), Abstract, 1 page.
Melamed et al., "Recombinant human hyaluronidase facilitates dispersion of subcutaneously administered gammagard liquid and enables administration of a full monthly dose in a single site to patients with immunodeficiency diseases," J Allergy and Clin Immunol 121(2, suppl.):S83 (2008), Abstract, 1 page.
Skoda-Smith et al., "Subcutaneous inununoglobulin replacement therapy in the treatment of patients with primary immunodeficiency disease," Ther Clin Risk Manag 6:1-10 (2010).
McCoy et al., "Pharmacokinetics of 10% immunoglobulin administered intravenously or subcutaneously alone or following recombinant human hyaluronidase in subjects with PID," XIVth Meeting of the European Society for Immunodeficienies (ESID) Istanbul, Turkey Oct. 6-10, 2010. Poster, 1 page.
Schiff et al., "Tolerability of immunoglobulin subcutaneous 10% administered SC following administration of recombinant human hyaluronidase in subjects with PID," XIVth Meeting of the European Society for Immunodeficienies (ESID) Istanbul, Turkey Oct. 6-10, 2010, Poster, 1 page.
Stein et al., "Tolerability and efficacy of recombinant human hyaluronidase (rHuPH20)—facilitated subcutaneous infusion of immune globulin (Human), 10% (IGHy) in patients with Primary Immunodeficiency Disease (PI)," American College of Allergy, Asthma, & Immunology Meeting, Boston, MA, Nov. 5, 2011, Poster, 1 page.
Wasserman et al., "Pharmacokinetics of recombinant human hyaluronidase (rHuPH20)—facilitated subcutaneous infusion of immune globulin (Human), 10% (IGHy) in patients with Primary Immunodeficiency Disease (PI)," American College of Allergy, Asthma, & Immunology Meeting, Boston, MA, Nov. 5, 2011, Poster, 1 page.
"Products & Pipeline: Baxter-HyQ," Halozyme website[online][retrieved on Jan. 25, 2012] Retrieved from:<URL:halozyme.com/Products-And-Pipeline/Pipeline/Baxter-HyQ/default.aspx[1 page].
News Release, "Baxter and Halozyme announce top-line results of phase III study of HyQ in patients with primary immunodeficiency," Published on Jul. 8, 2011 [online][retrieved on Jan. 25, 2012] Retrieved from:<URL:baxter.com/downloads/press_room/press_releases/2011/07_08_11_hyq.pdf [3 pages].
News Release, "Baxter presents data from interim analyses of phase III clinical trial HyQ at European Society for Immunodeficiencies meeting," Published on Oct. 6, 2010 [online][retrieved on Jan. 25, 2012] Retrieved from: <URL:baxter.com/press_room/press_releases/2010/10_06_10_hyq.html [5 pages].
News Release, "Baxter presents phase III HyQ efficacy and tolerability data at American College of Allergy, Asthma & Immunology meeting," Published on Jul. 11, 2011 [online][retrieved on Jan. 25, 2012] Retrieved from:<URL:baxter.com/press_room/press_releases/2011/11_07_11_hyq_acaai.html [3 pages].
News Release, "Data Presented at AAAAI reinforce Baxter's commitment to making Gammagard Liquid Therapy more convenient," Published on Mar. 16, 2009 [online][retrieved on Nov. 30, 2011] Retrieved from:<URL:baxter.com/press_room/press_releases/2009/03_16_09 aaaai.html [5 pages].
News Release, "Phase III trial begins for Gammagard Liquid Plus rHuPH20 in primary immunodeficiency patients," Published on Jan. 5, 2009 [online][retrieved on Jan. 25, 2012] Retrieved from:<URL:baxter.com/press_room/press_releases/2009/01_05_09_halozyme.html [4 pages].
Office Action, dated Feb. 17, 2011, in connection with related U.S. Appl. No. 12/378,969, 12 pages.
Response dated Aug. 17, 2011 to Office Action, dated Feb. 17,2011, in connection with related U.S. Appl. No. 12/378,969, 16 pages.
Examiner's Report, dated Oct. 5, 2011, in connection with corresponding Australian Patent Application No. 2009226141, 2 pages.
Notice of Opposition, submitted Oct. 24. 2011, in connection with corresponding Chilean Patent Application No. 633-2009, 7 pages.
Response to Notice of Opposition, submitted Oct. 24, 2011, in connection with Chilean Patent Application No. 633-2009, 27 pages.
Search Report and Written Opinion, dated Dec. 2, 2011 (received Jan. 19, 2012), in connection with Singapore Patent Application No. 201005998-8, 15 pages.
Examination Report, dated Nov. 22, 2012 (received Dec. 20, 2012), in connection with European Patent Application No. 09721669.1, 6 pages.
Letter/Written Disclosure of the Supplemental Information Disclosure Statement for the above-referenced application, filed herewith on Sep. 9, 2016, 4 pages.
Hylenex recombinant (hyaluronidase recombinant human) injection, solution. Published on Feb. 29, 2008 in Dosage and Administration: Subcutaneous Urography. Retrieved from <URL: dailymed.nlm.nih.gov/dailymed/archives/fdaDrugInfo.cfm?archiveid=7523 [Retrieved on Jul. 27, 2016], 6 pages.
Muckenschnabel et al., "Pharmacokinetics and tissue distribution of bovine testicular hyaluronidase and Vinblastine in mice: an attempt to optimize the mode of adjuvant hyaluronidase administration in cancer chemotherapy," Cancer Lett 131:71-84 (1998).
Written Opinion, dated Jul. 1, 2016, in connection with Singapore Patent Application No. 10201503296Q, 7 pages.
Office Action, dated Aug. 29, 2016, in connection with Argentinian Patent Application No. P090100943 [English translation and original document in Spanish], 7 pages.
Letter/Written Disclosure of the Supplemental Information Disclosure Statement for the above-referenced application, filed herewith Jan. 23, 2017, 2 pages.
Moon et al., "Limited growth of severed CNS axons after treatment of adult rat brain with hyaluronidase," J Neurosci Res 71(1):23-37 (2003).
Mouthon et al., "Intravenous immunoglobulins in autoimmune- or paroviius B19-mediated pure red cell aplasia," Autoimmunity Reviews 4(5):264-269 (2005).
Yasuda et al., "Effect of hyaluronidase on experimental cerebral infarct size and mortality," Lab Invest 46(4):400-404 (1982).
Greenway, "The Next Chapter Begins: Creating Value Through Growth," Presented at the IMP Securities 2015 Life Sciences Conference, Jun. 24, 2015, 24 pages.
News Release, Halozyme Therapeutics, Inc., "Halozyme Announces First Clinical Dosing Of Janssen's Daratumumab Using ENHANZE™ Technology," Published Nov. 4, 2015 [online], Retrieved from: <URL:halozyme.com/Investors/News-Releases/News-Release-Details/2015/Halozyme-Announces-First-Clinical-Dosing-Of-Janssens-Daratumumab-Using-ENHANZE-Technology/default.aspx [retrieved on Nov. 5, 2015], 3 pages.
News Release, Halozyme Therapeutics, Inc., "Halozyme Reports Second Quarter 2016 Financial Results," Published Aug. 9, 2016 [online], Retrieved from: <URL:pmewswire.com/news-releases/

(56) References Cited

OTHER PUBLICATIONS halozyme-reports-second-quarter-2016-financial-results-300311374.html [retrieved on Aug, 31, 2016], 10 pages.
Response, filed Nov. 30, 2016, to Office Action, dated Aug. 29, 2016, in connection with Argentinian Patent Application No. P090100943 [English instructions and document as filed in Spanish], 25 pages.
Response, filed Jun. 6, 2016, to Written Opinion, dated Jan. 6, 2016, in connection with Singapore Patent Application No. 10201503296Q, 46 pages.
Letter/Written Disclosure ofthe Supplemental Information Disclosure Statement for the above-referenced application, filed herewith Jun. 3, 2016, 2 pages.
Arming et a1., "In vitro mutagenesis of PH-20 hyaluronidase from human sperm," Eur J Biochem 247(3):810-814 (1997).
Gardulf and Hammarstrom, "Subcutaneous Administration of Immunoglobulins. What are the advantages?" Clin Immunother 6:108-116 (1996).
Response, filed Feb. 10, 2016, to Examiner's Report, dated Aug. 10, 2015, in connection with Canadian Patent Application No. 2,714,708, 57 pages.
Notification of Reexamination, dated Mar. 7, 2016, in connection with Chinese Patent Application No. 2009801095059 [English Translation and original document in Chinese], 14 pages.
Response, filed Dec. 29, 2015, to Examination Report, dated Oct. 21, 2015, in connection with European Patent Application No. 09721669.1, 8 pages.
Communication under Rule 71(3) Intention to Grant, dated Mar. 16, 2016, in connection with European Patent Application No. 09721669.1, 5 pages.
Response, filed Mar. 21, 2016, to Examination Report, dated Apr. 30, 2015, in connection with Indian Patent Application No. 7321/DELNP/2010, 47 pages.
Response, filed Sep. 28, 2015, to Office Action, dated Jun. 30, 2105, in connection with Japanese Patent Application No. 2014-192938 [English language instructions and document as filed in Japanese], 18 pages.
Office Action, dated Dec. 22, 2015, in connection with Japanese Patent Application No. 2014-192938 [English translation and original document in Japanese], 3 pages.
Response, filed Jan. 21, 2016, to Office Action, dated Dec. 22, 2105, in connection with Japanese Patent Application No. 2014-192938 [English language instructions and document as filed in Japanese], 34 pages.
Letter, dated Feb. 17, 2016, reporting Decision to Grant, dated Feb. 16, 2016, in connection with Japanese Patent Application No. 2014-192938 [English letter and original document in Japanese], 4 pages.
Response, filed May 29, 2015, to Official Action, dated Jan. 28, 2015, in connection with Mexican Patent Application No. MX/a/2010/009478 [English language instructions and document as filed in Spanish], 35 pages.
Response, filed Feb. 2, 2016, to Office Action, dated Sep. 17, 2015, in connection with Mexican Patent Application No. MX/a/2010/009478 [English language instructions and document as filed in Spanish], 31 pages.
Letter, dated Apr. 13, 2016, reporting a Notice of Allowance issued in connection with Mexican Patent Application No. MX/a/2010/009478, 1 page.
Search Report, dated Nov. 6, 2015, and Written Opinion, dated Dec. 11, 2015, issued in connection with Singapore Patent Application No. 10201503296Q, 10 pages.
Letter, dated Feb. 19, 2016, reporting Allowance of Patent Application- issued in connection with Taiwanese Patent Application No. 102142761 [English letter], 2 pages.
Response, filed Nov. 24, 2015, to Office Action, dated Jul. 27, 2015, in connection with Vietnamese Patent Application No. 1-2010-02743 [English instructions and document as filed in Vietnamese], 6 pages.
Letter, dated Mar. 31, 2016, reporting Decision to Grant, dated Mar. 23, 2016, in connection with Eurasian Patent Application No. 201200490 [English letter and document as issued in Russian], 9 pages.
Notice of Grant, dated Aug. 10, 2015, in connection with Mexican Patent Application No. MX/a/2012/003282 [Letter Reporting Notice of Allowance and Letters Patent], 3 pages.
Letter/Written Disclosure of the Supplemental Information Disclosure Statement for the above-referenced application, dated Sep. 10, 2012, 2 pages.
Lu, H. and E, Wimmer., "Poliovirus chimeras replicating under the translational control of genetic elements of hepatitis C virus reveal unusual properties of the internal ribosomal entry site of hepatitis C virus," Proc. Natl. Acad. Sci. USA 93:1412-1417 (1996).
Melamed et al., "Long-term safety and pharmacokinetics of facilitated subcutaneous infusion of immuneglobulin (HUMAN) 10% and recombinant human hyaluronidase (IGHy) in a phase III extension study in patients with primary immunodeficiency (PI)" Presented May 18, 2012 at the Clinical Immunolgy Society Annual Meeting: Primary Immune Deficiency Disease North American Conference, Chicago, IL, Abstract, 1 page.
Stein et al., "Pharmacokinetic (PK) of human immuneglobulin 10% (IgG) administered intraveneously (IGIV), subcutaneously (IGSC) or facilitated subcutaneously with recombinant human hyaluronidase hyaluronidase (IGHy) in a subset of patients with primary immunodeficiency (PI)," Presented May 18, 2012 at the Clinical Immunolgy Society Annual Meeting: Primary Immune Deficiency Disease North American Conference, Chicago, IL. Abstract, 2 pages.
Stein et al., "Tolerability and efficacy of facilitated-subcutaneous infusion of immuneglobulin (HUMAN) 10% and recombinant human hyaluronidase (IGHy) in patients with primary immunodeficiency (PI)," Presented May 18, 2012 at the Clinical Immunolgy Society Annual Meeting: Primary Immune Deficiency Disease North American Conference, Chicago, IL. Abstract, 1 page.
Teschner et al., "Preclinical Characterization of a New Liquid "Immune Globulin Intravenous (Human), 10% Triple Virally Reduced Solution"(IGIV, 10%TVR)," The Journal of Allergy and Clinical Immunology. 113(2):S45 (2004). Abstract 79, 1 page.
Wasserman et al., Pharrnacokinetic (PK) of human immuneglobulin 10% (IgG) administered intraveneously (IGIV), subcutaneously (IGSC) or facilitated subcutaneously with recombinant human hyaluronidase hyaluronidase (IGHy) in a subset of patients with primary immunodeficiency (PI) Presented May 18, 2012 at the Clinical Immunology Society Annual Meeting: Primary Immune Deficiency Disease Nonh American Conference May 17-20, 2012, Chicago, IL. Abstract, 1 page.
Wasserman et al., "Tolerability and efficacy of facilitated-subcutaneous infusion of immuneglobulin (HUMAN) 10% and recombinant human hyaluronidase (IGHy) in patients with primary immunodeficiency (PI)," Presented May 18, 2012 at the Clinical lmmunolgy Society Annual Meeting: Primary Immune Deficiency Disease North American Conference, Chicago, IL. Abstract, 2 pages.
Weber et al., "Intravenous immunoglobulin gammagard liquid contains anti-Rage IgG and sLRP," Presented at the 19th Meeting of the European Neurological Society, Jun. 23, 2009. Abstract, 1 page.
News Release, Baxter International Inc., "Baxter and Halozyme Provide Update on HyQ Biologics License Application," Published on Apr. 16. 2012 [online][retrieved on Jul. 27, 2012] Retrieved from: <URL:finance.yahoo.com/news/baxter-halozyme-hyq-biologics-license-120000974.html [2 pages].
News Release, Baxter International Inc., "Baxter Announces FDA Approval for GAMMAGARD Liquid as a Treatment for Multifocal Motor Neuropathy," Published on Jun. 25, 2012 [online][retrieved on Jul. 27, 2012] Retrieved from: <URL: finance.yahoo.com/news/baxter-announces-fda-approval-gammagard-130000672.html [3 pages].
News Release, Baxter International Inc., "Baxter Presents Phase III HyQ Efficacy and Tolerability Data at American College of Allergy, Asthma & Immunology Meeting,"Published 2012 [online] [retrieved on Jul. 27, 2012] Retrieved from: <URL:fiercebiotech.com/press-releases/baxter-presents-phase-iii-HyQ-efficacy-and-tolerability-data-American-colle [4 pages].

(56) References Cited

OTHER PUBLICATIONS

News Release, Baxter International Inc., "Baxter shares fall on news of FDA delay: Regulator requests more long-term data before approving HyQ immune system treatment," Chicago Tribune. Published Apr. 16, 2012 [online][retrieved on Jul, 27, 2012] Retrieved from: <URL: articles.chicagotribune.com/2012-04-16/business/ct-biz-0417-baxter-20120416_1_baxter-shares-gammagard-baxter-stock [2 pages].
News Release, Baxter International Inc., Baxter Gets FDA Nod for Gammagard, Published on Jun. 27, 2012 [online][retrieved on Jul. 27, 2012] Retrieved from:<URL: finance.yahoo.com/news/baxter-gets-fda-nod-gammagard-181520622.html [3 pages].
Response to Written Opinion, dated Aug. 31. 2009. in connection with International Application No. PCT/U82009/001670 (3058PC), 32 pages.
International Search Report and Written Opinion, dated Oct. 13, 2011, in connection with International Patent Application No. PCT/US2010/002545 (3088PC), 17 pages.
English translation of Examiniation Report dated Apr. 24, 2012 in connection with Taiwanese Patent Application No. 098108166 (30581W), 5 pages.
Response to Search Report and Written Opinion, dated Dec. 2, 2011, in connection with Singapore Patent Application No. 201005998-8 (30588G), 9 pages.
Office Action and Search Report, dated Jul. 4, 2012 (received Aug. 10, 2012) in connection with Chinese Patent Application No. 200980109505.9 (3058CN) [English Translation], 8 pages.
Letter/Written Disclosure of the Supplemental Information Disclosure Statement for the above-referenced application, filed herewith on May 10, 2017, 3 pages.
Communication under Rule 97(1) Decision to Grant, dated Apr. 6, 2017, in connection with European Patent Application No. 09721669. 1, 3 pages.
Final Examination Report, dated Apr. 10, 2017, and Notice of Eligibility for Grant, dated Apr. 24, 2017, issued in connection with Singapore Patent Application No. 10201503296Q [Original documents and cited references], 54 pages.
Examiner's Report, dated Mar. 31, 2017, in connection with Canadian Patent Application No. 2,714,708, 3 pages.
Letter/Written Disclosure of the Supplemental Information Disclosure Statement for the above-referenced application, filed herewith Aug. 31, 2017, 3 pages.
Office Action, dated Jun, 30, 2017, in connection with Argentinian Patent Application No. P090100943 [English translation and original document in Spanish; D1=Melamed et al., J Allergy and Clin Immunol (2008), D2=WO 2006/091871, D3=Bookbinder et al., J Controlled Release (2006)], 8 pages.
Office Action, dated Jul. 27, 2017, in connection with Chilean Patent Application No. 2009-00633 [English translation and original document in Spanish], 6 pages.
Certificate of Grant, dated Jun. 6, 2107, issued in connection with Singapore Patent Application No. 10201503296Q, 2 pages.
Office Action, dated Jul, 18, 2017, in connection with Vietnamese Patent Application No. 1-2010-02743 [English translation and original document in Vietnamese], 2 pages.
Letter/Written Disclosure of the Supplemental Information Disclosure Statement for the above-referenced application, filed herewith Dec. 14, 2017, 3 pages.
Notice of Allowance, dated Nov. 20, 2017 and received on Nov. 26, 2017, in connection with corresponding Chilean Patent Application No. 633-2009 [English reporting letter with Original document in Spanish], 5 pages.
Notice of Grant, dated Oct. 9, 2017 and corresponding Indonesian Patent Application received on Nov. 15, 2017, issued in connection with No. 201003534, 2 pages.
Letter/Written Disclosure of the Supplemental Information Disclosure Statement for the abovevreferenced application, filed herewith Dec. 13, 2018, 3 pages.
Office Action, dated Oct. 8, 2018, in connection with Chinese Patent Application No. 2016102582824 [English Translation and original document in Chinese], 18 pages.
Letter/Written Disclosure of the Supplemental Information Disclosure Statement for the above-referenced application, filed herewith Dec. 27, 2017, 2 pages.
"Immunoglobulin—overview" retrieved from <URIL:webmd.com/cancer/tc/immune-globulin-overview [retrieved on Apr. 12, 2017], 4 pages.
Kazatchkine, M. and S. Kaveri, "Immunomodulation of Autoimmune and Inflammatory Diseases with Intravenous Immune Globulin," Mackay and Rosen eds., N. Engl. J. Med. 345(10):747-755 (2001).
Muckenschnabel et al., "Hyaluronidase pretreatment produces selective melphalan enrichment in malignant melanoma implanted in nude mice," Cancer Chemother Pharmacol 38(1):88-94 (1996).
News Release, "Bristol-Myers Squibb and Halozyme Enter Global Collaboration and License Agreement for ENHANZE Technology," Published Sep. 14. 2017 [online] Retrieved from:<URL: halozyme.com/investors/news-releases/news-release-details/2017/Bristol-Myers-Squibb-and-Halozyme-Enter-Global-Collaboration-and-License-Agreement-for-ENHANZE-Technology/defaultaspx [retrieved on Sep. 14, 2017], 7 pages.
News Release, "ENHAZE draws EMS and Roche money; Halozyme could receive $2B+," Published Sep. 14, 2017 [online] Retrieved from:<URL: bioworld.com/content/enhanze-draws-bms-and-roche-money-halozyme-could-receive-2b [retrieved on Sep. 18, 2017], 2 pages.
News Release, "Bristol, Roche tap Halozyme for tech platform," Published Sep. 14, 2017 [online] Retrieved from:<URL: biopharmadive.com/news/bristol-roche-tap-halozyme-for-tech-platform/504958/ [retrieved on Sep, 18, 2017], 3 pages.
Notice of Allowance, dated Nov. 20, 2017, in connection with Chilean Patent Application No. 633-2009 [English translation and original document in Spanish], 10 pages.
Notice of Grant, dated Oct, 9, 2017, issued in connection with Indonesian Patent Application No. 201003534, 2 pages.
Examination Repor/ Hearing Notice, dated Dec. 14, 2017, in connection with Indian Patent Application No. 7321/DELNP/2010, 3 pages.
Notice of Allowance, dated Dec. 1, 2017, in connection with Vietnamese Patent Application No. 1-2010-02743 [English reporting letter and original document in Vietnamese], 4 pages.
Letter/Written Disclosure ofthe Supplemental Information Disclosure Statement for the above-referenced application, filed herewith on Aug. 23, 2018, 2 pages.
Office Action, dated May 23, 2018, in connection with Argentinian Patent Application No, P090100943 [English translation and original document in Spanish, D1=Melamed et al., J Allergy and Clin Immunol (2008), D2=WO 2006/091871, D3=Bookbinder et al., J Controlled Release (2006)], 6 pages.
Response, filed Aug. 9, 2018, to Office Action, dated May 23, 2018, in connection with Argentinian Patent Application No. P090100943 [English instructions and document as-filed in Spanish], 72 pages.
Letter/Written Disclosure of the Supplemental Information Disclosure Statement for the above-referenced application, filed herewith Oct. 25, 2017, 2 pages.
Response, filed Oct. 4, 2017, to Office Action, dated Jun. 30, 2017, in connection with Argentinian Patent Application No. P090100943 [English instructions and document as-filed in Spanish], 68 pages.
Response, filed Sep. 27, 2017, to Examiner's Report, dated Mar, 31, 2017, in connection with Canadian Patent Application No. 2,714,708 [Response as-filed and cited references], 43 pages.
Response, filed Sep. 8, 2017, to Office Action, dated Jul. 27, 2017, in connection with Chilean Patent Application No. 633-2009 [English instructions and document as filed in Spanish], 35 pages.
Response, filed Sep. 18, 2017, to Office Action, dated Jul. 18, 2017, in connection with Vietnamese Patent Application No. 1-2010-02743 [English instructions and document as filed in Vietnamese], 4 pages.
Letter/Written Disclosure of the Supplemental Information Disclosure Statement for the above-referenced application, filed herewith Jan. 15, 2019, 3 pages.

(56) References Cited

OTHER PUBLICATIONS

Office Action, dated Dec. 5, 2018, in connection with Argentinian Patent Application No. P090100943 [English translation and original document in Spanish, D1=Melamed et al., J Allergy and Clin Immunol (2008), D2=WO 2006/091871, D3=Bookbinder et al., J Controlled Release (2006)], 14 pages.

* cited by examiner

COMBINATIONS AND METHODS FOR SUBCUTANEOUS ADMINISTRATION OF IMMUNE GLOBULIN AND HYALURONIDASE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

RELATED APPLICATIONS

*The present application is a reissue of U.S. Pat. No. 10,301,376, which issued on May 28, 2019, which was filed as U.S. application Des. No. 12/381,844 on Mar. 16, 2009.* Benefit of priority is claimed to U.S. Provisional Application Ser. No. 61/069,841, to Richard Schiff, Heinz Leibl and Gregory Frost, entitled "Combinations and Methods for Subcutaneous Administration of Immune Globulin and Hyaluronidase," filed Mar. 17, 2008. The subject matter of the above-noted application is incorporated by reference in its entirety.

This application is related to International PCT Application Serial No. PCT/US2009/001670, filed the same day herewith, entitled "Combinations and Methods for Subcutaneous Administration of Immune Globulin and Hyaluronidase," which claims priority to U.S. Provisional Application Ser. No. 61/069,841. The subject matter of the above-noted related application is incorporated by reference in its entirety.

FIELD OF THE INVENTION

Provided are combinations, compositions and kits containing an immune globulin (IG) composition and a soluble hyaluronidase composition formulated for subcutaneous administration. Such products can be used in methods of treating IG-treatable diseases or conditions. Also provided are methods for subcutaneous administration of immune globulin whereby the dosing regimen is substantially the same as for intravenous administration of the same dosage for treatment of the same IG-treatable disease or condition.

BACKGROUND

The intravenous (IV) administration of immune globulin (WIG) is the primary treatment of individuals with immune deficiencies. Although the initial IVIG preparations caused severe side effects, the IVIG preparations available at the present time are well tolerated in the majority of immune deficient patients. Nonetheless, a small proportion of patients continue to have unpleasant, even disabling, reactions such as headache, fatigue, and myalgia. Fever and chills remains a problem, especially when patients have intercurrent infections. The reactions often persist despite trying other IVIG preparations or pre-medicating with acetaminophen, diphenhydramine, and corticosteroids. Further, due to the requirement for IV administration, there are issues with patient compliance.

Subcutaneous (SQ) administration of immune globulin is an alternative to intravenous administration. Compared to IV infusions, SQ administration of immune globulin has several advantages. For example, it reduces the incidence of systemic reactions, does not require sometimes-difficult IV access, improves trough levels, and gives patients more independence. Because of the difficulty in administering large quantities of fluid in a single site, it is necessary to do SQ infusions once or twice a week, using two to as many as 5 sites at a time. Thus, unlike WIG, which is given once a month, subcutaneous administration is usually done weekly. Hence, there is a need for alternative methods for administering immune globulin.

SUMMARY

Provided herein are methods, compositions, combinations and kits for subcutaneous administration of immune globulin and for treating IG-treatable diseases or conditions. Provided are methods for treating an IG-treatable disease or condition in a subject by subcutaneously administering to the subject soluble hyaluronidase and an immune globulin (IG) for treating the disease or condition. Co-administration of IG and hyaluronidase increases the bioavailability of subcutaneously administered IG to permit administration of IG subcutaneously using a dosing regime substantially the same as intravenous IG (IVIG) administration for the particular disease or condition. The administration of the IG is effected such that the amount administered and frequency of administration is substantially the same as for IV (intravenous) administration of the same amount via IV for the same disease or condition. The amount administered via IV can be predetermined or is known for a particular disease or condition. Typically, in the presence of a soluble hyaluronidase, for subcutaneous administration, the rate of administration can be greater than for IV administration. Hence, the time for administration of a particular dose can be reduced. Rate of administration can be controlled, such as by a pump, or can rely on gravity.

Thus, among the methods provided are methods for treating an IG-treatable disease or condition in a subject in need of such treatment by subcutaneously administering to the subject a soluble hyaluronidase and an amount of immune globulin (IG) effective for treating the disease or condition. The administration is performed with a dosage regimen in which: (a) a quantity of IG; and (b) a dosing frequency for successive administrations of IG to the subject are selected such that the therapeutic effect of the subcutaneous IG administration upon the subject is at least substantially equivalent to intravenous administration of the IG to the subject using the same dosing regimen.

In some examples of the methods provided herein, bioavailability of the subcutaneously administered IG is at least about 90% of the bioavailability of the same dosage administered via IV administration. The amount of soluble hyaluronidase administered can be sufficient to effect subcutaneous administration of the IG at a dosage administered no more than once a month. In other examples, administration of IG is no more than once monthly.

The soluble hyaluronidase used in the methods and uses provided herein can be PH20 or a truncated form thereof. For example, the soluble hyaluronidase can an ovine or bovine or truncated human PH20. In instances where a truncated human PH20 is used in the methods and uses provided herein, the truncated human PH20 can be selected from among polypeptides having a sequence of amino acids set forth in any of SEQ ID NOS:4-9, or allelic variants or other variants thereof. In one example, the soluble hyaluronidase is rHuPH20.

The IG administered using the methods and uses herein can be purified from human plasma, such as by alcohol fractionation. In some examples, the IG is further purified by any one or more of a chemical modification, incubation at pH 4.0 with or without pepsin, polyethylene glycol (PEG) precipitation, ion-exchange chromatography, enzymatic cleavage, solvent detergent treatment, diafiltration or ultrafiltration. The methods and uses provided herein can employ IG that contains IgG, IgA and IgM. In some examples, the IG contains greater than 95% IgG. Further, the IgG can be monomeric. Protein-stabilizing excipients, such as one or more of glycine, maltose, a polyol, human serum albumin, mannitol, and non-ionic detergent, also can be present in the IG. In some examples, the pH of the IG preparation is at or about 4.2 to 5.4, 4.6 to 5.1 or 4.8 to 5.0, and the protein concentration is or is about 5 to 15% w/v, 6 to 15% w/v, or 8 to 12% w/v of IG composition. In one example, the protein concentration of the 1G is 10% w/v.

Provided herein are methods and uses for treating an IG-treatable disease or condition, in which soluble hyaluronidase and an immune globulin (IG) for treating the disease or condition are subcutaneously administered, and the IG is infused at a rate of 10 ml/hr to 300 ml/hr, such as at or about 10 ml/hr, 20 ml/hr, 30 ml/hr, 40 ml/hr, 50 ml/hr, 60 ml/hr, 70 ml/hr, 80 ml/hr, 90 ml/hr, 100 ml/hr, 150 ml/hr, 200 ml/hr, 250 ml/hr and 300 ml/hr. The rate can be controlled by a pump or gravity. In some examples, the IG and hyaluronidase are administered separately, simultaneously or intermittently. For example, the hyaluronidase can be administered prior to administration of IG, such as 0.5 minutes, 1 minute, 2 minutes, 3 minutes, 4 minutes, 5 minutes, 6 minutes, 7 minutes, 8 minutes, 9 minutes, 10 minutes, 20 minutes or 30 minutes prior to administration of IG. In other examples, the IG and hyaluronidase are in a single composition. In further examples, about or 5 grams (g), 10 g, 15 g, 20 g, 21 g, 22 g, 23 g, 24 g, 25 g, 26 g, 27 g, 28 g, 29 g, 30 g, 31 g, 32 g, 33 g, 34 g, 35 g, 36 g, 37 g, 38 g, 39 g or 40 g of IG is administered, and the hyaluronidase is administered at a ratio (units hyaluronidase/grams of IG) at or about 10 U/gram (g), 20 U/g, 30 U/g, 35 U/g, 40 U/g, 50 U/g, 60 U/g, 70 U/g, 80 U/g, 90 U/g, 100 U/g, 150 U/g, or 300 U/g.

Soluble hyaluronidase and IG can be administered using the methods and uses provided herein to treat, for example, immunodeficiency; acquired hypogammaglobulinemia secondary to hematological malignancies; Kawasaki's disease; chronic inflammatory demyelinating polyneuropathy (CIDP); Guillain-Barre Syndrome; Idiopathic thrombocytopenic purpura; inflammatory myopathies; Lambert-Eaton myasthenic syndrome; multifocal motor neuropathy; Myasthenia Gravis; Moersch-Wohmann syndrome; secondary hypogammaglobulinaemia (including iatrogenic immunodeficiency); specific antibody deficiency; Acute disseminated encephalomyelitis; ANCA-positive systemic necrotizing vasculitis; Autoimmune haemolytic anaemia; Bullous pemphigoid; Cicatricial pemphigoid; Evans syndrome (including autoimmune haemolytic anaemia with immune thrombocytopenia); Foeto-maternal/neonatal alloimmune thrombocytopenia (FMAIT/NAIT); Haemophagocytic syndrome; High-risk allogeneic haemopoietic stem cell transplantation; IgM paraproteinaemic neuropathy; kidney transplantation; multiple sclerosis; Opsoclonus myoclonus ataxia; Pemphigus foliaceus; Pemphigus vulgaris; Post-transfusion purpura; Toxic epidermal necrolysis/Steven Johnson syndrome (TEN/SJS); Toxic shock syndrome; Alzheimer's Disease; Systemic lupus erythrematosus; multiple myeloma; sepsis; B cell tumors; trauma; and a bacterial, viral or fugal infection. In instances where the IG and hyaluronidase are administered to treat an immunodeficiency, the immunodeficiency can be selected from among common variable immunodeficiency (CVID), congenital agammaglobulinemia, Wiskott-Aldrich syndrome, severe combined immunodeficiency (SCID), primary hypogammaglobulinemia, primary immunodeficiency diseases with antibody deficiency, X-linked agammaglobulinemia (XLA), hypogammaglobulinemia of infancy, and paraneoplastic cerebellar degeneration with no antibodies.

In instances where the IG-treatable disease or condition is acquired hypogammaglobulinemia secondary to hematological malignancies, and the hematological malignancy can be chronic lymphocytic leukemia (CLL), multiple myeloma (MM) or non-Hodgkin's lymphoma (NHL). In instances where the IG-treatable disease or condition is an inflammatory myopathy, the inflammatory myopathy can be polymyositis, dermatomyositis or inclusion body myositis.

In some examples, soluble hyaluronidase and IG is administered subcutaneously to treat a bacteria, viral or fungal condition, such as, for example, Haemophilus influenzae type B, Psuedomonas aeruginosa types A and B, Staphylococcus aureus, Group B Streptococcus, Streptococcus pneumoniae types 1, 3, 4, 6, 7, 8, 9, 12, 14, 18, 19, and 23, Adenovirus types 2 and 5, Cytomegalovirus, Epstein Barr virus VCA, Hepatitis A virus, Hepatitis B virus, Herpes simplex virus-1, Herpes simplex virus-2, Influenza A, Measles, Parainfluenza types 1, 2 and 3, Polio, Varicella zoster virus, Apergillus and Candida albicans.

Provided herein are combinations of compositions, containing a first composition containing IG formulated for subcutaneous single dosage administration no more than once per month, and a second composition containing a soluble hyaluronidase formulated for single dosage administration no more than once per month. The compositions can be in a dual chamber container or in single container separated from each other. In some examples, the hyaluronidase is positioned in the container to be administered before the IG. The container can be a syringe, tube or bottle, and can further contain a needle for injection.

The combinations of compositions provided herein can contain PH20, or a truncated form thereof. For example, ovine, bovine or truncated human PH20, such as a polypeptide having a sequence of amino acids set forth in any of SEQ ID NOS:4-9, or allelic variants or other variants thereof, can be included in the combinations of compositions provided herein. In some examples, the soluble hyaluronidase in the combination is rHuPH20. Further, the IG in the combinations of compositions can be purified from human plasma, and can be lyophilized or a liquid.

In some examples, the volume of liquid in the combinations of compositions provided herein is or is about 100 ml, 150 ml, 200 ml, 300 ml, 400 ml, 500 ml, 600 ml or 700 ml. The IG in the combinations of compositions can have a protein concentration that is or is about 5 to 15% w/v, 6 to 15% w/v, or 8 to 12% w/v of IG composition, such as, for example, 10% w/v. In some examples, the IG in the composition is or is about 5 grams (g), 10 g, 15 g, 20 g, 21 g, 22 g, 23 g, 24 g, 25 g, 26 g 27 g, 28 g, 29 g, 30 g, 31 g, 32 g, 33 g, 34 g, 35 g, 36 g, 37 g, 38 g, 39 g or 40 g. The hyaluronidase can be a liquid. In some examples, the volume of the hyaluronidase liquid is or is about 1 ml, 2 ml, 3 ml, 4 ml, 5 ml, 6 ml, 7 ml, 8 ml, 9 ml, 10 ml, 20 ml or 30 ml, and the hyaluronidase is at or about 10 Units to 500,000 Units, 100 Units to 100,000 Units, 500 Units to 50,000 Units, 1000 Units to 10,000 Units, 5000 Units to 7500 Units, 5000 Units to 50,000 Units, or 1,000 Units to 10,000 Units. Provided herein are compositions containing immune globulin (IG) and a soluble hyaluronidase formulated for single dosage administration once a month. The soluble hyaluronidase contained in the composition can be PH20, or a truncated form thereof. For example, ovine, bovine or tamcated human PH20, such as a polypeptide having a sequence of amino acids set forth in any of SEQ ID NOS:4-9, or allelic variants or other variants thereof, can be included in the compositions formulated for single dosage administration provided herein. In some examples, the soluble hyaluronidase in the composition is rHuPH20. The IG in the compositions can be purified from human plasma, and can be a liquid.

In exemplary embodiments, the IG in the compositions formulated for single dosage administration provided herein has a protein concentration that is or is about 5 to 15% w/v, 6 to 15% w/v, or 8 to 12% w/v of IG composition, such as, for example, 10% w/v. The IG in the composition is or is about 5 grams (g), 10 g, 15 g, 20 g, 21 g, 22 g, 23 g, 24 g, 25 g, 26 g, 27 g, 28 g, 29 g, 30 g, 31 g, 32 g, 33 g, 34 g, 35 g, 36 g, 37 g, 38 g, 39 g or 40 g, and the hyaluronidase is at or about 10 Units to 500,000 Units, 100 Units to 100,000 Units, 500 Units to 50,000 Units, 1000 Units to 10,000 Units, 5000 Units to 7500 Units, 5000 Units to 50,000 Units, or 1,000 Units to 10,000 Units. The volume of liquid in the composition can be at or about 100 ml, 150 ml, 200 ml, 300 ml, 400 ml, 500 ml, 600 ml or 700 ml.

Provided herein are kits containing combinations of compositions, containing a first composition containing IG formulated for subcutaneous single dosage administration no more than once per month, and a second composition containing a soluble hyaluronidase formulated for single dosage administration no more than once per month. Also provided herein are compositions containing illumine globulin (IG) and a soluble hyaluronidase formulated for single dosage administration once a month. Optionally, instructions can be included in the kits.

DETAILED DESCRIPTION

Outline

A. Definitions
B. Subcutaneous Administration of Immune Globulin (IG)
C. Immune Globulin
D. Hyaluronidase
Soluble Hyaluronidase
Soluble Human PH20
Soluble Recombinant Human PH20 (rHuPH20)
E. Methods of Producing Nucleic Acids encoding a soluble Hyaluronidase and Polypeptides Thereof
1. Vectors and Cells
2. Expression
a. Prokaryotic Cells
b. Yeast Cells
c. Insect Cells
d. Mammalian Cells
e. Plants
3. Purification Techniques
F. Preparation, Formulation and Administration of Immune Globulins and Soluble Hyaluronidase Polypeptides
1. Formulations
Lyophilized powders
2. Dosage and Administration
G. Methods of Assessing Activity, Bioavailability and Pharmacokinetics
1. Pharmacokinetics and tolerability
2. Biological Activity
a. Immune globulin
b. Hyaluronidase
H. Therapeutic Uses
1. Primary immune deficiency with antibody deficiency
2. Acquired hypogammaglobulinemia secondary to hematological malignancies
3. Kawasaki's disease
4. Chronic inflammatory demyelinating polyneuropathy
5. Guillain-Barre Syndrome
6. Idiopathic thrombocytopenic purpura
7. Inflammatory myopathies: polymyositis, dermatomyositis and inclusion body myositis
8. Lambert-Eaton myasthenic syndrome
9. Multifocal motor neuropathy
10. Myasthenia Gravis
11. Moersch-Woltmann syndrome
12. Alzheimer's Disease
13. Other diseases and conditions
I. Articles of manufacture and kits
J. Examples

A. Definitions

Unless defined otherwise, all technical and scientific terms used herein have the same meaning as is commonly understood by one of skill in the art to which the invention(s) belong. All patents, patent applications, published applications and publications, Genbank sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

As used herein, "immunoglobulin," "immune globulin," "gamma globulin" refer to preparations of plasma proteins derived from the pooled plasma of adult donors. IgG antibodies predominate; other antibody subclasses, such as IgA and IgM are present. Therapeutic immune globulin can provide passive immunization by increasing a recipient's serum levels of circulating antibodies. IgG antibodies can, for example, bind to and neutralize bacterial toxins; opsonize pathogens; activate complement; and suppress pathogenic cytokines and phagocytes through interaction with cytokines and receptors thereof, such as CD5, interleukin-1a (IL-1a), interleukin 6 (IL-6), tumor necrosis factor-alpha (TNF-alpha), and T-cell receptors. Therapeutic immune globulin can inhibit the activity of autoantibodies. Immune globulin preparations also include, but are not limited to, immune globulin intravenous (IGIV), immune globulin IV, therapeutic immunoglobulin. Immune globulin preparation are well known, and include brand names, such as BayGam®, Gamimune® N, Gammagard® S/D, Gammar®-P, Iveegam® EN, Panglobulin®, Polygam® S/D, Sandoglobulin®, Venoglobulin®-I, Venoglobulin®-S, WinRho® SDF and others. Immune globulin preparations can be derived from human plasma, or are recombinantly produced.

As used herein, IG-treatable diseases or conditions refer to any disease or condition for which immune globulin preparations are used. Such diseases and conditions, include, but are not limited to, any disease in which an increase in circulating antibodies is ameliorative, such as, for example, immunodeficiency; acquired hypogammaglobulinemia secondary to hematological malignancies; Kawasaki's disease;

chronic inflammatory demyelinating polyneuropathy (CIDP); Guillain-Barre Syndrome; Idiopathic thrombocytopenic purpura; inflammatory myopathies; Lambert-Eaton myasthenic syndrome; multifocal motor neuropathy; Myasthenia Gravis; Moersch-Woltmann syndrome; secondary hypogammaglobulinaemia (including iatrogenic iinmunodeficiency); specific antibody deficiency; Acute disseminated encephalomyelitis; ANCA-positive systemic necrotizing vasculitis; Autoimmune haemolytic anaemia; Bullous pemphigoid; Cicatricial pemphigoid; Evans syndrome (including autoimmune haemolytic anaemia with immune thrombocytopenia); Foeto-maternal/neonatal alloimmune thrombocytopenia (FMAIT/NAIT); Haemophagocytic syndrome; High-risk allogeneic haemopoietic stem cell transplantation; IgM paraproteinaemic neuropathy; kidney transplantation; multiple sclerosis; Opsoclonus myoclonus ataxia; Pemphigus foliaceus; Pemphigus vulgaris; Post-transfusion purpura; Toxic epidermal necrolysis/Steven Johnson syndrome (TEN/SJS); Toxic shock syndrome; Alzheimer's Disease; Systemic lupus erythematosus; multiple myeloma; sepsis; B cell tumors; trauma; and a bacterial viral or fugal infection.

As used herein, dosing regime refers to the amount of immune globulin administered and the frequency of administration. The dosing regime is a function of the disease or condition to be treated, and thus can vary.

As used herein, "substantially the same as an intravenous IG (IVIG) dosing regime" refers to a regimen in which the dose and/or frequency is within an amount that is effective for treating a particular disease or condition, typically is about or 10%, of the IV dose or frequency. Amounts of IVIG that are effective for treating a particular disease or condition are known or can be empirically determined by one of skill in the art. For example, as exemplified below, 300 mg/kg (i.e. 21 grams assuming the average adult weighs 70 kg) to 600 mg/kg (i.e. 42 grams) is the typical monthly dose of IVIG administered to patients having primary immunodeficiency diseases. Hence, IG, when administered in combination with hyaluronidase, is administered subcutaneously at doses that are or are about 300 mg/kg to 600 mg/kg for treatment of primary immunodeficiency diseases.

As used herein, frequency of administration refers to the time between successive doses of immune globulin. For example, frequency can be one, two, three, four weeks, and is a function of the particular disease or condition treated. Generally, frequency is a least every two or three weeks, and typically no more than once a month.

As used herein, hyaluronidase refers to an enzyme that degrades hyaluronic acid. Hyaluronidases include bacterial hyaluronidases (EC 4.2.99.1), hyaluronidases from leeches, other parasites, and crustaceans (EC 3.2.1.36), and mammalian-type hyaluronidases (EC 3.2.1.35). Hyaluronidases also include any of non-human origin including, but not limited to, murine, canine, feline, leporine, avian, bovine, ovine, porcine, equine, piscine, ranine, bacterial, and any from leeches, other parasites, and crustaceans. Exemplary non-human hyaluronidases include, hyaluronidases from cows (SEQ ID NO:10 and 11), yellow jacket wasp (SEQ ID NOS:12 and 13), honey bee (SEQ ID NO:14), white-face hornet (SEQ ID NO:15), paper wasp (SEQ ID NO:16), mouse (SEQ ID NOS:17-19, 32), pig (SEQ ID NOS:20-21), rat (SEQ ID NOS:22-24, 31), rabbit (SEQ ID NO:25), sheep (SEQ ID NO:26 and 27), orangutan (SEQ ID NO:28), cynomolgus monkey (SEQ ID NO:29), guinea pig (SEQ ID NO: 30), Staphylococcus aureus (SEQ ID NO:33), Streptococcus pyogenes (SEQ ID NO:34), and Clostridium perfringens (SEQ ID NO:35). Hyaluronidases also include those of human origin. Exemplary human hyaluronidases include HYAL1 (SEQ ID NO:36), HYAL2 (SEQ ID NO:37), HYAL3 (SEQ ID NO:38), HYAL4 (SEQ ID NO:39), and PH20 (SEQ ID NO:1). Also included amongst hyaluronidases are soluble hyaluronidases, including, ovine and bovine PH20, soluble human PH20 and soluble rHuPH20.

Reference to hyaluronidases includes precursor hyaluronidase polypeptides and mature hyaluronidase polypeptides (such as those in which a signal sequence has been removed), truncated forms thereof that have activity, and includes allelic variants and species variants, variants encoded by splice variants, and other variants, including polypeptides that have at least 40%, 45%, 50%, 55%, 60%, 65%, 70%, 75%, 80%, 85%, 90%, 95%, 96%, 97%, 98%, 99% or more sequence identity to the precursor polypeptides set forth in SEQ ID NOS: 1 and 10-39, or the mature form thereof. For example, reference to hyaluronidase also includes the human PH20 precursor polypeptide variants set forth in SEQ ID NOS:50-51. Hyaluronidases also include those that contain chemical or posttranslational modifications and those that do not contain chemical or posttranslational modifications. Such modifications include, but are not limited to, pegylation, albumination, glycosylation, farnesylation, carboxylation, hydroxylation, phosphorylation, and other polypeptide modifications known in the art.

As used herein, a soluble hyaluronidase refers to a polypeptide characterized by its solubility under physiologic conditions. Soluble hyaluronidases can be distinguished, for example, by its partitioning into the aqueous phase of a Triton X-114 solution warmed to 37° C. (Bordier et al., (1981) J. Biol. Chem., 256:1604-7). Membrane-anchored, such as lipid anchored hyaluronidases, will partition into the detergent rich phase, but will partition into the detergent-poor or aqueous phase following treatment with Phospholipase-C. Included among soluble hyaluronidases are membrane anchored hyaluronidases in which one or more regions associated with anchoring of the hyaluronidase to the membrane has been removed or modified, where the soluble form retains hyaluronidase activity. Soluble hyaluronidases include recombinant soluble hyaluronidases and those contained in or purified from natural sources, such as, for example, testes extracts from sheep or cows. Exemplary of such soluble hyaluronidases are soluble human PH20. Other soluble hyaluronidases include ovine (SEQ ID NO:27) and bovine (SEQ ID NO:11) PH20.

As used herein, soluble human PH20 or sHuPH20 include mature polypeptides lacking all or a portion of the glycosylphospatidylinositol (GPI) attachment site at the C-tenninus such that upon expression, the polypeptides are soluble. Exemplary sHuPH20 polypeptides include mature polypeptides having an amino acid sequence set forth in any one of SEQ ID NOS:4-9 and 47-48. The precursor polypeptides for such exemplary sHuPH20 polypeptides include a signal sequence. Exemplary of the precursors are those set forth in SEQ ID NOS:3 and 40-46, each of which contains a 35 amino acid signal sequence at amino acid positions 1-35. Soluble HuPH20 polypeptides also include those degraded during or after the production and purification methods described herein.

As used herein, soluble recombinant human PH20 (rHuPH20) refers to a soluble fonn of human PH20 that is recombinantly expressed in Chinese Hamster Ovary (CHO) cells. Soluble rHuPH20 is encoded by nucleic acid that includes the signal sequence and is set forth in SEQ ID NO:49. Also included are DNA molecules that are allelic variants thereof and other soluble variants. The nucleic acid encoding soluble rHuPH20 is expressed in CHO cells which secrete the mature polypeptide. As produced in the culture medium there is heterogeneity at the C-terminus so that the product includes a mixture of species that can include any one or more of SEQ ID NOS: 4-9 in various abundance. Corresponding allelic variants and other variants also are included, including those corresponding to the precursor human PH20 polypeptides set forth in SEQ ID NOS:50-51. Other variants can have 60%, 70%, 80%, 85%, 90%, 91%, 92%, 93%, 94%, 95%, 96%, 97%, 98%, 99% or more sequence identity with any of SEQ ID NOS:4-9 and 47-48 as long they retain a hyaluronidase activity and are soluble.

As used herein, activity refers to a functional activity or activities of a polypeptide or portion thereof associated with a full-length (complete) protein. Functional activities include, but are not limited to, biological activity, catalytic or enzymatic activity, antigenicity (ability to bind or compete with a polypeptide for binding to an anti-polypeptide antibody), immunogenicity, ability to form multimers, and the ability to specifically bind to a receptor or ligand for the polypeptide.

As used herein, hyaluronidase activity refers to the ability of hyaluronidase to cleave hyaluronic acid. In vitro assays to determine the hyaluronidase activity of hyaluronidases, such as soluble rHuPH20, are known in the art and described herein. Exemplary assays include the microturbidity assay described below (see e.g. Example 3) that measures cleavage of hyaluronic acid by hyaluronidase indirectly by detecting the insoluble precipitate formed when the uncleaved is hyaluronic acid binds with serum albumin.

As used herein, the residues of naturally occurring α-amino acids are the residues of those 20 α-amino acids found in nature which are incorporated into protein by the specific recognition of the charged tRNA molecule with its cognate mRNA codon in humans.

As used herein, nucleic acids include DNA, RNA and analogs thereof, including peptide nucleic acids (PNA) and mixtures thereof. Nucleic acids can be single or double-stranded. When referring to probes or primers, which are optionally labeled, such as with a detectable label, such as a fluorescent or radiolabel, single-stranded molecules are contemplated. Such molecules are typically of a length such that their target is statistically unique or of low copy number (typically less than 5, generally less than 3) for probing or priming a library. Generally a probe or primer contains at least 14, 16 or 30 contiguous nucleotides of sequence complementary to or identical to a gene of interest. Probes and primers can be 10, 20, 30, 50, 100 or more nucleic acids long.

As used herein, a peptide refers to a polypeptide that is from 2 to 40 amino acids in length.

As used herein, the amino acids which occur in the various sequences of amino acids provided herein are identified according to their known, three-letter or one-letter abbreviations (Table 1). The nucleotides which occur in the various nucleic acid fragments are designated with the standard single-letter designations used routinely in the art.

As used herein, an "amino acid" is an organic compound containing an amino group and a carboxylic acid group. A polypeptide contains two or more amino acids. For purposes herein, amino acids include the twenty naturally-occurring amino acids, non-natural amino acids and amino acid analogs (i.e., amino acids wherein the α-carbon has a side chain).

As used herein, "amino acid residue" refers to an amino acid formed upon chemical digestion (hydrolysis) of a polypeptide at its peptide linkages. The amino acid residues described herein are presumed to be in the "L" isomeric form. Residues in the "D" isomeric form, which are so designated, can be substituted for any L-amino acid residue as long as the desired functional property is retained by the polypeptide. $NH_2$ refers to the free amino group present at the amino terminus of a polypeptide. COOH refers to the free carboxy group present at the carboxyl terminus of a polypeptide. In keeping with standard polypeptide nomenclature described in J. Biol. Chem., 243: 3557-3559 (1968), and adopted 37 C.F.R. §§ 1.821-1.822, abbreviations for amino acid residues are shown in Table 1:

TABLE 1

Table of Correspondence

| SYMBOL | | |
|---|---|---|
| 1-Letter | 3-Letter | AMINO ACID |
| Y | Tyr | Tyrosine |
| G | Gly | Glycine |
| F | Phe | Phenylalanine |
| M | Met | Methionine |
| A | Ala | Alanine |
| S | Ser | Serine |
| I | Ile | Isoleucine |
| L | Leu | Leucine |
| T | Thr | Threonine |
| V | Val | Valine |
| P | Pro | proline |
| K | Lys | Lysine |
| H | His | Histidine |
| Q | Gln | Glutamine |
| E | Glu | glutamic acid |
| Z | Glx | Glu and/or Gln |
| W | Trp | Tryptophan |
| R | Arg | Arginine |
| D | Asp | aspartic acid |
| N | Asn | asparagine |
| B | Asx | Asn and/or Asp |
| C | Cys | Cysteine |
| X | Xaa | Unknown or other |

It should be noted that all amino acid residue sequences represented herein by formulae have a left to right orientation in the conventional direction of amino-terminus to carboxyl-terminus. In addition, the phrase "amino acid residue" is broadly defined to include the amino acids listed in the Table of Correspondence (Table 1) and modified and unusual amino acids, such as those referred to in 37 C.F.R. §§ 1.821-1.822, and incorporated herein by reference. Furthermore, it should be noted that a dash at the beginning or end of an amino acid residue sequence indicates a peptide bond to a further sequence of one or more amino acid residues, to an amino-terminal group such as $NH_2$ or to a carboxyl-terminal group such as COOH.

As used herein, "naturally occurring amino acids" refer to the 20 L-amino acids that occur in polypeptides.

As used herein, "non-natural amino acid" refers to an organic compound that has a structure similar to a natural amino acid but has been modified structurally to mimic the structure and reactivity of a natural amino acid. Non-naturally occurring amino acids thus include, for example, amino acids or analogs of amino acids other than the 20 naturally-occurring amino acids and include, but are not limited to, the D-isostereomers of amino acids. Exemplary non-natural amino acids are described herein and are known to those of skill in the art.

As used herein, a DNA construct is a single or double stranded, linear or circular DNA molecule that contains segments of DNA combined and juxtaposed in a manner not found in nature. DNA constructs exist as a result of human manipulation, and include clones and other copies of manipulated molecules.

As used herein, a DNA segment is a portion of a larger DNA molecule having specified attributes. For example, a DNA segment encoding a specified polypeptide is a portion of a longer DNA molecule, such as a plasmid or plasmid fragment, which, when read from the 5' to 3' direction, encodes the sequence of amino acids of the specified polypeptide.

As used herein, the term polynucleotide means a single- or double-stranded polymer of deoxyribonucleotides or ribonucleotide bases read from the 5' to the 3' end. Polynucleotides include RNA and DNA, and can be isolated from natural sources, synthesized in vitro, or prepared from a combination of natural and synthetic molecules. The length of a polynucleotide molecule is given herein in terms of nucleotides (abbreviated "nt") or base pairs (abbreviated "bp"). The term nucleotides is used for single- and double-stranded molecules where the context permits. When the term is applied to double-stranded molecules it is used to denote overall length and will be understood to be equivalent to the term base pairs. It will be recognized by those skilled in the art that the two strands of a double-stranded polynucleotide can differ slightly in length and that the ends thereof can be staggered; thus all nucleotides within a double-stranded polynucleotide molecule can not be paired. Such unpaired ends will, in general, not exceed 20 nucleotides in length.

As used herein, "similarity" between two proteins or nucleic acids refers to the relatedness between the sequence of amino acids of the proteins or the nucleotide sequences of the nucleic acids. Similarity can be based on the degree of identity and/or homology of sequences of residues and the residues contained therein. Methods for assessing the degree of similarity between proteins or nucleic acids are known to those of skill in the art. For example, in one method of assessing sequence similarity, two amino acid or nucleotide sequences are aligned in a manner that yields a maximal level of identity between the sequences. "Identity" refers to the extent to which the amino acid or nucleotide sequences are invariant. Alignment of amino acid sequences, and to some extent nucleotide sequences, also can take into account conservative differences and/or frequent substitutions in amino acids (or nucleotides). Conservative differences are those that preserve the physico-chemical properties of the residues involved. Alignments can be global (alignment of the compared sequences over the entire length of the sequences and including all residues) or local (the alignment of a portion of the sequences that includes only the most similar region or regions).

"Identity" per se has an art-recognized meaning and can be calculated using published techniques. (See, e.g.: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). While there exists a number of methods to measure identity between two polynucleotide or polypeptides, the term "identity" is well known to skilled artisans (Carillo, H. & Lipton, D., SIAM J Applied Math 48:1073 (1988)).

As used herein, homologous (with respect to nucleic acid and/or amino acid sequences) means about greater than or equal to 25% sequence homology, typically greater than or equal to 25%, 40%, 50%, 60%, 70%, 80%, 85%, 90% or 95% sequence homology; the precise percentage can be specified if necessary. For purposes herein the terms "homology" and "identity" are often used interchangeably, unless otherwise indicated. In general, for determination of the percentage homology or identity, sequences are aligned so that the highest order match is obtained (see, e.g.: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; Carillo et al. (1988) SIAM J Applied Math 48:1073). By sequence homology, the number of conserved amino acids is determined by standard alignment algorithms programs, and can be used with default gap penalties established by each supplier. Substantially homologous nucleic acid molecules would hybridize typically at moderate stringency or at high stringency all along the length of the nucleic acid of interest. Also contemplated are nucleic acid molecules that contain degenerate codons in place of codons in the hybridizing nucleic acid molecule.

Whether any two molecules have nucleotide sequences or amino acid sequences that are at least 60%, 70%, 80%, 85%, 90%, 95%, 96%, 97%, 98% or 99% "identical" or "homologous" can be determined using known computer algorithms such as the "FASTA" program, using for example, the default parameters as in Pearson et al. (1988) Proc. Natl. Acad. Sci. USA 85:2444 (other programs include the GCG program package (Devereux, J., et al., Nucleic Acids Research 12(I):387 (1984)), BLASTP, BLASTN, FASTA (Atschul, S. F., et al., J Molec Biol 215:403 (1990)); Guide to Huge Computers, Martin J. Bishop, ed., Academic Press, San Diego, 1994, and Carillo et al. (1988) SIAM J Applied Math 48:1073). For example, the BLAST function of the National Center for Biotechnology Information database can be used to determine identity. Other commercially or publicly available programs include, DNAStar "MegAlign" program (Madison, Wis.) and the University of Wisconsin Genetics Computer Group (UWG) "Gap" program (Madison Wis.). Percent homology or identity of proteins and/or nucleic acid molecules can be determined, for example, by comparing sequence information using a GAP computer program (e.g., Needleman et al. (1970) J. Mol. Biol. 48:443, as revised by Smith and Waterman ((1981) Adv. Appl. Math. 2:482). Briefly, the GAP program defines similarity as the number of aligned symbols (i.e., nucleotides or amino acids), which are similar, divided by the total number of symbols in the shorter of the two sequences. Default parameters for the GAP program can include: (1) a unary comparison matrix (containing a value of 1 for identities and 0 for non-identities) and the weighted corn-parison matrix of Gribskov et al. (1986) Nucl. Acids Res. 14:6745, as described by Schwartz and Dayhoff, eds., ATLAS OF PROTEIN SEQUENCE AND STRUCTURE, National Biomedical Research Foundation, pp. 353-358 (1979); (2) a penalty of 3.0 for each gap and an additional 0.10 penalty for each symbol in each gap; and (3) no penalty for end gaps. Therefore, as used herein, the term "identity" or "homology" represents a comparison between a test and a reference polypeptide or polynucleotide. As used herein, the term at least "90% identical to" refers to percent identities from 90 to 99.99 relative to the reference nucleic acid or amino acid sequence of the polypeptide. Identity at a level of 90% or more is indicative of the fact that, assuming for exemplification purposes a test and reference polypeptide length of 100 amino acids are compared. No more than 10% (i.e., 10 out of 100) of the amino acids in the test polypeptide differs from that of the reference polypeptide. Similar comparisons can be made between test and reference polynucleotides. Such differences can be represented as point mutations randomly distributed over the entire length of a polypeptide or they can be clustered in one or more locations of varying length up to the maximum allowable, e.g. 10/100 amino acid difference (approximately 90% identity). Differences are defined as nucleic acid or amino acid substitutions, insertions or deletions. At the level of homologies or identities above about 85-90%, the result should be independent of the program and gap parameters set; such high levels of identity can be assessed readily, often by manual alignment without relying on software.

As used herein, an aligned sequence refers to the use of homology (similarity and/or identity) to align corresponding positions in a sequence of nucleotides or amino acids. Typically, two or more sequences that are related by 50% or more identity are aligned. An aligned set of sequences refers to 2 or more sequences that are aligned at corresponding positions and can include aligning sequences derived from RNAs, such as ESTs and other cDNAs, aligned with genomic DNA sequence.

As used herein, "primer" refers to a nucleic acid molecule that can act as a point of initiation of template-directed DNA synthesis under appropriate conditions (e.g., in the presence of four different nucleoside triphosphates and a polymerization agent, such as DNA polymerase, RNA polymerase or reverse transcriptase) in an appropriate buffer and at a suitable temperature. It will be appreciated that a certain nucleic acid molecules can serve as a "probe" and as a "primer." A primer, however, has a 3' hydroxyl group for extension. A primer can be used in a variety of methods, including, for example, polymerase chain reaction (PCR), reverse-transcriptase (RT)-PCR, RNA PCR, LCR, multiplex PCR, panhandle PCR, capture PCR, expression PCR, 3' and 5' RACE, in situ PCR, ligation-mediated PCR and other amplification protocols.

As used herein, "primer pair" refers to a set of primers that includes a 5' (upstream) primer that hybridizes with the 5' end of a sequence to be amplified (e.g. by PCR) and a 3' (downstream) primer that hybridizes with the complement of the 3' end of the sequence to be amplified.

As used herein, "specifically hybridizes" refers to annealing, by complementary base-pairing, of a nucleic acid molecule (e.g. an oligonucleotide) to a target nucleic acid molecule. Those of skill in the art are familiar with in vitro and in vivo parameters that affect specific hybridization, such as length and composition of the particular molecule. Parameters particularly relevant to in vitro hybridization further include annealing and washing temperature, buffer composition and salt concentration. Exemplary washing conditions for removing non-specifically bound nucleic acid molecules at high stringency are 0.1×SSPE, 0.1% SDS, 65° C., and at medium stringency are 0.2×SSPE, 0.1% SDS, 50° C. Equivalent stringency conditions are known in the art. The skilled person can readily adjust these parameters to achieve specific hybridization of a nucleic acid molecule to a target nucleic acid molecule appropriate for a particular application. Complementary, when referring to two nucleotide sequences, means that the two sequences of nucleotides are capable of hybridizing, typically with less than 25%, 15% or 5% mismatches between opposed nucleotides. If necessary, the percentage of complementarity will be specified. Typically the two molecules are selected such that they will hybridize under conditions of high stringency.

As used herein, substantially identical to a product means sufficiently similar so that the property of interest is sufficiently unchanged so that the substantially identical product can be used in place of the product.

As used herein, it also is understood that the terms "substantially identical" or "similar" varies with the context as understood by those skilled in the relevant art. As used herein, an allelic variant or allelic variation references any of two or more alternative forms of a gene occupying the same chromosomal locus. Allelic variation arises naturally through mutation, and can result in phenotypic polymorphism within populations. Gene mutations can be silent (no change in the encoded polypeptide) or can encode polypeptides having altered amino acid sequence. The term "allelic variant" also is used herein to denote a protein encoded by an allelic variant of a gene. Typically the reference form of the gene encodes a wildtype form and/or predominant form of a polypeptide from a population or single reference member of a species. Typically, allelic variants, which include variants between and among species typically have at least 80%, 90% or greater amino acid identity with a wildtype and/or predominant form from the same species; the degree of identity depends upon the gene and whether comparison is interspecies or intraspecies. Generally, intraspecies allelic variants have at least about 80%, 85%, 90% or 95% identity or greater with a wildtype and/or predominant form, including 96%, 97%, 98%, 99% or greater identity with a wildtype and/or predominant form of a polypeptide. Reference to an allelic variant herein generally refers to variations n proteins among members of the same species.

As used herein, "allele," which is used interchangeably herein with "allelic variant" refers to alternative forms of a gene or portions thereof. Alleles occupy the same locus or position on homologous chromosomes. When a subject has two identical alleles of a gene, the subject is said to be homozygous for that gene or allele. When a subject has two different alleles of a gene, the subject is said to be heterozygous for the gene. Alleles of a specific gene can differ from each other in a single nucleotide or several nucleotides, and can include substitutions, deletions and insertions of nucleotides. An allele of a gene also can be a form of a gene containing a mutation.

As used herein, species variants refer to variants in polypeptides among different species, including different mammalian species, such as mouse and human.

As used herein, a splice variant refers to a variant produced by differential processing of a primary transcript of genomic DNA that results in more than one type of mRNA.

As used herein, modification is in reference to modification of a sequence of amino acids of a polypeptide or a sequence of nucleotides in a nucleic acid molecule and includes deletions, insertions, and replacements of amino acids and nucleotides, respectively. Methods of modifying a polypeptide are routine to those of skill in the art, such as by using recombinant DNA methodologies.

As used herein, the term promoter means a portion of a gene containing DNA sequences that provide for the binding of RNA polymerase and initiation of transcription. Promoter sequences are commonly, but not always, found in the 5' non-coding region of genes.

As used herein, isolated or purified polypeptide or protein or biologically-active portion thereof is substantially free of cellular material or other contaminating proteins from the cell or tissue from which the protein is derived, or substantially free from chemical precursors or other chemicals when chemically synthesized. Preparations can be determined to be substantially free if they appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound, however, can be a mixture of stereoisomers. In such instances, further purification might increase the specific activity of the compound.

The term substantially free of cellular material includes preparations of proteins in which the protein is separated from cellular components of the cells from which it is isolated or recombinantly-produced. In one embodiment, the term substantially free of cellular material includes preparations of enzyme proteins having less that about 30% (by dry weight) of non-enzyme proteins (also referred to herein as a contaminating protein), generally less than about 20% of non-enzyme proteins or 10% of non-enzyme proteins or less that about 5% of non-enzyme proteins. When the enzyme protein is recombinantly produced, it also is substantially free of culture medium, i.e., culture medium represents less than about or at 20%, 10% or 5% of the volume of the enzyme protein preparation.

As used herein, the term substantially free of chemical precursors or other chemicals includes preparations of enzyme proteins in which the protein is separated from chemical precursors or other chemicals that are involved in the synthesis of the protein. The term includes preparations of enzyme proteins having less than about 30% (by dry weight) 20%, 10%, 5% or less of chemical precursors or non-enzyme chemicals or components.

As used herein, synthetic, with reference to, for example, a synthetic nucleic acid molecule or a synthetic gene or a synthetic peptide refers to a nucleic acid molecule or polypeptide molecule that is produced by recombinant methods and/or by chemical synthesis methods.

As used herein, production by recombinant means by using recombinant DNA methods means the use of the well known methods of molecular biology for expressing proteins encoded by cloned DNA.

As used herein, vector (or plasmid) refers to discrete elements that are used to introduce a heterologous nucleic acid into cells for either expression or replication thereof. The vectors typically remain episomal, but can be designed to effect integration of a gene or portion thereof into a chromosome of the genome. Also contemplated are vectors that are artificial chromosomes, such as yeast artificial chromosomes and mammalian artificial chromosomes. Selection and use of such vehicles are well known to those of skill in the art.

As used herein, an expression vector includes vectors capable of expressing DNA that is operatively linked with regulatory sequences, such as promoter regions, that are capable of effecting expression of such DNA fragments. Such additional segments can include promoter and terminator sequences, and optionally can include one or more origins of replication, one or more selectable markers, an enhancer, a polyadenylation signal, and the like. Expression vectors are generally derived from plasmid or viral DNA, or can contain elements of both. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein, vector also includes "virus vectors" or "viral vectors." Viral vectors are engineered viruses that are operatively linked to exogenous genes to transfer (as vehicles or shuttles) the exogenous genes into cells.

As used herein, operably or operatively linked when referring to DNA segments means that the segments are arranged so that they function in concert for their intended purposes, e.g., transcription initiates in the promoter and proceeds through the coding segment to the terminator.

As used herein the term assessing is intended to include quantitative and qualitative determination in the sense of obtaining an absolute value for the activity of a protease, or a domain thereof, present in the sample, and also of obtaining an index, ratio, percentage, visual or other value indicative of the level of the activity. Assessment can be direct or indirect and the chemical species actually detected need not of course be the proteolysis product itself but can for example be a derivative thereof or some further substance. For example, detection of a cleavage product of a complement protein, such as by SDS-PAGE and protein staining with Coomasie blue.

As used herein, biological activity refers to the in vivo activities of a compound or physiological responses that result upon in vivo administration of a compound, composition or other mixture. Biological activity, thus, encompasses therapeutic effects and pharmaceutical activity of such compounds, compositions and mixtures. Biological activities can be observed in in vitro systems designed to test or use such activities. Thus, for purposes herein a biological activity of a protease is its catalytic activity in which a polypeptide is hydrolyzed.

As used herein equivalent, when referring to two sequences of nucleic acids, means that the two sequences in question encode the same sequence of amino acids or equivalent proteins. When equivalent is used in referring to two proteins or peptides, it means that the two proteins or peptides have substantially the same amino acid sequence with only amino acid substitutions that do not substantially alter the activity or function of the protein or peptide. When equivalent refers to a property, the property does not need to be present to the same extent (e.g., two peptides can exhibit different rates of the same type of enzymatic activity), but the activities are usually substantially the same.

As used herein, "modulate" and "modulation" or "alter" refer to a change of an activity of a molecule, such as a protein. Exemplary activities include, but are not limited to, biological activities, such as signal transduction. Modulation can include an increase in the activity (i.e., up-regulation or agonist activity) a decrease in activity (i.e., down-regulation or inhibition) or any other alteration in an activity (such as a change in periodicity, frequency, duration, kinetics or other parameter). Modulation can be context dependent and typically modulation is compared to a designated state, for example, the wildtype protein, the protein in a constitutive state, or the protein as expressed in a designated cell type or condition.

As used herein, a composition refers to any mixture. It can be a solution, suspension, liquid, powder, paste, aqueous, non-aqueous or any combination thereof.

As used herein, a combination refers to any association between or among two or more items. The combination can be two or more separate items, such as two compositions or two collections, can be a mixture thereof, such as a single mixture of the two or more items, or any variation thereof. The elements of a combination are generally functionally associated or related.

As used herein, a kit is a packaged combination that optionally includes other elements, such as additional reagents and instructions for use of the combination or elements thereof.

As used herein, "disease or disorder" refers to a pathological condition in an organism resulting from cause or condition including, but not limited to, infections, acquired conditions, genetic conditions, and characterized by identifiable symptoms. Diseases and disorders of interest herein are those that are treatable by immune globulin.

As used herein, "treating" a subject with a disease or condition means that the subject's symptoms are partially or totally alleviated, or remain static following treatment. Hence treatment encompasses prophylaxis, therapy and/or cure. Prophylaxis refers to prevention of a potential disease and/or a prevention of worsening of symptoms or progression of a disease. Treatment also encompasses any phannaceutical use of an immune globulin preparation and compositions provided herein.

As used herein, a pharmaceutically effective agent, includes any therapeutic agent or bioactive agents, including, but not limited to, for example, anesthetics, vasoconstrictors, dispersing agents, conventional therapeutic drugs, including small molecule dnigs and therapeutic proteins.

As used herein, treatment means any manner in which the symptoms of a condition, disorder or disease or other indication, are ameliorated or otherwise beneficially altered.

As used herein therapeutic effect means an effect resulting from treatment of a subject that alters, typically improves or ameliorates the symptoms of a disease or condition or that cures a disease or condition. A therapeutically effective amount refers to the amount of a composition, molecule or compound which results in a therapeutic effect following administration to a subject.

As used herein, the term "subject" refers to an animal, including a mammal, such as a human being.

As used herein, a patient refers to a human subject.

As used herein, amelioration of the symptoms of a particular disease or disorder by a treatment, such as by administration of a pharmaceutical composition or other therapeutic, refers to any lessening, whether pennanent or temporary, lasting or transient, of the symptoms that can be attributed to or associated with administration of the composition or therapeutic.

As used herein, prevention or prophylaxis refers to methods in which the risk of developing disease or condition is reduced.

As used herein, a "therapeutically effective amount" or a "therapeutically effective dose" refers to the quantity of an agent, compound, material, or composition containing a compound that is at least sufficient to produce a therapeutic effect. Hence, it is the quantity necessary for preventing, curing, ameliorating, arresting or partially arresting a symptom of a disease or disorder.

As used herein, unit dose form refers to physically discrete units suitable for human and animal subjects and packaged individually as is known in the art.

As used herein, a single dosage formulation refers to a formulation for direct administration.

As used herein, an "article of manufacture" is a product that is made and sold.

As used throughout this application, the term is intended to encompass IG and hyaluronidase compositions contained in articles of packaging.

As used herein, fluid refers to any composition that can flow. Fluids thus encompass compositions that are in the form of semi-solids, pastes, solutions, aqueous mixtures, gels, lotions, creams and other such compositions.

As used herein, a "kit" refers to a combination of compositions provided herein and another item for a purpose including, but not limited to, activation, administration, diagnosis, and assessment of a biological activity or property. Kits optionally include instructions for use.

As used herein, a cellular extract or lysate refers to a preparation or fraction which is made from a lysed or disrupted cell.

As used herein, animal includes any animal, such as, but are not limited to primates including humans, gorillas and monkeys; rodents, such as mice and rats; fowl, such as chickens; nuninants, such as goats, cows, deer, sheep; ovine, such as pigs and other animals. Non-human animals exclude humans as the contemplated animal. The enzymes provided herein are from any source, animal, plant, prokaryotic and fungal. Most enzymes are of animal origin, including mammalian origin.

As used herein, a control refers to a sample that is substantially identical to the test sample, except that it is not treated with a test parameter, or, if it is a plasma sample, it can be from a normal volunteer not affected with the condition of interest. A control also can be an internal control.

As used herein, the singular forms "a," "an" and "the" include plural referents unless the context clearly dictates otherwise. Thus, for example, reference to a compound, comprising "an extracellular domain" includes compounds with one or a plurality of extracellular domains.

As used herein, ranges and amounts can be expressed as "about" a particular value or range. About also includes the exact amount. Hence "about 5 bases" means "about 5 bases" and also "5 bases."

As used herein, "optional" or "optionally" means that the subsequently described event or circumstance does or does not occur, and that the description includes instances where said event or circumstance occurs and instances where it does not. For example, an optionally substituted group means that the group is unsubstituted or is substituted.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) Biochem. 11:1726).

B. Subcutaneous Administration of Immune Globulin (IG)

Provided herein are methods and uses of treating IG-treatable diseases and conditions by subcutaneously administering immune globulin (IG) in combination with a soluble hyaluronidase. Hence, also provided are combinations of IG and a soluble hyaluronidase. By virtue of the ability of hyaluronidase to break down hyaluronic acid in the extracellular matrix, hyaluronidase facilitates subcutaneous infusions of therapeutic agents. Immune globulin is a therapeutic that is primarily given by intravenous administration to treat individuals with immune deficiencies, referred to as IVIG therapy. The bioavailability of IG in the presence of hyaluronidase is greater than 90% of the bioavailability of IG following IVIG treatment. Hence, in the methods and use provided herein, the combination therapy of hyaluronidase and IG permits the subcutaneous administration of immune globulin at dosages and frequencies that are similar to IVIG treatment. Thus, for example, in the methods and uses provided herein, IG, when administered subcutaneously in the presence of a soluble hyaluronidase, can be administered once monthly at prevailing IVIG doses for the particular indication. Further, because hyaluronidase acts to open flow channels in the skin it can speed infusion rates. Hence, methods of subcutaneously administering IG co-formulated and/or co-administered with hyaluronidase increases infusion rates, and thereby decreases time of delivery of IG therapy.

Defective antibody formation is the most common abnormality in the majority of primary immunodeficiency (PID) diseases; it is most often reflected by a decrease in serum immunoglobulins, which in turn leads to increased susceptibility to bacterial infections, especially of the sinopulmonary tract. Decreased immunoglobulin levels are found in individuals having antibody defects such as X-linked agammaglobulinemia, immunoglobulin heavy chain deletion, selective immunoglobulin G (IgG) subclass deficiency, common variable immunodeficiency, or X-linked hyperimmunoglobulin M syndrome. Decreased immunoglobulin levels also are found in individuals having combined immunodeficiencies due to defects in T and B cells, such as, but not limited to, severe combined immunodeficiency or Wiskott Aldrich Syndrome (IUIS Scientific Committee, 1999).

Individuals with these diseases require replacement therapy with immunoglobulin products to prevent or reduce the severity of infections. Initially, immunoglobulin replacement therapy was given by the intramuscular route, but starting in 1981 the overwhelming majority of patients have been treated by the intravenous (IV) route. Currently, the majority of immunoglobulin products in the United States are for IV administration. Immune globulin preparations have, however, been developed more recently for subcutaneous administration (Gardulf et al. (2006) Curr. Opin. Allergy Clin. Immunol., 6: 434-42; Gardulf et al. (2006) J Clin. Immunol., 26: 177-85; Ochs et al. (2006) J Clin. Immunol., 26:265-73). At least one product, Vivaglobin®, is approved for subcutaneous administration.

All of the immunoglobulin preparations presently used are formulated at 16%, compared to IVIG preparations formulated at 5 to 12%. The higher concentration relative to IV preparations allows smaller infusion volumes; such preparations cannot be infused intravenously. Such subcutaneous methods of immunoglobulin replacement therapy is considered to be effective, safe and also highly appreciated by patients as it has a low risk of systemic adverse reactions and leads to higher trough serum IgG concentrations compared to monthly IV infusions (Gardulf et al. (1995) J Adv. Nurs., 21: 917-27; Gardulf et al. (1993) Clin. Exp. Immunol., 92: 200-4; Gardulf et al. (1991) Lancet, 338: 162-6).

The bioavailability of immunoglobulin administered subcutaneously generally is less than that infused intravenously. Immunoglobulin is immediately available in the blood, and slowly equilibrates to the extra-vascular compartment over 3 to 5 days (Schiff et al. (1986) J. Clin. Immunol., 6:256-64). Subcutaneously administered immunoglobulin is slowly absorbed from the subcutaneous space into the blood and at the same time equilibrates with the extra-vascular compartment; there is no high IV spike. The bioavailability has not been extensively studied, but in a recent trial of the ZLB-Behring preparation (i.e. Vivaglobin®), it was determined by measuring the area under the curve (AUC) that only 67% of the immunoglobulin was absorbed and thus, the recommended dose was 137% of the IV dose (Ochs et al. (2006) J Clin. Immunol., 26:265-73). Despite the technical difficulties of comparing AUC for 2 different routes and frequency of administration, studies of intradermally administered immunoglobulin in rabbits suggests there is decreased bioavailability through the subcutaneous route. This may be due to the mode of absorption of large protein molecules, which cannot readily diffuse through the capillary walls and must be absorbed via the lymphatics (Supersaxo et al. (1990) Pharm. Res., 7: 167-9).

In addition to problems with bioavailability associated with subcutaneous administration of IG, the primary disadvantage of SC administration is that only small volumes can be infused in each site, necessitating the use of multiple sites on a weekly or biweekly (ever other week) basis. Generally, using a 16% solution, approximately 20 ml can be infused per site; and adult patient receiving 400 mg/kg body weight (BW) thus would require at least 3 sites per week or 12 sites per month. Even though weekly or biweekly administration has the added advantage of maintaining better trough levels than monthly IV infusions, the requirement of multiple needle insertions has been a deterrent for many patients.

The SC space is formed by a collagen network filled with a gel-like substance, hyaluronic acid. Hyaluronic acid is replaced with a half-life of approximately 5 h, and is largely responsible for the resistance to fluid flow through the tissues. Hyaluronidase temporarily digests the hyaluronic acid, thereby facilitating infusions into the subcutaneous space. The hyaluronic acid is restored within 24 hours, leaving no observable changes. Thus, due to the ability of hyaluronidase to open channels in the interstitial space through degradation of glycosaminoglycans, administration of a soluble hyaluronidase permits the diffusion of molecules, thereby improving the bioavailability, pharmacokinetics and/or pharmacodynamic characteristics of such co-formulated or co-administered molecules.

In some examples, the bioavailability of IG co-administered subcutaneously with hyaluronidase is 70%, 80%, 90%, 91%, 92%, 93%, 94%, 95%, 96%, 97%, 98%, 99%, or 100% of the bioavailability of IVIG. Typically, the bioavailability is greater than 90%. Further, co-administration with a soluble hyaluronidase permits infusion of large volumes at a single subcutaneous site. For example, volumes up to 600 ml or greater of IG can be administered at a single site in a single sitting, for example 200 ml, 300 ml, 400 ml, 500, ml, 600 ml or more can be administered at a single site in a single administration. Thus, an IG preparation formulated at or between 5-12% can be co-administered subcutaneously with a soluble hyaluronidase at dosages equivalent to once monthly IVIG doses, for example, at or about 100 mg/kg, 200 mg/kg, 300 mg/kg, 400 mg/kg, 500 mg/kg, 600 mg/kg or more. The dosages can be administered as a single dose or can be divided into multiple doses given daily or weekly, such as once a week or every two, three or four weeks or combinations thereof. Hence, by administering IG subcutaneously in the presence of a soluble hyaluronidase, one or all of the considerations and problems associated with subcutaneous administration of IG are addressed. Thus, by virtue of the dispersion properties of hyaluronidase, subcutaneously administering IG in the presence of a soluble hyaluronidase permits administration of IVIG doses at once monthly IVIG frequencies, while maintaining IVIG bioavailability.

The following sections describe exemplary immunoglobulins and soluble hyaluronidases in the combinations herein, methods of making them, and using them to treat IG-treatable diseases and conditions.

C. Immune Globulin

Provided herein are immune globulins (IG, also referred to as gamma globulin or IgG) that can be used for subcutaneous administration in combination with a soluble hyaluronidase. IG acts to strengthen the immune system by modulating the activity of complement, suppressing autoantibody production, saturating or blocking Fc receptors on macrophages and B lymphocytes, and suppressing the production of inflammatory mediators such as cytokines, chemokines and metalloproteinases.

IG is a protein fraction found in the plasma of higher animals and contains a large number of antibodies having varying specificities. Generally, IG contains serum immunoglobulins that can be any idiotype, such as IgG and various subclasses, IgA, IgM, IgD, IgE. The various immunoglobulins or subclasses can be present at various concentrations and specificities, which can differ between immune globulin preparations depending, for example, on the plasma donor's exposure to antigens (e.g., by way of vaccinations). Often, immunoglobulins are present in amounts normally found in the serum (see Table 2), although purification steps can be employed to alter ratios of particular immunoglobulin class or classes. Typically, IG preparations contain 90% or more IgG, such as 90%, 91%, 92%, 93%, 94%, 95%, 96%, 97%, 98%, 99% or more IgG. The immunoglobulins can be polyclonal or monoclonal. Typically, preparations include a high percentage of monomeric IgG and a low IgA content.

TABLE 2

Serum Immunoglobulin

| Ig Class | Serum Level mg/ml (%) | Function |
|---|---|---|
| IgG | 1200 (77) | Major Ig in Humans |
| IgA | 200 (13) | Protects Mucosa |
| IgM | 150 (9) | Major Ig for primary immune responses |
| IgD | 2 (<1) | Regulates B cells |
| IgE | <1 (trace) | Major Ig in Allergic Response |

Immune globulins can be isolated from human or animal blood or produced by other means, for example, by recombinant DNA technology or hybridoma technology. For example, immune globulin can be obtained from tissues, lymphocyte hybridoma cultures, blood plasma or senim, or recombinant cell cultures using any suitable fractionation procedure, e.g., alcohol precipitations or ion exchange separations. In general, IG is prepared from blood plasma by alcohol fractionation, such as was originally employed by Cohn and modified by Oncley (the Cohn-Oncley method, see e.g, Cohn et al. (1946) J. Am. Chem. Soc. 68: 459-475; Oncley et al. (1949) J Am. Chem. Soc., 71: 541-550). The use of alcohol in the purification can inactivate potentially contaminating viruses. The Cohn-Oncley method can result in denatured and aggregated proteins, which can result in high molecular weight forms that can act as antibody-antigen complexes having the capacity to freely fix complement.

To prevent such unwanted effects, modified Cohn-Oncley methods have been developed for the preparation and purification of IG. Various such procedures are known and can be adapted and modified for use of IG preparations herein. It is within the skill of the art to prepare IG preparations in view of the detailed methods known and available in the art. Typically, IG is manufactured using a primary cold ethanol fractionation and a secondary fractionation that can include any one or more of a chemical modification, incubation at pH 4.0 with or without pepsin, PEG precipitation, ion-exchange chromatography, enzymatic cleavage, solvent detergent treatment and diafiltration and ultrafiltration.

For example, the separation of IG aggregates by conventional techniques, such as ultra-centrifuging or exclusion chromatography, make it possible to obtain a product having a low anti-complementary activity. Other methods of IG preparation include, but are not limited to, a process for fractionating human plasma by means of ethyleneglycol polymers (Polson et al. (1964) Biochim. Biophys. Acta., 82: 463-475); incorporation of a polyethyleneglycol (PEG) as a purification agent starting from a material separated from the Cohn fractionation (fraction II or II+III, see e.g., U.S. Pat. Nos. 4,093,606 and 4,165,370); and other similar methods of purification processes with polyethyleneglycol (EP 0246579). In addition, processes have been described for obtaining IG that exhibits low anticomplement activity by treatment with enzymes such as pepsin, plasmin, immobilized trypsin, treatment at a moderate acidic pH, B-propiolactone treatment, fractionation methods which use polyethylene glycol as a precipitating agent, and other techniques described in U.S. Pat. Nos. 4,093,606, 4,126,605, 3,966,906, and 4,124,576. Other processes are based on chemically and partially modifying the IG molecules by treating them with reducing agents, alchoholization, alkylation and sulphonation (see e.g., U.S. Pat. No. 6,875,848). Ion exchange chromatography can be used to eliminate undesirable contaminants from the starting materials used to obtain the IG preparations (see e.g., U.S. Pat. No. 3,869,436, EP 91300790 and WO 94/29334). EP0440483 describes a combination of techniques useful for facilitating the intravenous preparation of the product based on ion exchange chromatography and diafiltration at a weak acid pH. Other methods also are described in the art and are known to one of skill in the art (see e.g., U.S. Pat. Nos. 5,177,194 and 6,875,848).

The IG preparations should be treated to remove viral load. There are two methods of decreasing viral load: viral inactivation and viral partitioning or removal. Exemplary of viral inactivation methods include, but are not limited to, cold ethanol fractionation, heating (pasterurization), solvent/detergent and acidic environment (low pH). For example, solvent/detergent process has been demonstrated to have virucidal action against VSV (vesicular stomatitits virus), Sindbis virus, HIV, HBV (hepatitis B virus, and HCV (hepatic C virus). Exemplary of viral partitioning or removal include, but are not limited to, cold ethanol fractionation, phase partitioning or PEG precipitation, affinity chromatography, ion exchange or gel exclusion chromatography and filtration.

The final purified formulation also must be prepared to avoid excessive aggregation and to stabilize the protein. Aggregation of IG preparation can be minimized by preparing lyophilized preparations for improved stability on storage, for reconstitution with a diluent before use. Another way of increasing the stability of IG preparations that is well known in the art is the addition of protein-stabilizing excipients to the IG preparation. Known excipients include, but are not limited to, sugars, polyols, amino acids, amines, salts, polymers and surfactants. For example, U.S. Pat. No. 4,499,073 describes stabilization through the selection of pH and ionic strength; JP Patent 54020124 discloses the addition of an amino acid to an intramuscular preparation to render it storage stable and safe; JP 57031623 and JP 57128635 disclose the use of arginine and/or lysine with NaCl in 5 to 15% IG preparations to achieve long-term stability in an intramuscular preparation; JP 4346934 discloses the use of low conductivity (less than mmho), pH 5.3 to 5.7 and optionally one or more stabilizer including PEG, human senun albumin and mannitol; U.S. Pat. No. 4,439,421 teaches the addition of a hydrophilic macromolecule, a polyol and another protein to stabilize against anti-complement generation; U.S. Pat. No. 5,945,098 discloses the stabilization if isotonic solutions by the addition of amino acids (0.1 to 0.3 M glycine) and non-ionic detergents (polysorbate and PEG); U.S. Pat. No. 4,186,192 discloses various additives including amino acids; WO 2005/049078 discloses the stabilization with maltose and additionally glycine to 0.1 M; U.S. Pat. No. 4,362,661 discloses the use of neutral and basic amino acids to impart stability on a 5% IG preparation. Stable liquid formulations also can be prepared, which use carbohydrates in an aqueous medium having a very low ionic strength and a pH of 4.25 (U.S. Pat. No. 4,396,608) or a weakly acidic pH of 5-6 (EP 0278422).

Dimer formation of IG preparations also can be controlled. For example, U.S. Pat. No. 5,871,736 discloses IG preparations, particularly liquid preparations, containing one or more amphiphilic stabilizer in order to stabilize against dimer formation. The amphiphilic stabilizers include nicotinic acid and its derivatives, in particular nicotinamide, and mainly in conjunction with the above, amino acids having uncharged lipophilic side chains, e.g., phenylalanine, methionine, leucine, isoleucine, proline and valine.

The preparations can be prepared by methods known in the art, such as any described herein. Generally, however, the pH of the final preparation is adjusted to a relatively high but acidic pH, namely in the range of about pH 4.2 to 5.4, such as a pH range of 4.6 to 5.1. It has been found that this pH range is particularly useful for improving the storage of IG preparations.

Generally, final IG preparations have a protein concentration of about 5 to 25% w/v, generally 6 to 15% w/v, 8 to 12% w/v, and typically 10% w/v. The final protein concentration will depend on various factors, such as the administration route the patient to be treated, and the type of condition to be treated.

It is contemplated herein that any IG preparation used for IV administration can be used in the methods provided herein in combination with a soluble hyaluronidase for subcutaneous administration. Preparations include lyophilized and liquid formulations. Immune globulin (IVIG) is commercially available as Carimune® NF, Flebogamma® 5%, Gammagard® Liquid, Gammagard® S/D, Gamunex®, Iveegam® EN, Octagam® and Polygam® S/D. Typically, such preparations all use a method of cold alcohol fractionation, but use different methods to isolate and purify the immune globulin and different methods to reduce the potential virus contamination. Further, other preparations presently formulated for intramuscular or subcutaneous administration can be used in the combinations and methods provided herein.

Exemplary of an IG preparation is Immune Globulin Intravenous (Human), 10% (IVIG, 10%, marketed as Gammagard® liquid, Baxter Healthcare Corporation), which is a liquid unmodified IgG preparation with a distribution of IgG subclasses similar to that of normal plasma. The preparation contains intact fragment crystallizable (Fc) and Fab regions. The preparations contains 100 mg/ml proteins, with at least 98% being IgG; IgA is present at a concentration of 37 μg/ml, and IgM is present only in trace amounts. It has an osmolality that is similar to physiologic osmolality and contains no added sugars, sodium or preservatives. It is formulated with glycine for stabilization at a pH of 4.6 to 5.1. The manufacturing process employs a modified Cohn-Oncley cold alcohol fractionation procedure and further purifications by a continuous process through the use of weak cation exchange chromatography and weak anion exchange chromatography. The manufacturing process also includes 3 independent viral inactivation or removal steps: solvent/detergent (S/D) treatment, nanofiltration and incubation at a low pH and elevated temperature.

D. Hyaluronidase

Provided herein are combinations containing immunoglobulin and a soluble hyaluronidase, and methods of using such combinations for subcutaneous administration for the treatment of IG-mediated diseases and conditions. Hyaluronidases are a family of enzymes that degrade hyaluronic acid, which is an essential component of the extracellular matrix and a major constituent of the interstitial barrier. By catalyzing the hydrolysis of hyaluronic acid, a major constituent of the interstitial barrier, hyaluronidase lowers the viscosity of hyaluronic acid, thereby increasing tissue permeability. As such, hyaluronidases have been used, for example, as a spreading or dispersing agent in conjunction with other agents, drugs and proteins to enhance their dispersion and delivery. Exemplary of hyaluronidases in the combinations and methods provided herein are soluble hyaluronidases.

There are three general classes of hyaluronidases; mammalian hyaluronidase, bacterial hyaluronidase and hyaluronidase from leeches, other parasites and crustaceans. Mammalian-type hyaluronidases (EC 3.2.1.35) are endo-β-N-acetyl-hexosaminidases that hydrolyze the β1→4 glycosidic bond of hyaluronan into various oligosaccharide lengths such as tetrasaccharides and hexasaccharides. They have both hydrolytic and transglycosidase activities, and can degrade hyaluronan and chondroitin sulfates (CS), generally C4-S and C6-S. Hyaluronidases of this type include, but are not limited to, hyaluronidases from cows (bovine) (SEQ ID NOS:10 and 11), mouse (SEQ ID NOS:17-19, 32), pig (SEQ ID NOS:20-21), rat (SEQ ID NOS:22-24, 31), rabbit (SEQ ID NO:25), sheep (ovine) (SEQ ID NOS:26 and 27), orangutan (SEQ ID NO:28), cynomolgus monkey (SEQ ID NO:29), guinea pig (SEQ ID NO: 30), and human hyaluronidases.

Mammalian hyaluronidases can be further subdivided into those that are neutral active, predominantly found in testes extracts, and acid active, predominantly found in organs such as the liver. Exemplary neutral active hyaluronidases include PH20, including but not limited to, PH20 derived from different species such as ovine (SEQ ID NO:27), bovine (SEQ ID NO:11) and human (SEQ ID NO:1). Human PH20 (also known as SPAM1 or sperm surface protein PH20), is generally locked to the plasma membrane via a glycosylphosphatidyl inositol (GPI) anchor. It is naturally involved in sperm-egg adhesion and aids penetration by sperm of the layer of cumulus cells by digesting hyaluronic acid. The PH20 mRNA transcript is normally translated to generate a 509 amino acid precursor polypeptide (SEQ ID NO:1) containing a 35 amino acid signal sequence at the N-terminus (amino acid residue positions 1-35) and a 19 amino acid GPI anchor at the C-terminus (amino acid residue positions 491-509) The mature PH20 is, therefore, a 474 amino acid polypeptide set forth in SEQ ID NO:2). Bovine PH20 is a 553 amino acid precursor polypeptide (SEQ ID NO:11). Alignment of bovine PH20 with the human PH20 shows only weak homology, with multiple gaps existing from amino acid 470 through to the respective carboxy termini due to the absence of a GPI anchor in the bovine polypeptide (see e.g., Frost GI (2007) Expert Opin. Drug. Deliv. 4: 427-440). In fact, no clear GPI anchor is predicted in any other PH20 species besides humans. Thus, PH20 polypeptides produced from ovine and bovine exist as soluble forms. Though bovine PH20 exists very loosely attached to the plasma membrane, it is not anchored via a phospholipase sensitive anchor (Lalancette et al, Biol Reprod. 2001 August; 65(2):628-36.). This unique feature of bovine hyaluronidase has permitted the use of the soluble bovine testes hyaluronidase enzyme as an extract for clinical use (Wydase™, Hyalase™)

Besides human PH20 (also termed SPAM1), five hyaluronidase-like genes have been identified in the human genome, HYAL1, HYAL2, HYAL3, HYAL4 and HYALP1. HYALP1 is a pseudogene, and HYAL3 (SEQ ID NO:38) has not been shown to possess enzyme activity toward any known substrates. HYAL4 (precursor polypeptide set forth in SEQ ID NO:39) is a chondroitinase and exhibits little activity towards hyaluronan. HYAL(precursor polypeptide set forth in SEQ ID NO:36) is the prototypical acid-active enzyme and PH20 (precursor polypeptide set forth in SEQ ID NO:1) is the prototypical neutral-active enzyme. Acid-active hyaluronidases, such as HYAL1 and HYAL2 (precursor polypeptide set forth in SEQ ID NO:37) generally lack catalytic activity at neutral pH (i.e. pH 7). For example, HYAL1 has little catalytic activity in vitro over pH 4.5 (Frost et al. (1997) Anal. Biochemistry, 251:263-269). HYAL2 is an acid-active enzyme with a very low specific activity in vitro. The hyaluronidase-like enzymes can also be characterized by those which are generally locked to the plasma membrane via a glycosylphosphatidyl inositol anchor such as human HYAL2 and human PH20 (Danilkovitch-Miagkova, et al. (2003) Proc Natl Acad Sci USA. 100(8):4580-5), and those which are generally soluble such as human HYAL1 (Frost et al, (1997) Biochem Biophys Res Commun. 236(1):10-5).

Glycosylation, including N- and O-linked glycosylation, of some hyaluronidases can be very important for their catalytic activity and stability. While altering the type of glycan modifying a glycoprotein can have dramatic affects on a protein's antigenicity, structural folding, solubility, and stability, most enzymes are not thought to require glycosylation for optimal enzyme activity. Such hyaluronidases are unique in this regard, in that removal of N-linked glycosylation can result in near complete inactivation of the hyaluronidase activity. For such hyaluronidases, the presence of N-linked glycans is critical for generating an active enzyme.

N-linked oligosaccharides fall into several major types (oligomannose, complex, hybrid, sulfated), all of which have (Man) 3-GlcNAc-GlcNAc-cores attached via the amide nitrogen of Asn residues that fall within-Asn-Xaa-Thr/Ser-sequences (where Xaa is not Pro). Glycosylation at an-Asn-Xaa-Cys-site has been reported for coagulation protein C. In some instances, the hyaluronidase can contain both N-glycosidic and O-glycosidic linkages. For example, PH20 has O-linked oligosaccharides as well as N-linked oligosaccharides.

There are seven potential N-linked glycosylation sites at N82, N166, N235, N254, N368, N393, N490 of human PH20 exemplified in SEQ ID NO: 1. Disulfide bonds form between the cysteine residues C60 and C351 and between C224 and C238 to form the core hyaluronidase domain. However, additional cysteines are required in the carboxy terminus for neutral enzyme catalytic activity such that amino acids 36 to 464 of SEQ ID NO:1 contains the minimally active human PH20 hyaluronidase domain. Thus, N-linked glycosylation site N-490 is not required for proper hyaluronidase activity.

Soluble Hyaluronidase

Provided in the combinations and methods herein are soluble hyaluronidases. Soluble hyaluronidases include any that exist in soluble form, including, but not limited to, Hyall, bovine PH20 and ovine PH20, allelic variants thereof and other variants. Also included among soluble hyaluronidase are any hyaluronidase that has been modified to be soluble. For example, human PH20, which is normally membrane anchored via a GPI anchor, can be made soluble by truncation of and removal of all or a portion of the GPI anchor at the C-terminus. Soluble hyaluronidases also include neutral active and acid active hyaluronidases, however, neutral active hyaluronidases are contemplated for use herein for purposes of subcutaneous administration.

Thus, exemplary of a soluble hyaluronidase is PH20 from any species, such as any set forth in any of SEQ ID NOS: 1, 2, 11, 25, 27, 30 and 31, or truncated forms thereof lacking all or a portion of the C-terminal GPI anchor, so long as the hyaluronidase is soluble and retains hyaluronidase activity. Also included among soluble hyaluronidases are allelic variants or other variants of any of SEQ ID NOS: 1, 2, 11, 25, 27, 30 and 31, or truncated forms thereof. Allelic variants and other variants are known to one of skill in the art, and include polypeptides having 60%, 70%, 80%, 90%, 91%, 92%, 93%, 94%, 95% or more sequence identify to any of SEQ ID NOS: 1, 2, 11, 25, 27, 30 and 31, or truncated forms thereof.

Typically, for use in the methods herein, a soluble human PH20 is used. Although PH20 from other animals can be utilized, such preparations are potentially immunogenic, since they are animal proteins. For example, a significant proportion of patients demonstrate prior sensitization secondary to ingested foods, and since these are animal proteins, all patients have a risk of subsequent sensitization. Thus, non-human preparations may not be suitable for chronic use. If non-human preparations are desired, it is contemplated herein that such polypeptides can be prepared to have reduced immunogenicity. Such modifications are within the level of one of skill in the art. Hyaluronidases, including PH20, used in the methods herein can be recombinantly produced or can be purified or partially-purified from natural sources, such as, for example, from testes extracts.

Soluble Human PH20

Exemplary of a soluble hyaluronidase is soluble human PH20. Soluble forms of recombinant human PH20 have been produced and can be used in the methods described herein for co-administration or co-formulation with immunoglobulin for subcutaneous administration to treat IG-treatable diseases and conditions. The production of such soluble forms of PH20 is described in application Ser. Nos. 11/065,716 and 11/238,171, and in Examples 2-6, below. Soluble forms include, but are not limited to, any having C-terminal truncations to generate polypeptides containing amino acid 1 to amino acid 347, 372, 394, 413, 430, 447, 467, 477, 478, 479, 480, 481, 482 and 483 of the sequence of amino acids set forth in SEQ ID NOS 1. When expressed in mammalian cells, the 35 amino acid N-terminal signal sequence is cleaved during processing, and the mature form of the protein is secreted. Thus, the mature soluble polypeptides contain amino acids 36 to 347, 372, 394, 413, 430, 447, 467, 477, 478, 479, 480, 481, 482 and 483 of SEQ ID NO:1. Deletion mutants ending at amino acid position 477 to 483 (corresponding to the precursor polypeptide set forth in SEQ ID NO:1) exhibit higher secreted hyaluronidase activity than the full length GPI-anchored form. Hence, exemplary of soluble hyaluronidases are those that are 442, 443, 444, 445, 446 or 447 amino acids in length, such as set forth in any of SEQ ID NOS:4-9, or allelic or species variants or other variants thereof. Generally soluble forms of PH20 are produced using protein expression systems that facilitate correct N-glycosylation to ensure the polypeptide retains activity, since glycosylation is important for the catalytic activity and stability of hyaluronidases. Such cells include, for example Chinese Hamster Ovary (CHO) cells (e.g. DG44 CHO cells).

Recombinant Soluble Human PH20 (rHuPH20)

Recombinant soluble forms of human PH20 (soluble rHuPH20) have been generated and can be produced and purified using the methods described herein. The generation of such soluble forms of rHuPH20 are described in U.S. patent application Ser. Nos. 11/065,716 and 11/238,171 (published as U.S. published patent application Nos. US20050260186 and US 20060104968), and in Examples 2-6, below. Exemplary of such polypeptides are those generated from a nucleic acid molecule encoding amino acids 1-482 set forth in SEQ ID NO:3. Post translational processing removes the 35 amino acid signal sequence, resulting in the secretion of a 447 amino acid soluble rHuPH20 (SEQ ID NO:4). Resulting purified rHuPH20 can be heterogenous due to peptidases present in the culture medium upon production and purification. Typically, rHuPH20 is produced in cells that facilitate correct N-glycosylation to retain activity, such as CHO cells (e.g. DG44 CHO cells).

E. Methods of Producing Nucleic Acids Encoding a Soluble Hyaluronidase and Polypeptides thereof Polypeptides of a soluble hyaluronidase set forth herein, can be obtained by methods well known in the art for protein purification and recombinant protein expression. Any method known to those of skill in the art for identification of nucleic acids that encode desired genes can be used. Any method available in the art can be used to obtain a full length (i.e., encompassing the entire coding region) cDNA or genomic DNA clone encoding a hyaluronidase, such as from a cell or tissue source. Modified or variant soluble hyaluronidases, can be engineered from a wildtype polypeptide, such as by site-directed mutagenesis.

Polypeptides can be cloned or isolated using any available methods known in the art for cloning and isolating nucleic acid molecules. Such methods include PCR amplification of nucleic acids and screening of libraries, including nucleic acid hybridization screening, antibody-based screening and activity-based screening.

Methods for amplification of nucleic acids can be used to isolate nucleic acid molecules encoding a desired polypeptide, including for example, polymerase chain reaction (PCR) methods. A nucleic acid containing material can be used as a starting material from which a desired polypeptide-encoding nucleic acid molecule can be isolated. For example, DNA and mRNA preparations, cell extracts, tissue extracts, fluid samples (e.g. blood, serum, saliva), samples from healthy and/or diseased subjects can be used in amplification methods. Nucleic acid libraries also can be used as a source of starting material. Primers can be designed to amplify a desired polypeptide. For example, primers can be designed based on expressed sequences from which a desired polypeptide is generated. Primers can be designed based on back-translation of a polypeptide amino acid sequence. Nucleic acid molecules generated by amplification can be sequenced and confirmed to encode a desired polypeptide.

Additional nucleotide sequences can be joined to a polypeptide-encoding nucleic acid molecule, including linker sequences containing restriction endonuclease sites for the purpose of cloning the synthetic gene into a vector, for example, a protein expression vector or a vector designed for the amplification of the core protein coding DNA sequences. Furthermore, additional nucleotide sequences specifying functional DNA elements can be operatively linked to a polypeptide-encoding nucleic acid molecule. Examples of such sequences include, but are not limited to, promoter sequences designed to facilitate intracellular protein expression, and secretion sequences, for example heterologous signal sequences, designed to facilitate protein secretion. Such sequences are known to those of skill in the art. Additional nucleotide residues sequences such as sequences of bases specifying protein binding regions also can be linked to enzyme-encoding nucleic acid molecules. Such regions include, but are not limited to, sequences of residues that facilitate or encode proteins that facilitate uptake of an enzyme into specific target cells, or otherwise alter pharmacokinetics of a product of a synthetic gene. For example, enzymes can be linked to PEG moieties.

In addition, tags or other moieties can be added, for example, to aid in detection or affinity purification of the polypeptide. For example, additional nucleotide residues sequences such as sequences of bases specifying an epitope tag or other detectable marker also can be linked to enzyme-encoding nucleic acid molecules. Exemplary of such sequences include nucleic acid sequences encoding a His tag (e.g., 6×His, HHHHHH; SEQ ID NO:54) or Flag Tag (DYKDDDDK; SEQ ID NO:55).

The identified and isolated nucleic acids can then be inserted into an appropriate cloning vector. A large number of vector-host systems known in the art can be used. Possible vectors include, but are not limited to, plasmids or modified viruses, but the vector system must be compatible with the host cell used. Such vectors include, but are not limited to, bacteriophages such as lambda derivatives, or plasmids such as pCMV4, pBR322 or pUC plasmid derivatives or the Bluescript vector (Stratagene, La Jolla, Calif.). Other expression vectors include the HZ24 expression vector exemplified herein. The insertion into a cloning vector can, for example, be accomplished by ligating the DNA fragment into a cloning vector which has complementary cohesive termini. Insertion can be effected using TOPO cloning vectors (INVITROGEN, Carlsbad, Calif.). If the complementary restriction sites used to fragment the DNA are not present in the cloning vector, the ends of the DNA molecules can be enzymatically modified. Alternatively, any site desired can be produced by ligating nucleotide sequences (linkers) onto the DNA termini; these ligated linkers can contain specific chemically synthesized oligonucleotides encoding restriction endonuclease recognition sequences. In an alternative method, the cleaved vector and protein gene can be modified by homopolymeric tailing. Recombinant molecules can be introduced into host cells via, for example, transformation, transfection, infection, electroporation and sonoporation, so that many copies of the gene sequence are generated.

In specific embodiments, transformation of host cells with recombinant DNA molecules that incorporate the isolated protein gene, cDNA, or synthesized DNA sequence enables generation of multiple copies of the gene. Thus, the gene can be obtained in large quantities by growing transformants, isolating the recombinant DNA molecules from the transformants and, when necessary, retrieving the inserted gene from the isolated recombinant DNA.

1. Vectors and Cells

For recombinant expression of one or more of the desired proteins, such as any described herein, the nucleic acid containing all or a portion of the nucleotide sequence encoding the protein can be inserted into an appropriate expression vector, i.e., a vector that contains the necessary elements for the transcription and translation of the inserted protein coding sequence. The necessary transcriptional and translational signals also can be supplied by the native promoter for enzyme genes, and/or their flanking regions.

Also provided are vectors that contain a nucleic acid encoding the enzyme. Cells containing the vectors also are provided. The cells include eukaryotic and prokaryotic cells, and the vectors are any suitable for use therein.

Prokaryotic and eukaryotic cells, including endothelial cells, containing the vectors are provided. Such cells include bacterial cells, yeast cells, fungal cells, Archea, plant cells, insect cells and animal cells. The cells are used to produce a protein thereof by growing the above-described cells under conditions whereby the encoded protein is expressed by the cell, and recovering the expressed protein. For purposes herein, for example, the enzyme can be secreted into the medium.

Provided are vectors that contain a sequence of nucleotides that encodes the soluble hyaluronidase polypeptide coupled to the native or heterologous signal sequence, as well as multiple copies thereof. The vectors can be selected for expression of the enzyme protein in the cell or such that the enzyme protein is expressed as a secreted protein.

A variety of host-vector systems can be used to express the protein coding sequence. These include but are not limited to mammalian cell systems infected with virus (e.g. vaccinia virus, adenovirus and other viruses); insect cell systems infected with virus (e.g. baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system used, any one of a number of suitable transcription and translation elements can be used.

Any methods known to those of skill in the art for the insertion of DNA fragments into a vector can be used to construct expression vectors containing a chimeric gene containing appropriate transcriptional/translational control signals and protein coding sequences. These methods can include in vitro recombinant DNA and synthetic techniques and in vivo recombinants (genetic recombination). Expression of nucleic acid sequences encoding protein, or domains, derivatives, fragments or homologs thereof, can be regulated by a second nucleic acid sequence so that the genes or fragments thereof are expressed in a host transformed with the recombinant DNA molecule(s). For example, expression of the proteins can be controlled by any promoter/enhancer known in the art. In a specific embodiment, the promoter is not native to the genes for a desired protein. Promoters which can be used include but are not limited to the SV40 early promoter (Bemoist and Chambon, Nature 290:304-310 (1981)), the promoter contained in the 3' long terminal repeat of Rous sarcoma virus (Yamamoto et al. Cell 22:787-797 (1980)), the herpes thymidine kinase promoter (Wagner et al., Proc. Natl. Acad. Sci. USA 78:1441-1445 (1981)), the regulatory sequences of the metallothionein gene (Brinster et al., Nature 296:39-42 (1982)); prokaryotic expression vectors such as the β-lactamase promoter (Jay et al., (1981) Proc. Natl. Acad. Sci. USA 78:5543) or the tac promoter (DeBoer et al., Proc. Natl. Acad. Sci. USA 80:21-25 (1983)); see also "Useful Proteins from Recombinant Bacteria": in Scientific American 242:79-94 (1980)); plant expression vectors containing the nopaline synthetase promoter (Herrara-Estrella et al., Nature 303:209-213 (1984)) or the cauliflower mosaic virus 35S RNA promoter (Garder et al., Nucleic Acids Res. 9:2871 (1981)), and the promoter of the photosynthetic enzyme ribulose bisphosphate carboxylase (Herrera-Estrella et al., Nature 310:115-120 (1984)); promoter elements from yeast and other fungi such as the Ga14 promoter, the alcohol dehydrogenase promoter, the phosphoglycerol kinase promoter, the alkaline phosphatase promoter, and the following animal transcriptional control regions that exhibit tissue specificity and have been used in transgenic animals: elastase I gene control region which is active in pancreatic acinar cells (Swift et al., Cell 38:639-646 (1984); Ornitz et al., Cold Spring Harbor Symp. Quant. Biol. 50:399-409 (1986); MacDonald, Hepatology 7:425-515 (1987)); insulin gene control region which is active in pancreatic beta cells (Hanahan et al., Nature 315:115-122 (1985)), immunoglobulin gene control region which is active in lymphoid cells (Grosschedl et al., Cell 38:647-658 (1984); Adams et al., Nature 318:533-538 (1985); Alexander et al., Mol. Cell Biol. 7:1436-1444 (1987)), mouse mammary tumor virus control region which is active in testicular, breast, lymphoid and mast cells (Leder et al., Cell 45:485-495 (1986)), albumin gene control region which is active in liver (Pinckert et al., Genes and Devel. 1:268-276 (1987)), alpha-fetoprotein gene control region which is active in liver (Krumlauf et al., Mol. Cell. Biol. 5:1639-1648 (1985); Hammer et al., Science 235:53-58 1987)), alpha-1 antitrypsin gene control region which is active in liver (Kelsey et al., Genes and Devel. 1:161-171 (1987)), beta globin gene control region which is active in myeloid cells (Magram et al., Nature 315:338-340 (1985); Kollias et al., Cell 46:89-94 (1986)), myelin basic protein gene control region which is active in oligodendrocyte cells of the brain (Readhead et al., Cell 48:703-712 (1987)), myosin light chain-2 gene control region which is active in skeletal muscle (Shani, Nature 314:283-286 (1985)), and gonadotrophic releasing hormone gene control region which is active in gonadotrophs of the hypothalamus (Mason et al., Science 234:1372-1378 (1986)).

In a specific embodiment, a vector is used that contains a promoter operably linked to nucleic acids encoding a desired protein, or a domain, fragment, derivative or homolog, thereof, one or more origins of replication, and optionally, one or more selectable markers (e.g., an antibiotic resistance gene). Exemplary plasmid vectors for transformation of E. coli cells, include, for example, the pQE expression vectors (available from Qiagen, Valencia, Calif.; see also literature published by Qiagen describing the system). pQE vectors have a phage T5 promoter (recognized by E. coli RNA polymerase) and a double lac operator repression module to provide tightly regulated, high-level expression of recombinant proteins in E. coli, a synthetic ribosomal binding site (RBS II) for efficient translation, a 6× His tag coding sequence, $t_0$ and T1 transcriptional tenninators, ColE1 origin of replication, and a beta-lactamase gene for conferring ampicillin resistance. The pQE vectors enable placement of a 6× His tag at either the N- or C-terminus of the recombinant protein. Such plasmids include pQE 32, pQE 30, and pQE 31 which provide multiple cloning sites for all three reading frames and provide for the expression of N-terminally 6× His-tagged proteins. Other exemplary plasmid vectors for transformation of E. coli cells, include, for example, the pET expression vectors (see, U.S. Pat. No. 4,952,496; available from NOVAGEN, Madison, Wis.; see, also literature published by Novagen describing the system).

Such plasmids include pET 11 a, which contains the T7lac promoter, T7 terminator, the inducible E. coli lac operator, and the lac repressor gene; pET 12a-c, which contains the T7 promoter, T7 terminator, and the E. coli ompT secretion signal; and pET 15b and pET19b (NOVAGEN, Madison, Wis.), which contain a His-Tag™ leader sequence for use in purification with a His column and a thrombin cleavage site that permits cleavage following purification over the column, the T7-lac promoter region and the T7 terminator.

Exemplary of a vector for mammalian cell expression is the HZ24 expression vector. The HZ24 expression vector was derived from the pCI vector backbone (Promega). It contains DNA encoding the Beta-lactamase resistance gene (AmpR), an F1 origin of replication, a Cytomegalovirus immediate-early enhancer/promoter region (CMV), and an SV40 late polyadenylation signal (SV40). The expression vector also has an internal ribosome entry site (IRES) from the ECMV virus (Clontech) and the mouse dihydrofolate reductase (DHFR) gene.

2. Expression

Soluble hyaluronidase polypeptides can be produced by any method known to those of skill in the art including in vivo and in vitro methods. Desired proteins can be expressed in any organism suitable to produce the required amounts and forms of the proteins, such as for example, needed for administration and treatment. Expression hosts include prokaryotic and eukaryotic organisms such as E. coli, yeast, plants, insect cells, mammalian cells, including human cell lines and transgenic animals. Expression hosts can differ in their protein production levels as well as the types of post-translational modifications that are present on the expressed proteins. The choice of expression host can be made based on these and other factors, such as regulatory and safety considerations, production costs and the need and methods for purification.

Many expression vectors are available and known to those of skill in the art and can be used for expression of proteins. The choice of expression vector will be influenced by the choice of host expression system. In general, expression vectors can include transcriptional promoters and optionally enhancers, translational signals, and transcriptional and translational termination signals. Expression vectors that are used for stable transformation typically have a selectable marker which allows selection and maintenance of the transformed cells. In some cases, an origin of replication can be used to amplify the copy number of the vector.

Soluble hyaluronidase polypeptides also can be utilized or expressed as protein fusions. For example, an enzyme fusion can be generated to add additional functionality to an enzyme. Examples of enzyme fusion proteins include, but are not limited to, fusions of a signal sequence, a tag such as for localization, e.g. a $his_6$ tag or a myc tag, or a tag for purification, for example, a GST fusion, and a sequence for directing protein secretion and/or membrane association.

a. Prokaryotic Cells

Prokaryotes, especially E. coli, provide a system for producing large amounts of proteins. Transformation of E. coli is simple and rapid technique well known to those of skill in the art. Expression vectors for E. coli can contain inducible promoters, such promoters are useful for inducing high levels of protein expression and for expressing proteins that exhibit some toxicity to the host cells. Examples of inducible promoters include the lac promoter, the trp promoter, the hybrid tac promoter, the T7 and SP6 RNA promoters and the temperature regulated APL promoter.

Proteins, such as any provided herein, can be expressed in the cytoplasmic environment of E. coli. The cytoplasm is a reducing environment and for some molecules, this can result in the formation of insoluble inclusion bodies. Reducing agents such as dithiothreitol and β-mercaptoethanol and denaturants, such as guanidine-HCl and urea can be used to resolubilize the proteins. An alternative approach is the expression of proteins in the periplasmic space of bacteria which provides an oxidizing environment and chaperonin-like and disulfide isomerases and can lead to the production of soluble protein. Typically, a leader sequence is fused to the protein to be expressed which directs the protein to the periplasm. The leader is then removed by signal peptidases inside the periplasm. Examples of periplasmic-targeting leader sequences include the pelB leader from the pectate lyase gene and the leader derived from the alkaline phosphatase gene. In some cases, periplasmic expression allows leakage of the expressed protein into the culture medium. The secretion of proteins allows quick and simple purification from the culture supernatant. Proteins that are not secreted can be obtained from the periplasm by osmotic lysis. Similar to cytoplasmic expression, in some cases proteins can become insoluble and denaturants and reducing agents can be used to facilitate solubilization and refolding. Temperature of induction and growth also can influence expression levels and solubility, typically temperatures between 25° C. and 37° C. are used. Typically, bacteria produce aglycosylated proteins. Thus, if proteins require glycosylation for function, glycosylation can be added in vitro after purification from host cells.

b. Yeast Cells

Yeasts such as Saccharomyces cerevisae, Schizosaccharomyces pombe, Yarrowia lipolytica, Kluyveromyces lactis and Pichia pastoris are well known yeast expression hosts that can be used for production of proteins, such as any described herein. Yeast can be transformed with episomal replicating vectors or by stable chromosomal integration by homologous recombination. Typically, inducible promoters are used to regulate gene expression. Examples of such promoters include GAL1, GALT and GALS and metallothionein promoters, such as CUP1, AOX1 or other Pichia or other yeast promoter. Expression vectors often include a selectable marker such as LEU2, TRP1, HIS3 and URA3 for selection and maintenance of the transformed DNA. Proteins expressed in yeast are often soluble. Co-expression with chaperonins such as Bip and protein disulfide isomerase can improve expression levels and solubility. Additionally, proteins expressed in yeast can be directed for secretion using secretion signal peptide fusions such as the yeast mating type alpha-factor secretion signal from Saccharomyces cerevisae and fusions with yeast cell surface proteins such as the Aga2p mating adhesion receptor or the Arxula adeninivorans glucoamylase. A protease cleavage site such as for the Kex-2 protease, can be engineered to remove the fused sequences from the expressed polypeptides as they exit the secretion pathway. Yeast also is capable of glycosylation at Asn-X-Ser/Thr motifs.

c. Insect Cells

Insect cells, particularly using baculovirus expression, are useful for expressing polypeptides such as hyaluronidase polypeptides. Insect cells express high levels of protein and are capable of most of the post-translational modifications used by higher eukaryotes. Baculovirus have a restrictive host range which improves the safety and reduces regulatory concerns of eukaryotic expression. Typical expression vectors use a promoter for high level expression such as the polyhedrin promoter of baculovirus. Commonly used baculovirus systems include the baculoviruses such as Autographa californica nuclear polyhedrosis virus (AcNPV), and the Bombyx morn nuclear polyhedrosis virus (BmNPV) and an insect cell line such as Sf9 derived from Spodoptera frugiperda, Pseudaletia unipuncta (A7S) and Danaus plexippus (DpN1). For high-level expression, the nucleotide sequence of the molecule to be expressed is fused immediately downstream of the polyhedrin initiation codon of the virus. Mammalian secretion signals are accurately processed in insect cells and can be used to secrete the expressed protein into the culture medium. In addition, the cell lines Pseudaletia unipuncta (A7S) and Danaus plexippus (DpN1) produce proteins with glycosylation patterns similar to mammalian cell systems.

An alternative expression system in insect cells is the use of stably transformed cells. Cell lines such as the Schneider 2 (S2) and Kc cells (Drosophila melanogaster) and C7 cells (Aedes albopictus) can be used for expression. The Drosophila metallothionein promoter can be used to induce high levels of expression in the presence of heavy metal induction with cadmium or copper. Expression vectors are typically maintained by the use of selectable markers such as neomycin and hygromycin.

d. Mammalian Cells

Mammalian expression systems can be used to express proteins including soluble hyaluronidase polypeptides. Expression constructs can be transferred to mammalian cells by viral infection such as adenovirus or by direct DNA transfer such as liposomes, calcium phosphate, DEAE-dextran and by physical means such as electroporation and microinjection. Expression vectors for mammalian cells typically include an mRNA cap site, a TATA box, a translational initiation sequence (Kozak consensus sequence) and polyadenylation elements. IRES elements also can be added to permit bicistronic expression with another gene, such as a selectable marker. Such vectors often include transcriptional promoter-enhancers for high-level expression, for example the SV40 promoter-enhancer, the human cytomegalovirus (CMV) promoter and the long terminal repeat of Rous sarcoma virus (RSV). These promoter-enhancers are active in many cell types. Tissue and cell-type promoters and enhancer regions also can be used for expression. Exemplary promoter/enhancer regions include, but are not limited to, those from genes such as elastase I, insulin, immunoglobulin, mouse mammary tumor virus, albumin, alpha fetoprotein, alpha 1 antitrypsin, beta globin, myelin basic protein, myosin light chain 2, and gonadotropic releasing hormone gene control. Selectable markers can be used to select for and maintain cells with the expression construct. Examples of selectable marker genes include, but are not limited to, hygromycin B phosphotransferase, adenosine deaminase, xanthine-guanine phosphoribosyl transferase, aminoglycoside phosphotransferase, dihydrofolate reductase (DHFR) and thymidine kinase. For example, expression can be performed in the presence of methotrexate to select for only those cells expressing the DHFR gene. Fusion with cell surface signaling molecules such as TCR-ζ and $Fc_{\epsilon}RI-_{\gamma}$ can direct expression of the proteins in an active state on the cell surface.

Many cell lines are available for mammalian expression including mouse, rat human, monkey, chicken and hamster cells. Exemplary cell lines include but are not limited to CHO, Balb/3T3, HeLa, MT2, mouse NSO (nonsecreting) and other myeloma cell lines, hybridoma and heterohybridoma cell lines, lymphocytes, fibroblasts, Sp2/0, COS, NIH3T3, HEK293, 293S, 2B8, and HKB cells. Cell lines also are available adapted to serum-free media which facilitates purification of secreted proteins from the cell culture media. Examples include CHO-S cells (Invitrogen, Carlsbad, Calif., cat #11619-012) and the serum free EBNA-1 cell line (Pham et al., (2003) Biotechnol. Bioeng. 84:332-42.). Cell lines also are available that are adapted to grow in special mediums optimized for maximal expression. For example, DG44 CHO cells are adapted to grow in suspension culture in a chemically defined, animal product-free medium.

e. Plants

Transgenic plant cells and plants can be used to express proteins such as any described herein. Expression constructs are typically transferred to plants using direct DNA transfer such as microprojectile bombardment and PEG-mediated transfer into protoplasts, and with agrobacterium-mediated transformation. Expression vectors can include promoter and enhancer sequences, transcriptional termination elements and translational control elements. Expression vectors and transformation techniques are usually divided between dicot hosts, such as Arabidopsis and tobacco, and monocot hosts, such as corn and rice. Examples of plant promoters used for expression include the cauliflower mosaic virus promoter, the nopaline synthase promoter, the ribose bisphosphate carboxylase promoter and the ubiquitin and UBQ3 promoters. Selectable markers such as hygromycin, phosphomannose isomerase and neomycin phosphotransferase are often used to facilitate selection and maintenance of transformed cells. Transformed plant cells can be maintained in culture as cells, aggregates (callus tissue) or regenerated into whole plants. Transgenic plant cells also can include algae engineered to produce hyaluronidase polypeptides. Because plants have different glycosylation patterns than mammalian cells, this can influence the choice of protein produced in these hosts.

3. Purification Techniques

Method for purification of polypeptides, including soluble hyaluronidase polypeptides or other proteins, from host cells will depend on the chosen host cells and expression systems. For secreted molecules, proteins are generally purified from the culture media after removing the cells. For intracellular expression, cells can be lysed and the proteins purified from the extract. When transgenic organisms such as transgenic plants and animals are used for expression, tissues or organs can be used as starting material to make a lysed cell extract. Additionally, transgenic animal production can include the production of polypeptides in milk or eggs, which can be collected, and if necessary, the proteins can be extracted and further purified using standard methods in the art.

Proteins, such as soluble hyaluronidase polypeptides, can be purified using standard protein purification techniques known in the art including but not limited to, SDS-PAGE, size fraction and size exclusion chromatography, ammonium sulfate precipitation and ionic exchange chromatography, such as anion exchange. Affinity purification techniques also can be utilized to improve the efficiency and purity of the preparations. For example, antibodies, receptors and other molecules that bind hyaluronidase enzymes can be used in affinity purification. Expression constructs also can be engineered to add an affinity tag to a protein such as a myc epitope, GST fusion or $His_6$ and affinity purified with myc antibody, glutathione resin and Ni-resin, respectively. Purity can be assessed by any method known in the art including gel electrophoresis and staining and spectrophotometric techniques.

F. Preparation, Formulation and Administration of Immune Globulins and Soluble Hyaluronidase Polypeptides Pharmaceutical compositions of immune globulins and soluble hyaluronidases are provided herein for subcutaneous administration. Formulations of pharmaceutical compositions of soluble hyaluronidases, for example, PH20, are known in the art (see e.g. published U.S. Application Nos. US20040268425, US20050260186 and US20060104968). Soluble hyaluronidases are co-formulated or co-administered with pharmaceutical formulations of immune globulin to enhance the delivery of immune globulins to desired sites within the body by increasing the bioavailability of immune globulins. For example, co-administration or co-formulation of IG with a hyaluronidase can improve the extent and/or rate of absorption and thus bioavailability of an agent by causing more of it to reach the bloodstream and/or less of it being degraded after administration by more rapid permeation. Increased absorption and bioavailability can be achieved, for example, by accelerating interstitial flow and potentially connective transport following administration by applying hydrostatic pressure associated with the volume injection combined with a reduction in impedance to flow associated with degradation of hyaluronan. Thus, soluble hyaluronidases can be used to achieve elevated and/or more rapidly achieved concentrations of the immune globulin following subcutaneous administration compared to conventional methods of subcutaneous administration, to provide, for example, a more potent and/or more rapid response for a given dose. Alternatively, the soluble hyaluronidase can be used to allow a given response to be achieved with a lower dose of administered IG. The ability of a soluble hyaluronidase to enhance bulk fluid flow at and near a site of injection or infusion also can improve other aspects of associated pharmacologic delivery. For example, the increase in bulk fluid flow can help to allow the volume of fluid injected to be more readily dispersed from the site of injection (reducing potentially painful or other adverse consequences of injection). This is particularly important for subcutaneous infusions to permit higher doses to be administered. In addition to increased bioavailability, co-administration or co-formulation of IG with soluble hyaluronidase provides for a safer or more convenient route of administration compared to conventional intravenous routes of administration.

Thus, by virtue of the increased bioavailability, immune globulins can be administered subcutaneously at dosages and frequencies for which current intravenous (IVIG) preparations are prepared and administered. The advantages over current subcutaneous formulations of IG is that co-administered or co-formulated hyaluronidase/IG can result in more favorable dosing regimens, for example, less frequent dosing. By less frequent or lower dosing, side effects associated with toxicity can be reduced. Generally, the pharmacokinetic and/or phannacodynamics of subcutaneous IG therapy is improved. In addition, subcutaneous administrations of IG also has advantages over current intravenous infusions. For example, subcutaneous infusion permits infusion by the patient or family as opposed to a skilled nurse; infusion can be achieved at higher rates such that IG is infused in 1-3 hours compared to 5-10 hours for conventional IVIG therapies; there is no requirement for functional veins; there is no infusion related side effects such as thrombosis, headache, thrombophlebitis, and nausea and less probability of adverse events; and infusion can be performed at home or anywhere.

The compositions can be formulated in lyophilized or liquid form. Where the compositions are provided in lyophilized form they can be reconstituted just prior to use by an appropriate buffer, for example, a sterile saline solution. The compositions can be provided together or separately. For purposes herein, such compositions typically are provided separately. The soluble hyaluronidase and IG can be packaged as separate compositions for administration together, sequentially or intermittently. The combinations can be packaged as a kit.

1. Formulations

The compounds can be formulated into any suitable pharmaceutical preparations for subcutaneous administration such as solutions, suspensions, powders, or sustained release formulations. Typically, the compounds are formulated into pharmaceutical compositions using techniques and procedures well known in the art (see e.g., Ansel Introduction to Pharmaceutical Dosage Forms, Fourth Edition, 1985, 126). Pharmaceutically acceptable compositions are prepared in view of approvals for a regulatory agency or other agency prepared in accordance with generally recognized pharmacopeia for use in animals and in humans. The formulation should suit the mode of administration.

Pharmaceutical compositions can include carriers such as a diluent, adjuvant, excipient, or vehicle with which a hyaluronidase or IG is administered. Examples of suitable pharmaceutical carriers are described in "Remington's Pharmaceutical Sciences" by E. W. Martin. Such compositions will contain a therapeutically effective amount of the compound, generally in purified form or partially purified form, together with a suitable amount of carrier so as to provide the form for proper administration to the patient. Such pharmaceutical carriers can be sterile liquids, such as water and oils, including those of petroleum, animal, vegetable or synthetic origin, such as peanut oil, soybean oil, mineral oil, and sesame oil. Water is a typical carrier when the pharmaceutical composition is administered intravenously. Saline solutions and aqueous dextrose and glycerol solutions also can be employed as liquid carriers, particularly for injectable solutions. Compositions can contain along with an active ingredient: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polyvinylpyn-°lidine, celluloses and derivatives thereof, povidone, crospovidones and other such binders known to those of skill in the art. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, and ethanol. A composition, if desired, also can contain minor amounts of wetting or emulsifying agents, or pH buffering agents, for example, acetate, sodium citrate, cyclodextrine derivatives, sorbitan monolaurate, triethanolamine sodium acetate, triethanolamine oleate, and other such agents.

Pharmaceutically therapeutically active compounds and derivatives thereof are typically formulated and administered in unit dosage forms or multiple dosage forms. Each unit dose contains a predetermined quantity of therapeutically active compound sufficient to produce the desired therapeutic effect, in association with the required pharmaceutical carrier, vehicle or diluent. Examples of unit dose forms include ampoules and syringes and individually packaged tablets or capsules. Unit dose forms can be administered in fractions or multiples thereof. A multiple dose form is a plurality of identical unit dosage forms packaged in a single container to be administered in segregated unit dose form. Examples of multiple dose forms include vials, bottles of tablets or capsules or bottles of pints or gallons. Hence, multiple dose form is a multiple of unit doses that are not segregated in packaging. Generally, dosage forms or compositions, containing active ingredient in the range of 0.005% to 100% with the balance made up from non-toxic carrier can be prepared.

Compositions provided herein typically are formulated for administration by subcutaneous route, although other routes of administration are contemplated, such as any route known to those of skill in the art including intramuscular, intravenous, intradermal, intralesional, intraperitoneal injection, epidural, nasal, oral, vaginal, rectal, topical, local, otic, inhalational, buccal (e.g., sublingual), and transdermal administration or any route. Formulations suited for such routes are known to one of skill in the art. Administration can be local, topical or systemic depending upon the locus of treatment. Local administration to an area in need of treatment can be achieved by, for example, but not limited to, local infusion during surgery, topical application, e.g., in conjunction with a wound dressing after surgery, by injection, by means of a catheter, by means of a suppository, or by means of an implant. Compositions also can be administered with other biologically active agents, either sequentially, intermittently or in the same composition. Administration also can include controlled release systems including controlled release formulations and device controlled release, such as by means of a pump.

The most suitable route in any given case depends on a variety of factors, such as the nature of the disease, the progress of the disease, the severity of the disease the particular composition which is used. For purposes herein, it is desired that hyaluronidases are administered so that they reach the interstitium of skin or tissues, thereby degrading the interstitial space for subsequent delivery of immunoglobulin. Thus, direct administration under the skin, such as by subcutaneous administration methods, is contemplated. Thus, in one example, local administration can be achieved by injection, such as from a syringe or other article of manufacture containing a injection device such as a needle. In another example, local administration can be achieved by infusion, which can be facilitated by the use of a pump or other similar device. Other modes of administration also are contemplated. Pharmaceutical composition can be formulated in dosage forms appropriate for each route of administration.

Subcutaneous administration, generally characterized by injection or infusion, is contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. The pharmaceutical compositions may contain other minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e. g., U.S. Pat. No. 3,710,795) is also contemplated herein. The percentage of active compound contained in such compositions is highly dependent on the specific nature thereof, as well as the activity of the compound and the needs of the subject.

Injectables are designed for local and systemic administration. For purposes herein, local administration is desired for direct administration to the affected interstitium. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous. If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers, which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEENs 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art. The unit-dose parenteral preparations are packaged in an ampoule, a vial or a syringe with a needle. The volume of liquid solution or reconstituted powder preparation, containing the pharmaceutically active compound, is a function of the disease to be treated and the particular article of manufacture chosen for package. All preparations for parenteral administration must be sterile, as is known and practiced in the art.

In one example, pharmaceutical preparation can be in liquid form, for example, solutions, syrups or suspensions. If provided in liquid form, the pharmaceutical preparations can be provided as a concentrated preparation to be diluted to a therapeutically effective concentration before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). In another example, pharmaceutical preparations can be presented in lyophilized form for reconstitution with water or other suitable vehicle before use.

Administration methods can be employed to decrease the exposure of selected compounds to degradative processes, such as proteolytic degradation and immunological intervention via antigenic and immunogenic responses. Examples of such methods include local administration at the site of treatment. Pegylation of therapeutics has been reported to increase resistance to proteolysis, increase plasma half-life, and decrease antigenicity and immunogenicity. Examples of pegylation methodologies are known in the art (see for example, Lu and Felix, Int. J. Peptide Protein Res., 43: 127-138, 1994; Lu and Felix, Peptide Res., 6: 142-6, 1993; Felix et al., Int. J. Peptide Res., 46: 253-64, 1995; Benhar et al., J. Biol. Chem., 269: 13398-404, 1994; Brumeanu et al., J Immunol., 154: 3088-95, 1995; see also, Caliceti et al. (2003) Adv. Drug Deily. Rev. 55(10):1261-77 and Molineux (2003) Pharmacotherapy 23 (8 Pt 2):3S-8S). Pegylation also can be used in the delivery of nucleic acid molecules in vivo. For example, pegylation of adenovirus can increase stability and gene transfer (see, e.g., Cheng et al. (2003) Pharm. Res. 20(9): 1444-51).

Lyophilized Powders

Of interest herein are lyophilized powders, which can be reconstituted for administration as solutions, emulsions and other mixtures. They may also be reconstituted and formulated as solids or gels.

The sterile, lyophilized powder is prepared by dissolving an active compound in a buffer solution. The buffer solution may contain an excipient which improves the stability or other pharmacological component of the powder or reconstituted solution, prepared from the powder. Subsequent sterile filtration of the solution followed by lyophilization under standard conditions known to those of skill in the art provides the desired formulation. Briefly, the lyophilized powder is prepared by dissolving an excipient, such as dextrose, sorbital, fructose, corn syrup, xylitol, glycerin, glucose, sucrose or other suitable agent, in a suitable buffer, such as citrate, sodium or potassium phosphate or other such buffer known to those of skill in the art. Then, a selected enzyme is added to the resulting mixture, and stirred until it dissolves. The resulting mixture is sterile filtered or treated to remove particulates and to insure sterility, and apportioned into vials for lyophilization. Each vial will contain a single dosage or multiple dosages of the compound. The lyophilized powder can be stored under appropriate conditions, such as at about 4° C. to room temperature. Reconstitution of this lyophilized powder with a buffer solution provides a formulation for use in parenteral administration.

2. Dosage and Administration

The soluble hyaluronidase provided herein can be formulated as pharmaceutical compositions, typically for single dosage administration, in combination with IG. The selected soluble hyaluronidase is included in an amount sufficient to exert a therapeutically useful effect of the IG in the absence of undesirable side effects on the patient treated. The therapeutically effective concentration can be determined empirically by testing the polypeptides in known in vitro and in vivo systems such as by using the assays provided herein or known in the art (see e.g., Taliani et al. (1996) Anal. Biochem., 240: 60-67; Filocamo et al. (1997) J Virology, 71: 1417-1427; Sudo et al. (1996) Antiviral Res. 32: 9-18; Buffard et al. (1995) Virology, 209:52-59; Bianchi et al. (1996) Anal. Biochem., 237: 239-244; Hamatake et al. (1996) Intervirology 39:249-258; Steinkuhler et al. (1998) Biochem., 37:8899-8905; D'Souza et al. (1995) J Gen. Virol., 76:1729-1736; Takeshita et al. (1997) Anal. Biochem., 247:242-246; see also e.g, Shimizu et al. (1994) J. Virol. 68:8406-8408; Mizutani et al. (1996) J. Virol. 70:7219-7223; Mizutani et al. (1996) Biochem. Biophys. Res. Conunun., 227:822-826; Lu et al. (1996) Proc. Natl. Acad. Sci (USA), 93:1412-1417; Hahm et al., (1996) Virology, 226:318-326; Ito et al. (1996) J. Gen. Virol., 77:1043-1054; Mizutani et al. (1995) Biochem. Biophys. Res. Commun., 212:906-911; Cho et al. (1997) J. Virol. Meth. 65:201-207 and then extrapolated therefrom for dosages for humans.

Typically, a therapeutically effective dose is at or about 500 Units to 100,000 Units of a soluble hyaluronidase. For example, soluble hyaluronidase can be administered subcutaneously at or about 500 Units, 1000 Units, 2000 Units, 5000 Units, 10,000 Units, 30,000 Units, 40,000 Units, 50,000 Units, 60,000 Units, 70,000 Units, 80,000 Units, 90,000 Units, 100,000 Units or more. In some examples, dosages can be provided as a ratio IG administered. For example, hyaluronidase can be administered at 10 U/gram to 500 U/g or more of IG, for example, at or about 10 U/g, 20 U/g, 30 U/g, 40 U/g, 50 U/g, 60 U/g, 70 U/g, 80 U/g, 90 U/g, 100 U/g, 150 U/g, 200 U/g, 300 U/g, 400 U/g, 500 U/g or more. Typically, volumes of injections or infusions of hyaluronidase contemplated herein are from at or about 0.5 ml, 1 ml, 2 ml, 3 ml, 4 ml, 5 ml, 6 ml, 7 ml, 8 ml, 9 ml, 10 ml, 15 ml, 20 ml, 30 ml, 40 ml, 50 ml or more. The hyaluronidase can be provided as a stock solution at or about 50 U/ml, 100 U/ml, 150 U/ml, 200 U/ml, 400 U/ml or 500 U/ml or can be provided in a more concentrated fonn, for example at or about 1000 U/ml, 1500 Units/ml, 2000 U/ml, 4000 U/ml or 5000 U/ml for use directly or for dilution to the effective concentration prior to use. The soluble hyaluronidase can be provided as a liquid or lyophilized formulation. Lyophilized fonnulations are ideal for storage of large Units doses of soluble hyaluronidase.

The immune globulin preparations provided herein can be formulated as pharmaceutical compositions for single or multiple dosage use. Generally, the IG preparations are formulated in pharmaceutical compositions to achieve dosage regimes (doses and frequencies) for which current intravenous (IVIG) preparations are prepared and administered for particular IG-treatable diseases or conditions. One of skill in the art is familiar with dosage regimes for IVIG administration of particular diseases or conditions. For example, Section H below provides exemplary dosage regimes (doses and frequencies) of IG for particular diseases and conditions. Other dosage regimes are well known to those of skill in the art. In some examples, the dosage frequency can be daily over an interval of time given over consecutive or alternate days, for example, 1, 2, 3, 4, 5, 6, 7, 8, 9, 10 or more days. In other examples, the dosage regime is weekly, for example, once every week, every two weeks, every three weeks, every four weeks, every five weeks, every six weeks or more. Typically, immune globulin preparations are formulated for single dose administration in an amount sufficient to provide a once monthly dose, but can be provided in lesser amounts for multiple dosage administrations. For example, once monthly doses of IG preparations can be administered daily, weekly, biweekly or once a month. Dosage regimes can be continued for months or years. The IG preparations can be provided in lyophilized or liquid form as discussed elsewhere herein.

The immune globulin is provided in a therapeutically effective dose. Therapeutically effective concentration can be determined empirically by testing the compounds in known in vitro and in vivo systems, such as the assays provided herein. The concentration of a selected immune globulin in the composition depends on absorption, inactivation and excretion rates of the complex, the physicochemical characteristics of the complex, the dosage schedule, and amount administered as well as other factors known to those of skill in the art. For example, it is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope thereof. The amount of a selected immune globulin preparation to be administered for the treatment of a disease or condition, for example an IG-treatable disease or condition, can be determined by standard clinical techniques. In addition, in vitro assays and animal models can be employed to help identify optimal dosage ranges.

Hence, the precise dosage, which can be determined empirically, can depend on the particular immune globulin preparation, the regime and dosing schedule with the soluble hyaluronidase, the route of administration, the type of disease to be treated and the seriousness of the disease. Generally, the IG preparations have a protein concentration that is or is about 5 to 15% w/v, 6 to 15% w/v, or 8 to 12% w/v of IG composition, such as, for example, 10% w/v. For example, IG is provided in an amount that permits subcutaneous administration of a dose equivalent to a once monthly IV dose for the particular indication being treated. The particular once monthly IV dose is a function of the disease to be treated, and thus can vary. Exemplary dosages ranges for subcutaneous administration of IG are from at or about 1 gram (g), 5 g, 10 g, 20 g, 30 g, 40 g, 50 g, 60 g, 70 g, 80 g, 90 g, 100 g or 200 g. The particular dosage and formulation thereof depends upon the indication and individual. For example, dosages can be administered at 50 mg/kg body weight (BW), 100 mg/kg BW, 200 mg/kg BW, 300 mg/kg BW, 400 mg/kg BW, 500 mg/kg BW, 600 mg/kg BW, or more. If necessary dosage can be empirically determined. To achieve such dosages, volumes of IG preparations administered subcutaneously can be at or about 50 ml, 100 ml, 200 ml, 300 ml, 400 ml, 500 ml, 600 ml, 700 ml or more. For example, a 10% liquid IG formulation (100 mg/ml) for indications described herein can be administered in a volume of 50 ml to 700 ml to achieve a dosage of 0.5 g to 70 g of IG.

Where large volumes are administered, administration is typically by infusion. Subjects can be dosed at rates of infusion at or about 0.5 ml/kg/BW/h, 1 ml/kg/BW/h, 2 ml/kg/BW/h, 3 ml/kg/BW/h, 4 ml/kg/BW/h, or 5 ml/kg/BW/h. The infusion rate can be empirically determined, and typically is a function of the tolerability of the subject. If an adverse reaction occurs during the infusion, the rate of infusion can be slowed to the rate immediately below that at which the adverse event occurred. If the adverse event resolves in response to the reduction in rate, the infusion rate can be slowly increased at the discretion of the physician. Subcutaneous IG infusion can be facilitated by gravity, pump infusion or injection of a full 20-30 gram dose. Generally, for infusions intravenous infusion pumps can be employed. IG can be infused at rates at or about 5 ml/h, 10 ml/h, 30 ml/h, 60 ml/h, 120 ml/h, 240 ml/h or 300 ml/h. Infusion rates can be increased during the course of treatment so long as the infusion is tolerated by the patient. Generally, time of administration of infusion is at or about 0.5 h, 1 h, 1.5 h, 2 h, 2.5 h, 3 h, 4 h or more. Due to the high rate of infusion achieved by subcutaneous administration of IG coformulated and/or co-administered with hyaluronidase, the time of infusion is significantly less than for conventional IVIG therapies. Where infusion time exceeds the desired limit, a second infusion site can be started at the physician and subject's discretion. The second site typically is started at least 10 cm from the initial site.

Techniques for infusion are known to one of skill in the art, and are within the skill of a treating physician. Generally, the appropriate dose of IG can be pooled into a standard IV bag. For example, a non-vented infusion set can be used that has a Y-port near its terminus. A 24-gauge subcutaneous infusion needle can be inserted at a site of the subject's preferences, but the abdomen and secondarily the thighs are recommended because of the volume of solution to be infused. The hyaluronidase and IG can be provided in the same Y port apparatus. Other articles of manufacture also can be used herein for purposes of infusion by gravity or a pump, and include, but are not limited to tubes, bottles, syringes or other containers.

The soluble hyaluronidase can be administered subsequently, intermittently or simultaneously from the IG preparation. Generally, the hyaluronidase is administered prior to administration of the IG preparation to permit the hyaluronidase to degrade the hyaluronic acid in the interstitial space. For example, the soluble hyaluronidase can be administered 1 minute, 2 minute, 3 minute, 4 minute, 5 minute, 6 minute, 7 minutes, 8 minutes, 9 minutes, 10 minutes, 20 minutes or 30 minutes prior to administration of the IG preparation. In some examples, the hyaluronidase is administered together with the immune globulin preparation. As will be appreciated by those of skill in the art, the desired proximity of co-administration depends in significant part on the effective half lives of the agents in the particular tissue setting, and the particular disease being treated, and can be readily optimized by testing the effects of administering the agents at varying times in suitable models, such as in suitable animal models. In some situations, the optimal timing of administration of the hyaluronidase will exceed 60 minutes.

Generally, prior to infusion of IG, a soluble hyaluronidase is injected at a rate of at or about 0.2 ml/min, 0.5 ml/min, 1 ml/min. 2 ml/min, 5 ml/min, 10 ml/min or more. For example, the soluble hyaluronidase can be injected through the same Y-port used for subsequent infusion of IG. As noted above, the volume of soluble hyaluronidase administered is a function of the dosage required, but can be varied depending on the concentration of a soluble hyaluronidase stock formulation available. For example, it is contemplated herein that soluble hyaluronidase is not administered in volumes greater than about 50 ml, and typically is administered in a volume of 5-30 ml. A syringe pump can be used for the higher volumes, at the discretion of the physician.

In the event that an infusion is not tolerated (e.g., it causes moderate to severe local reactions), a second infusion site can be started so that the subject receives the full dosage.

An IG preparation can be administered at once, or can be divided into a number of smaller doses to be administered at intervals of time. Selected IG preparations can be administered in one or more doses over the course of a treatment time for example over several hours, days, weeks, or months. In some cases, continuous administration is useful. It is understood that the precise dosage and course of administration depends on the indication and patients tolerability.

Also, it is understood that the precise dosage and duration of treatment is a function of the disease being treated and can be determined empirically using known testing protocols or by extrapolation from in vivo or in vitro test data. It is to be noted that concentrations and dosage values also can vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or use of compositions and combinations containing them. The compositions can be administered hourly, daily, weekly, monthly, yearly or once. Generally, dosage regimens are chosen to limit toxicity. It should be noted that the attending physician would know how to and when to terminate, interrupt or adjust therapy to lower dosage due to toxicity, or bone marrow, liver or kidney or other tissue dysfunctions. Conversely, the attending physician would also know how to and when to adjust treatment to higher levels if the clinical response is not adequate (precluding toxic side effects).

G. Methods of Assessing Activity, Bioavailability and Pharmacokinetics

Assays can be used to assess the in vitro and in vivo activities of immune globulin alone or in combination with a soluble hyaluronidase. Included among such assays are those that assess the pharmacokinetic properties of subcutaneously-administered immune globulin, including bioavailability, and tolerability. The biological activity of both immune globulin and hyaluronidase also can be assessed using assays well known in the art. Such assays can be used, for example, to determine appropriate dosages of immune globulin and hyaluronidase, and the frequency of dosing, for treatment.

1. Pharmacokinetics and Tolerability

Pharmacokinetic and tolerability studies, such as those described in Examples 1, below, can be performed using animal models or can be performed during clinical studies with patients. Animal models include, but are not limited to, mice, rats, rabbits, dogs, guinea pigs and non-human primate models, such as cynomolgus monkeys or rhesus macaques. In some instances, pharmacokinetic and tolerability studies are performed using healthy animals. In other examples, the studies are performed using animal models of a disease for which therapy with immune globulin is considered, such as animal models of any of the diseases and conditions described below.

The pharmacokinetics of subcutaneously administered immune globulin can be assessed by measuring such parameters as the maximum (peak) plasma immune globulin concentration ($C_{max}$), the peak time (i.e. when maximum plasma immune globulin concentration occurs; $T_{max}$), the minimum plasma immune globulin concentration (i.e. the minimum plasma concentration between doses of immune globulin; $C_{min}$), the elimination half-life ($T_{1/2}$) and area under the curve (i.e. the area under the curve generated by plotting time versus plasma inunune globulin concentration; AUC), following administration. The absolute bioavailability of subcutaneously administered immune globulin is determined by comparing the area under the curve of immune globulin following subcutaneous delivery ($AUC_{sc}$) with the AUC of immune globulin following intravenous delivery ($AUC_{iv}$). Absolute bioavailability (F), can be calculated using the formula: $F=([AUC]_{sc}\times dose_{sc})/([AUC]_{iv}\times dose_{iv})$. The concentration of in globulin in the plasma following subcutaneous administration can be measured using any method known in the art suitable for assessing concentrations of inunune globulin in samples of blood. Exemplary methods include, but are not limited to, ELISA and nephelometry.

A range of doses and different dosing frequency of dosing can be administered in the pharmacokinetic studies to assess the effect of increasing or decreasing concentrations of immune globulin and/or hyaluronidase in the dose. Pharmacokinetic properties of subcutaneously administered immune globulin, such as bioavailability, also can be assessed with or without co-administration of hyaluronidase. For example, dogs, such as beagles, can be administered imnnme globulin subcutaneously in combination with hyaluronidase, or alone. Intravenous doses of immune globulin also are given to another group of beagles. Blood samples can then be taken at various time points and the amount of immune globulin in the plasma determine, such as by nephelometry. The AUC can then be measured and the bioavailability of subcutaneously administered immune globulin administered with or without hyaluronidase can be determined. Such studies can be performed to assess the effect of co-administration with hyaluronidase on pharmacokinetic properties, such as bioavailability, of subcutaneously administered immune globulin.

Studies to assess safety and tolerability also are known in the art and can be used herein. Following subcutaneous administration of immune globulin, with or without co-administration of hyaluronidase, the development of any adverse reactions can be monitored. Adverse reactions can include, but are not limited to, injection site reactions, such as edema or swelling, headache, fever, fatigue, chills, flushing, dizziness, urticaria, wheezing or chest tightness, nausea, vomiting, rigors, back pain, chest pain, muscle cramps, seizures or convulsions, changes in blood pressure and anaphylactic or severe hypersensitivity responses. Typically, a range of doses and different dosing frequencies are be administered in the safety and tolerability studies to assess the effect of increasing or decreasing concentrations of immune globulin and/or hyaluronidase in the dose.

2. Biological Activity a. Immune Globulin

The ability of immune globulin to act as a therapeutic agent can be assessed in vitro or in vivo. For example, in vitro assays can be performed to assess the ability of inunune globulin to neutralize viral or bacterial infectivity (Hiemstra et al., (1994) J Lab Clin Med 123:241-6). Other in vitro assays can be utilized to assess other biological activities of immune globulin. For example, the ability of immune globulin preparations to interact with and modulate complement activation products, bind idiotypic antibody, bind Fc receptors on macrophages, and suppress various inflammatory mediators including cytokines, chemokines, and metalloproteinases, can be assessed using any method known in the art, including, but not limited to, ELISA, Western blot, Northern blot, and flow cytometry to assess marker expression. For example, the effect of immune globulin on the expression of chemokine receptors on peripheral blood mononuclear cells can be assessed using flow cytomtery (Trebst et al., (2006) Eur J Neurology). In another example, the effect of immune globulin on metalloproteinase expression in macrophages can be assessed using Northern blot analysis (Shapiro et al., (2002) Cancer 95:2032-2037).

In vivo studies using animal models also can be performed to assess the therapeutic activity of immune globulin. Irnmune globulin can be administered to animal models infected with one or more microorganisms and the effect on progression of infection can be assessed, such as by measuring the number of microorganisms or measuring weight as a marker of morbidity. The therapeutic effect of immune globulin also can be assessed using animal models of the diseases and conditions for which therapy using immune globulin is considered. Such animal models are known in the art, and include, but are not limited to, small animal models for X-linked agammaglobulinemia (XLA), SCID, Wiskott-Aldrich syndrome, Kawasaki disease, Guillain-Barré syndrome, ITP, polymyositis, Lambert-Eaton myasthenic syndrome, Myasthenia gravis and Moersch-Woltmann syndrome (Czitrom et al (1985) J Immunol 134:2276-2280, Ellmeier et al., (2000) J Exp Med. 192: 1611-1624, Ohno (2006) Drug Discovery Today: Disease Models 3:83-89, Oyaizu et al (1988) J Exp Med 2017-2022, Hansen et al., (2002) Blood 100:2087-2093, Strongwater et al., (1984) Arthritis Rheum. 27:433-42, Kim et al. (1998) Annals NY Acad Sci 841:670-676, Christadoss et al. (2000) 94:75-87, Sommer et al., (2005)

Lancet 365:1406-1411, U.S. Pat. No. 7,309,810)

b. Hyaluronidase

Hyaluronidase activity can be assessed using methods well known in the art. In one example, activity is measured using a microturbidity assay. This is based on the formation of an insoluble precipitate when hyaluronic acid binds with serum albumin. The activity is measured by incubating hyaluronidase with sodium hyaluronate (hyaluronic acid) for a set period of time (e.g. 10 minutes) and then precipitating the undigested sodium hyaluronate with the addition of acidified serum albumin. The turbidity of the resulting sample is measured at 640 nm after an additional development period. The decrease in turbidity resulting from hyaluronidase activity on the sodium hyaluronate substrate is a measure of hyaluronidase enzymatic activity. In another example, hyaluronidase activity is measured using a microtiter assay in which residual biotinylated hyaluronic acid is measured following incubation with hyaluronidase (see e.g. Frost and Stern (1997) Anal. Biochem. 251:263-269, U.S. Patent Publication No. 20050260186). The free carboxyl groups on the glucuronic acid residues of hyaluronic acid are biotinylated, and the biotinylated hyaluronic acid substrate is covalently couple to a microtiter plate. Following incubation with hyaluronidase, the residual biotinylated hyaluronic acid substrate is detected using an avidin-peroxidase reaction, and compared to that obtained following reaction with hyaluronidase standards of known activity. Other assays to measure hyaluronidase activity also are known in the art and can be used in the methods herein (see e.g. Delpech et al., (1995) Anal. Biochem. 229:35-41; Takahashi et al., (2003) Anal. Biochem. 322:257-263).

The ability of hyaluronidase to act as a spreading or diffusing agent also can be assessed. For example, trypan blue dye can be injected subcutaneously with or without hyaluronidase into the lateral skin on each side of nude mice. The dye area is then measured, such as with a microcaliper, to determine the ability of hyaluronidase to act as a spreading agent (U.S. Patent No. 20060104968).

H. Therapeutic Uses

The methods described herein can be used for treatment of any condition for which immune globulin is employed. Immune globulin (IG) can be administered subcutaneously, in combination with hyaluronidase, to treat any condition that is amendable to treatment with inunune globulin. This section provides exemplary therapeutic uses of IG. The therapeutic uses described below are exemplary and do not limit the applications of the methods described herein. Therapeutic uses include, but are not limited to, immunoglobulin replacement therapy and immunomodulation therapy for various immunological, hematological, neurological, inflammatory, dermatological and/or infectious diseases and conditions. In some examples, immune globulin is administered to augment the inumme response in healthy patients, such as following possible exposure to infectious disease (e.g. accidental needle stick injury). It is within the skill of a treating physician to identify such diseases or conditions.

Immune globulin can be co-administered with hyaluronidase subcutaneously, in combination with other agents used in the treatment of these diseases and conditions. For example, other agents that can be administered include, but are not limited to, antibiotics, chemotherapeutics, steroidal anti-inflammatories, non-steroidal anti-inflammatories, and other immunomodulatory agents such as cytokines, chemokines and growth factors.

If necessary, a particular dosage and duration and treatment protocol can be empirically determined or extrapolated. For example, exemplary doses of intravenously administered immune globulin can be used as a starting point to determine appropriate dosages. Dosage levels can be determined based on a variety of factors, such as body weight of the individual, general health, age, the activity of the specific compound employed, sex, diet, time of administration, rate of excretion, drug combination, the severity and course of the disease, and the patient's disposition to the disease and the judgment of the treating physician. Generally, dosages of immune globulin are from or about 100 mg per kg body weight (i.e. 100 mg/kg BW) to 2 g/kg BW, and dosages of hyaluronidase are from or about 10 U/gram to 500 U/g or more of immune globulin, for example, at or about 10 U/g, 20 U/g, 30 U/g, 40 U/g, 50 U/g, 60 U/g, 70 U/g, 80 U/g, 90 U/g, 100 U/g, 150 U/g, 200 U/g, 300 U/g, 400 U/g, 500 U/g or more. It is understood that the amount to administer will be a function of the indication treated, and possibly side effects that will be tolerated. Dosages can be empirically determined using recognized models for each disorder.

Upon improvement of a patient's condition, a maintenance dose of immune globulin can be administered subcutaneously in combination with hyaluronidase, if necessary, and the dosage, the dosage form, or frequency of administration, or a combination thereof can be modified. In some cases, a subject can require intermittent treatment on a long-term basis upon any recurrence of disease symptoms.

1. Primary Immune Deficiency with Antibody Deficiency

Immune globulin can be used to treat primary immune deficiency with antibody deficiency. Primary immune deficiency encompasses many disorders that are characterized by a deficiency of one or more proteins of the immune system. Typically, primary immune deficiencies are inherited disorders, and many are manifest by failure of protective antibody production. Thus, immune globulin can be administered as immunoglobulin replacement therapy to patients presenting with such diseases. Exemplary of primary immune deficiencies include, but are not limited to, common variable immunodeficiency (CVID), congenital agammaglobulinemia, Wiskott-Aldrich syndrome, severe combined inummodeficiency (SCID), primary hypogammaglobulinemia, primary immunodeficiency diseases with antibody deficiency, X-linked agammaglobulinaemia (XLA), hypogammaglobulinaemia of infancy, and paraneoplastic cerebellar degeneration with no antibodies. Immune globulin can be administered subcutaneously, in combination with hyaluronidase, to patients with primary immune deficiency with antibody deficiency at doses similar to the doses used for intravenous administration of immune globulin. Exemplary doses include, for example, between 100 mg/kg BW and 800 mg/kg BW immune globulin, at four week intervals. The dose can be increased or decreased, as can the frequency of the doses, depending on the clinical response.

2. Acquired Hypogammaglobulinemia Secondary to Hematological Malignancies

Patients with acquired hypogammaglobulinemia secondary to hematological malignancies, such as Chronic Lymphocytic Leukemia (CLL), multiple myeloma (MM), non-Hodgkin's lymphoma (NHL) & other relevant malignancies and post-hematopoietic stem cell transplantation, are susceptible to bacterial infections due to. Hypogammaglobulinemia is caused by a lack of B-lymphocytes and a resulting low level of antibodies in the blood, and can occur in patients with CLL, MM, NHL and as a result of both leukemia-related immune dysfunction and therapy-related immunosuppression. The deficiency in humoral immunity is largely responsible for the increased risk of infection-related morbidity and mortality in these patients, especially by encapsulated microorganisms. For example, Streptococcus pneumoniae, Haemophilus influenzae, and Staphyloccus aureus, as well as Legionella and Nocardia spp. are frequent bacterial pathogens that cause pneumonia in patients with CLL. Opportunistic infections such as Pneumocystis carinii, fungi, viruses, and mycobacteria also have been observed. The number and severity of infections in these patients can be significantly reduced by administration of immune globulin (Griffiths et al., (1989) Blood 73:366-368, Chapel et al. (1994) Lancet 343:1059-1063). Such patients, therefore, can be administered immune globulin subcutaneously in combination with hyaluronidase using the methods described herein to prevent recurrent infections. Exemplary dosages include those used for intravenous administration of immune globulin to patients with acquired hypogammaglobulinemia secondary to hematological malignancies. For example, about 400 mg/kg BW immune globulin, in combination with hyaluronidase, can be administered subcutaneously every 3 to 4 weeks. In a further example, an additional dose of 400 mg/kg BW can be administered in the first month of therapy where the patient's serum IgG is less than 4 g/L. The amount of immune globulin administered, and the frequency of the doses, can be increased or decreased as appropriate.

3. Kawasaki's Disease

Kawasaki disease is an acute, febrile, multi-system disease of children and young infants often involving the coronary arteries. It also is known as lymph node syndrome, mucocutaneous node disease, infantile polyarteritis and Kawasaki syndrome, and is a poorly understood self-limited vasculitis that affects many organs, including the skin and mucous membranes, lymph nodes, blood vessel walls, and the heart. Coronary artery aneurysms can occur from the second week of illness during the convalescent stage. Although the cause of the condition is unknown, there is evidence that the characteristic vasculitis results from an immune reaction characterized by T-cell and macrophage activation to an unknown antigen, secretion of cytokines, polyclonal B-cell hyperactivity, and the formation of autoantibodies to endothelial cells and smooth muscle cells. In genetically susceptible individuals, one or more uncharacterized common infectious agents, possibly with superantigen activity, may trigger the disease. Immune globulin administered early in Kawasaki disease can prevent coronary artery pathology. Subcutaneous administration of immune globulin in combination with hyaluronidase to patients with ongoing inflammation associated with Kawasaki disease can ameliorate symptoms. Exemplary dosages include those used for intravenous administration of immune globulin to patients with Kawasaki disease. For example, a patient with Kawasaki disease can be administered about 1-2 g per kg patient body weight of immune globulin. This can be administered, for example, in four doses of 400 mg/kg BW for four consecutive days. In another example, 1 g/kg BW immune globulin is administered as a single dose over a 10 hour period. The amount of immune globulin administered can be increased or decreased as appropriate.

4. Chronic Inflammatory Demyelinating Polyneuropathy

Chronic inflammatory demyelinating polyneuropathy (CIDP) is a neurological disorder characterized by progressive weakness and impaired sensory function in the legs and arms. The disorder, which is sometimes called chronic relapsing polyneuropathy, is caused by damage to the myelin sheath of the peripheral nerves. Although it can occur at any age and in both genders, CIDP is more common in young adults and in men more so than women. It often presents with symptoms that include tingling or numbness (beginning in the toes and fingers), weakness of the arms and legs, loss of deep tendon reflexes (areflexia), fatigue, and abnormal sensations. CIDP is closely related to Guillain-Barre syndrome and it is considered the chronic counterpart of that acute disease. There is no specific diagnostic test but characteristic clinical and laboratory findings help distinguish this disorder from other immune mediated neuropathic syndromes. Studies indicate that treatment with immune globulin reduces symptoms (van Schaik et al., (2002) Lancet Neurol. 1:497-498). Thus, immune globulin can be co-administered with hyaluronidase subcutaneously to patients presenting with CIDP using the methods described herein. Exemplary dosages include those used for intravenous administration of immune globulin to patients with CIDP. In one example, a patient with CIDP is administered about 2 g/kg BW of immune globulin subcutaneously, in combination with hyaluronidase. This can be administered, for example, in five doses of 400 mg/kg BW for five consecutive days. The amount of inunune globulin administered can be increased or decreased as appropriate.

5. Guillain-Barré Syndrome

Guillain-Barré syndrome is a neurologic autoimmune disorder involving inflammatory demyelination of peripheral nerves. The first symptoms include varying degrees of weakness or tingling sensations in the legs, which can spread to the arms and upper body. These symptoms can increase in intensity until the muscles cannot be used at all and the patient is almost totally paralyzed, resulting in a life-threatening condition. Although recovery is generally good or complete in the majority of patients, persistent disability has been reported to occur in about 20% and death in 4 to 15% of patients. Guillain-Barré syndrome can occur a few days or weeks after symptoms of a respiratory or gastrointestinal viral infection. In some instances, surgery or vaccinations can trigger the syndrome. The disorder can develop over the course of hours or days, or it may take up to 3 to 4 weeks. A nerve conduction velocity (NCV) test can give a doctor clues to aid the diagnosis. In some instances, a spinal tap can be used in diagnosis as the cerebrospinal fluid in Guillain-Barré syndrome patients typically contains more protein than normal subjects.

Although there is no known cure for Guillain-Barre syndrome, treatment with immune globulin can lessen the severity of the illness and accelerate recovery. Immune globulin can be administered subcutaneously to patients in combination with hyaluronidase at an appropriate dose, such as, for example, a dose similar to the dose use to administer immune globulin intravenously to patients with Guillain-Barre syndrome. For example, a patient with Guillain-Barre syndrome can administered about 2 g/kg BW of immune globulin, in combination with hyaluronidase, subcutaneously. This can be administered, for example, in five doses of 400 mg/kg BW for five consecutive days. The amount of immune globulin administered can be increased or decrease depending on, for example, the severity of the disease and the clinical response to therapy, which can be readily evaluated by one of skill in the art. 6. Idiopathic Thrombocytopenic Purpura Idiopathic thrombocytopenic purpura (ITP), also known as primary immune thrombocytopenic purpura and autoimmune thrombocytopenic purpura, is a reduction in platelet count (thrombocytopenia) resulting from shortened platelet survival due to anti-platelet antibodies. When platelet counts are very low (e.g. $<30\times10^9$/L), bleeding into the skin (purpura) and mucous membranes can occur. Bone marrow platelet production (megakaryopoiesis) in patients with ITP is morphologically normal. In some instances, there is additional impainnent of platelet function related to antibody binding to glycoproteins on the platelet surface. ITP can present as chronic and acute forms. Approximately 80% of adults with ITP have the chronic form of disease. The highest incidence of chronic ITP is in women aged 15-50 years, although some reports suggest increasing incidence with age. ITP is relatively common in patients with HIV. While ITP can be found at any stage of the infection, its prevalence increases as HIV disease advances.

Studies have demonstrated that immune globulin can be used to treat patients with ITP (Godeau et al. (1993) Blood 82(5):1415-21, Godeau et al. (1999) Br J Haematol 1999; 107(4):716-9). Immune globulin can be administered subcutaneously to patients in combination with hyaluronidase at a dose similar to the dose use to administer immune globulin intravenously, to treat patients with ITP. For example, a patient with ITP can administered about 1 to 2 g/kg of immune globulin, in combination with hyaluronidase, subcutaneously. This can be administered over several days, or can be administered in one dose. In some examples, five doses of 400 mg/kg BW immune globulin on consecutive days is administered. In another example, 1 g/kg BW is administered for 1-2 consecutive days, depending on platelet count and clinical response. The amount of immune globulin administered, and the frequency of the doses, can be increased or decrease depending on, for example, platelet count and the clinical response to therapy, which can be readily evaluated by one of skill in the art.

7. Inflammatory Myopathies: Polymyositis, Dermatomyositis and Inclusion Body Myositis Inflammatory myopathies are a group of muscle diseases involving the inflammation and degeneration of skeletal muscle tissues. These disorders are acquired and all present with significant muscle weakness and the presence of an inflammatory response within the muscle. Dermatomyositis (DM) is the most easily recognized of the inflammatory myopathies due to its distinctive rash, which occurs as a patchy, dusky, reddish or lilac rash on the eyelids, cheeks, and bridge of the nose, and on the back or upper chest, elbows, knees and knuckles. In some patients, calcified nodules or hardened bumps develop under the skin. The rash often precedes muscle weakness, which typically develops over a period of weeks but may develop over months or even days. Dennatomyositis can occur at any age from childhood to adulthood and is more common in females than males. Approximately one third of DM patients report difficulty swallowing. Muscle pain and tenderness generally occurs in less than 25% of adults with DM, but more than 50% of children with DM complain of muscle pain and tenderness.

Polymyositis (PM) does not have the characteristic rash of dermatomyositis, and the onset of muscle weakness usually progresses slower than DM. Many PM patients present have difficulty in swallowing. In some instances, the patients also have difficulty breathing due to muscle failure. As many as one third of PM patients have muscle pain. PM. The disease affects more women than men, and rarely affects people under the age of 20, although cases of childhood and infant polymyositis have been reported.

Inclusion body myositis (IBM) is very similar to polymyositis. Onset of muscle weakness in IBM is usually very gradual, taking place over months or years. It is different from PM in that both proximal and distal muscles are affected, while generally only the proximal muscles are affected in PM. Typical findings include weakness of the wrist flexors and finger flexors. Atrophy of the forearms is characteristic of the disease, and atrophy of the quadriceps muscle is common with varying degrees of weakness in other muscles. Approximately half of the patients afflicted with IBM have difficulty swallowing. Symptoms of IBM usually begin after age 50, although no age group is excluded. IBM occurs more frequently in men than women. About one in ten cases of IBM may be hereditary.

Studies indicate that administration of immune globulin can benefit patients with these inflammatory myopathies. Immune globulin can improve muscle strength, reduce inflammation and reduce disease progression and severity (Dalakas et al. (1993) N Engl J Med 329(27):1993-2000; Dalakas et al. (2001) Neurology 56(3):323-7, Dalakas (2004) Pharmacol Ther 102(3):177-93, Walter et al. (2000) J Neurol 247(1):22-8). Immune globulin can be administered subcutaneously to patients with DM, PM or IBM in combination with hyaluronidase at a dose similar to the dose used to administer immune globulin intravenously. For example, 2 g/kg BW of immune globulin can be administered, typically over several days, such as, for example, five doses of 400 mg/kg BW on consecutive days.

8. Lambert-Eaton Myasthenic Syndrome

Lambert-Eaton myasthenic syndrome (LEMS) is a rare autoimmune disorder of neuromuscular transmission first recognized clinically in association with lung cancer and subsequently in cases in which no neoplasm was detected. Patients with LEMS have a presynaptic neuromuscular junction defect. The disease is characterized clinically by proximal muscle weakness with augmentation of strength after exercise, mild oculomotor signs, depressed deep tendon reflexes and autonomic dysfunction (dry mouth, constipation, erectile failure). Subcutaneous administration of immune globulin in combination with hyaluronidase to patients with LEMS can ameliorate symptoms. Exemplary dosages include those used for intravenous administration of immune globulin to patients with LEMS. For example, a patient with LEMS can be administered 2 g per kg patient body weight of immune globulin over several doses. For example, five doses of 400 mg/kg BW immune globulin can be administered on five consecutive days. The amount of immune globulin administered can be increased or decreased as appropriate.

9. Multifocal Motor Neuropathy

Multifocal motor neuropathy (MMN) with conduction block is an acquired immune-mediated demyelinating neuropathy with slowly progressive weakness, fasciculations, and cramping, without significant sensory involvement. The duration of disease prior to diagnosis ranges from several months to more than 15 years. The precise cause of MMN is unknown. Histopathologic and electrodiagnostic studies demonstrate the presence of both demyelinating and axonal injury. Motor nerves are primarily affected, although mild demyelination has been demonstrated in sensory nerves as well. Efficacy of immunomodulatory and immunosuppressive treatment further supports the immune nature of MMN. Titers of anti-GM1 antibodies are elevated in over half of the patients with MMN. Although the role of the anti-GM1 antibodies in the disease in unknown, their presence can be used as a diagnostic marker for MMN.

Subcutaneous administration of immune globulin in combination with hyaluronidase to patients with MMN can to ameliorate symptoms. Exemplary dosages include those used for intravenous administration of immune globulin to patients with MMN. For example, a patient with MMN can be administered 2 g per kg patient body weight of immune globulin over several doses. For example, five doses of 400 mg/kg BW immune globulin can be administered on five consecutive days. In another example, 1 g/kg BW can be administered on 2 consecutive days. Some patients can be given maintenance therapy, which can include, for example, doses of 400 mg/kg BW to 2 g/kg BW, given every 2-6 weeks. The amount of immune globulin administered can be increased or decreased as appropriate, taking into account the patients response.

10. Myasthenia Gravis

Myasthenia gravis (MG) is a chronic autoimmune neuromuscular disease characterized by varying degrees of weakness of the skeletal muscles of the body. It is associated with the presence of antibodies to acetylcholine receptors (AChR) or to muscle-specific tyrosine kinase (MuSK) at the neuromuscular junction, although some patients are antibody negative. The clinical features of MG include fluctuating weakness and fatigability of voluntary muscles, particularly levator palpebrae, extraocular, bulbar, limb and respiratory muscles. Patients usually present with unilateral or bilateral drooping of eyelid (ptosis), double vision (diplopia), difficulty in swallowing (dysphagia) and proximal muscle weakness. Weakness of respiratory muscles can result in respiratory failure in severe cases or in acute severe exacerbations (myasthenic crisis). Myasthenia gravis occurs in all ethnic groups and both genders. It most commonly affects young adult women under 40 and older men over 60, but it can occur at any age. In some instances, thymectomy is performed to reduce symptoms.

Immune globulin can be used, for example, as maintenance therapy for patients with moderate to severe MG, typically when other treatments have been ineffective caused severe side effects, and also can be administered prior to thymectomy or during an acute exacerbation of the disease (myasthemic crisis). Immune globulin can be administered subcutaneously, in combination with hyaluronidase, to patients with Myasthenia gravis using the methods described herein. Exemplary dosages include those used for intravenous administration of immune globulin to patients with MG. For example, a patient with MG can be administered doses of 400 mg/kg BW to 2 g/kg BW every 4-6 weeks for maintenance therapy. Prior to thymectomy or during myasthemic crisis, 1-2 g/kg BW can be administered over several doses, such as, for example, five doses of 400 mg/kg BW on five consecutive days. In another example, 1 g/kg BW can be administered on 2 consecutive days.

11. Moersch-Woltmann Syndrome

Moersch-Woltmann syndrome, also known as stiff person syndrome or stiffman syndrome, is a rare neurological disorder with features of an autoimmune disease. Patients present with symptoms related to muscular rigidity and superimposed episodic spasms. Muscle rigidity spreads to involve axial muscles, primarily abdominal and thoracolumbar, as well as proximal limb muscles. Typically, co-contraction of truncal agonist and antagonistic muscles leads to a board-like appearance with hyperlordosis. Less frequently, respiratory muscle involvement leads to breathing difficulty and facial muscle involvement to a mask-like face. Treatment with immune globulin can effect decreased stiffness and heightened sensitivity scores in patients with Moersch-Woltmann syndrome (Dalakas et al. (2001) N Engl J Med 345(26):1870-6). Immune globulin can be administered subcutaneously, in combination with hyaluronidase, to patients with Moersch-Woltmann syndrome using the methods described herein. Exemplary dosages include those used for intravenous administration of immune globulin to patients with Moersch-Woltmann syndrome. For example, immune globulin can be administered at doses of 400 mg/kg BW on five consecutive days. Some patients can be given maintenance therapy, which can include, for example, 1-2 g/kg BW immune globulin every 4-6 weeks. The amount of immune globulin administered can be increased or decreased as appropriate.

12. Alzheimer's Disease

Treatment for Alzheimer's disease includes treatment with intravenous inuminoglobulin (see e.g. Dodel et al. (2004) J Neural Neurosurg. Psychiatry, 75:1472-4; Solomon et al. (2007) Curr. Opin. Mol. Ther., 9:79-85; Relkin et al. (2008) Neurobiol Aging). IG contains antibodies that bind to beta amyloid (AB), which is a central component of the plaque in the brains of Alzheimer's patients. Thus, IG can help to promote the clearance of AB from the brain and block AB's toxic effects on brain cells. Hence, immune globulin can be administered subcutaneously, in combination with hyaluronidase, to patients with Alzheimer's disease using the methods described herein. Subjects to be treated include patients having mild, moderate or advanced Alzheimer's disease. It is within the level of skill of a treating physician to identify patients for treatment. Immune globulin in combination with hyaluronidase can be administered every week, every two weeks or once a month. Treatment can continue over the course of months or years. IG can be administered at doses at or between 200 mg/kg BW to 2 g/kg BW every week or every two weeks, and generally at least 200 mg/kg to 2 g/kg BW at least once a month. Treatment with immune globulin can effect an increase in patients' anti-amyloid beta antibody levels compared to levels before treatment.

13. Other Diseases and Conditions

Clinical data indicate that immune globulin can be used in the treatment of many conditions. In some instances, immune globulin can be used a the primary treatment, while in other cases, it is administered as second-line therapy when standard therapies have proven ineffective, have become intolerable, or are contraindicated. It is within the skill of a treating physician to identify such diseases or conditions. Exemplary of these include, but are not limited to, secondary hypogammaglobulinaemia (including iatrogenic immunodeficiency); specific antibody deficiency; Acute disseminated encephalomyelitis; ANCA-positive systemic necrotizing vasculitis; Autoimmune haemolytic anaemia; Bullous pemphigoid; Cicatricial pemphigoid; Evans syndrome (including autoimmune haemolytic anaemia with immune thrombocytopenia); Foeto-maternal/neonatal alloimmune thrombocytopenia (FMAIT/NAIT); Alzheimer's Disease, Haemophagocytic syndrome; High-risk allogeneic haemopoietic stem cell transplantation; IgM paraproteinaemic neuropathy; kidney transplantation; multiple sclerosis; Opsoclonus myoclonus ataxia; Pemphigus foliaceus; Pemphigus vulgaris; Post-transfusion purpura; Toxic epidermal necrolysis/Steven Johnson syndrome (TEN/SJS); Toxic shock syndrome; Systemic lupus erythematosus; multiple myeloma; sepsis; bone marrow transplantation, B cell tumors; and trauma.

Immune globulin also has been shown to have antimicrobial activity against a number of bacterial, viral and fungal infections, including, but not limited to, Haemophilus influenzae type B, Psuedomonas aeruginosa types A and B, Staphylococcus aureus, Group B Streptococcus, Streptococcus pneumoniae types 1, 3, 4, 6, 7, 8, 9, 12, 14, 18, 19, and 23, Adenovirus types 2 and 5, Cytomegalovirus, Epstein Barr virus VCA, Hepatitis A virus, Hepatitis B virus, Herpes simplex virus-1, Herpes simplex virus-2, Influenza A, Measles, Parainfluenza types 1, 2 and 3, Polio, Varicella zoster virus, Apergillus and Candida albicans. Thus, immune globulin can be administered subcutaneously in combination with hyaluronidase to patients with bacterial, viral and fungal infections to augment the patient's immune system and treat the disease. In some examples, antibiotics or other antimicrobials also are administered.

I. Articles of Manufacture and Kits

Pharmaceutical compositions of immune globulin and a soluble hyaluronidase, provided together or separately, can be packaged as articles of manufacture containing packaging material, a pharmaceutical composition which is effective for treating a IG-treatable disease or condition, and a label that indicates that the composition and combinations are to be used for treating a IG-treatable diseases and conditions. Exemplary of articles of manufacture are containers including single chamber and dual chamber containers. The containers include, but are not limited to, tubes, bottles and syringes. The containers can further include a needle for subcutaneous administration.

The articles of manufacture provided herein contain packaging materials. Packaging materials for use in packaging pharmaceutical products are well known to those of skill in the art. See, for example, U.S. Pat. Nos. 5,323,907, 5,033,252 and 5,052,558, each of which is incorporated herein in its entirety. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any IG-treatable disease or condition.

Compositions of immune globulin and a soluble hyaluronidase, provided together or separately, also can be provided as kits. Kits can include a pharmaceutical composition described herein and an item for administration. For example compositions can be supplied with a device for administration, such as a syringe, an inhaler, a dosage cup, a dropper, or an applicator. The kit can, optionally, include instructions for application including dosages, dosing regimens and instructions for modes of administration. Kits also can include a pharmaceutical composition described herein and an item for diagnosis. For example, such kits can include an item for measuring the concentration, amount or activity of IG.

J. Examples

The following examples are included for illustrative purposes only and are not intended to limit the scope of the invention.

Example 1

Soluble Recombinant Human PH20 (rHuPH20) Facilitates Subcutaneous Administration of Immune Globulin (IG) and Bioavailability Subcutaneous (SQ) administration of immune globulin (IG) results in reduced bioavailability compared to intravenous (IV) administration. One study reported 63% bioavailability compared to IV administration, thereby requiring an SQ dose of 137% of the IV does to be used to achieve an equivalent bioavailability, i.e. area under the time-concentration curve (AUC) (Ochs et al. (2006) J Clin. Iminunol., 26:265-273). Thus, experiments were performed to determine if subcutaneous administration of IG (GAMMAGARD LIQUID (GGL), Baxter Biosciences) in the presence of soluble recombinant human PH20 (rHuPH20) increased the bioavailability of IG upon SQ administration, obviating the need for increased doses. The experimental study was designed to assess 1) the ability of subjects to tolerate a monthly dose of GGL in a single site via subcutaneous (SQ) route; 2) the dose of rHuPH20 per gram of GGL required to tolerate a monthly dose of GGL with no more than mild local adverse drug reactions; 3) the time required for SC administration; and 3) a comparison of the bioavailability measured by area under the curve (AUC) of GGL IV versus SQ.

Briefly, eleven adult immunodeficient patients who were on stable doses of intravenous gammaglobulin (WIG) were enrolled in the study. All patients remained on the same monthly doses of IVIG as they received prior to the study. For subcutaneous administration, patients that were receiving up to 600 mg/kg body weight of GGL every four weeks IV, received SQ infusions in a single site beginning at a dose that was ¼ of the 4-week IV dose, i.e. a 1-week dose, to determine the dose of rHuPH20 required to tolerate the 1-week dose. Subsequently, dosages of rHuPH20 were reduced and patients received the 2, 3, and finally a full four-week dose of GGL to determine the minimum rHuPH20 required to tolerate a once monthly infusion of GGL SQ.

Initial infusions were conducted using 150 U of rHuPH20 per gram of GGL. The rHuPH20 was administered through a 24-gauge SQ needle at a concentration of 150 U/ml or 1500 U/ml at a rate of 1-2 ml/min., prior to the infusion of the GGL. If 1500 U/ml rHuPH20 was used, it was diluted as follows: a) if the volume of the concentrated (1500 U/ml) rHuPH20 solution needed was 1.5 ml of below, it was diluted 1:10 using normal saline for injection; b) if the volume of the concentrated (1500 U/ml) rHuPH20 needed was above 1.5 ml but below 15 ml, it was diluted to 15 l with normal saline for injection; c) if the volume of the concentrated (1500 U/ml) rHuPH20 solution needed was 15 ml or above, it was used undiluted.

Immediately after the infusion of rHuPH20 (and within 5 minutes), the GGL was infused through the same 24-gauge SQ needle beginning at a dose that was ¼ of the 4-week dose (i.e. 1 week dose) to determine the amount of rHuPH20 needed to give one fourth of the 4-week dose in a single site. Each patient was assessed to determine if the infusion was tolerated; the infusion was deemed not to be tolerated if there were moderate or severe local reactions requiring more than one site of administration or an inability to complete the infusion in less than 3 hours. If the weekly dose of GGL was tolerated, the one-half dose (two week dose) was administered using rHuPH20 at 100 U/g GGL, and the dose of rHuPH20 was further reduced to 66 U/g GGL, then 50 U/g GGL. The dose of rHuPH20 was repeated, on a per-gram GGL basis, with increased amounts of GGL until a full 4-week dose of GGL in a single site was tolerated. If the amount of rHuPH20 was not tolerated at any point, then that weekly dose of GGL was repeated at the next interval and the amount of rHuPH20 increased until the dose was tolerated. If a subject fails to tolerate a dose for 2 successive increases in rHuPH20 dose (i.e. 3 attempts at a distinct dose of GGL), then the previously tolerated dose was determined to be the maximum tolerated dose.

The first 4 patients were evaluated for tolerability only; the last 7 patients had an IV infusion, followed by a pharmacokinetic (PK) study to compare the IV infusion to the subsequent SQ infusions. For the SQ infusions, after a monthly dose administration of GGL was achieved, the same monthly dose was repeated and a PK study performed to evaluate the T1/2, Tmax, and AUC. If AUC(SQ) was not within 90% of the AUC(IV), the dose of rHuPH20 was increased 4-fold at the next infusion, and the PK assessment was repeated.

Ten of the 11 patients achieved monthly doses of 25.5 to 61.2 grams of GGL (255 to 612 ml) in a single SQ site, at rates of 120 to 300 ml/hour. The eleventh patient withdrew following the 1-week infusion citing local discomfort. For the first patient (39001), the initial infusions were done by gravity, however, the rates were not acceptable despite increasing the dose of rHuPH20 from 150 to 300 U/g GGL. Therefore, all subsequent infusions were done using an IV peristaltic pump. The remaining 9 patients achieved the GGL monthly dose without the need to repeat doses or increase the concentration of rHuPH20. Thus, all 9 patients in whom an attempt was made to reduce the dose of rHuPH20 completed the study and were able to tolerate the infusions using 50 U/g GGL. To determine if 50 U/g GGL was the minimum rHuPH20 that could be administered, a dose of 25 U/g GGL was attempted in two patients without success: one had discomfort and the other had reduced tolerability and required administration at two sites. Thus, the minimum amount of rHuPH20 that permitted a monthly dose administration of GGL SQ was 50 U/g GGL. The results are summarized in Table 3 below. The results show that all but the first two patients were infused at rates up to 300 ml/hr with infusion times of 1.64 h (270 ml) to 3.55 h (537 ml). The rate of administration was limited primarily by the type of pump used. The IV pump frequently alarmed at rapid infusion rates. One infusion was slowed and one was interrupted due to mild infusion-site pain. Both infusions resumed and were completed.

TABLE 3

Infusion Parameters for Patients Successfully Completing Monthly SC Infusions

| Subjects (N = 10) | Number of monthly-dose infusions | Dose IgG (g) infused (mean) | Volume (mL) IgG infused (mean) | Final rHuPH20 conc. (U/g) | Max infusion rate (mL/hr) | Time (hrs) to infuse (mean) |
|---|---|---|---|---|---|---|
| 390001 | 1 | 25.5 | 255 | 305.9 | 175 | 2.13 |
| 390003 | 1 | 30.1 | 301 | 46.9 | 200 | 2.38 |
| 400001 | 1 | 44.5 | 445 | 49.8 | 300 | 3.05 |
| 340001 | 3 | 30.3 | 303 | 52.5 | 300 | 3.02 |
| 340002 | 4 | 39.9 | 399 | 50.0 | 300 | 3.20 |
| 390004 | 4 | 29.3 | 293 | 50.8 | 300 | 1.92 |
| 390005 | 3 | 27.2 | 272 | 50.6 | 300 | 1.64 |
| 390006 | 3 | 61.4 | 614 | 50.0 | 300 | 2.75 |
| 400002 | 3 | 53.7 | 537 | 51.5 | 300 | 3.55 |
| 400003 | 3 | 42.1 | 421 | 48.8 | 300 | 2.29 |

1. Tolerability Assessment

The subjects were assessed for their tolerability to the SQ infusions. Most infusions were associated with only mild infusion-related reactions (Table 4). Most common mild reactions were infusion site erythema, pain, swelling, warmth and pruritus. Moderate infusion site reactions included three cases of pain, and one case each of pruritus, swelling and warmth. No severe reactions were reported. There were complaints of transient burning during the infusion of the rHuPH20 in 10 of the infusions, with five occurring in one patient.

TABLE 4

Adverse events, regardless of causality, by periods corresponding to dose categories

| MeDRA System Organ Class | SC ¼ dose | SC ½ dose | SC ¾ dose | SC full dose |
|---|---|---|---|---|
| Ear and labyrinth disorders | 0 | 0 | 0 | 1 |
| Eye disorders | 0 | 1 | 0 | 3 |
| Gastrointestinal disorders | 0 | 1 | 0 | 2 |
| General disorders and administration site conditions | 26 | 15 | 20 | 29 |
| Immune system disorders | 0 | 0 | 0 | 1 |
| Infections and infestations | 1 | 1 | 1 | 3 |
| Musculoskeletal and connective tissue disorders | 1 | 1 | 1 | 0 |
| Nervous system disorders | 2 | 1 | 0 | 0 |
| Respiratory, thoracic and mediastinal disorders | 0 | 0 | 0 | 4 |
| Skin and subcutaneous tissue disorders | 0 | 0 | 3 | 1 |
| Total | 30 | 20 | 25 | 44 |

Systemic adverse events considered to be possibly or probably related to the infusions are listed in Table 5. Three were moderate and none were severe. Only the episode of mild chest pain was associated with interruption of the infusion, but the infusion was completed and subsequent infusions were well tolerated. Table 6 depicts the proportion of subcutaneous infusions that were completed without interruption for an adverse event.

One serious adverse event, an anaphylactic reaction, occurred in one patient, unrelated to study therapy. The patient, who had a history of previous allergic reactions to antibiotics, received an antibiotic on the day following her infusion with GGL/rHuPH20, and subsequently developed anaphylaxis. This patient recovered completely and was able to successfully complete the study.

There were no documented bacterial infections during this trial of PID patients. There were 9 reported cases of viral infections, all deemed not related to study therapy: 2 cases of viral gastroenteritis, 1 case of herpetic keratitis, 2 cases of sinusitis, 1 case of conjunctivitis, and 3 cases (in one patient) of influenza-like illness.

TABLE 5

Systemic non-serious, related adverse events

| Adverse events by MEDRA term | Mild | Mod | Severe | Total |
|---|---|---|---|---|
| Dry eye | 1 | 0 | 0 | 1 |
| Night sweats | 1 | 0 | 0 | 1 |
| Musculoskeletal discomfort | 0 | 1 | 0 | 1 |
| Headache | 1 | 2 | 0 | 3 |
| Lethargy | 1 | 0 | 0 | 1 |
| Chest pain | 1 | 0 | 0 | 1 |
| Oedema peripheral | 1 | 0 | 0 | 1 |
| Pain | 1 | 0 | 0 | 1 |
| Back pain | 2 | 0 | 0 | 2 |
| Total related adverse events | 9 | 3 | 0 | 12 |

TABLE 6

Proportion of SC infusions completed without interruption for an adverse event

| Patient | Without interruption | Percent (%) | Inter-rupted | Stopped | Percent % | Total infusions |
|---|---|---|---|---|---|---|
| 390001 | 4 | 80 | 1* | 0 | 20 | 5 |
| 390002 | 2 | 100 | 0 | 0 | 0 | 2 |
| 390003 | 4 | 100 | 0 | 0 | 0 | 4 |
| 400001 | 4 | 100 | 0 | 0 | 0 | 4 |
| 340001 | 6 | 100 | 0 | 0 | 0 | 6 |
| 340002 | 6 | 86 | 1† | 0 | 14 | 7 |
| 390004 | 7 | 100 | 0 | 0 | 0 | 7 |
| 390005 | 7 | 100. | 0 | 0 | 0 | 7 |
| 390006 | 6 | 100. | 0 | 0 | 0 | 6 |
| 400002 | 6 | 100. | 0 | 0 | 0 | 6 |
| 400003 | 7 | 100. | 0 | 0 | 0 | 7 |
| Total | 59 | N/A | 2 | 0 | N/A | 61 |

*interrupted due to mild infusion-site pain

†interrupted due to mild transient chest pain

2. Pharmacokinetic Assessment

Pharmacokinetic (PK) analysis was performed on serum IgG levels. The 7 patients enrolled in the PK assessment phase of this study achieved monthly doses of 27 to 61 grams of GGL in a single site using 50 U of rHuPH20 per gram GGL (see Table 3). The PK study was performed after receiving a second monthly dose infusion of GGL. Serum samples were collected pre-infusion, 1 h post-infusion and on days 1, 2, 3, 4, 5, 7, 14, 21 and 28 (if on 28 day schedule) post-infusion. The pharmacokinetic parameters of the 7 patients are depicted in Table 7. The ratio of AUC(SQ) to AUC(IV) for the 7 patients is shown in Table 8. The results show that five of the 7 patients had AUC(SQ) within 90% of AUC (IV). Increasing the dose or rHuPH20 four-fold in the 2 subjects with a ratio less than 90% did not further improve bioavailability.

TABLE 7

Pharmacokinetic parameters of individual subjects

| Patients | AUC (days * g/L) | $T_{1/2}$ (days) | $T_{max}$ (days) | $C_{min}$ (g/L) |
|---|---|---|---|---|
| 34001 | 461.2 | 61.3 | 3.0 | 12.9 |
| 34002* | 387.1 | 114.1 | 4.9 | 11.3 |
| | 356.7 | 43.9 | 4.0 | 11.3 |
| 39004* | 256.9 | 113.8 | 5.0 | 7.9 |
| | 264.2 | 44.3 | 6.9 | 7.7 |
| 39005 | 369.6 | 59.3 | 3.1 | 10.9 |
| 39006 | 368.9 | 40.3 | 4.8 | 10.8 |
| 40002 | 375.2 | 33.7 | 6.8 | 10.6 |
| 40003 | 356.2 | 37.9 | 4.9 | 9.7 |
| Median | 368.9 | 43.93 | 4.8 | 10.8 |

*Patients with repeated PK assessments following administration with an increased dose of rHuPH20.

TABLE 8

Ratio $AUC_{(SQ)}$ to $AUC_{(IV)}$ (%)

| | rHuPH20 concentration | |
|---|---|---|
| Patient | 50 U/g | 200 U/g |
| 34001 | 101.0 | N/A |
| 34002 | 86.5 | 79.6 |
| 39004 | 75.8 | 77.8 |
| 39005 | 102.7 | N/A |
| 39006 | 94.7 | N/A |
| 40002 | 97.3 | N/A |
| 40003 | 90.5 | N/A |
| Mean | 92.6 | N/A |

3. Summary of Results

The use of rHuPH20 by injection prior to infusion with GGL made it possible to infuse as much as 600 ml of GGL in a single subcutaneous site at infusion rates up to 300 ml per hour in this study. The rate was limited primarily by the IV pumps that were used, which are designed to alarm and shut off when the IV infiltrates and pressure increases. Although pump shut off did not occur until rates approached the 300 ml/h, the need to restart the pump did increase the time of infusion. Since there is no need to pressure alarms for subcutaneous administration, the problem of shutting off should be eliminated by switching to pumps capable of generating more pressure without alarming.

Although most of the infusions were associated with some swelling, redness, or occasionally pain or itching, all but a few were mild. Two of the six moderate reactions occurred in infusions where the rHuPH20 was reduced in an effort to find the minimum effective dose; the rHuPH20 dose of 50 U/g GGL was tolerated by 10 of the 11 subjects. One subject, who had not previously experienced subcutaneous infusions, withdrew after the first one week dose citing discomfort at the site of the lower abdomen. All other infusions were completed despite the mild reactions, with 97% of the infusions being completed without interruption. Most reactions were treated with cool packs and only a few required acetaminophen or diphenhydramine.

The mean bioavailability of GGL upon subcutaneously administering in combination with rHuPH20 was 92% of the bioavailability of GGL following IV administration. This study suggests that the increased diffusion afforded by the rHuPH20 improved absorption of GGL. Further, the trough levels achieved by monthly subcutaneous dosing of GGL in this study are identical to those achieved by IV administration. Thus, there is no need to increase the frequency of administration of GGL by subcutaneous dosing versus IV dosing; subcutaneous administration of GGL in combination with rHuPH20 requires only a single SQ site and can be achieved at rates of infusion up to 300 ml/h.

In conclusion, rHuPH20 facilitated administration of a full monthly dose of GGL in a single site at rates up to 300 ml/h in a group of adult immunodeficient subjects. The bioavailability of the combination was 92% of the IV bioavailability, based on AUC of the time versus IgG concentration curve. This suggests that rHuPH20 improves absorption of subcutaneous administered GGL. Most of the local side effects were mild and did not result in slowing or interrupting the infusions.

Example 2

Generation of a Soluble rHuPH20-Expressing Cell Line

The HZ24 plasmid (set forth in SEQ ID NO:52) was used to transfect Chinese Hamster Ovary (CHO cells) (see e.g. application Ser. Nos. 10,795,095, 11/065,716 and 11/238,171). The HZ24 plasmid vector for expression of soluble rHuPH20 contains a pCI vector backbone (Promega), DNA encoding amino acids 1-482 of human PH20 hyaluronidase (SEQ ID NO:49), an internal ribosomal entry site (IRES) from the ECMV virus (Clontech), and the mouse dihydrofolate reductase (DHFR) gene. The pCl vector backbone also includes DNA encoding the Beta-lactamase resistance gene (AmpR), an f1 origin of replication, a Cytomegalovirus immediate-early enhancer/promoter region (CMV), a chimeric intron, and an SV40 late polyadenylation signal (SV40). The DNA encoding the soluble rHuPH20 construct contains an NheI site and a Kozak consensus sequence prior to the DNA encoding the methionine at amino acid position 1 of the native 35 amino acid signal sequence of human PH20, and a stop codon following the DNA encoding the tyrosine corresponding to amino acid position 482 of the human PH20 hyaluronidase set forth in SEQ ID NO:1), followed by a BamHI restriction site. The construct pCI-PH20-IRES-DHER-SV40pa (HZ24), therefore, results in a single mRNA species driven by the CMV promoter that encodes amino acids 1-482 of human PH20 (set forth in SEQ ID NO:3) and amino acids 1-186 of mouse dihydrofolate reductase (set forth in SEQ ID NO:53), separated by the internal ribosomal entry site (IRES).

Non-transfected DG44 CHO cells growing in GIBCO Modified CD-CHO media for DHFR(−) cells, supplemented with 4 mM Glutamine and 18 ml/L Plurionic F68/L (Gibco), were seeded at $0.5\times10^6$ cells/ml in a shaker flask in preparation for transfection. Cells were grown at 37° C. in 5% $CO_2$ in a humidified incubator, shaking at 120 rpm. Exponentially growing non-transfected DG44 CHO cells were tested for viability prior to transfection.

Sixty million viable cells of the non-transfected DG44 CHO cell culture were pelleted and resuspended to a density of $2\times10^7$ cells in 0.7 mL of 2× transfection buffer (2× HeBS: 40 mM Hepes, pH 7.0, 274 mM NaCl, 10 mM KCl, 1.4 mM $Na_2HPO_4$, 12 mM dextrose). To each aliquot of resuspended cells, 0.09 mL (250 μg) of the linear HZ24 plasmid (linearized by overnight digestion with Cla I (New England Biolabs) was added, and the cell/DNA solutions were transferred into 0.4 cm gap BTX (Gentronics) electroporation cuvettes at room temperature. A negative control electroporation was performed with no plasmid DNA mixed with the cells. The cell/plasmid mixes were electroporated with a capacitor discharge of 330 V and 960 μF or at 350 V and 960 μF.

The cells were removed from the cuvettes after electroporation and transferred into 5 mL of Modified CD-CHO media for DHFR(−) cells, supplemented with 4 mM Glutamine and 18 ml/L Plurionic F68/L (Gibco), and allowed to grow in a well of a 6-well tissue culture plate without selection for 2 days at 37° C. in 5% $CO_2$ in a humidified incubator.

Two days post-electroporation, 0.5 mL of tissue culture media was removed from each well and tested for the presence of hyaluronidase activity, using the microturbidity assay described in Example 3.

TABLE 9

Initial Hyaluronidase Activity of HZ24 Transfected DG44 CHO cells at 40 hours post-transfection

| | Dilution | Activity Units/ml |
|---|---|---|
| Transfection 1 330 V | 1 to 10 | 0.25 |
| Transfection 2 350 V | 1 to 10 | 0.52 |
| Negative Control | 1 to 10 | 0.015 |

Cells from Transfection 2 (350V) were collected from the tissue culture well, counted and diluted to $1\times10^4$ to $2\times10^4$ viable cells per mL. A 0.1 mL aliquot of the cell suspension was transferred to each well of five, 96 well round bottom tissue culture plates. One hundred microliters of CD-CHO media (GIBCO) containing 4 mM GlutaMAX™-1 supplement (GIBCO™, Invitrogen Corporation) and without hypoxanthine and thymidine supplements were added to the wells containing cells (final volume 0.2 mL). Ten clones were identified from the 5 plates grown without methotrexate.

TABLE 10

Hyaluronidase activity of identified clones

| Plate/Well ID | Relative Hyaluronidase |
|---|---|
| 1C3 | 261 |
| 2C2 | 261 |
| 3D3 | 261 |
| 3E5 | 243 |
| 3C6 | 174 |
| 2G8 | 103 |
| 1B9 | 304 |
| 2D9 | 273 |
| 4D10 | 302 |

Six HZ24 clones were expanded in culture and transferred into shaker flasks as single cell suspensions. Clones 3D3, 3E5, 2G8, 2D9, 1E11, and 4D10 were plated into 96-well round bottom tissue culture plates using a two-dimensional infinite dilution strategy in which cells were diluted 1:2 down the plate, and 1:3 across the plate, starting at 5000 cells in the top left hand well. Diluted clones were grown in a background of 500 non-transfected DG44 CHO cells per well, to provide necessary growth factors for the initial days in culture. Ten plates were made per subclone, with 5 plates containing 50 nM methotrexate and 5 plates without methotrexate.

Clone 3D3 produced 24 visual subclones (13 from the no methotrexate treatment, and 11 from the 50 nM methotrexate treatment. Significant hyaluronidase activity was measured in the supernatants from 8 of the 24 subclones (>50 Units/mL), and these 8 subclones were expanded into T-25 tissue culture flasks. Clones isolated from the methotrexate treatment protocol were expanded in the presence of 50 nM methotrexate. Clone 3D35M was further expanded in 500 nM methotrexate giving rise to clones producing in excess of 1,000 Units/ml in shaker flasks (clone 3D35M; or Gen1 3D35M). A master cell bank (MCB) of the 3D35M cells was then prepared.

Example 3

Determination of Hyaluronidase Activity of Soluble rHuPH20

Hyaluronidase activity of soluble rHuPH20 in samples such as cell cultures, purification fractions and purified solutions was determined using a tubidometric assay, which based on the formation of an insoluble precipitate when hyaluronic acid binds with serum albumin. The activity is measured by incubating soluble rHuPH20 with sodium hyaluronate (hyaluronic acid) for a set period of time (10 minutes) and then precipitating the undigested sodium hyaluronate with the addition of acidified serum albumin. The turbidity of the resulting sample is measured at 640 nm after a 30 minute development period. The decrease in turbidity resulting from enzyme activity on the sodium hyaluronate substrate is a measure of the soluble rHuPH20 hyaluronidase activity. The method is performed using a calibration curve generated with dilutions of a soluble rHuPH20 assay working reference standard, and sample activity measurements are made relative to this calibration curve.

Dilutions of the sample were prepared in Enzyme Diluent Solutions. The Enzyme Diluent Solution was prepared by dissolving 33.0±0.05 mg of hydrolyzed gelatin in 25.0 mL of the 50 mM PIPES Reaction Buffer (140 mM NaCl, 50 mM PIPES, pH 5.5) and 25.0 mL of SWFI, and diluting 0.2 mL of 25% Buminate solution into the mixture and vortexing for 30 seconds. This was performed within 2 hours of use and stored on ice until needed. The samples were diluted to an estimated 1-2 U/mL. Generally, the maximum dilution per step did not exceed 1:100 and the initial sample size for the first dilution was not be less than 20 μL. The minimum sample volumes needed to perform the assay were: In-process Samples, FPLC Fractions: 80 μL; Tissue Culture Supernatants:1 mL; Concentrated Material 80 μL; Purified or Final Step Material: 80 μL. The dilutions were made in in triplicate in a Low Protein Binding 96-well plate, and 30 μL of each dilution was transferred to Optilux black/clear bottom plates (BD BioSciences).

Dilutions of known soluble rHuPH20 with a concentration of 2.5 U/mL were prepared in Enzyme Diluent Solution to generate a standard curve and added to the Optilux plate in triplicate. The dilutions included 0 U/mL, 0.25 U/mL, 0.5 U/mL, 1.0 U/mL, 1.5 U/mL, 2.0 U/mL, and 2.5 U/mL. "Reagent blank" wells that contained 60 μL of Enzyme Diluent Solution were included in the plate as a negative control. The plate was then covered and warmed on a heat block for 5 minutes at 37° C. The cover was removed and the plate was shaken for 10 seconds. After shaking, the plate was returned to the plate to the heat block and the MULTIDROP 384 Liquid Handling Device was primed with the warm 0.25 mg/mL sodium hyaluronate solution (prepared by dissolving 100 mg of sodium hyaluronate (LifeCore Biomedical) in 20.0 mL of SWFI. This was mixed by gently rotating and/or rocking at 2-8° C. for 2-4 hours, or until completely dissolved). The reaction plate was transferred to the MULTIDROP 384 and the reaction was initiated by pressing the start key to dispense 30 μL sodium hyaluronate into each well. The plate was then removed from the MULTIDROP 384 and shaken for 10 seconds before being transferred to a heat block with the plate cover replaced. The plate was incubated at 37° C. for 10 minutes The MULTIDROP 384 was prepared to stop the reaction by priming the machine with Serum Working Solution and changing the volume setting to 240 μL. (25 mL of Serum Stock Solution [1 volume of Horse Serum (Sigma) was diluted with 9 volumes of 500 mM Acetate Buffer Solution and the pH was adjusted to 3.1 with hydrochloric acid] in 75 mL of 500 mM Acetate Buffer Solution). The plate was removed from the heat block and placed onto the MULTIDROP 384 and 240 μL of serum Working Solutions was dispensed into the wells. The plate was removed and shaken on a plate reader for 10 seconds. After a further 15 minutes, the turbidity of the samples was measured at 640 nm and the hyaluronidase activity (in U/mL) of each sample was determined by fitting to the standard curve.

Specific activity (Units/mg) was calculated by dividing the hyaluronidase activity (U/ml) by the protein concentration (mg/mL).

Example 4

Production and Purification of Gen1 Human sPH20

A. 5 L Bioreactor Process

A vial of 3D35M was thawed and expanded from shaker flasks through 1 L spinner flasks in CD-CHO media (Invitrogen, Carlsbad Calif.) supplemented with 100 nM Methotrexate and GlutaMAX™-1 (Invitrogen). Cells were transferred from spinner flasks to a 5 L bioreactor (Braun) at an inoculation density of $4\times10^5$ viable cells per ml. Parameters were temperature Setpoint 37° C., pH 7.2 (starting Setpoint), with Dissolved Oxygen Setpoint 25% and an air overlay of 0-100 cc/min. At 168 hrs, 250 ml of Feed #1 Medium (CD CHO with 50 g/L Glucose) was added. At 216 hours, 250 ml of Feed #2 Medium (CD CHO with 50 g/L Glucose and 10 mM Sodium Butyrate) was added, and at 264 hours 250 ml of Feed #2 Medium was added. This process resulted in a final productivity of 1600 Units per ml with a maximal cell density of $6\times10^6$ cells/ml. The addition of sodium butyrate was to dramatically enhance the production of soluble rHuPH20 in the final stages of production.

Conditioned media from the 3D35M clone was clarified by depth filtration and tangential flow diafiltration into 10 mM Hepes pH 7.0. Soluble rHuPH20 was then purified by sequential chromatography on Q Sepharose (Pharmacia) ion exchange, Phenyl Sepharose (Pharmacia) hydrophobic interaction chromatography, phenyl boronate (Prometics) and Hydroxapatite Chromatography (Biorad, Richmond, Calif.).

Soluble rHuPH20 bound to Q Sepharose and eluted at 400 mM NaCl in the same buffer. The eluate was diluted with 2M ammonium sulfate to a final concentration of 500 mM ammonium sulfate and passed through a Phenyl Sepharose (low sub) column, followed by binding under the same conditions to a phenyl boronate resin. The soluble rHuPH20 was eluted from the phenyl sepharose resin in Hepes pH 6.9 after washing at pH 9.0 in 50 mM bicine without ammonium sulfate. The eluate was loaded onto a ceramic hydroxyapatite resin at pH 6.9 in 5 mM potassium phosphate and 1 mM $CaCl_2$ and eluted with 80 mM potassium phosphate, pH 7.4 with 0.1 mM $CaCl_2$.

The resultant purified soluble rHuPH20 possessed a specific activity in excess of 65,000 USP Units/mg protein by way of the microturbidity assay (Example 16) using the USP reference standard. Purified sPH20 eluted as a single peak from 24 to 26 minutes from a Pharmacia 5RPC styrene divinylbenzene column with a gradient between 0.1% TFA/$H_2O$ and 0.1% TFA/90% acetonitrile/10% $H_2O$ and resolved as a single broad 61 kDa band by SDS electrophoresis that reduced to a sharp 51 kDa band upon treatment with PNGASE-F. N-terminal amino acid sequencing revealed that the leader peptide had been efficiently removed.

B. Upstream Cell Culture Expansion Process into 100 L Bioreactor Cell Culture

A scaled-up process was used to separately purify soluble rHuPH20 from four different vials of 3D35M cell to produce 4 separate batches of sHuPH20; HUA0406C, HUA0410C, HUA0415C and HUA0420C. Each vial was separately expanded and cultured through a 125 L bioreactor, then purified using column chromatography. Samples were taken throughout the process to assess such parameters as enzyme yield. The description of the process provided below sets forth representative specifications for such things as bioreactor starting and feed media volumes, transfer cell densities, and wash and elution volumes. The exact numbers vary slightly with each batch, and are detailed in Tables 11 to 18.

Four vials of 3D35M cells were thawed in a 37° C. water bath, CD CHO containing 100 nM methotrexate and 40 mL/L GlutaMAX was added and the cells were centrifuged. The cells were re-suspended in a 125 mL shake flask with 20 mL of fresh media and placed in a 37° C., 7% $CO_2$ incubator. The cells were expanded up to 40 mL in the 125 mL shake flask. When the cell density reached 1.5-2.5×$10^6$ cells/mL, the culture was expanded into a 125 mL spinner flask in a 100 mL culture volume. The flask was incubated at 37° C., 7% $CO_2$. When the cell density reached 1.5-2.5×$10^6$ cells/mL, the culture was expanded into a 250 mL spinner flask in 200 mL culture volume, and the flask was incubated at 37° C., 7% $CO_2$, When the cell density reached 1.5-2.5×$10^6$ cells/mL, the culture was expanded into a 1 L spinner flask in 800 mL culture volume and incubated at 37° C., 7% $CO_2$. When the cell density reached 1.5-2.5×$10^6$ cells/mL, the culture was expanded into a 6 L spinner flask in 5 L culture volume and incubated at 37° C., 7% $CO_2$. When the cell density reached 1.5-2.5×$10^6$ cells/mL, the culture was expanded into a 36 L spinner flask in 20 L culture volume and incubated at 37° C., 7% $CO_2$.

A 125 L reactor was sterilized with steam at 121° C., 20 PSI and 65 L of CD CHO media was added. Before use, the reactor was checked for contamination. When the cell density in the 36 L spinner flasks reached 1.8-2.5×$10^6$ cells/mL, 20 L cell culture were transferred from the 36 L spinner flasks to the 125 L bioreactor (Braun), resulting a final volume of 85 L and a seeding density of approximately 4×$10^5$ cells/mL. Parameters were temperature setpoint, 37° C.; pH: 7.2; Dissolved oxygen: 25%±10%; Impeller Speed 50 rpm; Vessel Pressure 3 psi; Air Sparge 1 L/min.; Air Overlay: 1 L/min. The reactor was sampled daily for cell counts, pH verification, media analysis, protein production and retention. Nutrient feeds were added during the run. At Day 6, 3.4 L of Feed #1 Medium (CD CHO+50 g/L Glucose+40 mL/L GlutaMAX™-1) was added, and culture temperature was changed to 36.5° C. At day 9, 3.5 L of Feed #2 (CD CHO+50 g/L Glucose+40 mL/L GlutaMAX™-1+1.1 g/L Sodium Butyrate) was added, and culture temperature was changed to 36° C. At day 11, 3.7. L of Feed #3 (CD CHO+50 g/L Glucose+40 mL/L GlutaMAX™-1+1.1 g/L Sodium Butyrate) was added, and the culture temperature was changed to 35.5° C. The reactor was harvested at 14 days or when the viability of the cells dropped below 50%. The process resulted in production of soluble rHuPH20 with an enzymatic activity of 1600 Units/ml with a maximal cell density of 8 million cells/mL. At harvest, the culture was sampled for mycoplasma, bioburden, endotoxin, and virus in vitro and in vivo, transmission electron microscopy (TEM) for viral particles, and enzyme activity.

The one hundred liter bioreactor cell culture harvest was filtered through a series of disposable capsule filters having a polyethersulfone medium (Sartorius): first through a 8.0 μm depth capsule, a 0.65 μm depth capsule, a 0.22 μm capsule, and finally through a 0.22 μm Sartopore 2000 $cm^2$ filter and into a 100 L sterile storage bag. The culture was concentrated 10× using two TFF with Spiral Polyethersulfone 30 kDa MWCO filters (Millipore), followed by a 6× buffer exchange with 10 mM HEPES, 25 mM $Na_2SO_4$, pH 7.0 into a 0.22 μm final filter into a 20 L sterile storage bag. Table 11 provides monitoring data related to the cell culture, harvest, concentration and buffer exchange steps.

TABLE 11

Monitoring data for cell culture, harvest, concentration and buffer exchange steps.

| Parameter | HUA0406C | HUA04010C | HUA0415C | HUA0420C |
|---|---|---|---|---|
| Time from thaw to inoculate 100 L bioreactor (days) | 21 | 19 | 17 | 18 |
| 100 L inoculation density (×$10^6$ cells/mL) | 0.45 | 0.33 | 0.44 | 0.46 |
| Doubling time in logarithmic growth (hr) | 29.8 | 27.3 | 29.2 | 23.5 |
| Max. cell density (×$10^6$ cells/mL) | 5.65 | 8.70 | 6.07 | 9.70 |
| Harvest viability (%) | 41 | 48 | 41 | 41 |
| Harvest titer (U/ml) | 1964 | 1670 | 991 | 1319 |
| Time in 100-L bioreactor (days) | 13 | 13 | 12 | 13 |
| Clarified harvest volume (mL) | 81800 | 93300 | 91800 | 89100 |
| Clarified harvest enzyme assay (U/mL) | 2385 | 1768 | 1039 | 1425 |
| Concentrate enzyme assay (U/mL) | 22954 | 17091 | 8561 | 17785 |
| Buffer exchanged concentrate enzyme assay (U/mL) | 15829 | 11649 | 9915 | 8679 |
| Filtered buffer exchanged concentrate enzyme assay (U/mL) | 21550 | 10882 | 9471 | 8527 |

TABLE 11-continued

| Monitoring data for cell culture, harvest, concentration and buffer exchange steps. | | | | |
|---|---|---|---|---|
| Parameter | HUA0406C | HUA04010C | HUA0415C | HUA0420C |
| Buffer exchanged concentrate volume (mL) | 10699 | 13578 | 12727 | 20500 |
| Ratio enzyme units concentration/harvest | 0.87 | 0.96 | 1.32 | 1.4 |

A Q Sepharose (Pharmacia) ion exchange column (3 L resin, Height=20 cm, Diameter=14 cm) was prepared. Wash samples were collected for a determination of pH, conductivity and endotoxin (LAL) assay. The column was equilibrated with 5 column volumes of 10 mM Tris, 20 mM $Na_2SO_4$, pH 7.5. The concentrated, diafiltered harvest was loaded onto the Q column at a flow rate of 100 cm/hr. The column was washed with 5 column volumes of 10 mM Tris, 20 mM $Na_2SO_4$, pH 7.5 and 10 mM Hepes, 50 mM NaCl, pH 7.0. The protein was eluted with 10 mM Hepes, 400 mM NaCl, pH 7.0 and filtered through a 0.22 μm final filter into a sterile bag.

Phenyl-Sepharose (Pharmacia) hydrophobic interaction chromatography was next performed. A Phenyl-Sepharose (PS) column (9.1 L resin, Height=29 cm, Diameter=20 cm) was prepared. The column was equilibrated with 5 column volumes of 5 mM potassium phosphate, 0.5 M ammonium sulfate, 0.1 mM $CaCl_2$, pH 7.0. The protein eluate from above was supplemented with 2M ammonium sulfate, 1 M potassium phosphate and 1 M $CaCl_2$ stock solutions to final concentrations of 5 mM, 0.5 M and 0.1 mM, respectively. The protein was loaded onto the PS column at a flow rate of 100 cm/hr. 5 mM potassium phosphate, 0.5 M ammonium sulfate and 0.1 mM $CaCl_2$ pH 7.0 was added at 100 cm/hr. The flow through was passed through a 0.22 μm final filter into a sterile bag.

The PS-purified protein was the loaded onto an aminophenyl boronate column (ProMedics) (6.3 L resin, Height=20 cm, Diameter=20 cm) that had been equilibrated with 5 column volumes of 5 mM potassium phosphate, 0.5 M ammonium sulfate. The protein was passed through the column at a flow rate of 100 cm/hr, and the column was washed with 5 mM potassium phosphate, 0.5 M ammonium sulfate, pH 7.0. The column was then washed with 20 mM bicine, 100 mM NaCl, pH 9.0 and the protein eluted with 50 mM Hepes, 100 mM NaCl pH 6.9 through a sterile filter and into a 20 L sterile bag. The eluate was tested for bioburden, protein concentration and enzyme activity.

A hydroxyapatite (HAP) column (BioRad) (1.6 L resin, Height=10 cm, Diameter=14 cm) was equilibrated with 5 mM potassium phosphate, 100 mM NaCl, 0.1 mM $CaCl_2$ pH 7.0. Wash samples were collected and tested for pH, conductivity and endotoxin (LAL assay). The aminophenyl boronate purified protein was supplemented with potassium phosphate and $CaCl_2$ to yield final concentrations of 5 mM potassium phosphate and 0.1 mM $CaCl_2$ and loaded onto the HAP column at a flow rate of 100 cm/hr. The column was washed with 5 mM potassium phosphate pH 7.0, 100 mM NaCl, 0.1 mM $CaCl_2$, then 10 mM potassium phosphate pH 7.0, 100 mM NaCl, 0.1 mM $CaCl_2$ pH. The protein was eluted with 70 mM potassium phosphate pH 7.0 and filtered through a 0.22 μm filter into a 5 L sterile storage bag. The eluate was tested for bioburden, protein concentration and enzyme activity.

The HAP-purified protein was then pumped through a 20 nM viral removal filter via a pressure tank. The protein was added to the DV20 pressure tank and filter (Pall Corporation), passing through an Ultipor DV20 Filter with 20 nm pores (Pall Corporation) into a sterile 20 L storage bag. The filtrate was tested for protein concentration, enzyme activity, oligosaccharide, monosaccharide and sialic acid profiling, and process-related impurities. The protein in the filtrate was then concentrated to 1 mg/mL using a 10 kD molecular weight cut off (MWCO) Sartocon Slice tangential flow filtration (TFF) system (Sartorius). The filter was first prepared by washing with a Hepes/saline solution (10 mM Hepes, 130 mM NaCl, pH 7.0) and the permeate was sampled for pH and conductivity. Following concentration, the concentrated protein was sampled and tested for protein concentration and enzyme activity. A 6× buffer exchange was performed on the concentrated protein into the final buffer: 10 mM Hepes, 130 mM NaCl, pH 7.0. The concentrated protein was passed though a 0.22 μm filter into a 20 L sterile storage bag. The protein was sampled and tested for protein concentration, enzyme activity, free sulfhydryl groups, oligosaccharide profiling and osmolarity.

Tables 12 to 18 provide monitoring data related to each of the purification steps described above, for each 3D35M cell lot.

TABLE 12

| Q sepharose column data | | | | |
|---|---|---|---|---|
| Parameter | HUA0406C | HUA0410C | HUA0415C | HUA0420C |
| Load volume (mL) | 10647 | 13524 | 12852 | 20418 |
| Load Volume/ Resin Volume ratio | 3.1 | 4.9 | 4.5 | 7.3 |
| Column Volume (mL) | 2770 | 3840 | 2850 | 2880 |
| Eluate volume (mL) | 6108 | 5923 | 5759 | 6284 |
| Protein Conc. of Eluate (mg/mL) | 2.8 | 3.05 | 2.80 | 2.86 |
| Eluate Enzyme Assay (U/mL) | 24493 | 26683 | 18321 | 21052 |
| Enzyme Yield (%) | 65 | 107 | 87 | 76 |

TABLE 13

| Phenyl Sepharose column data | | | | |
|---|---|---|---|---|
| Parameter | HUA0406C | HUA0410C | HUA0415C | HUA0420C |
| Volume Before Stock Solution Addition (mL) | 5670 | 5015 | 5694 | 6251 |
| Load Volume (mL) | 7599 | 6693 | 7631 | 8360 |

TABLE 13-continued

| Phenyl Sepharose column data | | | | |
|---|---|---|---|---|
| Parameter | HUA0406C | HUA0410C | HUA0415C | HUA0420C |
| Column Volume (mL) | 9106 | 9420 | 9340 | 9420 |
| Load Volume/ Resin Volume ratio | 0.8 | 0.71 | 0.82 | 0.89 |
| Eluate volume (mL) | 16144 | 18010 | 16960 | 17328 |
| Protein Cone of Eluate (mg/mL) | 0.4 | 0.33 | 0.33 | 0.38 |
| Eluate Enzyme Assay (U/mL) | 8806 | 6585 | 4472 | 7509 |
| Protein Yield (%) | 41 | 40 | 36 | 37 |
| Enzyme Yield (%) | 102 | 88 | 82 | 96 |

TABLE 14

| Amino Phenyl Boronate column data | | | | |
|---|---|---|---|---|
| Parameter | HUA0406C | HUA0410C | HUA0415C | HUA0420C |
| Load Volume (mL) | 16136 | 17958 | 16931 | 17884 |
| Load Volume/ Resin Volume ratio | 2.99 | 3.15 | 3.08 | 2.98 |
| Column Volume (mL) | 5400 | 5700 | 5500 | 5300 |
| Eluate volume (mL) | 17595 | 22084 | 20686 | 19145 |
| Protein Conc. of Eluate (mg/mL) | 0.0 | 0.03 | 0.03 | 0.04 |
| Protein Conc. of Filtered Eluate (mg/mL) | not tested | 0.03 | 0.00 | 0.04 |
| Eluate Enzyme Assay (U/mL) | 4050 | 2410 | 1523 | 4721 |
| Protein Yield (%) | 0 | 11 | 11 | 12 |
| Enzyme Yield (%) | not determined | 41 | 40 | 69 |

TABLE 15

| Hydroxyapatite column data | | | | |
|---|---|---|---|---|
| Parameter | HUA0406C | HUA0410C | HUA0415C | HUA0420C |
| Volume Before Stock Solution Addition (mL) | 16345 | 20799 | 20640 | 19103 |
| Load Volume/ Resin Volume ratio | 10.95 | 13.58 | 14.19 | 12.81 |
| Column Volume (mL) | 1500 | 1540 | 1462 | 1500 |
| Load volume (mL) | 16429 | 20917 | 20746 | 19213 |
| Eluate volume (mL) | 4100 | 2415 | 1936 | 2419 |
| Protein Conc. of Eluate (mg/mL) | not tested | 0.24 | 0.17 | 0.23 |
| Protein Conc. of Filtered Eluate (mg/mL) | NA | NA | 0.17 | NA |

TABLE 15-continued

| Hydroxyapatite column data | | | | |
|---|---|---|---|---|
| Parameter | HUA0406C | HUA0410C | HUA0415C | HUA0420C |
| Eluate Enzyme Assay (U/mL) | 14051 | 29089 | 20424 | 29826 |
| Protein Yield (%) | Not tested | 93 | 53 | 73 |
| Enzyme Yield (%) | 87 | 118 | 140 | 104 |

TABLE 16

| DV20 filtration data | | | | |
|---|---|---|---|---|
| Parameter | HUA0406C | HUA0410C | HUA0415C | HUA0420C |
| Start volume (mL) | 4077 | 2233 | 1917 | 2419 |
| Filtrate Volume (mL) | 4602 | 3334 | 2963 | 3504 |
| Protein Conc. of Filtrate (mg/mL) | 0.1 | NA | 0.09 | NA |
| Protein Conc. of Filtered Eluate (mg/mL) | NA | 0.15 | 0.09 | 0.16 |
| Protein Yield (%) | not tested | 93 | 82 | 101 |

TABLE 17

| Final concentration data | | | | |
|---|---|---|---|---|
| Parameter | HUA0406C | HUA0410C | HUA0415C | HUA0420C |
| Start volume (mL) | 4575 | 3298 | 2963 | 3492 |
| Concentrate Volume (mL) | 562 | 407 | 237 | 316 |
| Protein Conc. of Concentrate (mg/mL) | 0.9 | 1.24 | 1.16 | 1.73 |
| Protein Yield (%) | 111 | 102 | 103 | 98 |

TABLE 18

| Buffer Exchange into Final Formulation data | | | | |
|---|---|---|---|---|
| Parameter | HUA0406C | HUA0410C | HUA0415C | HUA0420C |
| Start Volume (mL) | 562 | 407 | 237 | 316 |
| Final Volume Buffer Exchanged Concentrate (mL) | 594 | 516 | 310 | 554 |
| Protein Conc. of Concentrate (mg/mL) | 1.00 | 0.97 | 0.98 | 1.00 |
| Protein Conc. of Filtered Concentrate (mg/mL) | 0.95 | 0.92 | 0.95 | 1.02 |
| Protein Yield (%) | 118 | 99 | 110 | 101 |

The purified and concentrated soluble rHuPH20 protein was aseptically filled into sterile vials with 5 mL and 1 mL fill volumes. The protein was passed though a 0.22 μm filter to an operator controlled pump that was used to fill the vials using a gravimetric readout. The vials were closed with stoppers and secured with crimped caps. The closed vials were visually inspected for foreign particles and then labeled. Following labeling, the vials were flash-frozen by submersion in liquid nitrogen for no longer than 1 minute and stored at ≤15° C. (−20±5° C.).

Example 5

Production Gen2 Cells Containing Soluble Human PH20 (rHuPH20)

The Gen1 3D35M cell line described in Example 2 was adapted to higher methotrexate levels to produce generation 2 (Gen2) clones. 3D35M cells were seeded from established methotrexate-containing cultures into CD CHO medium containing 4 mM GlutaMAX-1™ and 1.0 μM methotrexate. The cells were adapted to a higher methotrexate level by growing and passaging them 9 times over a period of 46 days in a 37° C., 7% $CO_2$ humidified incubator. The amplified population of cells was cloned out by limiting dilution in 96-well tissue culture plates containing medium with 2.0 μM methotrexate. After approximately 4 weeks, clones were identified and clone 3E10B was selected for expansion. 3E10B cells were grown in CD CHO medium containing 4 mM GlutaMAX-1™ and 2.0 μM methotrexate for 20 passages. A master cell bank (MCB) of the 3E10B cell line was created and frozen and used for subsequent studies.

Amplification of the cell line continued by culturing 3E10B cells in CD CHO medium containing 4 mM GlutaMAX-1™ and 4.0 μM methotrexate. After the $12^{th}$ passage, cells were frozen in vials as a research cell bank (RCB). One vial of the RCB was thawed and cultured in medium containing 8.0 μM methotrexate. After 5 days, the methotrexate concentration in the medium was increased to 16.0 μM, then 20.0 μM 18 days later. Cells from the $8^{th}$ passage in medium containing 20.0 μM methotrexate were cloned out by limiting dilution in 96-well tissue culture plates containing CD CHO medium containing 4 mM GlutaMAX-1™ and 20.0 μM methotrexate. Clones were identified 5-6 weeks later and clone 2B2 was selected for expansion in medium containing 20.0 μM methotrexate. After the 11th passage, 2B2 cells were frozen in vials as a research cell bank (RCB).

The resultant 2B2 cells are dihydrofolate reductase deficient (dhfr-) DG44 CHO cells that express soluble recombinant human PH20 (rHuPH20). The soluble PH20 is present in 2B2 cells at a copy number of approximately 206 copies/cell. Southern blot analysis of Spe I-, Xba I- and BamH I/Hind III-digested genomic 2B2 cell DNA using a rHuPH20-specific probe revealed the following restriction digest profile: one major hybridizing band of ~7.7 kb and four minor hybridizing bands (~13.9, ~6.6, ~5.7 and ~4.6 kb) with DNA digested with Spe I; one major hybridizing band of ~5.0 kb and two minor hybridizing bands (~13.9 and ~6.5 kb) with DNA digested with Xba I; and one single hybridizing band of ~1.4 kb observed using 2B2 DNA digested with BamH I/Hind III. Sequence analysis of the mRNA transcript indicated that the derived cDNA (SEQ ID NO:56) was identical to the reference sequence (SEQ ID NO:49) except for one base pair difference at position 1131, which was observed to be a thymidine (T) instead of the expected cytosine (C). This is a silent mutation, with no effect on the amino acid sequence.

Example 6

A. Production of Gen2 Soluble rHuPH20 in 300 L Bioreactor Cell Culture

A vial of HZ24-2B2 was thawed and expanded from shaker flasks through 36 L spinner flasks in CD-CHO media (Invitrogen, Carlsbad, Calif.) supplemented with 20 μM methotrexate and GlutaMAX-1™ (Invitrogen). Briefly, the a vial of cells was thawed in a 37° C. water bath, media was added and the cells were centrifuged. The cells were resuspended in a 125 mL shake flask with 20 mL of fresh media and placed in a 37° C., 7% $CO_2$ incubator. The cells were expanded up to 40 mL in the 125 mL shake flask. When the cell density reached greater than $1.5\times10^6$ cells/mL, the culture was expanded into a 125 mL spinner flask in a 100 mL culture volume. The flask was incubated at 37° C., 7% $CO_2$. When the cell density reached greater than $1.5\times10^6$ cells/mL, the culture was expanded into a 250 mL spinner flask in 200 mL culture volume, and the flask was incubated at 37° C., 7% $CO_2$. When the cell density reached greater than $1.5\times10^6$ cells/mL, the culture was expanded into a 1 L spinner flask in 800 mL culture volume and incubated at 37° C., 7% $CO_2$. When the cell density reached greater than $1.5\times10^6$ cells/mL the culture was expanded into a 6 L spinner flask in 5000 mL culture volume and incubated at 37° C., 7% $CO_2$. When the cell density reached greater than $1.5\times10^6$ cells/mL the culture was expanded into a 36 L spinner flask in 32 L culture volume and incubated at 37° C., 7% $CO_2$.

A 400 L reactor was sterilized and 230 mL of CD-CHO media was added. Before use, the reactor was checked for contamination. Approximately 30 L cells were transferred from the 36 L spinner flasks to the 400 L bioreactor (Braun) at an inoculation density of $4.0\times10^5$ viable cells per ml and a total volume of 260 L. Parameters were temperature setpoint, 37° C.; Impeller Speed 40-55 RPM; Vessel Pressure: 3 psi; Air Sparge 0.5-1.5 L/Min.; Air Overlay: 3 L/min. The reactor was sampled daily for cell counts, pH verification, media analysis, protein production and retention. Also, during the run nutrient feeds were added. At 120 hrs (day 5), 10.4 L of Feed #1 Medium (4×CD-CHO+33 g/L Glucose+160 mL/L Glutamax-1™+83 mL/L Yeastolate+33 mg/L rHulnsulin) was added. At 168 hours (day 7), 10.8 L of Feed #2 (2×CD-CHO+33 g/L Glucose+80 mL/L Glutamax-1™+167 mL/L Yeastolate+0.92 g/L Sodium Butyrate) was added, and culture temperature was changed to 36.5° C. At 216 hours (day 9), 10.8 L of Feed #3 (1×CD-CHO+50 g/L Glucose+50 mL/L Glutamax-1™+250 mL/L Yeastolate+1.80 g/L Sodium Butyrate) was added, and culture temperature was changed to 36° C. At 264 hours (day 11), 10.8 L of Feed #4 (1×CD-CHO+33 g/L Glucose+33 mL/L Glutamax-1™+250 mL/L Yeastolate+0.92 g/L Sodium Butyrate) was added, and culture temperature was changed to 35.5° C. The addition of the feed media was observed to dramatically enhance the production of soluble rHuPH20 in the final stages of production. The reactor was harvested at 14 or 15 days or when the viability of the cells dropped below 40%. The process resulted in a final productivity of 17,000 Units per ml with a maximal cell density of 12 million cells/mL. At harvest, the culture was sampled for mycoplasma, bioburden, endotoxin and viral in vitro and in vivo, Transmission Electron Microscopy (TEM) and enzyme activity.

The culture was pumped by a peristaltic pump through four Millistak filtration system modules (Millipore) in parallel, each containing a layer of diatomaceous earth graded to 4-8 μm and a layer of diatomaceous earth graded to 1.4-1.1 μm, followed by a cellulose membrane, then through a second single Millistak filtration system (Millipore) containing a layer of diatomaceous earth graded to 0.4-0.11 μm and a layer of diatomaceous earth graded to <0.1 μm, followed by a cellulose membrane, and then through a 0.22 μm final filter into a sterile single use flexible bag with a 350

L capacity. The harvested cell culture fluid was supplemented with 10 mM EDTA and 10 mM Tris to a pH of 7.5. The culture was concentrated 10× with a tangential flow filtration (TFF) apparatus using four Sartoslice TFF 30 kDa molecular weight cut-off (MWCO) polyether sulfone (PES) filter (Sartorious), followed by a 10× buffer exchange with 10 mM Tris, 20 mM $Na_2SO_4$, pH 7.5 into a 0.22 μm final filter into a 50 L sterile storage bag.

The concentrated, diafiltered harvest was inactivated for virus. Prior to viral inactivation, a solution of 10% Triton X-100, 3% tri (n-butyl) phosphate (TNBP) was prepared. The concentrated, diafiltered harvest was exposed to 1% Triton X-100, 0.3% TNBP for 1 hour in a 36 L glass reaction vessel immediately prior to purification on the Q column.

B. Purification of Gent soluble rHuPH20

A Q Sepharose (Pharmacia) ion exchange column (9 L resin, H=29 cm, D=20 cm) was prepared. Wash samples were collected for a determination of pH, conductivity and endotoxin (LAL) assay. The column was equilibrated with 5 column volumes of 10 mM Tris, 20 mM Na2SO4, pH 7.5. Following viral inactivation, the concentrated, diafiltered harvest was loaded onto the Q column at a flow rate of 100 cm/hr. The column was washed with 5 column volumes of 10 mM Tris, 20 mM Na2SO4, pH 7.5 and 10 mM Hepes, 50 mM NaCl, pH7.0. The protein was eluted with 10 mM Hepes, 400 mM NaCl, pH 7.0 into a 0.22 μm final filter into sterile bag. The eluate sample was tested for bioburden, protein concentration and hyaluronidase activity. $A_{280}$ absorbance reading were taken at the beginning and end of the exchange.

Phenyl-Sepharose (Pharmacia) hydrophobic interaction chromatography was next performed. A Phenyl-Speharose (PS) column (19-21 L resin, H=29 cm, D=30 cm) was prepared. The wash was collected and sampled for pH, conductivity and endotoxin (LAL assay). The column was equilibrated with 5 column volumes of 5 mM potassium phosphate, 0.5 M ammonium sulfate, 0.1 mM CaCl2, pH 7.0. The protein eluate from the Q sepharose column was supplemented with 2M anunonium sulfate, 1 M potassium phosphate and 1 M $CaCl_2$ stock solutions to yield final concentrations of 5 mM, 0.5 M and 0.1 mM, respectively. The protein was loaded onto the PS column at a flow rate of 100 cm/hr and the column flow thru collected. The column was washed with 5 mM potassium phosphate, 0.5 M ammonium sulfate and 0.1 mM CaCl2 pH 7.0 at 100 cm/hr and the wash was added to the collected flow thru. Combined with the column wash, the flow through was passed through a 0.22 μm final filter into a sterile bag. The flow through was sampled for bioburden, protein concentration and enzyme activity.

An aminophenyl boronate column (Promtics) was prepared. The wash was collected and sampled for pH, conductivity and endotoxin (LAL assay). The column was equilibrated with 5 column volumes of 5 mM potassium phosphate, 0.5 M ammonium sulfate. The PS flow through containing purified protein was loaded onto the aminophenyl boronate column at a flow rate of 100 cm/hr. The column was washed with 5 mM potassium phosphate, 0.5 M ammonium sulfate, pH 7.0. The column was washed with 20 mM bicine, 0.5 M ammonium sulfate, pH 9.0. The column was washed with 20 mM bicine, 100 mM sodium chloride, pH 9.0. The protein was eluted with 50 mM Hepes, 100 mM NaCl, pH 6.9 and passed through a sterile filter into a sterile bag. The eluted sample was tested for bioburden, protein concentration and enzyme activity.

The hydroxyapatite (HAP) column (Biorad) was prepared. The wash was collected and test for pH, conductivity and endotoxin (LAL assay). The column was equilibrated with 5 mM potassium phosphate, 100 mM NaCl, 0.1 mM $CaCl_2$, pH 7.0. The aminophenyl boronate purified protein was supplemented to final concentrations of 5 mM potassium phosphate and 0.1 mM $CaCl_2$ and loaded onto the HAP column at a flow rate of 100 cm/hr. The column was washed with 5 mM potassium phosphate, pH 7, 100 mM NaCl, 0.1 mM $CaCl_2$. The column was next washed with 10 mM potassium phosphate, pH 7, 100 mM NaCl, 0.1 mM $CaCl_2$. The protein was eluted with 70 mM potassium phosphate, pH 7.0 and passed through a 0.22 μm sterile filter into a sterile bag. The eluted sample was tested for bioburden, protein concentration and enzyme activity.

The HAP purified protein was then passed through a viral removal filter. The sterilized Virosart filter (Sartorius) was first prepared by washing with 2 L of 70 mM potassium phosphate, pH 7.0. Before use, the filtered buffer was sampled for pH and conductivity. The HAP purified protein was pumped via a peristaltic pump through the 20 nM viral removal filter. The filtered protein in 70 mM potassium phosphate, pH 7.0 was passed through a 0.22 μm final filter into a sterile bag. The viral filtered sample was tested for protein concentration, enzyme activity, oligosaccharide, monosaccharide and sialic acid profiling. The sample also was tested for process related impurities.

The protein in the filtrate was then concentrated to 10 mg/mL using a 10 kD molecular weight cut off (MWCO) Sartocon Slice tangential flow filtration (TFF) system (Sartorius). The filter was first prepared by washing with 10 mM histidine, 130 mM NaCl, pH 6.0 and the permeate was sampled for pH and conductivity. Following concentration, the concentrated protein was sampled and tested for protein concentration and enzyme activity. A 6× buffer exchange was performed on the concentrated protein into the final buffer: 10 mM histidine, 130 mM NaCl, pH 6.0. Following buffer exchange, the concentrated protein was passed though a 0.22 μm filter into a 20 L sterile storage bag. The protein was sampled and tested for protein concentration, enzyme activity, free sulfhydryl groups, oligosaccharide profiling and osmolarity.

The sterile filtered bulk protein was then aseptically dispensed at 20 mL into 30 mL sterile Teflon vials (Nalgene). The vials were then flash frozen and stored at −20±5° C.

C. Comparison of Production and Purification of Gen1 Soluble rHuPH20 and Gen2 Soluble rHuPH20

The production and purification of Gen2 soluble rHuPH20 in a 300 L bioreactor cell culture contained some changes in the protocols compared to the production and purification Gen1 soluble rHuPH20 in a 100 L bioreactor cell culture (described in Example 4.B). Table 19 sets forth exemplary differences, in addition to simple scale up changes, between the methods.

TABLE 19

| Process Difference | Gen1 soluble rHuPH20 | Gen2 soluble rHuPH20 |
|---|---|---|
| Cell line | 3D35M | 2B2 |
| Media used to expand cell inoculum | Contains 0.10 μM methotrexate (0.045 mg/L) | Contains 20 μM methotrexate (9 mg/L) |
| Media in 6 L cultures onwards | Contains 0.10 μM methotrexate | Contains no methotrexate |
| 36 L spinner flask | No instrumentation<br>20 L operating volume. | Equipped with instrumentation that monitors and controls pH, dissolved oxygen, sparge and overlay gas flow rate.<br>32 L operating volume |
| Final operating volume in bioreactor | Approx. 100 L in a 125 L bioreactor (initial culture volume + 65 L) | Approx. 300 L in a 400 L bioreactor (initial culture volume + 260 L) |
| Culture media in final bioreactor | No rHuInsulin | 5.0 mg/L rHuInsulin |
| Media feed volume | Scaled at 4% of the bioreactor cell culture volume i.e. 3.4, 3.5 and 3.7 L, resulting in a target bioreactor volume of ~92 L. | Scaled at 4% of the bioreactor cell culture volume i.e. 10.4, 10.8, 11.2 and 11.7 L, resulting in a target bioreactor volume of ~303 L. |
| Media feed | Feed #1 Medium: CD CHO + 50 g/L Glucose + 8 mM GlutaMAX ™-1<br>Feed #2 (CD CHO + 50 g/L Glucose + 8 mM GlutaMAX + 1.1 g/L Sodium Butyrate<br>Feed #3: CD CHO + 50 g/L Glucose + 8 mM GlutaMAX + 1.1 g/L Sodium Butyrate | Feed #1 Medium: 4 × CD CHO + 33 g/L Glucose + 32 mM Glutamax + 16.6 g/L Yeastolate + 33 mg/L rHuInsulin<br>Feed #2: 2 × CD CHO + 33 g/L Glucose + 16 mM Glutamax + 33.4 g/L Yeastolate + 0.92 g/L Sodium Butyrate<br>Feed #3: 1 × CD CHO + 50 g/L Glucose + 10 mM Glutamax + 50 g/L Yeastolate + 1.80 g/L Sodium Butyrate<br>Feed #4: 1 × CD CHO + 33 g/L Glucose + 6.6 mM Glutamax + 50 g/L Yeastolate + 0.92 g/L Sodium Butyrate |
| Filtration of bioreactor cell culture | Four polyethersulfone filters (8.0 μm, 0.65 μm, 0.22 μm and 0.22 μm) in series<br>100 L storage bag | 1st stage - Four modules in parallel, each with a layer of diatomaceous earth graded to 4-8 μm and a layer of diatomaceous earth graded to 1.4-1.1 μm, followed by a cellulose membrane.<br>2nd stage - single module containing a layer of diatomaceous earth graded to 0.4-0.11 μm and a layer of diatomaceous earth graded to <0.1 μm, followed by a cellulose membrane.<br>3rd stage - 0.22 μm polyethersulfone filter<br>300 L storage bag<br>Harvested cell culture is supplemented with 10 mM EDTA, 10 mM Tris to a pH of 7.5. |
| Concentration and buffer exchange prior to chromatography | Concentrate with 2 TFF with Millipore Spiral Polyethersulfone 30K MWCO Filter<br>Buffer Exchange the Concentrate 6 × with 10 mM Hepes, 25 mM NaCl, pH 7.0<br>20 L sterile storage bag | Concentrate using four Sartorius Sartoslice TFF 30K MWCO Filter<br>Buffer Exchange the Concentrate 10 × with 10 mM Tris, 20 mM Na2SO4, pH 7.5<br>50 L sterile storage bag |

TABLE 19-continued

| Process Difference | Gen1 soluble rHuPH20 | Gen2 soluble rHuPH20 |
|---|---|---|
| Viral inactivation prior to chromatography | None | Viral inactivation performed with the addition of a 1% Triton X-100, 0.3% Tributyl Phosphate, pH 7.5, |
| 1st purification step (Q sepharose) | No absorbance reading | A280 measurements at the beginning and end |
| Viral filtration after chromatography | Pall DV-20 filter (20 nm) | Sartorius Virosart filter (20 nm) |
| Concentration and buffer exchange after chromatography | Hepes/saline pH 7.0 buffer Protein concentrated to 1 mg/ml | Histidine/saline, pH 6.0 buffer Protein concentrated to 10 mg/ml |

Since modifications will be apparent to those of skill in this art, it is intended that this invention be limited only by the scope of the appended claims.

SEQUENCE LISTING

```
<160> NUMBER OF SEQ ID NOS: 56

<210> SEQ ID NO 1
<211> LENGTH: 509
<212> TYPE: PRT
<213> ORGANISM: Homo sapiens
<220> FEATURE:
<223> OTHER INFORMATION: precursor human PH20

<400> SEQUENCE: 1

Met Gly Val Leu Lys Phe Lys His Ile Phe Phe Arg Ser Phe Val Lys
1               5                   10                  15

Ser Ser Gly Val Ser Gln Ile Val Phe Thr Phe Leu Leu Ile Pro Cys
            20                  25                  30

Cys Leu Thr Leu Asn Phe Arg Ala Pro Pro Val Ile Pro Asn Val Pro
        35                  40                  45

Phe Leu Trp Ala Trp Asn Ala Pro Ser Glu Phe Cys Leu Gly Lys Phe
    50                  55                  60

Asp Glu Pro Leu Asp Met Ser Leu Phe Ser Phe Ile Gly Ser Pro Arg
65                  70                  75                  80

Ile Asn Ala Thr Gly Gln Gly Val Thr Ile Phe Tyr Val Asp Arg Leu
                85                  90                  95

Gly Tyr Tyr Pro Tyr Ile Asp Ser Ile Thr Gly Val Thr Val Asn Gly
            100                 105                 110

Gly Ile Pro Gln Lys Ile Ser Leu Gln Asp His Leu Asp Lys Ala Lys
        115                 120                 125

Lys Asp Ile Thr Phe Tyr Met Pro Val Asp Asn Leu Gly Met Ala Val
    130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
        195                 200                 205

Leu Leu Arg Pro Asn His Leu Trp Gly Tyr Tyr Leu Phe Pro Asp Cys
    210                 215                 220

Tyr Asn His His Tyr Lys Lys Pro Gly Tyr Asn Gly Ser Cys Phe Asn
```

225 230 235 240

Val Glu Ile Lys Arg Asn Asp Asp Leu Ser Trp Leu Trp Asn Glu Ser
245 250 255

Thr Ala Leu Tyr Pro Ser Ile Tyr Leu Asn Thr Gln Gln Ser Pro Val
260 265 270

Ala Ala Thr Leu Tyr Val Arg Asn Arg Val Arg Glu Ala Ile Arg Val
275 280 285

Ser Lys Ile Pro Asp Ala Lys Ser Pro Leu Pro Val Phe Ala Tyr Thr
290 295 300

Arg Ile Val Phe Thr Asp Gln Val Leu Lys Phe Leu Ser Gln Asp Glu
305 310 315 320

Leu Val Tyr Thr Phe Gly Glu Thr Val Ala Leu Gly Ala Ser Gly Ile
325 330 335

Val Ile Trp Gly Thr Leu Ser Ile Met Arg Ser Met Lys Ser Cys Leu
340 345 350

Leu Leu Asp Asn Tyr Met Glu Thr Ile Leu Asn Pro Tyr Ile Ile Asn
355 360 365

Val Thr Leu Ala Ala Lys Met Cys Ser Gln Val Leu Cys Gln Glu Gln
370 375 380

Gly Val Cys Ile Arg Lys Asn Trp Asn Ser Ser Asp Tyr Leu His Leu
385 390 395 400

Asn Pro Asp Asn Phe Ala Ile Gln Leu Glu Lys Gly Gly Lys Phe Thr
405 410 415

Val Arg Gly Lys Pro Thr Leu Glu Asp Leu Glu Gln Phe Ser Glu Lys
420 425 430

Phe Tyr Cys Ser Cys Tyr Ser Thr Leu Ser Cys Lys Glu Lys Ala Asp
435 440 445

Val Lys Asp Thr Asp Ala Val Asp Val Cys Ile Ala Asp Gly Val Cys
450 455 460

Ile Asp Ala Phe Leu Lys Pro Pro Met Glu Thr Glu Glu Pro Gln Ile
465 470 475 480

Phe Tyr Asn Ala Ser Pro Ser Thr Leu Ser Ala Thr Met Phe Ile Val
485 490 495

Ser Ile Leu Phe Leu Ile Ile Ser Ser Val Ala Ser Leu
500 505

<210> SEQ ID NO 2
<211> LENGTH: 474
<212> TYPE: PRT
<213> ORGANISM: Homo sapiens
<220> FEATURE:
<223> OTHER INFORMATION: Mature PH20

<400> SEQUENCE: 2

Leu Asn Phe Arg Ala Pro Pro Val Ile Pro Asn Val Pro Phe Leu Trp
1 5 10 15

Ala Trp Asn Ala Pro Ser Glu Phe Cys Leu Gly Lys Phe Asp Glu Pro
20 25 30

Leu Asp Met Ser Leu Phe Ser Phe Ile Gly Ser Pro Arg Ile Asn Ala
35 40 45

Thr Gly Gln Gly Val Thr Ile Phe Tyr Val Asp Arg Leu Gly Tyr Tyr
50 55 60

Pro Tyr Ile Asp Ser Ile Thr Gly Val Thr Val Asn Gly Gly Ile Pro
65 70 75 80

Gln Lys Ile Ser Leu Gln Asp His Leu Asp Lys Ala Lys Lys Asp Ile

```
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Gln Asn Val Gln Leu
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Gly Thr Leu Ser Ile Met Arg Ser Met Lys Ser Cys Leu Leu Leu Asp
305                 310                 315                 320

Asn Tyr Met Glu Thr Ile Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu Pro Gln Ile Phe Tyr Asn
        435                 440                 445

Ala Ser Pro Ser Thr Leu Ser Ala Thr Met Phe Ile Val Ser Ile Leu
    450                 455                 460

Phe Leu Ile Ile Ser Ser Val Ala Ser Leu
465                 470


<210> SEQ ID NO 3
<211> LENGTH: 482
<212> TYPE: PRT
<213> ORGANISM: Homo sapiens
```

<220> FEATURE:
<223> OTHER INFORMATION: precursor soluble rHuPH20

<400> SEQUENCE: 3

Met Gly Val Leu Lys Phe Lys His Ile Phe Phe Arg Ser Phe Val Lys
1 5 10 15

Ser Ser Gly Val Ser Gln Ile Val Phe Thr Phe Leu Leu Ile Pro Cys
20 25 30

Cys Leu Thr Leu Asn Phe Arg Ala Pro Pro Val Ile Pro Asn Val Pro
35 40 45

Phe Leu Trp Ala Trp Asn Ala Pro Ser Glu Phe Cys Leu Gly Lys Phe
50 55 60

Asp Glu Pro Leu Asp Met Ser Leu Phe Ser Phe Ile Gly Ser Pro Arg
65 70 75 80

Ile Asn Ala Thr Gly Gln Gly Val Thr Ile Phe Tyr Val Asp Arg Leu
85 90 95

Gly Tyr Tyr Pro Tyr Ile Asp Ser Ile Thr Gly Val Thr Val Asn Gly
100 105 110

Gly Ile Pro Gln Lys Ile Ser Leu Gln Asp His Leu Asp Lys Ala Lys
115 120 125

Lys Asp Ile Thr Phe Tyr Met Pro Val Asp Asn Leu Gly Met Ala Val
130 135 140

Ile Asp Trp Glu Glu Trp Arg Pro Thr Trp Ala Arg Asn Trp Lys Pro
145 150 155 160

Lys Asp Val Tyr Lys Asn Arg Ser Ile Glu Leu Val Gln Gln Gln Asn
165 170 175

Val Gln Leu Ser Leu Thr Glu Ala Thr Glu Lys Ala Lys Gln Glu Phe
180 185 190

Glu Lys Ala Gly Lys Asp Phe Leu Val Glu Thr Ile Lys Leu Gly Lys
195 200 205

Leu Leu Arg Pro Asn His Leu Trp Gly Tyr Tyr Leu Phe Pro Asp Cys
210 215 220

Tyr Asn His His Tyr Lys Lys Pro Gly Tyr Asn Gly Ser Cys Phe Asn
225 230 235 240

Val Glu Ile Lys Arg Asn Asp Asp Leu Ser Trp Leu Trp Asn Glu Ser
245 250 255

Thr Ala Leu Tyr Pro Ser Ile Tyr Leu Asn Thr Gln Gln Ser Pro Val
260 265 270

Ala Ala Thr Leu Tyr Val Arg Asn Arg Val Arg Glu Ala Ile Arg Val
275 280 285

Ser Lys Ile Pro Asp Ala Lys Ser Pro Leu Pro Val Phe Ala Tyr Thr
290 295 300

Arg Ile Val Phe Thr Asp Gln Val Leu Lys Phe Leu Ser Gln Asp Glu
305 310 315 320

Leu Val Tyr Thr Phe Gly Glu Thr Val Ala Leu Gly Ala Ser Gly Ile
325 330 335

Val Ile Trp Gly Thr Leu Ser Ile Met Arg Ser Met Lys Ser Cys Leu
340 345 350

Leu Leu Asp Asn Tyr Met Glu Thr Ile Leu Asn Pro Tyr Ile Ile Asn
355 360 365

Val Thr Leu Ala Ala Lys Met Cys Ser Gln Val Leu Cys Gln Glu Gln
370 375 380

Gly Val Cys Ile Arg Lys Asn Trp Asn Ser Ser Asp Tyr Leu His Leu
385 390 395 400

```
Asn Pro Asp Asn Phe Ala Ile Gln Leu Glu Lys Gly Gly Lys Phe Thr
                405                 410                 415

Val Arg Gly Lys Pro Thr Leu Glu Asp Leu Glu Gln Phe Ser Glu Lys
            420                 425                 430

Phe Tyr Cys Ser Cys Tyr Ser Thr Leu Ser Cys Lys Glu Lys Ala Asp
        435                 440                 445

Val Lys Asp Thr Asp Ala Val Asp Val Cys Ile Ala Asp Gly Val Cys
    450                 455                 460

Ile Asp Ala Phe Leu Lys Pro Pro Met Glu Thr Glu Glu Pro Gln Ile
465                 470                 475                 480

Phe Tyr


<210> SEQ ID NO 4
<211> LENGTH: 447
<212> TYPE: PRT
<213> ORGANISM: Homo sapiens
<220> FEATURE:
<223> OTHER INFORMATION: soluble rHuPH20 1-447

<400> SEQUENCE: 4

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Gln Asn Val Gln Leu
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270
```

```
Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Gly Thr Leu Ser Ile Met Arg Ser Met Lys Ser Cys Leu Leu Leu Asp
305                 310                 315                 320

Asn Tyr Met Glu Thr Ile Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu Pro Gln Ile Phe Tyr
        435                 440                 445


<210> SEQ ID NO 5
<211> LENGTH: 446
<212> TYPE: PRT
<213> ORGANISM: Homo sapiens
<220> FEATURE:
<223> OTHER INFORMATION: soluble rHuPH20 1-446

<400> SEQUENCE: 5

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Gln Asn Val Gln Leu
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190
```

```
His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Gly Thr Leu Ser Ile Met Arg Ser Met Lys Ser Cys Leu Leu Leu Asp
305                 310                 315                 320

Asn Tyr Met Glu Thr Ile Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu Pro Gln Ile Phe
        435                 440                 445


<210> SEQ ID NO 6
<211> LENGTH: 445
<212> TYPE: PRT
<213> ORGANISM: Homo sapiens
<220> FEATURE:
<223> OTHER INFORMATION: soluble rHuPH20 1-445

<400> SEQUENCE: 6

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110
```

```
Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Gln Asn Val Gln Leu
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Gly Thr Leu Ser Ile Met Arg Ser Met Lys Ser Cys Leu Leu Leu Asp
305                 310                 315                 320

Asn Tyr Met Glu Thr Ile Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu Pro Gln Ile
        435                 440                 445


<210> SEQ ID NO 7
<211> LENGTH: 444
<212> TYPE: PRT
<213> ORGANISM: Homo sapiens
<220> FEATURE:
<223> OTHER INFORMATION: soluble rHuPH20 1-444

<400> SEQUENCE: 7

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30
```

```
Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Gln Asn Val Gln Leu
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Gly Thr Leu Ser Ile Met Arg Ser Met Lys Ser Cys Leu Leu Leu Asp
305                 310                 315                 320

Asn Tyr Met Glu Thr Ile Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu Pro Gln
        435                 440
```

<210> SEQ ID NO 8
<211> LENGTH: 443
<212> TYPE: PRT
<213> ORGANISM: Homo sapiens
<220> FEATURE:
<223> OTHER INFORMATION: soluble rHuPH20 1-443

<400> SEQUENCE: 8

Leu Asn Phe Arg Ala Pro Pro Val Ile Pro Asn Val Pro Phe Leu Trp
1 5 10 15

Ala Trp Asn Ala Pro Ser Glu Phe Cys Leu Gly Lys Phe Asp Glu Pro
20 25 30

Leu Asp Met Ser Leu Phe Ser Phe Ile Gly Ser Pro Arg Ile Asn Ala
35 40 45

Thr Gly Gln Gly Val Thr Ile Phe Tyr Val Asp Arg Leu Gly Tyr Tyr
50 55 60

Pro Tyr Ile Asp Ser Ile Thr Gly Val Thr Val Asn Gly Gly Ile Pro
65 70 75 80

Gln Lys Ile Ser Leu Gln Asp His Leu Asp Lys Ala Lys Lys Asp Ile
85 90 95

Thr Phe Tyr Met Pro Val Asp Asn Leu Gly Met Ala Val Ile Asp Trp
100 105 110

Glu Glu Trp Arg Pro Thr Trp Ala Arg Asn Trp Lys Pro Lys Asp Val
115 120 125

Tyr Lys Asn Arg Ser Ile Glu Leu Val Gln Gln Gln Asn Val Gln Leu
130 135 140

Ser Leu Thr Glu Ala Thr Glu Lys Ala Lys Gln Glu Phe Glu Lys Ala
145 150 155 160

Gly Lys Asp Phe Leu Val Glu Thr Ile Lys Leu Gly Lys Leu Leu Arg
165 170 175

Pro Asn His Leu Trp Gly Tyr Tyr Leu Phe Pro Asp Cys Tyr Asn His
180 185 190

His Tyr Lys Lys Pro Gly Tyr Asn Gly Ser Cys Phe Asn Val Glu Ile
195 200 205

Lys Arg Asn Asp Asp Leu Ser Trp Leu Trp Asn Glu Ser Thr Ala Leu
210 215 220

Tyr Pro Ser Ile Tyr Leu Asn Thr Gln Gln Ser Pro Val Ala Ala Thr
225 230 235 240

Leu Tyr Val Arg Asn Arg Val Arg Glu Ala Ile Arg Val Ser Lys Ile
245 250 255

Pro Asp Ala Lys Ser Pro Leu Pro Val Phe Ala Tyr Thr Arg Ile Val
260 265 270

Phe Thr Asp Gln Val Leu Lys Phe Leu Ser Gln Asp Glu Leu Val Tyr
275 280 285

Thr Phe Gly Glu Thr Val Ala Leu Gly Ala Ser Gly Ile Val Ile Trp
290 295 300

Gly Thr Leu Ser Ile Met Arg Ser Met Lys Ser Cys Leu Leu Leu Asp
305 310 315 320

Asn Tyr Met Glu Thr Ile Leu Asn Pro Tyr Ile Ile Asn Val Thr Leu
325 330 335

Ala Ala Lys Met Cys Ser Gln Val Leu Cys Gln Glu Gln Gly Val Cys
340 345 350

Ile Arg Lys Asn Trp Asn Ser Ser Asp Tyr Leu His Leu Asn Pro Asp
355 360 365

Asn Phe Ala Ile Gln Leu Glu Lys Gly Gly Lys Phe Thr Val Arg Gly

```
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu Pro
        435                 440


<210> SEQ ID NO 9
<211> LENGTH: 442
<212> TYPE: PRT
<213> ORGANISM: Homo sapiens
<220> FEATURE:
<223> OTHER INFORMATION: soluble rHuPH20 1-442

<400> SEQUENCE: 9

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Gln Asn Val Gln Leu
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
```

```
    290                 295                 300

Gly Thr Leu Ser Ile Met Arg Ser Met Lys Ser Cys Leu Leu Leu Asp
305                 310                 315                 320

Asn Tyr Met Glu Thr Ile Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu
        435                 440


<210> SEQ ID NO 10
<211> LENGTH: 450
<212> TYPE: PRT
<213> ORGANISM: Bos taurus
<220> FEATURE:
<223> OTHER INFORMATION: hyaluronidase

<400> SEQUENCE: 10

Met Arg Pro Phe Ser Leu Glu Val Ser Leu His Leu Pro Trp Ala Met
1               5                   10                  15

Ala Ala His Leu Leu Pro Val Cys Thr Leu Phe Leu Asn Leu Leu Ser
            20                  25                  30

Met Thr Gln Gly Ser Arg Asp Pro Val Val Pro Asn Gln Pro Phe Thr
        35                  40                  45

Thr Ile Trp Asn Ala Asn Thr Glu Trp Cys Met Lys Lys His Gly Val
    50                  55                  60

Asp Val Asp Ile Ser Ile Phe Asp Val Val Thr Asn Pro Gly Gln Thr
65                  70                  75                  80

Phe Arg Gly Pro Asn Met Thr Ile Phe Tyr Ser Ser Gln Leu Gly Thr
                85                  90                  95

Tyr Pro Tyr Tyr Thr Ser Ala Gly Glu Pro Val Phe Gly Gly Leu Pro
            100                 105                 110

Gln Asn Ala Ser Leu Asn Ala His Leu Ala Arg Thr Phe Gln Asp Ile
        115                 120                 125

Leu Ala Ala Met Pro Glu Pro Arg Phe Ser Gly Leu Ala Val Ile Asp
    130                 135                 140

Trp Glu Ala Trp Arg Pro Arg Trp Ala Phe Asn Trp Asp Thr Lys Asp
145                 150                 155                 160

Ile Tyr Arg Gln Arg Ser Arg Ala Leu Val Gln Lys Gln His Pro Asp
                165                 170                 175

Trp Leu Ala Pro Arg Val Glu Ala Ala Ala Gln Asp Gln Phe Glu Gly
            180                 185                 190

Ala Ala Glu Glu Trp Met Ala Gly Thr Leu Lys Leu Gly Gln Ala Leu
        195                 200                 205

Arg Pro Gln Gly Leu Trp Gly Phe Tyr Asn Phe Pro Glu Cys Tyr Asn
```

```
    210                 215                 220

Tyr Asp Phe Lys Ser Pro Asn Tyr Thr Gly Arg Cys Pro Leu Asn Ile
225                 230                 235                 240

Cys Ala Gln Asn Asp Gln Leu Gly Trp Leu Trp Gly Gln Ser Arg Ala
                245                 250                 255

Leu Tyr Pro Ser Ile Tyr Leu Pro Ala Ala Leu Glu Gly Thr Lys Lys
            260                 265                 270

Thr Gln Met Phe Val Gln His Arg Val Ala Glu Ala Phe Arg Val Ala
        275                 280                 285

Ala Gly Ala Gly Asp Pro Lys Leu Pro Val Leu Pro Tyr Met Gln Leu
    290                 295                 300

Phe Tyr Asp Met Thr Asn His Phe Leu Pro Ala Glu Glu Leu Glu His
305                 310                 315                 320

Ser Leu Gly Glu Ser Ala Ala Gln Gly Ala Ala Gly Val Val Leu Trp
                325                 330                 335

Val Ser Trp Leu Ser Thr Ser Thr Lys Glu Ser Cys Gln Ala Ile Lys
            340                 345                 350

Glu Tyr Val Asp Thr Thr Leu Gly Pro Ser Ile Leu Asn Val Thr Ser
        355                 360                 365

Gly Ala Arg Leu Cys Ser Gln Val Leu Cys Ser Gly His Gly Arg Cys
    370                 375                 380

Ala Arg Arg Pro Ser Tyr Pro Lys Ala Arg Leu Ile Leu Asn Ser Thr
385                 390                 395                 400

Ser Phe Ser Ile Lys Pro Thr Pro Gly Gly Gly Pro Leu Thr Leu Gln
                405                 410                 415

Gly Ala Leu Ser Leu Glu Asp Arg Leu Arg Met Ala Val Glu Phe Glu
            420                 425                 430

Cys Arg Cys Tyr Arg Gly Trp Arg Gly Thr Arg Cys Glu Gln Trp Gly
        435                 440                 445

Met Trp
    450


<210> SEQ ID NO 11
<211> LENGTH: 553
<212> TYPE: PRT
<213> ORGANISM: Bos taurus
<220> FEATURE:
<223> OTHER INFORMATION: PH20

<400> SEQUENCE: 11

Met Arg Met Leu Arg Arg His His Ile Ser Phe Arg Ser Phe Ala Gly
1               5                   10                  15

Ser Ser Gly Thr Pro Gln Ala Val Phe Thr Phe Leu Leu Leu Pro Cys
            20                  25                  30

Cys Leu Ala Leu Asp Phe Arg Ala Pro Pro Leu Ile Ser Asn Thr Ser
        35                  40                  45

Phe Leu Trp Ala Trp Asn Ala Pro Val Glu Arg Cys Val Asn Arg Arg
    50                  55                  60

Phe Gln Leu Pro Pro Asp Leu Arg Leu Phe Ser Val Lys Gly Ser Pro
65                  70                  75                  80

Gln Lys Ser Ala Thr Gly Gln Phe Ile Thr Leu Phe Tyr Ala Asp Arg
                85                  90                  95

Leu Gly Tyr Tyr Pro His Ile Asp Glu Lys Thr Gly Lys Thr Val Phe
            100                 105                 110

Gly Gly Ile Pro Gln Leu Gly Asn Leu Lys Ser His Met Glu Lys Ala
```

```
        115                 120                 125

Lys Asn Asp Ile Ala Tyr Tyr Ile Pro Asn Asp Ser Val Gly Leu Ala
    130                 135                 140

Val Ile Asp Trp Glu Asn Trp Arg Pro Thr Trp Ala Arg Asn Trp Lys
145                 150                 155                 160

Pro Lys Asp Val Tyr Arg Asp Glu Ser Val Glu Leu Val Leu Gln Lys
                165                 170                 175

Asn Pro Gln Leu Ser Phe Pro Glu Ala Ser Lys Ile Ala Lys Val Asp
            180                 185                 190

Phe Glu Thr Ala Gly Lys Ser Phe Met Gln Glu Thr Leu Lys Leu Gly
        195                 200                 205

Lys Leu Leu Arg Pro Asn His Leu Trp Gly Tyr Tyr Leu Phe Pro Asp
    210                 215                 220

Cys Tyr Asn His Asn His Asn Gln Pro Thr Tyr Asn Gly Asn Cys Pro
225                 230                 235                 240

Asp Val Glu Lys Arg Arg Asn Asp Asp Leu Glu Trp Leu Trp Lys Glu
                245                 250                 255

Ser Thr Ala Leu Phe Pro Ser Val Tyr Leu Asn Ile Arg Leu Lys Ser
            260                 265                 270

Thr Gln Asn Ala Ala Leu Tyr Val Arg Asn Arg Val Gln Glu Ala Ile
        275                 280                 285

Arg Leu Ser Lys Ile Ala Ser Val Glu Ser Pro Leu Pro Val Phe Val
    290                 295                 300

Tyr Ala Arg Pro Val Phe Thr Asp Gly Ser Ser Thr Tyr Leu Ser Gln
305                 310                 315                 320

Gly Asp Leu Val Asn Ser Val Gly Glu Ile Val Ser Leu Gly Ala Ser
                325                 330                 335

Gly Ile Ile Met Trp Gly Ser Leu Asn Leu Ser Leu Ser Met Gln Ser
            340                 345                 350

Cys Met Asn Leu Gly Thr Tyr Leu Asn Thr Thr Leu Asn Pro Tyr Ile
        355                 360                 365

Ile Asn Val Thr Leu Ala Ala Lys Met Cys Ser Gln Val Leu Cys His
    370                 375                 380

Asn Glu Gly Val Cys Thr Arg Lys His Trp Asn Ser Ser Asp Tyr Leu
385                 390                 395                 400

His Leu Asn Pro Met Asn Phe Ala Ile Gln Thr Gly Glu Gly Gly Lys
                405                 410                 415

Tyr Thr Val Pro Gly Thr Val Thr Leu Glu Asp Leu Gln Lys Phe Ser
            420                 425                 430

Asp Thr Phe Tyr Cys Ser Cys Tyr Ala Asn Ile His Cys Lys Lys Arg
        435                 440                 445

Val Asp Ile Lys Asn Val His Ser Val Asn Val Cys Met Ala Glu Asp
    450                 455                 460

Ile Cys Ile Asp Ser Pro Val Lys Leu Gln Pro Ser Asp His Ser Ser
465                 470                 475                 480

Ser Gln Glu Ala Ser Thr Thr Thr Phe Ser Ser Ile Ser Pro Ser Thr
                485                 490                 495

Thr Thr Ala Thr Val Ser Pro Cys Thr Pro Glu Lys His Ser Pro Glu
            500                 505                 510

Cys Leu Lys Val Arg Cys Ser Glu Val Ile Pro Asn Val Thr Gln Lys
        515                 520                 525

Ala Cys Gln Ser Val Lys Leu Lys Asn Ile Ser Tyr Gln Ser Pro Ile
    530                 535                 540
```

```
Gln Asn Ile Lys Asn Gln Thr Thr Tyr
545                 550


<210> SEQ ID NO 12
<211> LENGTH: 331
<212> TYPE: PRT
<213> ORGANISM: Vespula vulgaris
<220> FEATURE:
<223> OTHER INFORMATION: hyaluronidase A

<400> SEQUENCE: 12

Ser Glu Arg Pro Lys Arg Val Phe Asn Ile Tyr Trp Asn Val Pro Thr
1               5                   10                  15

Phe Met Cys His Gln Tyr Asp Leu Tyr Phe Asp Glu Val Thr Asn Phe
            20                  25                  30

Asn Ile Lys Arg Asn Ser Lys Asp Asp Phe Gln Gly Asp Lys Ile Ala
        35                  40                  45

Ile Phe Tyr Asp Pro Gly Glu Phe Pro Ala Leu Leu Ser Leu Lys Asp
    50                  55                  60

Gly Lys Tyr Lys Lys Arg Asn Gly Gly Val Pro Gln Glu Gly Asn Ile
65                  70                  75                  80

Thr Ile His Leu Gln Lys Phe Ile Glu Asn Leu Asp Lys Ile Tyr Pro
                85                  90                  95

Asn Arg Asn Phe Ser Gly Ile Gly Val Ile Asp Phe Glu Arg Trp Arg
            100                 105                 110

Pro Ile Phe Arg Gln Asn Trp Gly Asn Met Lys Ile His Lys Asn Phe
        115                 120                 125

Ser Ile Asp Leu Val Arg Asn Glu His Pro Thr Trp Asn Lys Lys Met
    130                 135                 140

Ile Glu Leu Glu Ala Ser Lys Arg Phe Glu Lys Tyr Ala Arg Phe Phe
145                 150                 155                 160

Met Glu Glu Thr Leu Lys Leu Ala Lys Lys Thr Arg Lys Gln Ala Asp
                165                 170                 175

Trp Gly Tyr Tyr Gly Tyr Pro Tyr Cys Phe Asn Met Ser Pro Asn Asn
            180                 185                 190

Leu Val Pro Glu Cys Asp Val Thr Ala Met His Glu Asn Asp Lys Met
        195                 200                 205

Ser Trp Leu Phe Asn Asn Gln Asn Val Leu Leu Pro Ser Val Tyr Val
    210                 215                 220

Arg Gln Glu Leu Thr Pro Asp Gln Arg Ile Gly Leu Val Gln Gly Arg
225                 230                 235                 240

Val Lys Glu Ala Val Arg Ile Ser Asn Asn Leu Lys His Ser Pro Lys
                245                 250                 255

Val Leu Ser Tyr Trp Trp Tyr Val Tyr Gln Asp Glu Thr Asn Thr Phe
            260                 265                 270

Leu Thr Glu Thr Asp Val Lys Lys Thr Phe Gln Glu Ile Val Ile Asn
        275                 280                 285

Gly Gly Asp Gly Ile Ile Ile Trp Gly Ser Ser Ser Asp Val Asn Ser
    290                 295                 300

Leu Ser Lys Cys Lys Arg Leu Gln Asp Tyr Leu Leu Thr Val Leu Gly
305                 310                 315                 320

Pro Ile Ala Ile Asn Val Thr Glu Ala Val Asn
                325                 330


<210> SEQ ID NO 13
```

<211> LENGTH: 340
<212> TYPE: PRT
<213> ORGANISM: Vespula vulgaris
<220> FEATURE:
<223> OTHER INFORMATION: hyaluronidase B

<400> SEQUENCE: 13

Asp Arg Thr Ile Trp Pro Lys Lys Gly Phe Ser Ile Tyr Trp Asn Ile
1 5 10 15

Pro Thr His Phe Cys His Asn Phe Gly Val Tyr Phe Lys Glu Leu Lys
20 25 30

Gln Phe Asn Ile Lys Tyr Asn Ser Met Asn Asn Phe Arg Gly Glu Thr
35 40 45

Ile Ser Leu Phe Tyr Asp Pro Gly Asn Phe Pro Ser Met Val Leu Leu
50 55 60

Lys Asn Gly Thr Tyr Glu Ile Arg Asn Glu Gly Val Pro Gln Lys Gly
65 70 75 80

Asn Leu Thr Ile His Leu Glu Gln Phe Thr Lys Glu Leu Asp Glu Ile
85 90 95

Tyr Pro Lys Lys Ile Ala Gly Gly Ile Gly Val Ile His Phe His Asn
100 105 110

Trp Arg Pro Ile Phe Arg Arg Asn Val Asp Asn Leu Lys Ile Asn Lys
115 120 125

Asp Ile Ser Ile Asp Leu Val Arg Lys Glu His Pro Lys Trp Asp Lys
130 135 140

Ser Met Ile Glu Lys Glu Ala Ser Asn Arg Phe Glu Thr Ser Ala Lys
145 150 155 160

Ile Phe Met Glu Lys Thr Leu Lys Leu Ala Lys Glu Ile Arg Lys Lys
165 170 175

Thr Glu Trp Gly Tyr His Gly Tyr Pro His Cys Leu Ser Gly Ser Thr
180 185 190

Asp Lys Pro Ser Phe Asp Cys Asp Ala Leu Ser Met Ser Glu Asn Asp
195 200 205

Lys Met Ser Trp Leu Phe Asn Asn Gln Asn Val Leu Leu Pro Ser Ile
210 215 220

Tyr Leu Lys Asn Val Leu Lys Pro Asp Glu Lys Ile His Leu Val Gln
225 230 235 240

Glu Arg Leu Lys Glu Ala Ile Arg Ile Ser Lys Asn Phe Lys His Leu
245 250 255

Pro Lys Val Leu Pro Tyr Trp Trp Tyr Thr Tyr Gln Asp Lys Glu Ser
260 265 270

Ile Phe Leu Thr Glu Ala Asp Val Lys Asn Thr Phe Lys Glu Ile Leu
275 280 285

Thr Asn Gly Ala Asp Gly Ile Ile Ile Trp Gly Val Ser Tyr Glu Leu
290 295 300

Thr Asp Arg Lys Arg Cys Glu Lys Leu Lys Glu Tyr Leu Met Lys Ile
305 310 315 320

Leu Gly Pro Ile Ala Phe Lys Val Thr Lys Ala Val Lys Glu Asn Thr
325 330 335

Pro Leu Asn Phe
340

<210> SEQ ID NO 14
<211> LENGTH: 382
<212> TYPE: PRT
<213> ORGANISM: Apis mellifera <220> FEATURE:
<223> OTHER INFORMATION: hyaluronidase

<400> SEQUENCE: 14

```
Met Ser Arg Pro Leu Val Ile Thr Glu Gly Met Met Ile Gly Val Leu
1               5                   10                  15

Leu Met Leu Ala Pro Ile Asn Ala Leu Leu Leu Gly Phe Val Gln Ser
            20                  25                  30

Thr Pro Asp Asn Asn Lys Thr Val Arg Glu Phe Asn Val Tyr Trp Asn
        35                  40                  45

Val Pro Thr Phe Met Cys His Lys Tyr Gly Leu Arg Phe Glu Glu Val
    50                  55                  60

Ser Glu Lys Tyr Gly Ile Leu Gln Asn Trp Met Asp Lys Phe Arg Gly
65                  70                  75                  80

Glu Glu Ile Ala Ile Leu Tyr Asp Pro Gly Met Phe Pro Ala Leu Leu
                85                  90                  95

Lys Asp Pro Asn Gly Asn Val Val Ala Arg Asn Gly Gly Val Pro Gln
            100                 105                 110

Leu Gly Asn Leu Thr Lys His Leu Gln Val Phe Arg Asp His Leu Ile
        115                 120                 125

Asn Gln Ile Pro Asp Lys Ser Phe Pro Gly Val Gly Val Ile Asp Phe
    130                 135                 140

Glu Ser Trp Arg Pro Ile Phe Arg Gln Asn Trp Ala Ser Leu Gln Pro
145                 150                 155                 160

Tyr Lys Lys Leu Ser Val Glu Val Val Arg Arg Glu His Pro Phe Trp
                165                 170                 175

Asp Asp Gln Arg Val Glu Gln Glu Ala Lys Arg Arg Phe Glu Lys Tyr
            180                 185                 190

Gly Gln Leu Phe Met Glu Glu Thr Leu Lys Ala Ala Lys Arg Met Arg
        195                 200                 205

Pro Ala Ala Asn Trp Gly Tyr Tyr Ala Tyr Pro Tyr Cys Tyr Asn Leu
    210                 215                 220

Thr Pro Asn Gln Pro Ser Ala Gln Cys Glu Ala Thr Thr Met Gln Glu
225                 230                 235                 240

Asn Asp Lys Met Ser Trp Leu Phe Glu Ser Glu Asp Val Leu Leu Pro
                245                 250                 255

Ser Val Tyr Leu Arg Trp Asn Leu Thr Ser Gly Glu Arg Val Gly Leu
            260                 265                 270

Val Gly Gly Arg Val Lys Glu Ala Leu Arg Ile Ala Arg Gln Met Thr
        275                 280                 285

Thr Ser Arg Lys Lys Val Leu Pro Tyr Tyr Trp Tyr Lys Tyr Gln Asp
    290                 295                 300

Arg Arg Asp Thr Asp Leu Ser Arg Ala Asp Leu Glu Ala Thr Leu Arg
305                 310                 315                 320

Lys Ile Thr Asp Leu Gly Ala Asp Gly Phe Ile Ile Trp Gly Ser Ser
                325                 330                 335

Asp Asp Ile Asn Thr Lys Ala Lys Cys Leu Gln Phe Arg Glu Tyr Leu
            340                 345                 350

Asn Asn Glu Leu Gly Pro Ala Val Lys Arg Ile Ala Leu Asn Asn Asn
        355                 360                 365

Ala Asn Asp Arg Leu Thr Val Asp Val Ser Val Asp Gln Val
    370                 375                 380
```

<210> SEQ ID NO 15

<211> LENGTH: 331
<212> TYPE: PRT
<213> ORGANISM: Dolichovespula maculata
<220> FEATURE:
<223> OTHER INFORMATION: hyaluronidase

<400> SEQUENCE: 15

Ser Glu Arg Pro Lys Arg Val Phe Asn Ile Tyr Trp Asn Val Pro Thr
1 5 10 15

Phe Met Cys His Gln Tyr Gly Leu Tyr Phe Asp Glu Val Thr Asn Phe
20 25 30

Asn Ile Lys His Asn Ser Lys Asp Asp Phe Gln Gly Asp Lys Ile Ser
35 40 45

Ile Phe Tyr Asp Pro Gly Glu Phe Pro Ala Leu Leu Pro Leu Lys Glu
50 55 60

Gly Asn Tyr Lys Ile Arg Asn Gly Gly Val Pro Gln Glu Gly Asn Ile
65 70 75 80

Thr Ile His Leu Gln Arg Phe Ile Glu Asn Leu Asp Lys Thr Tyr Pro
85 90 95

Asn Arg Asn Phe Asn Gly Ile Gly Val Ile Asp Phe Glu Arg Trp Arg
100 105 110

Pro Ile Phe Arg Gln Asn Trp Gly Asn Met Met Ile His Lys Lys Phe
115 120 125

Ser Ile Asp Leu Val Arg Asn Glu His Pro Phe Trp Asp Lys Lys Met
130 135 140

Ile Glu Leu Glu Ala Ser Lys Arg Phe Glu Lys Tyr Ala Arg Leu Phe
145 150 155 160

Met Glu Glu Thr Leu Lys Leu Ala Lys Lys Thr Arg Lys Gln Ala Asp
165 170 175

Trp Gly Tyr Tyr Gly Tyr Pro Tyr Cys Phe Asn Met Ser Pro Asn Asn
180 185 190

Leu Val Pro Asp Cys Asp Ala Thr Ala Met Leu Glu Asn Asp Lys Met
195 200 205

Ser Trp Leu Phe Asn Asn Gln Asn Val Leu Leu Pro Ser Val Tyr Ile
210 215 220

Arg His Glu Leu Thr Pro Asp Gln Arg Val Gly Leu Val Gln Gly Arg
225 230 235 240

Val Lys Glu Ala Val Arg Ile Ser Asn Asn Leu Lys His Ser Pro Lys
245 250 255

Val Leu Ser Tyr Trp Trp Tyr Val Tyr Gln Asp Asp Thr Asn Thr Phe
260 265 270

Leu Thr Glu Thr Asp Val Lys Lys Thr Phe Gln Glu Ile Ala Ile Asn
275 280 285

Gly Gly Asp Gly Ile Ile Ile Trp Gly Ser Ser Ser Asp Val Asn Ser
290 295 300

Leu Ser Lys Cys Lys Arg Leu Arg Glu Tyr Leu Leu Thr Val Leu Gly
305 310 315 320

Pro Ile Thr Val Asn Val Thr Glu Thr Val Asn
325 330

<210> SEQ ID NO 16
<211> LENGTH: 367
<212> TYPE: PRT
<213> ORGANISM: Polistes annularis
<220> FEATURE:
<223> OTHER INFORMATION: hyaluronidase

<400> SEQUENCE: 16

Tyr Val Ser Leu Ser Pro Asp Ser Val Phe Asn Ile Ile Thr Asp Asp
1 5 10 15

Ile Ser His Gln Ile Leu Ser Arg Ser Asn Cys Glu Arg Ser Lys Arg
20 25 30

Pro Lys Arg Val Phe Ser Ile Tyr Trp Asn Val Pro Thr Phe Met Cys
35 40 45

His Gln Tyr Gly Met Asn Phe Asp Glu Val Thr Asp Phe Asn Ile Lys
50 55 60

His Asn Ser Lys Asp Asn Phe Arg Gly Glu Thr Ile Ser Ile Tyr Tyr
65 70 75 80

Asp Pro Gly Lys Phe Pro Ala Leu Met Pro Leu Lys Asn Gly Asn Tyr
85 90 95

Glu Glu Arg Asn Gly Gly Val Pro Gln Arg Gly Asn Ile Thr Ile His
100 105 110

Leu Gln Gln Phe Asn Glu Asp Leu Asp Lys Met Thr Pro Asp Lys Asn
115 120 125

Phe Gly Gly Ile Gly Val Ile Asp Phe Glu Arg Trp Lys Pro Ile Phe
130 135 140

Arg Gln Asn Trp Gly Asn Thr Glu Ile His Lys Lys Tyr Ser Ile Glu
145 150 155 160

Leu Val Arg Lys Glu His Pro Lys Trp Ser Glu Ser Met Ile Glu Ala
165 170 175

Glu Ala Thr Lys Lys Phe Glu Lys Tyr Ala Arg Tyr Phe Met Glu Glu
180 185 190

Thr Leu Lys Leu Ala Lys Lys Thr Arg Lys Arg Ala Lys Trp Gly Tyr
195 200 205

Tyr Gly Phe Pro Tyr Cys Tyr Asn Val Thr Pro Asn Asn Pro Gly Pro
210 215 220

Asp Cys Asp Ala Lys Ala Thr Ile Glu Asn Asp Arg Leu Ser Trp Met
225 230 235 240

Tyr Asn Asn Gln Glu Ile Leu Phe Pro Ser Val Tyr Val Arg His Glu
245 250 255

Gln Lys Pro Glu Glu Arg Val Tyr Leu Val Gln Gly Arg Ile Lys Glu
260 265 270

Ala Val Arg Ile Ser Asn Asn Leu Glu His Ser Pro Ser Val Leu Ala
275 280 285

Tyr Trp Trp Tyr Val Tyr Gln Asp Lys Met Asp Ile Tyr Leu Ser Glu
290 295 300

Thr Asp Val Glu Lys Thr Phe Gln Glu Ile Val Thr Asn Gly Gly Asp
305 310 315 320

Gly Ile Ile Ile Trp Gly Ser Ser Ser Asp Val Asn Ser Leu Ser Lys
325 330 335

Cys Lys Arg Leu Arg Glu Tyr Leu Leu Asn Thr Leu Gly Pro Phe Ala
340 345 350

Val Asn Val Thr Glu Thr Val Asn Gly Arg Ser Ser Leu Asn Phe
355 360 365

<210> SEQ ID NO 17
<211> LENGTH: 462
<212> TYPE: PRT
<213> ORGANISM: Mus musculus
<220> FEATURE:
<223> OTHER INFORMATION: hyaluronidase

<400> SEQUENCE: 17

Met Leu Gly Leu Thr Gln His Ala Gln Lys Val Trp Arg Met Lys Pro
1 5 10 15

Phe Ser Pro Glu Val Ser Pro Gly Ser Ser Pro Ala Thr Ala Gly His
20 25 30

Leu Leu Arg Ile Ser Thr Leu Phe Leu Thr Leu Leu Glu Leu Ala Gln
35 40 45

Val Cys Arg Gly Ser Val Val Ser Asn Arg Pro Phe Ile Thr Val Trp
50 55 60

Asn Gly Asp Thr His Trp Cys Leu Thr Glu Tyr Gly Val Asp Val Asp
65 70 75 80

Val Ser Val Phe Asp Val Val Ala Asn Lys Glu Gln Ser Phe Gln Gly
85 90 95

Ser Asn Met Thr Ile Phe Tyr Arg Glu Glu Leu Gly Thr Tyr Pro Tyr
100 105 110

Tyr Thr Pro Thr Gly Glu Pro Val Phe Gly Gly Leu Pro Gln Asn Ala
115 120 125

Ser Leu Val Thr His Leu Ala His Thr Phe Gln Asp Ile Lys Ala Ala
130 135 140

Met Pro Glu Pro Asp Phe Ser Gly Leu Ala Val Ile Asp Trp Glu Ala
145 150 155 160

Trp Arg Pro Arg Trp Ala Phe Asn Trp Asp Ser Lys Asp Ile Tyr Arg
165 170 175

Gln Arg Ser Met Glu Leu Val Gln Ala Glu His Pro Asp Trp Pro Glu
180 185 190

Thr Leu Val Glu Ala Ala Ala Lys Asn Gln Phe Gln Glu Ala Ala Glu
195 200 205

Ala Trp Met Ala Gly Thr Leu Gln Leu Gly Gln Val Leu Arg Pro Arg
210 215 220

Gly Leu Trp Gly Tyr Tyr Gly Phe Pro Asp Cys Tyr Asn Asn Asp Phe
225 230 235 240

Leu Ser Leu Asn Tyr Thr Gly Gln Cys Pro Val Phe Val Arg Asp Gln
245 250 255

Asn Asp Gln Leu Gly Trp Leu Trp Asn Gln Ser Tyr Ala Leu Tyr Pro
260 265 270

Ser Ile Tyr Leu Pro Ala Ala Leu Met Gly Thr Gly Lys Ser Gln Met
275 280 285

Tyr Val Arg His Arg Val Gln Glu Ala Leu Arg Val Ala Ile Val Ser
290 295 300

Arg Asp Pro His Val Pro Val Met Pro Tyr Val Gln Ile Phe Tyr Glu
305 310 315 320

Met Thr Asp Tyr Leu Leu Pro Leu Glu Glu Leu Glu His Ser Leu Gly
325 330 335

Glu Ser Ala Ala Gln Gly Val Ala Gly Ala Val Leu Trp Leu Ser Ser
340 345 350

Asp Lys Thr Ser Thr Lys Glu Ser Cys Gln Ala Ile Lys Ala Tyr Met
355 360 365

Asp Ser Thr Leu Gly Pro Phe Ile Val Asn Val Thr Ser Ala Ala Leu
370 375 380

Leu Cys Ser Glu Ala Leu Cys Ser Gly His Gly Arg Cys Val Arg His
385 390 395 400

Pro Ser Tyr Pro Glu Ala Leu Leu Thr Leu Asn Pro Ala Ser Phe Ser
405 410 415

```
Ile Glu Leu Thr His Asp Gly Arg Pro Pro Ser Leu Lys Gly Thr Leu
            420                 425                 430

Ser Leu Lys Asp Arg Ala Gln Met Ala Met Lys Phe Arg Cys Arg Cys
        435                 440                 445

Tyr Arg Gly Trp Arg Gly Lys Trp Cys Asp Lys Arg Gly Met
    450                 455                 460


<210> SEQ ID NO 18
<211> LENGTH: 473
<212> TYPE: PRT
<213> ORGANISM: Mus musculus
<220> FEATURE:
<223> OTHER INFORMATION: Hyaluronidase 2

<400> SEQUENCE: 18

Met Arg Ala Gly Leu Gly Pro Ile Ile Thr Leu Ala Leu Val Leu Glu
1               5                   10                  15

Val Ala Trp Ala Gly Glu Leu Lys Pro Thr Ala Pro Pro Ile Phe Thr
            20                  25                  30

Gly Arg Pro Phe Val Val Ala Trp Asn Val Pro Thr Gln Glu Cys Ala
        35                  40                  45

Pro Arg His Lys Val Pro Leu Asp Leu Arg Ala Phe Asp Val Lys Ala
    50                  55                  60

Thr Pro Asn Glu Gly Phe Phe Asn Gln Asn Ile Thr Thr Phe Tyr Tyr
65                  70                  75                  80

Asp Arg Leu Gly Leu Tyr Pro Arg Phe Asp Ala Ala Gly Thr Ser Val
                85                  90                  95

His Gly Gly Val Pro Gln Asn Gly Ser Leu Cys Ala His Leu Pro Met
            100                 105                 110

Leu Lys Glu Ser Val Glu Arg Tyr Ile Gln Thr Gln Glu Pro Gly Gly
        115                 120                 125

Leu Ala Val Ile Asp Trp Glu Glu Trp Arg Pro Val Trp Val Arg Asn
    130                 135                 140

Trp Gln Glu Lys Asp Val Tyr Arg Gln Ser Ser Arg Gln Leu Val Ala
145                 150                 155                 160

Ser Arg His Pro Asp Trp Pro Ser Asp Arg Val Met Lys Gln Ala Gln
                165                 170                 175

Tyr Glu Phe Glu Phe Ala Ala Arg Gln Phe Met Leu Asn Thr Leu Arg
            180                 185                 190

Tyr Val Lys Ala Val Arg Pro Gln His Leu Trp Gly Phe Tyr Leu Phe
        195                 200                 205

Pro Asp Cys Tyr Asn His Asp Tyr Val Gln Asn Trp Glu Ser Tyr Thr
    210                 215                 220

Gly Arg Cys Pro Asp Val Glu Val Ala Arg Asn Asp Gln Leu Ala Trp
225                 230                 235                 240

Leu Trp Ala Glu Ser Thr Ala Leu Phe Pro Ser Val Tyr Leu Asp Glu
                245                 250                 255

Thr Leu Ala Ser Ser Val His Ser Arg Asn Phe Val Ser Phe Arg Val
            260                 265                 270

Arg Glu Ala Leu Arg Val Ala His Thr His His Ala Asn His Ala Leu
        275                 280                 285

Pro Val Tyr Val Phe Thr Arg Pro Thr Tyr Thr Arg Gly Leu Thr Gly
    290                 295                 300

Leu Ser Gln Val Asp Leu Ile Ser Thr Ile Gly Glu Ser Ala Ala Leu
305                 310                 315                 320
```

```
Gly Ser Ala Gly Val Ile Phe Trp Gly Asp Ser Glu Asp Ala Ser Ser
                325                 330                 335

Met Glu Thr Cys Gln Tyr Leu Lys Asn Tyr Leu Thr Gln Leu Leu Val
            340                 345                 350

Pro Tyr Ile Val Asn Val Ser Trp Ala Thr Gln Tyr Cys Ser Trp Thr
        355                 360                 365

Gln Cys His Gly His Gly Arg Cys Val Arg Arg Asn Pro Ser Ala Asn
    370                 375                 380

Thr Phe Leu His Leu Asn Ala Ser Ser Phe Arg Leu Val Pro Gly His
385                 390                 395                 400

Thr Pro Ser Glu Pro Gln Leu Arg Pro Glu Gly Gln Leu Ser Glu Ala
                405                 410                 415

Asp Leu Asn Tyr Leu Gln Lys His Phe Arg Cys Gln Cys Tyr Leu Gly
            420                 425                 430

Trp Gly Gly Glu Gln Cys Gln Arg Asn Tyr Lys Gly Ala Ala Gly Asn
        435                 440                 445

Ala Ser Arg Ala Trp Ala Gly Ser His Leu Thr Ser Leu Leu Gly Leu
    450                 455                 460

Val Ala Val Ala Leu Thr Trp Thr Leu
465                 470


<210> SEQ ID NO 19
<211> LENGTH: 412
<212> TYPE: PRT
<213> ORGANISM: Mus musculus
<220> FEATURE:
<223> OTHER INFORMATION: hyalurinidase 3

<400> SEQUENCE: 19

Met Ile Met His Leu Gly Leu Met Met Val Val Gly Leu Thr Leu Cys
1               5                   10                  15

Leu Met His Gly Gln Ala Leu Leu Gln Val Pro Glu His Pro Phe Ser
            20                  25                  30

Val Val Trp Asn Val Pro Ser Ala Arg Cys Lys Ala His Phe Gly Val
        35                  40                  45

His Leu Pro Leu Asp Ala Leu Gly Ile Val Ala Asn His Gly Gln His
    50                  55                  60

Phe His Gly Gln Asn Ile Ser Ile Phe Tyr Lys Asn Gln Phe Gly Leu
65                  70                  75                  80

Tyr Pro Tyr Phe Gly Pro Arg Gly Thr Ala His Asn Gly Gly Ile Pro
                85                  90                  95

Gln Ala Val Ser Leu Asp His His Leu Ala Arg Ala Ala His Gln Ile
            100                 105                 110

Leu His Ser Leu Gly Ser Ser Phe Ala Gly Leu Ala Val Leu Asp Trp
        115                 120                 125

Glu Glu Trp Tyr Pro Leu Trp Ala Gly Asn Trp Gly Pro His Arg Gln
    130                 135                 140

Val Tyr Leu Ala Ala Ser Trp Val Trp Thr Gln Gln Met Phe Pro Gly
145                 150                 155                 160

Leu Asp Pro Gln Glu Gln Leu His Lys Ala His Thr Ser Phe Glu Gln
                165                 170                 175

Ala Ala Arg Ala Leu Met Glu Tyr Thr Leu Gln Leu Gly Arg Thr Leu
            180                 185                 190

Arg Pro Ser Gly Leu Trp Gly Phe Tyr Arg Tyr Pro Ala Cys Gly Asn
        195                 200                 205
```

```
Gly Trp His Lys Met Ala Ser Asn Tyr Thr Gly His Cys His Ala Ala
    210                 215                 220

Ile Thr Thr Gln Asn Thr Gln Leu Arg Trp Leu Trp Ala Ala Ser Ser
225                 230                 235                 240

Ala Leu Phe Pro Ser Ile Tyr Leu Pro Pro Arg Leu Pro Leu Ala Tyr
                245                 250                 255

Arg Gln Ala Phe Val Arg His Arg Leu Glu Glu Ala Phe Arg Val Ala
            260                 265                 270

Leu Leu Glu His Ser His Pro Leu Pro Val Leu Ala Tyr Ser Arg Leu
        275                 280                 285

Thr His Arg Ser Ser Gly Arg Phe Leu Ser Leu Asp Asp Leu Met Gln
    290                 295                 300

Thr Ile Gly Val Ser Ala Ala Leu Gly Thr Ala Gly Val Val Leu Trp
305                 310                 315                 320

Gly Asp Leu Ser Phe Ser Ser Ser Glu Glu Lys Cys Trp Arg Leu His
                325                 330                 335

Asp Tyr Leu Val Gly Thr Leu Gly Pro Tyr Val Ile Asn Val Thr Lys
            340                 345                 350

Ala Asp Met Ala Cys Ser His Gln Arg Cys His Gly His Gly Arg Cys
        355                 360                 365

Ala Arg Lys Asp Pro Gly Gln Met Glu Ala Phe Leu His Leu Gln Pro
    370                 375                 380

Asp Asp Ser Leu Gly Ala Trp Asn Ser Phe Arg Cys His Cys Tyr Ser
385                 390                 395                 400

Gly Trp Ala Gly Pro Thr Cys Leu Glu Pro Lys Pro
                405                 410


<210> SEQ ID NO 20
<211> LENGTH: 435
<212> TYPE: PRT
<213> ORGANISM: Sus scrofa
<220> FEATURE:
<223> OTHER INFORMATION: hyalauronidase

<400> SEQUENCE: 20

Met Ala Ala His Leu Leu Pro Ile Cys Thr Leu Phe Leu Asn Leu Leu
1               5                   10                  15

Ser Val Ala Gln Gly Ser Arg Asp Pro Val Val Leu Asn Arg Pro Phe
            20                  25                  30

Thr Thr Ile Trp Asn Ala Asn Thr Gln Trp Cys Leu Lys Arg His Gly
        35                  40                  45

Val Asp Val Asp Val Ser Val Phe Glu Val Val Val Asn Pro Gly Gln
    50                  55                  60

Thr Phe Arg Gly Pro Asn Met Thr Ile Phe Tyr Ser Ser Gln Leu Gly
65                  70                  75                  80

Thr Tyr Pro Tyr Tyr Thr Ser Ala Gly Glu Pro Val Phe Gly Gly Leu
                85                  90                  95

Pro Gln Asn Ala Ser Leu Asp Val His Leu Asn Arg Thr Phe Lys Asp
            100                 105                 110

Ile Leu Ala Ala Met Pro Glu Ser Asn Phe Ser Gly Leu Ala Val Ile
        115                 120                 125

Asp Trp Glu Ala Trp Arg Pro Arg Trp Ala Phe Asn Trp Asp Ala Lys
    130                 135                 140

Asp Ile Tyr Arg Gln Arg Ser Arg Ala Leu Val Gln Lys Gln His Pro
145                 150                 155                 160
```

```
Asp Trp Pro Ala Pro Trp Val Glu Ala Ala Ala Gln Asp Gln Phe Gln
                165                 170                 175

Glu Ala Ala Gln Thr Trp Met Ala Gly Thr Leu Lys Leu Gly Gln Thr
            180                 185                 190

Leu Arg Pro His Gly Leu Trp Gly Phe Tyr Gly Phe Pro Asp Cys Tyr
        195                 200                 205

Asn Tyr Asp Phe Gln Ser Ser Asn Tyr Thr Gly Gln Cys Pro Pro Gly
    210                 215                 220

Val Ser Ala Gln Asn Asp Gln Leu Gly Trp Leu Trp Gly Gln Ser Arg
225                 230                 235                 240

Ala Leu Tyr Pro Ser Ile Tyr Leu Pro Ser Ala Leu Glu Gly Thr Asn
                245                 250                 255

Lys Thr Gln Leu Tyr Val Gln His Arg Val Asn Glu Ala Phe Arg Val
            260                 265                 270

Ala Ala Ala Ala Gly Asp Pro Asn Leu Pro Val Leu Pro Tyr Ala Gln
        275                 280                 285

Ile Phe His Asp Met Thr Asn Arg Leu Leu Ser Arg Glu Glu Leu Glu
    290                 295                 300

His Ser Leu Gly Glu Ser Ala Ala Gln Gly Ala Ala Gly Val Val Leu
305                 310                 315                 320

Trp Val Ser Trp Glu Asn Thr Arg Thr Lys Glu Ser Cys Gln Ser Ile
                325                 330                 335

Lys Glu Tyr Val Asp Thr Thr Leu Gly Pro Phe Ile Leu Asn Val Thr
            340                 345                 350

Ser Gly Ala Leu Leu Cys Ser Gln Ala Val Cys Ser Gly His Gly Arg
        355                 360                 365

Cys Val Arg Arg Pro Ser His Thr Glu Ala Leu Pro Ile Leu Asn Pro
    370                 375                 380

Ser Ser Phe Ser Ile Lys Pro Thr Pro Gly Gly Gly Pro Leu Thr Leu
385                 390                 395                 400

Gln Gly Ala Leu Ser Leu Lys Asp Arg Val Gln Met Ala Glu Glu Phe
                405                 410                 415

Gln Cys Arg Cys Tyr Pro Gly Trp Arg Gly Thr Trp Cys Glu Gln Gln
            420                 425                 430

Gly Thr Arg
        435


<210> SEQ ID NO 21
<211> LENGTH: 419
<212> TYPE: PRT
<213> ORGANISM: Sus scrofa
<220> FEATURE:
<223> OTHER INFORMATION: hyaluronidase 3

<400> SEQUENCE: 21

Met Thr Met Gln Leu Gly Leu Ala Leu Val Leu Gly Val Ala Met Cys
1               5                   10                  15

Leu Gly Cys Gly Gln Pro Leu Leu Arg Ala Pro Glu Arg Pro Phe Cys
            20                  25                  30

Val Leu Trp Asn Val Pro Ser Ala Arg Cys Lys Ala Arg Phe Gly Val
        35                  40                  45

His Leu Pro Leu Glu Ala Leu Gly Ile Thr Ala Asn His Gly Gln Arg
    50                  55                  60

Phe His Gly Gln Asn Ile Thr Ile Phe Tyr Lys Ser Gln Leu Gly Leu
65                  70                  75                  80
```

```
Tyr Pro Tyr Phe Gly Pro Arg Gly Thr Ala His Asn Gly Gly Ile Pro
                85                  90                  95

Gln Ala Val Ser Leu Asp His His Leu Ala Arg Ala Ala Tyr Gln Ile
            100                 105                 110

His Arg Ser Leu Arg Pro Gly Phe Thr Gly Leu Ala Val Leu Asp Trp
        115                 120                 125

Glu Glu Trp Cys Pro Leu Trp Ala Gly Asn Trp Gly Arg Arg Gln Ala
    130                 135                 140

Tyr Gln Ala Ala Ser Cys Ala Trp Ala Gln Arg Val Tyr Pro Asn Leu
145                 150                 155                 160

Asp Pro Gln Glu Gln Leu Cys Lys Ala Arg Ala Gly Phe Glu Glu Ala
                165                 170                 175

Ala Arg Ala Leu Met Glu Asp Thr Leu Arg Leu Gly Arg Met Leu Arg
            180                 185                 190

Pro His Gly Leu Trp Gly Phe Tyr His Tyr Pro Ala Cys Gly Asn Gly
        195                 200                 205

Trp His Gly Thr Ala Ser Asn Tyr Thr Gly His Cys His Ala Ala Ala
    210                 215                 220

Leu Ala Arg Asn Thr Gln Leu Tyr Trp Leu Trp Ala Ala Ser Ser Ala
225                 230                 235                 240

Leu Phe Pro Ser Ile Tyr Leu Pro Pro Gly Leu Pro Pro Ala Tyr His
                245                 250                 255

Gln Ala Phe Val Arg Tyr Arg Leu Glu Glu Ala Phe Arg Val Ala Leu
            260                 265                 270

Val Gly His Pro His Pro Leu Pro Val Leu Ala Tyr Ala Arg Leu Thr
        275                 280                 285

His Arg Asn Ser Gly Arg Phe Leu Ser Gln Asp Glu Leu Val Gln Thr
    290                 295                 300

Ile Gly Val Ser Ala Ala Leu Gly Ala Ser Gly Val Val Leu Trp Gly
305                 310                 315                 320

Asp Leu Ser Phe Ser Ser Ser Glu Glu Glu Cys Trp His Leu Arg Gly
                325                 330                 335

Tyr Leu Val Gly Thr Leu Gly Pro Tyr Val Ile Asn Val Thr Arg Ala
            340                 345                 350

Ala Met Ala Cys Ser His Gln Arg Cys His Gly His Gly Arg Cys Ala
        355                 360                 365

Trp Gln Asp Pro Gly Gln Leu Lys Val Phe Leu His Leu His Pro Gly
    370                 375                 380

Gly Ser Pro Gly Ala Trp Glu Ser Phe Ser Cys Arg Cys Tyr Trp Gly
385                 390                 395                 400

Trp Ala Gly Pro Thr Cys Gln Glu Pro Arg Pro Glu Leu Gly Pro Glu
                405                 410                 415

Glu Ala Thr


<210> SEQ ID NO 22
<211> LENGTH: 449
<212> TYPE: PRT
<213> ORGANISM: Rattus norvegicus
<220> FEATURE:
<223> OTHER INFORMATION: hyaluronidase 1

<400> SEQUENCE: 22

Met Lys Pro Phe Ser Pro Glu Val Ser Pro Asp Pro Cys Pro Ala Thr
1               5                   10                  15
```

```
Ala Ala His Leu Leu Arg Thr Tyr Thr Leu Phe Leu Thr Leu Leu Glu
            20                  25                  30

Leu Ala Gln Gly Cys Arg Gly Ser Met Val Ser Asn Arg Pro Phe Ile
        35                  40                  45

Thr Val Trp Asn Ala Asp Thr His Trp Cys Leu Lys Asp His Gly Val
    50                  55                  60

Asp Val Asp Val Ser Val Phe Asp Val Val Ala Asn Lys Glu Gln Asn
65                  70                  75                  80

Phe Gln Gly Pro Asn Met Thr Ile Phe Tyr Arg Glu Glu Leu Gly Thr
                85                  90                  95

Tyr Pro Tyr Tyr Thr Pro Thr Gly Glu Pro Val Phe Gly Gly Leu Pro
            100                 105                 110

Gln Asn Ala Ser Leu Val Thr His Leu Ala His Ala Phe Gln Asp Ile
        115                 120                 125

Lys Ala Ala Met Pro Glu Pro Asp Phe Ser Gly Leu Ala Val Ile Asp
    130                 135                 140

Trp Glu Ala Trp Arg Pro Arg Trp Ala Phe Asn Trp Asp Ser Lys Asp
145                 150                 155                 160

Ile Tyr Gln Gln Arg Ser Met Glu Leu Val Arg Ala Glu His Pro Asp
                165                 170                 175

Trp Pro Glu Thr Leu Val Glu Ala Glu Ala Gln Gly Gln Phe Gln Glu
            180                 185                 190

Ala Ala Glu Ala Trp Met Ala Gly Thr Leu Gln Leu Gly Gln Val Leu
        195                 200                 205

Arg Pro Arg Gly Leu Trp Gly Tyr Tyr Gly Phe Pro Asp Cys Tyr Asn
    210                 215                 220

Tyr Asp Phe Leu Ser Pro Asn Tyr Thr Gly Gln Cys Ser Leu Ser Ile
225                 230                 235                 240

His Asp Gln Asn Asp Gln Leu Gly Trp Leu Trp Asn Gln Ser Tyr Ala
                245                 250                 255

Leu Tyr Pro Ser Ile Tyr Leu Pro Ala Ala Leu Met Gly Thr Gly Lys
            260                 265                 270

Ser Gln Met Tyr Val Arg Tyr Arg Val Gln Glu Ala Phe Arg Leu Ala
        275                 280                 285

Leu Val Ser Arg Asp Pro His Val Pro Ile Met Pro Tyr Val Gln Ile
    290                 295                 300

Phe Tyr Glu Lys Thr Asp Tyr Leu Leu Pro Leu Glu Glu Leu Glu His
305                 310                 315                 320

Ser Leu Gly Glu Ser Ala Ala Gln Gly Ala Ala Gly Ala Val Leu Trp
                325                 330                 335

Ile Ser Ser Glu Lys Thr Ser Thr Lys Glu Ser Cys Gln Ala Ile Lys
            340                 345                 350

Ala Tyr Met Asp Ser Thr Leu Gly Pro Phe Ile Leu Asn Val Thr Ser
        355                 360                 365

Ala Ala Leu Leu Cys Ser Glu Ala Leu Cys Ser Gly Arg Gly Arg Cys
    370                 375                 380

Val Arg His Pro Ser Tyr Pro Glu Ala Leu Leu Thr Leu Ser Pro Ala
385                 390                 395                 400

Ser Phe Ser Ile Glu Pro Thr His Asp Gly Arg Pro Leu Ser Leu Lys
                405                 410                 415

Gly Thr Leu Ser Leu Lys Asp Arg Ala Gln Met Ala Met Lys Phe Lys
            420                 425                 430

Cys Arg Cys Tyr Arg Gly Trp Ser Gly Glu Trp Cys Lys Lys Gln Asp
```

```
        435                 440                 445

Met


<210> SEQ ID NO 23
<211> LENGTH: 473
<212> TYPE: PRT
<213> ORGANISM: Rattus norvegicus
<220> FEATURE:
<223> OTHER INFORMATION: hyaluronidase 2

<400> SEQUENCE: 23

Met Arg Ala Gly Leu Gly Pro Ile Ile Thr Leu Ala Leu Val Leu Glu
1               5                   10                  15

Val Ala Trp Ala Ser Glu Leu Lys Pro Thr Ala Pro Pro Ile Phe Thr
            20                  25                  30

Gly Arg Pro Phe Val Val Ala Trp Asn Val Pro Thr Gln Glu Cys Ala
        35                  40                  45

Pro Arg His Lys Val Pro Leu Asp Leu Arg Ala Phe Asp Val Glu Ala
    50                  55                  60

Thr Pro Asn Glu Gly Phe Phe Asn Gln Asn Ile Thr Thr Phe Tyr Tyr
65                  70                  75                  80

Asp Arg Leu Gly Leu Tyr Pro Arg Phe Asp Ala Ala Gly Met Ser Val
                85                  90                  95

His Gly Gly Val Pro Gln Asn Gly Ser Leu Cys Ala His Leu Pro Met
            100                 105                 110

Leu Lys Glu Ala Val Glu Arg Tyr Ile Gln Thr Gln Glu Pro Ala Gly
        115                 120                 125

Leu Ala Val Ile Asp Trp Glu Glu Trp Arg Pro Val Trp Val Arg Asn
    130                 135                 140

Trp Gln Glu Lys Asp Val Tyr Arg Gln Ser Ser Arg Gln Leu Val Ala
145                 150                 155                 160

Ser Arg His Pro Asp Trp Pro Ser Asp Arg Ile Val Lys Gln Ala Gln
                165                 170                 175

Tyr Glu Phe Glu Phe Ala Ala Arg Gln Phe Met Leu Asn Thr Leu Arg
            180                 185                 190

Tyr Val Lys Ala Val Arg Pro Gln His Leu Trp Gly Phe Tyr Leu Phe
        195                 200                 205

Pro Asp Cys Tyr Asn His Asp Tyr Val Gln Asn Trp Asp Ser Tyr Thr
    210                 215                 220

Gly Arg Cys Pro Asp Val Glu Val Ala Gln Asn Asp Gln Leu Ala Trp
225                 230                 235                 240

Leu Trp Ala Glu Asn Thr Ala Leu Phe Pro Ser Val Tyr Leu Asp Lys
                245                 250                 255

Thr Leu Ala Ser Ser Lys His Ser Arg Asn Phe Val Ser Phe Arg Val
            260                 265                 270

Gln Glu Ala Leu Arg Val Ala His Thr His His Ala Asn His Ala Leu
        275                 280                 285

Pro Val Tyr Val Phe Thr Arg Pro Thr Tyr Thr Arg Arg Leu Thr Glu
    290                 295                 300

Leu Asn Gln Met Asp Leu Ile Ser Thr Ile Gly Glu Ser Ala Ala Leu
305                 310                 315                 320

Gly Ser Ala Gly Val Ile Phe Trp Gly Asp Ser Val Tyr Ala Ser Ser
                325                 330                 335

Met Glu Asn Cys Gln Asn Leu Lys Lys Tyr Leu Thr Gln Thr Leu Val
            340                 345                 350
```

```
Pro Tyr Ile Val Asn Val Ser Trp Ala Thr Gln Tyr Cys Ser Trp Thr
        355                 360                 365

Gln Cys His Gly His Gly Arg Cys Val Arg Arg Asn Pro Ser Ala Ser
    370                 375                 380

Thr Phe Leu His Leu Ser Pro Ser Ser Phe Arg Leu Val Pro Gly Arg
385                 390                 395                 400

Thr Pro Ser Glu Pro Gln Leu Arg Pro Glu Gly Glu Leu Ser Glu Asp
                405                 410                 415

Asp Leu Ser Tyr Leu Gln Met His Phe Arg Cys His Cys Tyr Leu Gly
            420                 425                 430

Trp Gly Gly Glu Gln Cys Gln Trp Asn His Lys Arg Ala Ala Gly Asp
        435                 440                 445

Ala Ser Arg Ala Trp Ala Gly Ala His Leu Ala Ser Leu Leu Gly Leu
    450                 455                 460

Val Ala Met Thr Leu Thr Trp Thr Leu
465                 470


<210> SEQ ID NO 24
<211> LENGTH: 412
<212> TYPE: PRT
<213> ORGANISM: Rattus norvegicus
<220> FEATURE:
<223> OTHER INFORMATION: hyaluronidase 3

<400> SEQUENCE: 24

Met Ile Thr Gln Leu Gly Leu Thr Leu Val Val Gly Leu Thr Leu Cys
1               5                   10                  15

Leu Val His Val Gln Ala Leu Leu Gln Val Pro Glu Phe Pro Phe Ser
            20                  25                  30

Val Leu Trp Asn Val Pro Ser Ala Arg Cys Lys Thr Arg Phe Gly Val
        35                  40                  45

His Leu Pro Leu Asp Ala Leu Gly Ile Ile Ala Asn His Gly Gln Arg
    50                  55                  60

Phe His Gly Gln Asn Ile Thr Ile Phe Tyr Lys Asn Gln Phe Gly Leu
65                  70                  75                  80

Tyr Pro Tyr Phe Gly Pro Arg Gly Thr Ala His Asn Gly Gly Ile Pro
                85                  90                  95

Gln Ala Val Ser Leu Asp His His Leu Ala Gln Ala Ala His Gln Ile
            100                 105                 110

Leu His Asn Leu Gly Ser Ser Phe Ala Gly Leu Ala Val Leu Asp Trp
        115                 120                 125

Glu Glu Trp Tyr Pro Leu Trp Ala Gly Asn Trp Gly Thr His Arg Gln
    130                 135                 140

Val Tyr Gln Ala Ala Ser Trp Ala Trp Ala Gln Gln Met Phe Pro Asp
145                 150                 155                 160

Leu Asn Pro Gln Glu Gln Leu His Lys Ala Gln Thr Gly Phe Glu Gln
                165                 170                 175

Ala Ala Arg Ala Leu Met Glu His Thr Leu Arg Leu Gly Gln Met Leu
            180                 185                 190

Arg Pro His Gly Leu Trp Gly Phe Tyr Arg Tyr Pro Val Cys Gly Asn
        195                 200                 205

Gly Trp His Asn Met Ala Ser Asn Tyr Thr Gly His Cys His Pro Ala
    210                 215                 220

Ile Ile Thr Arg Asn Thr Gln Leu Arg Trp Leu Trp Ala Ala Ser Ser
225                 230                 235                 240
```

```
Ala Leu Phe Pro Ser Ile Tyr Leu Pro Pro Arg Leu Pro Pro Ala Tyr
                245                 250                 255

His Gln Thr Phe Val Arg His Arg Leu Glu Glu Ala Phe Arg Val Ala
            260                 265                 270

Leu Thr Gly His Ala His Pro Leu Pro Val Leu Ala Tyr Val Arg Leu
        275                 280                 285

Thr His Arg Ser Ser Gly Arg Phe Leu Ser Leu Asp Asp Leu Met Gln
    290                 295                 300

Thr Ile Gly Val Ser Ala Ala Leu Gly Ala Ala Gly Val Val Leu Trp
305                 310                 315                 320

Gly Asp Leu Ser Val Ser Ser Ser Glu Glu Glu Cys Trp Arg Leu His
                325                 330                 335

Asp Tyr Leu Val Gly Thr Leu Gly Pro Tyr Val Ile Asn Val Thr Lys
            340                 345                 350

Ala Ala Thr Ala Cys Ser His Gln Arg Cys His Gly His Gly Arg Cys
        355                 360                 365

Ser Trp Lys Asp Pro Gly Gln Met Glu Ala Phe Leu His Leu Gln Pro
    370                 375                 380

Asp Asp Asn Leu Gly Ala Trp Lys Ser Phe Arg Cys Arg Cys Tyr Leu
385                 390                 395                 400

Gly Trp Ser Gly Pro Thr Cys Leu Glu Pro Lys Pro
                405                 410


<210> SEQ ID NO 25
<211> LENGTH: 545
<212> TYPE: PRT
<213> ORGANISM: Oryctolagus cuniculus
<220> FEATURE:
<223> OTHER INFORMATION: PH20

<400> SEQUENCE: 25

Met Gly Val Leu Lys Phe Lys His Ile Phe Phe Gly Ser Ala Val Glu
1               5                   10                  15

Leu Ser Gly Val Phe Gln Ile Val Phe Ile Phe Leu Leu Ile Pro Cys
            20                  25                  30

Cys Leu Thr Ala Asn Phe Arg Ala Pro Pro Val Ile Pro Asn Val Pro
        35                  40                  45

Phe Leu Trp Ala Trp Asn Ala Pro Thr Glu Phe Cys Leu Gly Lys Ser
    50                  55                  60

Gly Glu Pro Leu Asp Met Ser Leu Phe Ser Leu Phe Gly Ser Pro Arg
65                  70                  75                  80

Lys Asn Lys Thr Gly Gln Gly Ile Thr Ile Phe Tyr Val Asp Arg Leu
                85                  90                  95

Gly Tyr Tyr Pro Tyr Ile Asp Pro His Thr Gly Ala Ile Val His Gly
            100                 105                 110

Arg Ile Pro Gln Leu Gly Pro Leu Gln Gln His Leu Thr Lys Leu Arg
        115                 120                 125

Gln Glu Ile Leu Tyr Tyr Met Pro Lys Asp Asn Val Gly Leu Ala Val
    130                 135                 140

Ile Asp Trp Glu Glu Trp Leu Pro Thr Trp Leu Arg Asn Trp Lys Pro
145                 150                 155                 160

Lys Asp Ile Tyr Arg Ile Lys Ser Ile Glu Leu Val Lys Ser Gln His
                165                 170                 175

Pro Gln Tyr Asn His Ser Tyr Ala Thr Glu Lys Ala Lys Arg Asp Phe
            180                 185                 190
```

```
Glu Lys Ala Gly Lys Asp Phe Met Glu Glu Thr Leu Lys Leu Gly Arg
        195                 200                 205

Leu Leu Arg Pro Asn His Leu Trp Gly Tyr Tyr Leu Phe Pro Asp Cys
    210                 215                 220

Tyr Asn His His Tyr Asp Lys Pro Asn Leu Tyr Lys Gly Ser Cys Phe
225                 230                 235                 240

Asp Ile Glu Lys Lys Arg Asn Asp Asp Leu Ser Trp Leu Trp Lys Glu
                245                 250                 255

Ser Thr Ala Leu Phe Pro Ser Val Tyr Leu Thr Ser Arg Ala Arg Ser
            260                 265                 270

Ala Thr Ala Leu Ser Lys Leu Tyr Val Val Arg Asn Arg Val His Glu
        275                 280                 285

Ala Ile Arg Val Ser Lys Ile Pro Asp Asp Lys Ser Pro Leu Pro Asn
    290                 295                 300

Phe Val Tyr Thr Arg Leu Val Phe Thr Asp Gln Ile Phe Gln Phe Leu
305                 310                 315                 320

Ser His His Asp Leu Val Tyr Thr Ile Gly Glu Ile Val Ala Leu Gly
                325                 330                 335

Ala Ser Gly Ile Val Val Trp Gly Ser Gln Ser Leu Ala Arg Ser Met
            340                 345                 350

Lys Ser Cys Leu His Leu Asp Asn Tyr Met Lys Thr Ile Leu Asn Pro
        355                 360                 365

Tyr Leu Ile Asn Val Thr Leu Ala Ala Lys Met Cys Asn Gln Val Leu
    370                 375                 380

Cys Gln Glu Gln Gly Val Cys Thr Arg Lys Asn Trp Asn Pro Asn Asp
385                 390                 395                 400

Tyr Leu His Leu Asn Pro Gly Asn Phe Ala Ile Gln Leu Gly Ser Asn
                405                 410                 415

Gly Thr Tyr Lys Val Asp Gly Lys Pro Thr Leu Thr Asp Leu Glu Gln
            420                 425                 430

Phe Ser Lys Asn Phe Gln Cys Ser Cys Tyr Thr Asn Leu Asn Cys Lys
        435                 440                 445

Glu Arg Thr Asp Met Asn Asn Val Arg Thr Val Asn Val Cys Ala Val
    450                 455                 460

Glu Asn Val Cys Ile Asp Thr Asn Val Gly Pro Gln Ala Val Thr Tyr
465                 470                 475                 480

Ala Pro Lys Glu Lys Lys Asp Val Ala His Ile Leu Ser Asn Thr Thr
                485                 490                 495

Ser Ile Asn Ser Ser Thr Thr Met Ser Leu Pro Phe Pro Arg Lys His
            500                 505                 510

Val Ser Gly Cys Leu Leu Val Leu Cys Met Tyr Ser Gln Tyr Leu Asn
        515                 520                 525

Ile Cys Tyr Arg Leu Val Ala Ile Gly Ile Gln His Gly Tyr Tyr Leu
    530                 535                 540

Lys
545


<210> SEQ ID NO 26
<211> LENGTH: 476
<212> TYPE: PRT
<213> ORGANISM: Ovis aries
<220> FEATURE:
<223> OTHER INFORMATION: hyaluronidase 2

<400> SEQUENCE: 26
```

```
Met Trp Thr Gly Leu Gly Pro Ala Val Thr Leu Ala Leu Val Leu Val
1               5                   10                  15

Val Ala Trp Ala Thr Glu Leu Lys Pro Thr Ala Pro Pro Ile Phe Thr
            20                  25                  30

Gly Arg Pro Phe Val Val Ala Trp Asp Val Pro Thr Gln Asp Cys Gly
        35                  40                  45

Pro Arg His Lys Met Pro Leu Asp Pro Lys Asp Met Lys Ala Phe Asp
    50                  55                  60

Val Gln Ala Ser Pro Asn Glu Gly Phe Val Asn Gln Asn Ile Thr Ile
65                  70                  75                  80

Phe Tyr Arg Asp Arg Leu Gly Met Tyr Pro His Phe Asn Ser Val Gly
                85                  90                  95

Arg Ser Val His Gly Gly Val Pro Gln Asn Gly Ser Leu Trp Val His
            100                 105                 110

Leu Glu Met Leu Lys Gly His Val Glu His Tyr Ile Arg Thr Gln Glu
        115                 120                 125

Pro Ala Gly Leu Ala Val Ile Asp Trp Glu Asp Trp Arg Pro Val Trp
    130                 135                 140

Val Arg Asn Trp Gln Asp Lys Asp Val Tyr Arg Arg Leu Ser Arg Gln
145                 150                 155                 160

Leu Val Ala Ser His His Pro Asp Trp Pro Pro Glu Arg Ile Val Lys
                165                 170                 175

Glu Ala Gln Tyr Glu Phe Glu Phe Ala Ala Arg Gln Phe Met Leu Glu
            180                 185                 190

Thr Leu Arg Phe Val Lys Ala Phe Arg Pro Arg His Leu Trp Gly Phe
        195                 200                 205

Tyr Leu Phe Pro Asp Cys Tyr Asn His Asp Tyr Val Gln Asn Trp Glu
    210                 215                 220

Thr Tyr Thr Gly Arg Cys Pro Asp Val Glu Val Ser Arg Asn Asp Gln
225                 230                 235                 240

Leu Ser Trp Leu Trp Ala Glu Ser Thr Ala Leu Phe Pro Ser Val Tyr
                245                 250                 255

Leu Glu Glu Thr Leu Ala Ser Ser Thr His Gly Arg Asn Phe Val Ser
            260                 265                 270

Phe Arg Val Gln Glu Ala Leu Arg Val Ala Asp Val His His Ala Asn
        275                 280                 285

His Ala Leu Pro Val Tyr Val Phe Thr Arg Pro Thr Tyr Ser Arg Gly
    290                 295                 300

Leu Thr Gly Leu Ser Glu Met Asp Leu Ile Ser Thr Ile Gly Glu Ser
305                 310                 315                 320

Ala Ala Leu Gly Ala Ala Gly Val Ile Leu Trp Gly Asp Ala Gly Phe
                325                 330                 335

Thr Thr Ser Asn Glu Thr Cys Arg Arg Leu Lys Asp Tyr Leu Thr Arg
            340                 345                 350

Ser Leu Val Pro Tyr Val Val Asn Val Ser Trp Ala Ala Gln Tyr Cys
        355                 360                 365

Ser Trp Ala Gln Cys His Gly His Gly Arg Cys Val Arg Arg Asp Pro
    370                 375                 380

Asn Ala His Thr Phe Leu His Leu Ser Ala Ser Ser Phe Arg Leu Val
385                 390                 395                 400

Pro Ser His Ala Pro Asp Glu Pro Arg Leu Arg Pro Glu Gly Glu Leu
                405                 410                 415
```

```
Ser Trp Ala Asp Arg Asn His Leu Gln Thr His Phe Arg Cys Gln Cys
            420                 425                 430

Tyr Leu Gly Trp Gly Gly Glu Gln Cys Gln Trp Asp Arg Arg Arg Ala
        435                 440                 445

Ala Gly Gly Ala Ser Gly Ala Trp Ala Gly Ser His Leu Thr Gly Leu
    450                 455                 460

Leu Ala Val Ala Val Leu Ala Phe Thr Trp Thr Ser
465                 470                 475


<210> SEQ ID NO 27
<211> LENGTH: 114
<212> TYPE: PRT
<213> ORGANISM: Ovis aries
<220> FEATURE:
<223> OTHER INFORMATION: PH20 partial sequence

<400> SEQUENCE: 27

Leu Tyr Val Arg Asn Arg Val Arg Glu Ala Ile Arg Leu Ser Lys Ile
1               5                   10                  15

Ala Ser Val Glu Ser Pro Leu Pro Val Phe Val Tyr His Arg Pro Val
            20                  25                  30

Phe Thr Asp Gly Ser Ser Thr Tyr Leu Ser Gln Gly Asp Leu Val Asn
        35                  40                  45

Ser Val Gly Glu Ile Val Ala Leu Gly Ala Ser Gly Ile Ile Met Trp
    50                  55                  60

Gly Ser Leu Asn Leu Ser Leu Thr Met Gln Ser Cys Met Asn Leu Gly
65                  70                  75                  80

Asn Tyr Leu Asn Thr Thr Leu Asn Pro Tyr Ile Ile Asn Val Thr Leu
                85                  90                  95

Ala Ala Lys Met Cys Ser Gln Val Leu Cys Gln Glu Gln Gly Val Cys
            100                 105                 110

Ile Arg


<210> SEQ ID NO 28
<211> LENGTH: 414
<212> TYPE: PRT
<213> ORGANISM: Pongo pygmaeus
<220> FEATURE:
<223> OTHER INFORMATION: hyaluronidase 3

<400> SEQUENCE: 28

Met Thr Thr Arg Leu Gly Pro Ala Leu Val Leu Gly Val Ala Leu Cys
1               5                   10                  15

Leu Gly Cys Gly Gln Pro Leu Pro Gln Val Pro Glu Arg Pro Phe Ser
            20                  25                  30

Val Leu Trp Asn Val Pro Ser Ala His Cys Lys Ser Arg Phe Gly Val
        35                  40                  45

His Leu Pro Leu Asn Ala Leu Gly Ile Ile Ala Asn Arg Gly Gln His
    50                  55                  60

Phe His Gly Gln Asn Met Thr Ile Phe Tyr Lys Asn Gln Leu Gly Leu
65                  70                  75                  80

Tyr Pro Tyr Phe Gly Pro Lys Gly Thr Ala His Asn Gly Gly Ile Pro
                85                  90                  95

Gln Ala Leu Pro Leu Asp Arg His Leu Ala Leu Ala Ala Tyr Gln Ile
            100                 105                 110

His His Ser Leu Arg Pro Gly Phe Ala Gly Pro Ala Val Leu Asp Trp
        115                 120                 125
```

```
Glu Glu Trp Cys Pro Leu Trp Ala Gly Asn Trp Gly Arg Arg Arg Ala
    130                 135                 140

Tyr Gln Ala Ala Ser Trp Ala Trp Ala Gln Gln Val Phe Pro Asp Leu
145                 150                 155                 160

Asp Pro Gln Glu Gln Leu Tyr Lys Ala Tyr Thr Gly Phe Glu Gln Ala
                165                 170                 175

Ala Arg Ala Leu Met Glu Asp Thr Leu Arg Val Ala Gln Ala Leu Arg
            180                 185                 190

Pro His Gly Leu Trp Gly Phe Tyr His Tyr Pro Ala Cys Gly Asn Gly
        195                 200                 205

Trp His Ser Met Ala Ser Asn Tyr Thr Gly Arg Cys His Ala Ala Thr
    210                 215                 220

Leu Ala Arg Asn Thr Gln Leu His Trp Leu Trp Ala Ala Ser Ser Ala
225                 230                 235                 240

Leu Phe Pro Ser Ile Tyr Leu Pro Pro Arg Leu Pro Pro Ala His His
                245                 250                 255

Gln Ala Phe Val Arg His Arg Leu Glu Glu Ala Phe Arg Val Ala Leu
            260                 265                 270

Val Gly His Leu Pro Val Leu Ala Tyr Val Arg Leu Thr His Arg Arg
        275                 280                 285

Ser Gly Arg Phe Leu Ser Gln Asp Asp Leu Val Gln Thr Ile Gly Val
    290                 295                 300

Ser Ala Ala Leu Gly Ala Ala Gly Val Val Leu Trp Gly Asp Leu Ser
305                 310                 315                 320

Leu Ser Ser Ser Glu Glu Glu Cys Trp His Leu His Asp Tyr Leu Val
                325                 330                 335

Asp Thr Leu Gly Pro Tyr Gly Ile Asn Val Thr Arg Ala Ala Met Ala
            340                 345                 350

Cys Ser His Gln Arg Cys His Gly His Gly Arg Cys Ala Arg Arg Asp
        355                 360                 365

Pro Gly Gln Met Glu Ala Phe Leu His Leu Trp Pro Asp Gly Ser Leu
    370                 375                 380

Gly Asp Trp Lys Ser Phe Ser Cys His Cys Tyr Trp Gly Trp Ala Gly
385                 390                 395                 400

Pro Thr Cys Gln Glu Pro Arg Leu Gly Pro Lys Glu Ala Val
                405                 410


<210> SEQ ID NO 29
<211> LENGTH: 510
<212> TYPE: PRT
<213> ORGANISM: Macaca fascicularis
<220> FEATURE:
<223> OTHER INFORMATION: PH20

<400> SEQUENCE: 29

Met Gly Val Leu Lys Phe Lys His Ile Phe Phe Arg Ser Phe Val Lys
1               5                   10                  15

Ser Ser Gly Val Ser Gln Ile Val Phe Thr Phe Leu Leu Ile Pro Cys
            20                  25                  30

Cys Leu Thr Leu Asn Phe Arg Ala Pro Pro Ile Ile Pro Asn Val Pro
        35                  40                  45

Phe Leu Trp Ala Trp Asn Ala Pro Ser Glu Phe Cys Leu Gly Lys Phe
    50                  55                  60

Asn Glu Pro Leu Asp Met Ser Leu Phe Thr Leu Met Gly Ser Pro Arg
65                  70                  75                  80
```

```
Ile Asn Val Thr Gly Gln Gly Val Thr Ile Phe Tyr Val Asp Arg Leu
                85                  90                  95

Gly Tyr Tyr Pro Tyr Ile Asp Leu Thr Thr Gly Val Thr Val His Gly
            100                 105                 110

Gly Ile Pro Gln Lys Val Ser Leu Gln Asp His Leu Asp Lys Ser Lys
        115                 120                 125

Gln Asp Ile Leu Phe Tyr Met Pro Val Asp Asn Leu Gly Met Ala Val
    130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Pro Gln Ala Thr Asp Lys Ala Lys Gln Glu Phe
            180                 185                 190

Glu Lys Ala Gly Lys Asp Phe Met Leu Glu Thr Ile Lys Leu Gly Arg
        195                 200                 205

Ser Leu Arg Pro Asn His Leu Trp Gly Tyr Tyr Leu Phe Pro Asp Cys
    210                 215                 220

Tyr Asn His His Tyr Arg Lys Pro Gly Tyr Asn Gly Ser Cys Phe Asp
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Val Val
            260                 265                 270

Val Ala Thr Leu Tyr Val Arg Asn Arg Val Arg Glu Ala Ile Arg Val
        275                 280                 285

Ser Lys Ile Pro Asp Ala Lys Asn Pro Leu Pro Val Phe Val Tyr Ala
    290                 295                 300

Arg Leu Val Phe Thr Asp Gln Val Leu Lys Phe Leu Ser Arg Glu Glu
305                 310                 315                 320

Leu Val Ser Thr Leu Gly Glu Thr Val Ala Leu Gly Ala Ser Gly Ile
                325                 330                 335

Val Ile Trp Gly Ser Leu Ser Ile Thr Arg Ser Met Lys Ser Cys Leu
            340                 345                 350

Leu Leu Asp Thr Tyr Met Glu Thr Ile Leu Asn Pro Tyr Ile Ile Asn
        355                 360                 365

Val Thr Leu Ala Ala Lys Met Cys Ser Gln Val Leu Cys Gln Glu Gln
    370                 375                 380

Gly Val Cys Ile Arg Lys Asp Trp Asn Ser Ser Asp Tyr Leu His Leu
385                 390                 395                 400

Asn Pro Asp Asn Phe Asp Ile Arg Leu Glu Lys Gly Gly Lys Phe Thr
                405                 410                 415

Val His Gly Lys Pro Thr Val Glu Asp Leu Glu Glu Phe Ser Glu Lys
            420                 425                 430

Phe Tyr Cys Ser Cys Tyr Thr Asn Leu Ser Cys Lys Glu Lys Ala Asp
        435                 440                 445

Val Lys Asp Thr Asp Ala Val Asp Val Cys Ile Ala Asp Gly Val Cys
    450                 455                 460

Ile Asp Ala Ser Leu Lys Pro Pro Val Glu Thr Glu Gly Ser Pro Pro
465                 470                 475                 480

Ile Phe Tyr Asn Thr Ser Ser Ser Thr Val Ser Thr Thr Met Phe Ile
                485                 490                 495

Val Asn Ile Leu Phe Leu Ile Ile Ser Ser Val Ala Ser Leu
```

```
            500                 505                 510


<210> SEQ ID NO 30
<211> LENGTH: 529
<212> TYPE: PRT
<213> ORGANISM: Cavia porcellus
<220> FEATURE:
<223> OTHER INFORMATION: PH20

<400> SEQUENCE: 30

Met Gly Ala Phe Thr Phe Lys His Ser Phe Phe Gly Ser Phe Val Glu
1               5                   10                  15

Cys Ser Gly Val Leu Gln Thr Val Phe Ile Phe Leu Leu Ile Pro Cys
            20                  25                  30

Cys Leu Ala Asp Lys Arg Ala Pro Pro Leu Ile Pro Asn Val Pro Leu
        35                  40                  45

Leu Trp Val Trp Asn Ala Pro Thr Glu Phe Cys Ile Gly Gly Thr Asn
    50                  55                  60

Gln Pro Leu Asp Met Ser Phe Phe Ser Ile Val Gly Thr Pro Arg Lys
65                  70                  75                  80

Asn Ile Thr Gly Gln Ser Ile Thr Leu Tyr Tyr Val Asp Arg Leu Gly
                85                  90                  95

Tyr Tyr Pro Tyr Ile Asp Pro His Thr Gly Ala Ile Val His Gly Gly
            100                 105                 110

Leu Pro Gln Leu Met Asn Leu Gln Gln His Leu Arg Lys Ser Arg Gln
        115                 120                 125

Asp Ile Leu Phe Tyr Met Pro Thr Asp Ser Val Gly Leu Ala Val Ile
    130                 135                 140

Asp Trp Glu Glu Trp Arg Pro Thr Trp Thr Arg Asn Trp Arg Pro Lys
145                 150                 155                 160

Asp Ile Tyr Arg Asn Lys Ser Ile Glu Leu Val Lys Ser Gln His Pro
                165                 170                 175

Gln Tyr Asn His Ser Tyr Ala Val Ala Val Ala Lys Arg Asp Phe Glu
            180                 185                 190

Arg Thr Gly Lys Ala Phe Met Leu Glu Thr Leu Lys Leu Gly Lys Ser
        195                 200                 205

Leu Arg Pro Ser Ser Leu Trp Gly Tyr Tyr Leu Phe Pro Asp Cys Tyr
    210                 215                 220

Asn Thr His Phe Thr Lys Pro Asn Tyr Asp Gly His Cys Pro Pro Ile
225                 230                 235                 240

Glu Leu Gln Arg Asn Asn Asp Leu Gln Trp Leu Trp Asn Asp Ser Thr
                245                 250                 255

Ala Leu Tyr Pro Ser Val Tyr Leu Thr Ser Arg Val Arg Ser Ser Gln
            260                 265                 270

Asn Gly Ala Leu Tyr Val Arg Asn Arg Val His Glu Ser Ile Arg Val
        275                 280                 285

Ser Lys Leu Met Asp Asp Lys Asn Pro Leu Pro Ile Tyr Val Tyr Ile
    290                 295                 300

Arg Leu Val Phe Thr Asp Gln Thr Thr Thr Phe Leu Glu Leu Asp Asp
305                 310                 315                 320

Leu Val His Ser Val Gly Glu Ile Val Pro Leu Gly Val Ser Gly Ile
                325                 330                 335

Ile Ile Trp Gly Ser Leu Ser Leu Thr Arg Ser Leu Val Ser Cys Ile
            340                 345                 350

Gly Leu Glu Asn Tyr Met Lys Gly Thr Leu Leu Pro Tyr Leu Ile Asn
```

```
        355                 360                 365

Val Thr Leu Ala Ala Lys Met Cys Gly Gln Val Leu Cys Lys Asn Gln
    370                 375                 380

Gly Ile Cys Thr Arg Lys Asp Trp Asn Thr Asn Thr Tyr Leu His Leu
385                 390                 395                 400

Asn Ala Thr Asn Phe Asp Ile Glu Leu Gln Gln Asn Gly Lys Phe Val
                405                 410                 415

Val His Gly Lys Pro Ser Leu Glu Asp Leu Gln Glu Phe Ser Lys Asn
            420                 425                 430

Phe His Cys Ser Cys Tyr Thr Asn Val Ala Cys Lys Asp Arg Leu Asp
        435                 440                 445

Val His Asn Val Arg Ser Val Asn Val Cys Thr Ala Asn Asn Ile Cys
    450                 455                 460

Ile Asp Ala Val Leu Asn Phe Pro Ser Leu Asp Asp Asp Asp Glu Pro
465                 470                 475                 480

Pro Ile Thr Asp Asp Thr Ser Gln Asn Gln Asp Ser Ile Ser Asp Ile
                485                 490                 495

Thr Ser Ser Ala Pro Pro Ser Ser His Ile Leu Pro Lys Asp Leu Ser
            500                 505                 510

Trp Cys Leu Phe Leu Leu Ser Ile Phe Ser Gln His Trp Lys Tyr Leu
        515                 520                 525

Leu


<210> SEQ ID NO 31
<211> LENGTH: 512
<212> TYPE: PRT
<213> ORGANISM: Rattus norvegicus
<220> FEATURE:
<223> OTHER INFORMATION: PH20

<400> SEQUENCE: 31

Met Gly Glu Leu Gln Phe Lys Trp Leu Phe Trp Arg Ser Phe Ala Glu
1               5                   10                  15

Ser Gly Gly Thr Phe Gln Thr Val Leu Ile Phe Leu Phe Ile Pro Tyr
            20                  25                  30

Ser Leu Thr Val Asp Tyr Arg Ala Thr Pro Val Leu Ser Asp Thr Thr
        35                  40                  45

Phe Val Trp Val Trp Asn Val Pro Thr Glu Ala Cys Val Glu Asn Val
    50                  55                  60

Thr Glu Pro Ile Asp Leu Ser Phe Phe Ser Leu Ile Gly Ser Pro Arg
65                  70                  75                  80

Lys Thr Ala Ile Gly Gln Pro Val Thr Leu Phe Tyr Val Asp Arg Leu
                85                  90                  95

Gly Asn Tyr Pro His Ile Asp Ala Gln Gln Thr Glu His His Gly Gly
            100                 105                 110

Ile Pro Gln Lys Gly Asp Leu Thr Thr His Leu Val Lys Ala Lys Glu
        115                 120                 125

Asp Val Glu Arg Tyr Ile Pro Thr Asp Lys Leu Gly Leu Ala Ile Ile
    130                 135                 140

Asp Trp Glu Glu Trp Arg Pro Thr Trp Met Arg Asn Trp Thr Pro Lys
145                 150                 155                 160

Asp Ile Tyr Arg Asn Lys Ser Ile Glu Leu Val Gln Ala Ala Asp Pro
                165                 170                 175

Ala Ile Asn Ile Thr Glu Ala Thr Val Arg Ala Lys Ala Gln Phe Glu
            180                 185                 190
```

```
Gly Ala Ala Lys Glu Phe Met Glu Gly Thr Leu Lys Leu Gly Lys His
        195                 200                 205

Ile Arg Pro Lys His Leu Trp Gly Phe Tyr Leu Phe Pro Asp Cys Tyr
    210                 215                 220

Asn Asn Lys Phe Gln Val Asp Asn Tyr Asp Gly Gln Cys Pro Asp Val
225                 230                 235                 240

Glu Lys Lys Arg Asn Asp Asp Leu Asp Trp Leu Trp Lys Glu Ser Thr
                245                 250                 255

Gly Leu Tyr Pro Ser Val Tyr Leu Lys Lys Asp Leu Lys Ser Ser Arg
            260                 265                 270

Lys Ala Thr Leu Tyr Val Arg Tyr Arg Val Leu Glu Ser Ile Arg Val
        275                 280                 285

Ser Lys Val Ser Asp Glu Ser Asn Pro Val Pro Ile Phe Val Tyr Ile
    290                 295                 300

Arg Leu Val Phe Thr Asp His Val Ser Glu Tyr Leu Leu Glu Asp Asp
305                 310                 315                 320

Leu Val Asn Thr Ile Gly Glu Ile Val Ala Gln Gly Thr Ser Gly Ile
                325                 330                 335

Ile Ile Trp Asp Ala Met Ser Leu Ala Gln Arg Ser Ala Gly Cys Pro
            340                 345                 350

Ile Leu Arg Gln Tyr Met Lys Thr Thr Leu Asn Pro Tyr Ile Val Asn
        355                 360                 365

Val Thr Leu Ala Ala Lys Met Cys Ser Gln Thr Leu Cys Lys Glu Lys
    370                 375                 380

Gly Met Cys Ser Arg Lys Thr Glu Ser Ser Asp Ala Tyr Leu His Leu
385                 390                 395                 400

Asp Pro Ser Ser Phe Ser Ile Asn Val Thr Glu Ala Gly Lys Tyr Glu
                405                 410                 415

Val Leu Gly Lys Pro Glu Val Lys Asp Leu Glu Tyr Phe Ser Glu His
            420                 425                 430

Phe Lys Cys Ser Cys Phe Ser Lys Met Thr Cys Glu Glu Thr Ser Asp
        435                 440                 445

Met Arg Ser Ile Gln Asp Val Asn Val Cys Met Gly Asp Asn Val Cys
    450                 455                 460

Ile Lys Ala Thr Leu Gly Pro Asn Ser Ala Phe His Leu Leu Pro Gly
465                 470                 475                 480

Lys Gly Leu Leu Leu Met Thr Thr Leu Ala His Ile Leu His His Leu
                485                 490                 495

Pro His Asp Ile Phe Val Phe Pro Trp Lys Met Leu Val Ser Thr Pro
            500                 505                 510


<210> SEQ ID NO 32
<211> LENGTH: 512
<212> TYPE: PRT
<213> ORGANISM: Mus musculus
<220> FEATURE:
<223> OTHER INFORMATION: PH20

<400> SEQUENCE: 32

Met Gly Glu Leu Arg Phe Lys His Leu Phe Trp Gly Ser Phe Val Glu
1               5                   10                  15

Ser Gly Gly Thr Phe Gln Thr Val Leu Ile Phe Leu Leu Ile Pro Cys
            20                  25                  30

Ser Leu Thr Val Asp Tyr Arg Ala Ala Pro Ile Leu Ser Asn Thr Thr
        35                  40                  45
```

```
Phe Leu Trp Ile Trp Asn Val Pro Thr Glu Arg Cys Val Gly Asn Val
    50                  55                  60

Asn Asp Pro Ile Asp Leu Ser Phe Phe Ser Leu Ile Gly Ser Pro Arg
65                  70                  75                  80

Lys Thr Ala Thr Gly Gln Pro Val Thr Leu Phe Tyr Val Asp Arg Leu
                85                  90                  95

Gly Leu Tyr Pro His Ile Asp Ala Asn Gln Ala Glu His Tyr Gly Gly
            100                 105                 110

Ile Pro Gln Arg Gly Asp Tyr Gln Ala His Leu Arg Lys Ala Lys Thr
        115                 120                 125

Asp Ile Glu His Tyr Ile Pro Asp Asp Lys Leu Gly Leu Ala Ile Ile
    130                 135                 140

Asp Trp Glu Glu Trp Arg Pro Thr Trp Leu Arg Asn Trp Lys Pro Lys
145                 150                 155                 160

Asp Asn Tyr Arg Asn Lys Ser Ile Glu Leu Val Gln Ser Thr Asn Pro
                165                 170                 175

Gly Leu Ser Ile Thr Glu Ala Thr Gln Lys Ala Ile Gln Gln Phe Glu
            180                 185                 190

Glu Ala Gly Arg Lys Phe Met Glu Gly Thr Leu His Leu Gly Lys Phe
        195                 200                 205

Leu Arg Pro Asn Gln Leu Trp Gly Tyr Tyr Leu Phe Pro Asp Cys Tyr
    210                 215                 220

Asn Asn Lys Phe Gln Asp Pro Lys Tyr Asp Gly Gln Cys Pro Ala Val
225                 230                 235                 240

Glu Lys Lys Arg Asn Asp Asn Leu Lys Trp Leu Trp Lys Ala Ser Thr
                245                 250                 255

Gly Leu Tyr Pro Ser Val Tyr Leu Lys Lys Asp Leu Lys Ser Asn Arg
            260                 265                 270

Gln Ala Thr Leu Tyr Val Arg Tyr Arg Val Val Glu Ala Ile Arg Val
        275                 280                 285

Ser Lys Val Gly Asn Ala Ser Asp Pro Val Pro Ile Phe Val Tyr Ile
    290                 295                 300

Arg Leu Val Phe Thr Asp Arg Thr Ser Glu Tyr Leu Leu Glu Asp Asp
305                 310                 315                 320

Leu Val Asn Thr Ile Gly Glu Ile Val Ala Leu Gly Thr Ser Gly Ile
                325                 330                 335

Ile Ile Trp Asp Ala Met Ser Leu Ala Gln Arg Ala Ala Gly Cys Pro
            340                 345                 350

Ile Leu His Lys Tyr Met Gln Thr Thr Leu Asn Pro Tyr Ile Val Asn
        355                 360                 365

Val Thr Leu Ala Ala Lys Met Cys Ser Gln Thr Leu Cys Asn Glu Lys
    370                 375                 380

Gly Met Cys Ser Arg Arg Lys Glu Ser Ser Asp Val Tyr Leu His Leu
385                 390                 395                 400

Asn Pro Ser His Phe Asp Ile Met Leu Thr Glu Thr Gly Lys Tyr Glu
                405                 410                 415

Val Leu Gly Asn Pro Arg Val Gly Asp Leu Glu Tyr Phe Ser Glu His
            420                 425                 430

Phe Lys Cys Ser Cys Phe Ser Arg Met Thr Cys Lys Glu Thr Ser Asp
        435                 440                 445

Val Lys Asn Val Gln Asp Val Asn Val Cys Val Gly Asp Asn Val Cys
    450                 455                 460
```

```
Ile Lys Ala Lys Val Glu Pro Asn Pro Ala Phe Tyr Leu Leu Pro Gly
465                 470                 475                 480

Lys Ser Leu Leu Phe Met Thr Thr Leu Gly His Val Leu Tyr His Leu
                485                 490                 495

Pro Gln Asp Ile Phe Val Phe Pro Arg Lys Thr Leu Val Ser Thr Pro
            500                 505                 510


<210> SEQ ID NO 33
<211> LENGTH: 807
<212> TYPE: PRT
<213> ORGANISM: Staphylococcus aureus
<220> FEATURE:
<223> OTHER INFORMATION: hyaluronidase

<400> SEQUENCE: 33

Met Thr Tyr Arg Ile Lys Lys Trp Gln Lys Leu Ser Thr Ile Thr Leu
1               5                   10                  15

Leu Met Ala Gly Val Ile Thr Leu Asn Gly Gly Glu Phe Arg Ser Val
            20                  25                  30

Asp Lys His Gln Ile Ala Val Ala Asp Thr Asn Val Gln Thr Pro Asp
        35                  40                  45

Tyr Glu Lys Leu Arg Asn Thr Trp Leu Asp Val Asn Tyr Gly Tyr Asp
    50                  55                  60

Lys Tyr Asp Glu Asn Asn Pro Asp Met Lys Lys Lys Phe Asp Ala Thr
65                  70                  75                  80

Glu Lys Glu Ala Thr Asn Leu Leu Lys Glu Met Lys Thr Glu Ser Gly
                85                  90                  95

Arg Lys Tyr Leu Trp Ser Gly Ala Glu Thr Leu Glu Thr Asn Ser Ser
            100                 105                 110

His Met Thr Arg Thr Tyr Arg Asn Ile Glu Lys Ile Ala Glu Ala Met
        115                 120                 125

Arg Asn Pro Lys Thr Thr Leu Asn Thr Asp Glu Asn Lys Lys Lys Val
    130                 135                 140

Lys Asp Ala Leu Glu Trp Leu His Lys Asn Ala Tyr Gly Lys Glu Pro
145                 150                 155                 160

Asp Lys Lys Val Lys Glu Leu Ser Glu Asn Phe Thr Lys Thr Thr Gly
                165                 170                 175

Lys Asn Thr Asn Leu Asn Trp Trp Asp Tyr Glu Ile Gly Thr Pro Lys
            180                 185                 190

Ser Leu Thr Asn Thr Leu Ile Leu Leu Asn Asp Gln Phe Ser Asn Glu
        195                 200                 205

Glu Lys Lys Lys Phe Thr Ala Pro Ile Lys Thr Phe Ala Pro Asp Ser
    210                 215                 220

Asp Lys Ile Leu Ser Ser Val Gly Lys Ala Glu Leu Ala Lys Gly Gly
225                 230                 235                 240

Asn Leu Val Asp Ile Ser Lys Val Lys Leu Leu Glu Cys Ile Ile Glu
                245                 250                 255

Glu Asp Lys Asp Met Met Lys Lys Ser Ile Asp Ser Phe Asn Lys Val
            260                 265                 270

Phe Thr Tyr Val Gln Asp Ser Ala Thr Gly Lys Glu Arg Asn Gly Phe
        275                 280                 285

Tyr Lys Asp Gly Ser Tyr Ile Asp His Gln Asp Val Pro Tyr Thr Gly
    290                 295                 300

Ala Tyr Gly Val Val Leu Leu Glu Gly Ile Ser Gln Met Met Pro Met
305                 310                 315                 320
```

```
Ile Lys Glu Thr Pro Phe Asn Asp Lys Thr Gln Asn Asp Thr Thr Leu
                325                 330                 335

Lys Ser Trp Ile Asp Asp Gly Phe Met Pro Leu Ile Tyr Lys Gly Glu
            340                 345                 350

Met Met Asp Leu Ser Arg Gly Arg Ala Ile Ser Arg Glu Asn Glu Thr
        355                 360                 365

Ser His Ser Ala Ser Ala Thr Val Met Lys Ser Leu Leu Arg Leu Ser
    370                 375                 380

Asp Ala Met Asp Asp Ser Thr Lys Ala Lys Tyr Lys Lys Ile Val Lys
385                 390                 395                 400

Ser Ser Val Glu Ser Asp Ser Ser Tyr Lys Gln Asn Asp Tyr Leu Asn
                405                 410                 415

Ser Tyr Ser Asp Ile Asp Lys Met Lys Ser Leu Met Thr Asp Asn Ser
            420                 425                 430

Ile Ser Lys Asn Gly Leu Thr Gln Gln Leu Lys Ile Tyr Asn Asp Met
        435                 440                 445

Asp Arg Val Thr Tyr His Asn Lys Asp Leu Asp Phe Ala Phe Gly Leu
    450                 455                 460

Ser Met Thr Ser Lys Asn Val Ala Arg Tyr Glu Ser Ile Asn Gly Glu
465                 470                 475                 480

Asn Leu Lys Gly Trp His Thr Gly Ala Gly Met Ser Tyr Leu Tyr Asn
                485                 490                 495

Ser Asp Val Lys His Tyr His Asp Asn Phe Trp Val Thr Ala Asp Met
            500                 505                 510

Lys Arg Leu Ser Gly Thr Thr Thr Leu Asp Asn Glu Ile Leu Lys Asp
        515                 520                 525

Thr Asp Asp Lys Lys Ser Ser Lys Thr Phe Val Gly Gly Thr Lys Val
    530                 535                 540

Asp Asp Gln His Ala Ser Ile Gly Met Asp Phe Glu Asn Gln Asp Lys
545                 550                 555                 560

Thr Leu Thr Ala Lys Lys Ser Tyr Phe Ile Leu Asn Asp Lys Ile Val
                565                 570                 575

Phe Leu Gly Thr Gly Ile Lys Ser Thr Asp Ser Ser Lys Asn Pro Val
            580                 585                 590

Thr Thr Ile Glu Asn Arg Lys Ala Asn Gly Tyr Thr Leu Tyr Thr Asp
        595                 600                 605

Asp Lys Gln Thr Thr Asn Ser Asp Asn Gln Glu Asn Asn Ser Val Phe
    610                 615                 620

Leu Glu Ser Thr Asp Thr Lys Lys Asn Ile Gly Tyr His Phe Leu Asn
625                 630                 635                 640

Lys Pro Lys Ile Thr Val Lys Lys Glu Ser His Thr Gly Lys Trp Lys
                645                 650                 655

Glu Ile Asn Lys Ser Gln Lys Asp Thr Gln Lys Thr Asp Glu Tyr Tyr
            660                 665                 670

Glu Val Thr Gln Lys His Ser Asn Ser Asp Asn Lys Tyr Gly Tyr Val
        675                 680                 685

Leu Tyr Pro Gly Leu Ser Lys Asp Val Phe Lys Thr Lys Lys Asp Glu
    690                 695                 700

Val Thr Val Val Lys Gln Glu Asp Asp Phe His Val Val Lys Asp Asn
705                 710                 715                 720

Glu Ser Val Trp Ala Gly Val Asn Tyr Ser Asn Ser Thr Gln Thr Phe
                725                 730                 735

Asp Ile Asn Asn Thr Lys Val Glu Val Lys Ala Lys Gly Met Phe Ile
```

```
            740                 745                 750

Leu Lys Lys Lys Asp Asp Asn Thr Tyr Glu Cys Ser Phe Tyr Asn Pro
        755                 760                 765

Glu Ser Thr Asn Ser Ala Ser Asp Ile Glu Ser Lys Ile Ser Met Thr
    770                 775                 780

Gly Tyr Ser Ile Thr Asn Lys Asn Thr Ser Thr Ser Asn Glu Ser Gly
785                 790                 795                 800

Val His Phe Glu Leu Thr Lys
                805


<210> SEQ ID NO 34
<211> LENGTH: 371
<212> TYPE: PRT
<213> ORGANISM: Streptococcus pyogenes
<220> FEATURE:
<223> OTHER INFORMATION: [bacteriophage H4489A] hyaluronidase

<400> SEQUENCE: 34

Met Thr Glu Asn Ile Pro Leu Arg Val Gln Phe Lys Arg Met Ser Ala
1               5                   10                  15

Asp Glu Trp Ala Arg Ser Asp Val Ile Leu Leu Glu Gly Glu Ile Gly
            20                  25                  30

Phe Glu Thr Asp Thr Gly Phe Ala Lys Phe Gly Asp Gly Gln Asn Thr
        35                  40                  45

Phe Ser Lys Leu Lys Tyr Leu Thr Gly Pro Lys Gly Pro Lys Gly Asp
    50                  55                  60

Thr Gly Leu Gln Gly Lys Thr Gly Gly Thr Gly Pro Arg Gly Pro Ala
65                  70                  75                  80

Gly Lys Pro Gly Thr Thr Asp Tyr Asp Gln Leu Gln Asn Lys Pro Asp
                85                  90                  95

Leu Gly Ala Phe Ala Gln Lys Glu Glu Thr Asn Ser Lys Ile Thr Lys
            100                 105                 110

Leu Glu Ser Ser Lys Ala Asp Lys Ser Ala Val Tyr Ser Lys Ala Glu
        115                 120                 125

Ser Lys Ile Glu Leu Asp Lys Lys Leu Ser Leu Thr Gly Gly Ile Val
    130                 135                 140

Thr Gly Gln Leu Gln Phe Lys Pro Asn Lys Ser Gly Ile Lys Pro Ser
145                 150                 155                 160

Ser Ser Val Gly Gly Ala Ile Asn Ile Asp Met Ser Lys Ser Glu Gly
                165                 170                 175

Ala Ala Met Val Met Tyr Thr Asn Lys Asp Thr Thr Asp Gly Pro Leu
            180                 185                 190

Met Ile Leu Arg Ser Asp Lys Asp Thr Phe Asp Gln Ser Ala Gln Phe
        195                 200                 205

Val Asp Tyr Ser Gly Lys Thr Asn Ala Val Asn Ile Val Met Arg Gln
    210                 215                 220

Pro Ser Ala Pro Asn Phe Ser Ser Ala Leu Asn Ile Thr Ser Ala Asn
225                 230                 235                 240

Glu Gly Gly Ser Ala Met Gln Ile Arg Gly Val Glu Lys Ala Leu Gly
                245                 250                 255

Thr Leu Lys Ile Thr His Glu Asn Pro Asn Val Glu Ala Lys Tyr Asp
            260                 265                 270

Glu Asn Ala Ala Ala Leu Ser Ile Asp Ile Val Lys Lys Gln Lys Gly
        275                 280                 285

Gly Lys Gly Thr Ala Ala Gln Gly Ile Tyr Ile Asn Ser Thr Ser Gly
```

```
    290                 295                 300

Thr Ala Gly Lys Met Leu Arg Ile Arg Asn Lys Asn Glu Asp Lys Phe
305                 310                 315                 320

Tyr Val Gly Pro Asp Gly Gly Phe His Ser Gly Ala Asn Ser Thr Val
                325                 330                 335

Ala Gly Asn Leu Thr Val Lys Asp Pro Thr Ser Gly Lys His Ala Ala
            340                 345                 350

Thr Lys Asp Tyr Val Asp Glu Lys Ile Ala Glu Leu Lys Lys Leu Ile
        355                 360                 365

Leu Lys Lys
    370


<210> SEQ ID NO 35
<211> LENGTH: 1628
<212> TYPE: PRT
<213> ORGANISM: Clostridium perfringens
<220> FEATURE:
<223> OTHER INFORMATION: hyaluronidase

<400> SEQUENCE: 35

Met Asn Lys Asn Ile Arg Lys Ile Ile Thr Ser Thr Val Leu Ala Ala
1               5                   10                  15

Met Thr Ile Ser Val Leu Pro Ser Asn Leu Val Val Phe Ala Thr Asp
            20                  25                  30

Gly Ile Thr Glu Asn Phe Tyr Glu Ile Tyr Pro Lys Pro Gln Glu Ile
        35                  40                  45

Ser Tyr Ser Gly Gly Glu Phe Gln Ile Ser Asp Glu Ile Asn Ile Val
    50                  55                  60

Tyr Asp Asp Gly Ile Asp Thr Tyr Thr Lys Lys Arg Val Asp Glu Val
65                  70                  75                  80

Leu Glu Ala Ser Asn Leu Glu Ala Thr Val Ser Asn Glu Ile Val Pro
                85                  90                  95

Gly Lys Thr Asn Phe Leu Val Gly Ile Asn Glu Ser Gly Gly Val Val
            100                 105                 110

Asp Asn Tyr Phe Asn Lys Asn Ile Pro His Asp Glu Ser Phe Phe Asp
        115                 120                 125

Glu Lys Met Asp Ala Asn Ile Val Ser Val Lys Asp Gly Val Ile Gly
    130                 135                 140

Val Ile Gly Glu Asp Thr Asp Ser Ala Phe Tyr Gly Val Thr Thr Leu
145                 150                 155                 160

Lys His Val Phe Asn Gln Leu Glu Glu Gly Asn Lys Ile Gln Ser Phe
                165                 170                 175

Arg Ala Asp Asp Tyr Ala Glu Val Ala His Arg Gly Phe Ile Glu Gly
            180                 185                 190

Tyr Tyr Gly Asn Pro Trp Ser Asn Glu Asp Arg Ala Glu Leu Met Lys
        195                 200                 205

Phe Gly Gly Asp Tyr Lys Leu Asn Gln Tyr Val Phe Ala Pro Lys Asp
    210                 215                 220

Asp Pro Tyr His Asn Ser Lys Trp Arg Asp Leu Tyr Pro Glu Glu Lys
225                 230                 235                 240

Leu Ser Glu Ile Lys Lys Leu Ala Gln Val Gly Asn Glu Thr Lys Asn
                245                 250                 255

Arg Tyr Val Tyr Ala Leu His Pro Phe Met Asn Asn Pro Val Arg Phe
            260                 265                 270

Asp Thr Glu Glu Asn Tyr Gln Asn Asp Leu Gly Val Ile Lys Ala Lys
```

```
        275                 280                 285

Phe Thr Gln Leu Leu Glu Asn Asp Val Arg Gln Phe Ala Ile Leu Ala
    290                 295                 300

Asp Asp Ala Ser Ala Pro Ala Gln Gly Ala Ser Met Tyr Val Lys Leu
305                 310                 315                 320

Leu Thr Asp Leu Thr Arg Trp Leu Glu Glu Gln Gln Ser Thr Tyr Pro
                325                 330                 335

Asp Leu Lys Thr Asp Leu Met Phe Cys Pro Ser Asp Tyr Tyr Gly Asn
            340                 345                 350

Gly Ser Ser Ala Gln Leu Lys Glu Leu Asn Lys Ala Glu Asp Asn Val
        355                 360                 365

Ser Ile Val Met Thr Gly Gly Arg Ile Trp Gly Glu Val Asp Glu Asn
    370                 375                 380

Phe Ala Asn Asn Phe Met Asn Asn Ile Ser Thr Glu Gly His Pro Gly
385                 390                 395                 400

Arg Ala Pro Phe Phe Trp Ile Asn Trp Pro Cys Ser Asp Asn Ser Lys
                405                 410                 415

Gln His Leu Ile Met Gly Gly Asn Asp Thr Phe Leu His Pro Gly Val
            420                 425                 430

Asp Pro Ser Lys Ile Asp Gly Ile Val Leu Asn Pro Met Gln Gln Ala
        435                 440                 445

Glu Ala Asn Lys Ser Ala Leu Phe Ala Ile Ala Asp Tyr Ala Trp Asn
    450                 455                 460

Ile Trp Asp Asn Lys Glu Glu Ala Asp Glu Asn Trp Asn Asp Ser Phe
465                 470                 475                 480

Lys Tyr Met Asp His Gly Thr Ala Glu Glu Thr Asn Ser Ser Leu Ala
                485                 490                 495

Leu Arg Glu Ile Ser Lys His Met Ile Asn Gln Asn Met Asp Gly Arg
            500                 505                 510

Val Arg Pro Leu Gln Glu Ser Val Glu Leu Ala Pro Lys Leu Glu Ala
        515                 520                 525

Phe Lys Gln Lys Tyr Asp Ser Gly Ala Ser Ile Lys Glu Asp Ala Leu
    530                 535                 540

Glu Leu Ile Ala Glu Phe Thr Asn Leu Gln Lys Ala Ala Asp Tyr Tyr
545                 550                 555                 560

Lys Asn Asn Pro Gly Asn Glu Arg Thr Arg Asp Gln Ile Ile Tyr Trp
                565                 570                 575

Leu Asn Cys Trp Glu Asp Thr Met Asp Ala Ala Ile Gly Tyr Leu Lys
            580                 585                 590

Ser Ala Ile Ala Ile Glu Glu Gly Asp Asp Glu Ala Ala Trp Ala Asn
        595                 600                 605

Tyr Ser Glu Ala Gln Gly Ala Phe Glu Lys Ser Lys Thr Tyr Gly Phe
    610                 615                 620

His Tyr Val Asp His Thr Glu Tyr Ala Glu Val Gly Val Gln His Ile
625                 630                 635                 640

Val Pro Phe Ile Lys Ser Met Gly Gln Asn Leu Ser Val Val Ile Gly
                645                 650                 655

Ser Ile Val Asp Pro Asn Arg Ile Ile Ala Thr Tyr Ile Ser Asn Arg
            660                 665                 670

Gln Asp Ala Pro Thr Gly Asn Pro Asp Asn Ile Phe Asp Asn Asn Ala
        675                 680                 685

Ser Thr Glu Leu Val Tyr Lys Asn Pro Asn Arg Ile Asp Val Gly Thr
    690                 695                 700
```

```
Tyr Val Gly Val Lys Tyr Ser Asn Pro Ile Thr Leu Asn Asn Val Glu
705                 710                 715                 720

Phe Leu Met Gly Ala Asn Ser Asn Pro Asn Asp Thr Met Gln Lys Ala
                725                 730                 735

Lys Ile Gln Tyr Thr Val Asp Gly Arg Glu Trp Ile Asp Leu Glu Glu
            740                 745                 750

Gly Val Glu Tyr Thr Met Pro Gly Ala Ile Lys Val Glu Asn Leu Asp
        755                 760                 765

Leu Lys Val Arg Gly Val Arg Leu Ile Ala Thr Glu Ala Arg Glu Asn
    770                 775                 780

Thr Trp Leu Gly Val Arg Asp Ile Asn Val Asn Lys Lys Glu Asp Ser
785                 790                 795                 800

Asn Ser Gly Val Glu Phe Asn Pro Ser Leu Ile Arg Ser Glu Ser Trp
                805                 810                 815

Gln Val Tyr Glu Gly Asn Glu Ala Asn Leu Leu Asp Gly Asp Asp Asn
            820                 825                 830

Thr Gly Val Trp Tyr Lys Thr Leu Asn Gly Asp Thr Ser Leu Ala Gly
        835                 840                 845

Glu Phe Ile Gly Leu Asp Leu Gly Lys Glu Ile Lys Leu Asp Gly Ile
    850                 855                 860

Arg Phe Val Ile Gly Lys Asn Gly Gly Gly Ser Ser Asp Lys Trp Asn
865                 870                 875                 880

Lys Phe Lys Leu Glu Tyr Ser Leu Asp Asn Glu Ser Trp Thr Thr Ile
                885                 890                 895

Lys Glu Tyr Asp Lys Thr Gly Ala Pro Ala Gly Lys Asp Val Ile Glu
            900                 905                 910

Glu Ser Phe Glu Thr Pro Ile Ser Ala Lys Tyr Ile Arg Leu Thr Asn
        915                 920                 925

Met Glu Asn Ile Asn Lys Trp Leu Thr Phe Ser Glu Phe Ala Ile Ile
    930                 935                 940

Ser Asp Glu Leu Glu Asn Ala Gly Asn Lys Glu Asn Val Tyr Thr Asn
945                 950                 955                 960

Thr Glu Leu Asp Leu Leu Ser Leu Ala Lys Glu Asp Val Thr Lys Leu
                965                 970                 975

Ile Pro Thr Asp Asp Ile Ser Leu Asn His Gly Glu Tyr Ile Gly Val
            980                 985                 990

Lys Leu Asn Arg Ile Lys Asp Leu Ser Asn Ile Asn Leu Glu Ile Ser
        995                 1000                1005

Asn Asp Thr Gly Leu Lys Leu Gln Ser Ser Met Asn Gly Val Glu Trp
    1010                1015                1020

Thr Glu Ile Thr Asp Lys Asn Thr Leu Glu Asp Gly Arg Tyr Val Arg
1025                1030                1035                1040

Leu Ile Asn Thr Ser Asn Glu Ala Val Asn Phe Asn Leu Thr Lys Phe
                1045                1050                1055

Glu Val Asn Ser Asn Glu Val Tyr Glu Pro Ser Leu Val Asp Ala Tyr
            1060                1065                1070

Val Gly Asp Asp Gly Ala Lys Lys Ala Val Asp Gly Asp Leu Lys Thr
        1075                1080                1085

Arg Val Lys Phe Leu Gly Ala Pro Ser Thr Gly Asp Thr Ile Val Tyr
    1090                1095                1100

Asp Leu Gly Gln Glu Ile Leu Val Asp Asn Leu Lys Tyr Val Val Leu
1105                1110                1115                1120
```

```
Asp Thr Glu Val Asp His Val Arg Asp Gly Lys Ile Gln Leu Ser Leu
                1125                1130                1135

Asp Gly Glu Thr Trp Thr Asp Ala Ile Thr Ile Gly Asp Gly Val Glu
            1140                1145                1150

Asn Gly Val Asp Asp Met Phe Ser Thr Pro Leu Lys Asn Gly Tyr Lys
        1155                1160                1165

His Gly Asn Gln Ser Gly Gly Ile Val Pro Ile Asp Ser Ala Tyr Val
    1170                1175                1180

Glu Gly Asp Asn Leu Asn Gln Lys Ala Arg Tyr Val Arg Ile Leu Phe
1185                1190                1195                1200

Thr Ala Pro Tyr Arg His Arg Trp Thr Val Ile Asn Glu Leu Met Ile
                1205                1210                1215

Asn Asn Gly Glu Tyr Ile Ser Thr Val Asn Asp Pro Thr Tyr Ile Ser
            1220                1225                1230

Asn Pro Ile Glu Glu Arg Gly Phe Ala Pro Ser Asn Leu Arg Asp Gly
        1235                1240                1245

Asn Leu Thr Thr Ser Tyr Lys Pro Asn Thr Asn Asn Gly Glu Ile Ser
    1250                1255                1260

Glu Gly Ser Ile Thr Tyr Arg Leu Ser Glu Lys Thr Asp Val Arg Lys
1265                1270                1275                1280

Val Thr Ile Val Gln Ser Gly Ser Ser Ile Ser Asn Ala Lys Val Met
                1285                1290                1295

Ala Arg Val Gly Asp Gly Ser Glu Asn Val Thr Asp Gln Trp Val Gln
            1300                1305                1310

Leu Gly Thr Leu Ser Asn Ser Leu Asn Glu Phe Ile Asn Arg Asp Tyr
        1315                1320                1325

Asn Asn Ile Tyr Glu Ile Lys Ile Glu Trp Thr Asp Val Ala Pro Asn
    1330                1335                1340

Ile Tyr Glu Ile Ile Thr Leu Asn Gln Glu Phe Glu Phe Pro Val Asn
1345                1350                1355                1360

Asp Ser Leu Lys Ala Lys Tyr Asp Glu Leu Ile Asn Leu Ser Gly Asp
                1365                1370                1375

Glu Tyr Thr Leu Ser Ser Phe Glu Thr Leu Lys Glu Ala Leu Asn Glu
            1380                1385                1390

Ala Lys Ser Ile Leu Asp Asp Ser Asn Ser Ser Gln Lys Lys Ile Asp
        1395                1400                1405

Lys Ala Leu Glu Lys Leu Asn Lys Ala Glu Glu Arg Leu Asp Leu Arg
    1410                1415                1420

Ala Thr Asp Phe Glu Asp Phe Asn Lys Val Leu Thr Leu Gly Asn Ser
1425                1430                1435                1440

Leu Val Glu Glu Glu Tyr Thr Ala Glu Ser Trp Ala Leu Phe Ser Glu
                1445                1450                1455

Val Leu Glu Ala Ala Asn Glu Ala Asn Lys Asn Lys Ala Asp Tyr Thr
            1460                1465                1470

Gln Asp Gln Ile Asn Gln Ile Val Ile Asp Leu Asp Ala Ser Ile Lys
        1475                1480                1485

Ala Leu Val Lys Glu Thr Pro Glu Val Asp Lys Thr Asn Leu Gly Glu
    1490                1495                1500

Leu Ile Asn Gln Gly Lys Ser Leu Leu Asp Glu Ser Val Glu Gly Phe
1505                1510                1515                1520

Asn Val Gly Glu Tyr His Lys Gly Ala Lys Asp Gly Leu Thr Val Glu
                1525                1530                1535

Ile Asn Lys Ala Glu Glu Val Phe Asn Lys Glu Asp Ala Thr Glu Glu
```

```
            1540                1545                1550

Glu Ile Asn Leu Ala Lys Glu Ser Leu Glu Gly Ala Ile Ala Arg Phe
        1555                1560                1565

Asn Ser Leu Leu Ile Glu Glu Ser Thr Gly Asp Phe Asn Gly Asn Gly
    1570                1575                1580

Lys Ile Asp Ile Gly Asp Leu Ala Met Val Ser Lys Asn Ile Gly Ser
1585                1590                1595                1600

Thr Thr Asn Thr Ser Leu Asp Leu Asn Lys Asp Gly Ser Ile Asp Glu
                1605                1610                1615

Tyr Glu Ile Ser Phe Ile Asn His Arg Ile Leu Asn
            1620                1625


<210> SEQ ID NO 36
<211> LENGTH: 435
<212> TYPE: PRT
<213> ORGANISM: Homo sapiens
<220> FEATURE:
<223> OTHER INFORMATION: Hyaluronidase-1 [Precursor]

<400> SEQUENCE: 36

Met Ala Ala His Leu Leu Pro Ile Cys Ala Leu Phe Leu Thr Leu Leu
1               5                   10                  15

Asp Met Ala Gln Gly Phe Arg Gly Pro Leu Leu Pro Asn Arg Pro Phe
            20                  25                  30

Thr Thr Val Trp Asn Ala Asn Thr Gln Trp Cys Leu Glu Arg His Gly
        35                  40                  45

Val Asp Val Asp Val Ser Val Phe Asp Val Val Ala Asn Pro Gly Gln
    50                  55                  60

Thr Phe Arg Gly Pro Asp Met Thr Ile Phe Tyr Ser Ser Gln Leu Gly
65                  70                  75                  80

Thr Tyr Pro Tyr Tyr Thr Pro Thr Gly Glu Pro Val Phe Gly Gly Leu
                85                  90                  95

Pro Gln Asn Ala Ser Leu Ile Ala His Leu Ala Arg Thr Phe Gln Asp
            100                 105                 110

Ile Leu Ala Ala Ile Pro Ala Pro Asp Phe Ser Gly Leu Ala Val Ile
        115                 120                 125

Asp Trp Glu Ala Trp Arg Pro Arg Trp Ala Phe Asn Trp Asp Thr Lys
    130                 135                 140

Asp Ile Tyr Arg Gln Arg Ser Arg Ala Leu Val Gln Ala Gln His Pro
145                 150                 155                 160

Asp Trp Pro Ala Pro Gln Val Glu Ala Val Ala Gln Asp Gln Phe Gln
                165                 170                 175

Gly Ala Ala Arg Ala Trp Met Ala Gly Thr Leu Gln Leu Gly Arg Ala
            180                 185                 190

Leu Arg Pro Arg Gly Leu Trp Gly Phe Tyr Gly Phe Pro Asp Cys Tyr
        195                 200                 205

Asn Tyr Asp Phe Leu Ser Pro Asn Tyr Thr Gly Gln Cys Pro Ser Gly
    210                 215                 220

Ile Arg Ala Gln Asn Asp Gln Leu Gly Trp Leu Trp Gly Gln Ser Arg
225                 230                 235                 240

Ala Leu Tyr Pro Ser Ile Tyr Met Pro Ala Val Leu Glu Gly Thr Gly
                245                 250                 255

Lys Ser Gln Met Tyr Val Gln His Arg Val Ala Glu Ala Phe Arg Val
            260                 265                 270

Ala Val Ala Ala Gly Asp Pro Asn Leu Pro Val Leu Pro Tyr Val Gln
```

```
        275                 280                 285

Ile Phe Tyr Asp Thr Thr Asn His Phe Leu Pro Leu Asp Glu Leu Glu
    290                 295                 300

His Ser Leu Gly Glu Ser Ala Ala Gln Gly Ala Ala Gly Val Val Leu
305                 310                 315                 320

Trp Val Ser Trp Glu Asn Thr Arg Thr Lys Glu Ser Cys Gln Ala Ile
                325                 330                 335

Lys Glu Tyr Met Asp Thr Thr Leu Gly Pro Phe Ile Leu Asn Val Thr
            340                 345                 350

Ser Gly Ala Leu Leu Cys Ser Gln Ala Leu Cys Ser Gly His Gly Arg
        355                 360                 365

Cys Val Arg Arg Thr Ser His Pro Lys Ala Leu Leu Leu Leu Asn Pro
    370                 375                 380

Ala Ser Phe Ser Ile Gln Leu Thr Pro Gly Gly Gly Pro Leu Ser Leu
385                 390                 395                 400

Arg Gly Ala Leu Ser Leu Glu Asp Gln Ala Gln Met Ala Val Glu Phe
                405                 410                 415

Lys Cys Arg Cys Tyr Pro Gly Trp Gln Ala Pro Trp Cys Glu Arg Lys
            420                 425                 430

Ser Met Trp
        435


<210> SEQ ID NO 37
<211> LENGTH: 473
<212> TYPE: PRT
<213> ORGANISM: Homo sapiens
<220> FEATURE:
<223> OTHER INFORMATION: Hyaluronidase-2 [Precursor]

<400> SEQUENCE: 37

Met Arg Ala Gly Pro Gly Pro Thr Val Thr Leu Ala Leu Val Leu Ala
1               5                   10                  15

Val Ala Trp Ala Met Glu Leu Lys Pro Thr Ala Pro Pro Ile Phe Thr
            20                  25                  30

Gly Arg Pro Phe Val Val Ala Trp Asp Val Pro Thr Gln Asp Cys Gly
        35                  40                  45

Pro Arg Leu Lys Val Pro Leu Asp Leu Asn Ala Phe Asp Val Gln Ala
    50                  55                  60

Ser Pro Asn Glu Gly Phe Val Asn Gln Asn Ile Thr Ile Phe Tyr Arg
65                  70                  75                  80

Asp Arg Leu Gly Leu Tyr Pro Arg Phe Asp Ser Ala Gly Arg Ser Val
                85                  90                  95

His Gly Gly Val Pro Gln Asn Val Ser Leu Trp Ala His Arg Lys Met
            100                 105                 110

Leu Gln Lys Arg Val Glu His Tyr Ile Arg Thr Gln Glu Ser Ala Gly
        115                 120                 125

Leu Ala Val Ile Asp Trp Glu Asp Trp Arg Pro Val Trp Val Arg Asn
    130                 135                 140

Trp Gln Asp Lys Asp Val Tyr Arg Arg Leu Ser Arg Gln Leu Val Ala
145                 150                 155                 160

Ser Arg His Pro Asp Trp Pro Pro Asp Arg Ile Val Lys Gln Ala Gln
                165                 170                 175

Tyr Glu Phe Glu Phe Ala Ala Gln Gln Phe Met Leu Glu Thr Leu Arg
            180                 185                 190

Tyr Val Lys Ala Val Arg Pro Arg His Leu Trp Gly Phe Tyr Leu Phe
```

```
        195                 200                 205

Pro Asp Cys Tyr Asn His Asp Tyr Val Gln Asn Trp Glu Ser Tyr Thr
    210                 215                 220

Gly Arg Cys Pro Asp Val Glu Val Ala Arg Asn Asp Gln Leu Ala Trp
225                 230                 235                 240

Leu Trp Ala Glu Ser Thr Ala Leu Phe Pro Ser Val Tyr Leu Asp Glu
                245                 250                 255

Thr Leu Ala Ser Ser Arg His Gly Arg Asn Phe Val Ser Phe Arg Val
            260                 265                 270

Gln Glu Ala Leu Arg Val Ala Arg Thr His His Ala Asn His Ala Leu
        275                 280                 285

Pro Val Tyr Val Phe Thr Arg Pro Thr Tyr Ser Arg Arg Leu Thr Gly
    290                 295                 300

Leu Ser Glu Met Asp Leu Ile Ser Thr Ile Gly Glu Ser Ala Ala Leu
305                 310                 315                 320

Gly Ala Ala Gly Val Ile Leu Trp Gly Asp Ala Gly Tyr Thr Thr Ser
                325                 330                 335

Thr Glu Thr Cys Gln Tyr Leu Lys Asp Tyr Leu Thr Arg Leu Leu Val
            340                 345                 350

Pro Tyr Val Val Asn Val Ser Trp Ala Thr Gln Tyr Cys Ser Arg Ala
        355                 360                 365

Gln Cys His Gly His Gly Arg Cys Val Arg Arg Asn Pro Ser Ala Ser
    370                 375                 380

Thr Phe Leu His Leu Ser Thr Asn Ser Phe Arg Leu Val Pro Gly His
385                 390                 395                 400

Ala Pro Gly Glu Pro Gln Leu Arg Pro Val Gly Glu Leu Ser Trp Ala
                405                 410                 415

Asp Ile Asp His Leu Gln Thr His Phe Arg Cys Gln Cys Tyr Leu Gly
            420                 425                 430

Trp Ser Gly Glu Gln Cys Gln Trp Asp His Arg Gln Ala Ala Gly Gly
        435                 440                 445

Ala Ser Glu Ala Trp Ala Gly Ser His Leu Thr Ser Leu Leu Ala Leu
    450                 455                 460

Ala Ala Leu Ala Phe Thr Trp Thr Leu
465                 470


<210> SEQ ID NO 38
<211> LENGTH: 417
<212> TYPE: PRT
<213> ORGANISM: Homo sapiens
<220> FEATURE:
<223> OTHER INFORMATION: Hyaluronidase-3 [Precursor]

<400> SEQUENCE: 38

Met Thr Thr Gln Leu Gly Pro Ala Leu Val Leu Gly Val Ala Leu Cys
1               5                   10                  15

Leu Gly Cys Gly Gln Pro Leu Pro Gln Val Pro Glu Arg Pro Phe Ser
            20                  25                  30

Val Leu Trp Asn Val Pro Ser Ala His Cys Glu Ala Arg Phe Gly Val
        35                  40                  45

His Leu Pro Leu Asn Ala Leu Gly Ile Ile Ala Asn Arg Gly Gln His
    50                  55                  60

Phe His Gly Gln Asn Met Thr Ile Phe Tyr Lys Asn Gln Leu Gly Leu
65                  70                  75                  80

Tyr Pro Tyr Phe Gly Pro Arg Gly Thr Ala His Asn Gly Gly Ile Pro
```

```
                85                  90                  95

Gln Ala Leu Pro Leu Asp Arg His Leu Ala Leu Ala Ala Tyr Gln Ile
            100                 105                 110

His His Ser Leu Arg Pro Gly Phe Ala Gly Pro Ala Val Leu Asp Trp
        115                 120                 125

Glu Glu Trp Cys Pro Leu Trp Ala Gly Asn Trp Gly Arg Arg Arg Ala
    130                 135                 140

Tyr Gln Ala Ala Ser Trp Ala Trp Ala Gln Gln Val Phe Pro Asp Leu
145                 150                 155                 160

Asp Pro Gln Glu Gln Leu Tyr Lys Ala Tyr Thr Gly Phe Glu Gln Ala
                165                 170                 175

Ala Arg Ala Leu Met Glu Asp Thr Leu Arg Val Ala Gln Ala Leu Arg
            180                 185                 190

Pro His Gly Leu Trp Gly Phe Tyr His Tyr Pro Ala Cys Gly Asn Gly
        195                 200                 205

Trp His Ser Met Ala Ser Asn Tyr Thr Gly Arg Cys His Ala Ala Thr
    210                 215                 220

Leu Ala Arg Asn Thr Gln Leu His Trp Leu Trp Ala Ala Ser Ser Ala
225                 230                 235                 240

Leu Phe Pro Ser Ile Tyr Leu Pro Pro Arg Leu Pro Pro Ala His His
                245                 250                 255

Gln Ala Phe Val Arg His Arg Leu Glu Glu Ala Phe Arg Val Ala Leu
            260                 265                 270

Val Gly His Arg His Pro Leu Pro Val Leu Ala Tyr Val Arg Leu Thr
        275                 280                 285

His Arg Arg Ser Gly Arg Phe Leu Ser Gln Asp Asp Leu Val Gln Ser
    290                 295                 300

Ile Gly Val Ser Ala Ala Leu Gly Ala Ala Gly Val Val Leu Trp Gly
305                 310                 315                 320

Asp Leu Ser Leu Ser Ser Ser Glu Glu Glu Cys Trp His Leu His Asp
                325                 330                 335

Tyr Leu Val Asp Thr Leu Gly Pro Tyr Val Ile Asn Val Thr Arg Ala
            340                 345                 350

Ala Met Ala Cys Ser His Gln Arg Cys His Gly His Gly Arg Cys Ala
        355                 360                 365

Arg Arg Asp Pro Gly Gln Met Glu Ala Phe Leu His Leu Trp Pro Asp
    370                 375                 380

Gly Ser Leu Gly Asp Trp Lys Ser Phe Ser Cys His Cys Tyr Trp Gly
385                 390                 395                 400

Trp Ala Gly Pro Thr Cys Gln Glu Pro Arg Pro Gly Pro Lys Glu Ala
                405                 410                 415

Val


<210> SEQ ID NO 39
<211> LENGTH: 481
<212> TYPE: PRT
<213> ORGANISM: Homo sapiens
<220> FEATURE:
<223> OTHER INFORMATION: Hyaluronidase-4

<400> SEQUENCE: 39

Met Lys Val Leu Ser Glu Gly Gln Leu Lys Leu Cys Val Val Gln Pro
1               5                   10                  15

Val His Leu Thr Ser Trp Leu Leu Ile Phe Phe Ile Leu Lys Ser Ile
            20                  25                  30
```

```
Ser Cys Leu Lys Pro Ala Arg Leu Pro Ile Tyr Gln Arg Lys Pro Phe
        35                  40                  45

Ile Ala Ala Trp Asn Ala Pro Thr Asp Gln Cys Leu Ile Lys Tyr Asn
    50                  55                  60

Leu Arg Leu Asn Leu Lys Met Phe Pro Val Ile Gly Ser Pro Leu Ala
65                  70                  75                  80

Lys Ala Arg Gly Gln Asn Val Thr Ile Phe Tyr Val Asn Arg Leu Gly
                85                  90                  95

Tyr Tyr Pro Trp Tyr Thr Ser Gln Gly Val Pro Ile Asn Gly Gly Leu
            100                 105                 110

Pro Gln Asn Ile Ser Leu Gln Val His Leu Glu Lys Ala Asp Gln Asp
        115                 120                 125

Ile Asn Tyr Tyr Ile Pro Ala Glu Asp Phe Ser Gly Leu Ala Val Ile
    130                 135                 140

Asp Trp Glu Tyr Trp Arg Pro Gln Trp Ala Arg Asn Trp Asn Ser Lys
145                 150                 155                 160

Asp Val Tyr Arg Gln Lys Ser Arg Lys Leu Ile Ser Asp Met Gly Lys
                165                 170                 175

Asn Val Ser Ala Thr Asp Ile Glu Tyr Leu Ala Lys Val Thr Phe Glu
            180                 185                 190

Glu Ser Ala Lys Ala Phe Met Lys Glu Thr Ile Lys Leu Gly Ile Lys
        195                 200                 205

Ser Arg Pro Lys Gly Leu Trp Gly Tyr Tyr Leu Tyr Pro Asp Cys His
    210                 215                 220

Asn Tyr Asn Val Tyr Ala Pro Asn Tyr Ser Gly Ser Cys Pro Glu Asp
225                 230                 235                 240

Glu Val Leu Arg Asn Asn Glu Leu Ser Trp Leu Trp Asn Ser Ser Ala
                245                 250                 255

Ala Leu Tyr Pro Ser Ile Gly Val Trp Lys Ser Leu Gly Asp Ser Glu
            260                 265                 270

Asn Ile Leu Arg Phe Ser Lys Phe Arg Val His Glu Ser Met Arg Ile
        275                 280                 285

Ser Thr Met Thr Ser His Asp Tyr Ala Leu Pro Val Phe Val Tyr Thr
    290                 295                 300

Arg Leu Gly Tyr Arg Asp Glu Pro Leu Phe Phe Leu Ser Lys Gln Asp
305                 310                 315                 320

Leu Val Ser Thr Ile Gly Glu Ser Ala Ala Leu Gly Ala Ala Gly Ile
                325                 330                 335

Val Ile Trp Gly Asp Met Asn Leu Thr Ala Ser Lys Ala Asn Cys Thr
            340                 345                 350

Lys Val Lys Gln Phe Val Ser Ser Asp Leu Gly Ser Tyr Ile Ala Asn
        355                 360                 365

Val Thr Arg Ala Ala Glu Val Cys Ser Leu His Leu Cys Arg Asn Asn
    370                 375                 380

Gly Arg Cys Ile Arg Lys Met Trp Asn Ala Pro Ser Tyr Leu His Leu
385                 390                 395                 400

Asn Pro Ala Ser Tyr His Ile Glu Ala Ser Glu Asp Gly Glu Phe Thr
                405                 410                 415

Val Lys Gly Lys Ala Ser Asp Thr Asp Leu Ala Val Met Ala Asp Thr
            420                 425                 430

Phe Ser Cys His Cys Tyr Gln Gly Tyr Glu Gly Ala Asp Cys Arg Glu
        435                 440                 445
```

```
Ile Lys Thr Ala Asp Gly Cys Ser Gly Val Ser Pro Ser Pro Gly Ser
    450                 455                 460

Leu Met Thr Leu Cys Leu Leu Leu Leu Ala Ser Tyr Arg Ser Ile Gln
465                 470                 475                 480

Leu


<210> SEQ ID NO 40
<211> LENGTH: 467
<212> TYPE: PRT
<213> ORGANISM: Homo sapiens
<220> FEATURE:
<223> OTHER INFORMATION: sHuPH20 precursor 1-467

<400> SEQUENCE: 40

Met Gly Val Leu Lys Phe Lys His Ile Phe Phe Arg Ser Phe Val Lys
1               5                   10                  15

Ser Ser Gly Val Ser Gln Ile Val Phe Thr Phe Leu Leu Ile Pro Cys
            20                  25                  30

Cys Leu Thr Leu Asn Phe Arg Ala Pro Pro Val Ile Pro Asn Val Pro
        35                  40                  45

Phe Leu Trp Ala Trp Asn Ala Pro Ser Glu Phe Cys Leu Gly Lys Phe
    50                  55                  60

Asp Glu Pro Leu Asp Met Ser Leu Phe Ser Phe Ile Gly Ser Pro Arg
65                  70                  75                  80

Ile Asn Ala Thr Gly Gln Gly Val Thr Ile Phe Tyr Val Asp Arg Leu
                85                  90                  95

Gly Tyr Tyr Pro Tyr Ile Asp Ser Ile Thr Gly Val Thr Val Asn Gly
            100                 105                 110

Gly Ile Pro Gln Lys Ile Ser Leu Gln Asp His Leu Asp Lys Ala Lys
        115                 120                 125

Lys Asp Ile Thr Phe Tyr Met Pro Val Asp Asn Leu Gly Met Ala Val
    130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
        195                 200                 205

Leu Leu Arg Pro Asn His Leu Trp Gly Tyr Tyr Leu Phe Pro Asp Cys
    210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
            260                 265                 270

Ala Ala Thr Leu Tyr Val Arg Asn Arg Val Arg Glu Ala Ile Arg Val
        275                 280                 285

Ser Lys Ile Pro Asp Ala Lys Ser Pro Leu Pro Val Phe Ala Tyr Thr
    290                 295                 300

Arg Ile Val Phe Thr Asp Gln Val Leu Lys Phe Leu Ser Gln Asp Glu
305                 310                 315                 320

Leu Val Tyr Thr Phe Gly Glu Thr Val Ala Leu Gly Ala Ser Gly Ile
```

```
                325                 330                 335

Val Ile Trp Gly Thr Leu Ser Ile Met Arg Ser Met Lys Ser Cys Leu
            340                 345                 350

Leu Leu Asp Asn Tyr Met Glu Thr Ile Leu Asn Pro Tyr Ile Ile Asn
        355                 360                 365

Val Thr Leu Ala Ala Lys Met Cys Ser Gln Val Leu Cys Gln Glu Gln
    370                 375                 380

Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr
                405                 410                 415

Val Arg Gly Lys Pro Thr Leu Glu Asp Leu Glu Gln Phe Ser Glu Lys
            420                 425                 430

Phe Tyr Cys Ser Cys Tyr Ser Thr Leu Ser Cys Lys Glu Lys Ala Asp
        435                 440                 445

Val Lys Asp Thr Asp Ala Val Asp Val Cys Ile Ala Asp Gly Val Cys
    450                 455                 460

Ile Asp Ala
465


<210> SEQ ID NO 41
<211> LENGTH: 477
<212> TYPE: PRT
<213> ORGANISM: Homo sapiens
<220> FEATURE:
<223> OTHER INFORMATION: sHuPH20 precursor 1-477

<400> SEQUENCE: 41

Met Gly Val Leu Lys Phe Lys His Ile Phe Phe Arg Ser Phe Val Lys
1               5                   10                  15

Ser Ser Gly Val Ser Gln Ile Val Phe Thr Phe Leu Leu Ile Pro Cys
            20                  25                  30

Cys Leu Thr Leu Asn Phe Arg Ala Pro Pro Val Ile Pro Asn Val Pro
        35                  40                  45

Phe Leu Trp Ala Trp Asn Ala Pro Ser Glu Phe Cys Leu Gly Lys Phe
    50                  55                  60

Asp Glu Pro Leu Asp Met Ser Leu Phe Ser Phe Ile Gly Ser Pro Arg
65                  70                  75                  80

Ile Asn Ala Thr Gly Gln Gly Val Thr Ile Phe Tyr Val Asp Arg Leu
                85                  90                  95

Gly Tyr Tyr Pro Tyr Ile Asp Ser Ile Thr Gly Val Thr Val Asn Gly
            100                 105                 110

Gly Ile Pro Gln Lys Ile Ser Leu Gln Asp His Leu Asp Lys Ala Lys
        115                 120                 125

Lys Asp Ile Thr Phe Tyr Met Pro Val Asp Asn Leu Gly Met Ala Val
    130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
        195                 200                 205

Leu Leu Arg Pro Asn His Leu Trp Gly Tyr Tyr Leu Phe Pro Asp Cys
```

```
    210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
            260                 265                 270

Ala Ala Thr Leu Tyr Val Arg Asn Arg Val Arg Glu Ala Ile Arg Val
        275                 280                 285

Ser Lys Ile Pro Asp Ala Lys Ser Pro Leu Pro Val Phe Ala Tyr Thr
    290                 295                 300

Arg Ile Val Phe Thr Asp Gln Val Leu Lys Phe Leu Ser Gln Asp Glu
305                 310                 315                 320

Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
            340                 345                 350

Leu Leu Asp Asn Tyr Met Glu Thr Ile Leu Asn Pro Tyr Ile Ile Asn
        355                 360                 365

Val Thr Leu Ala Ala Lys Met Cys Ser Gln Val Leu Cys Gln Glu Gln
    370                 375                 380

Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr
                405                 410                 415

Val Arg Gly Lys Pro Thr Leu Glu Asp Leu Glu Gln Phe Ser Glu Lys
            420                 425                 430

Phe Tyr Cys Ser Cys Tyr Ser Thr Leu Ser Cys Lys Glu Lys Ala Asp
        435                 440                 445

Val Lys Asp Thr Asp Ala Val Asp Val Cys Ile Ala Asp Gly Val Cys
    450                 455                 460

Ile Asp Ala Phe Leu Lys Pro Pro Met Glu Thr Glu Glu
465                 470                 475


<210> SEQ ID NO 42
<211> LENGTH: 478
<212> TYPE: PRT
<213> ORGANISM: Homo sapiens
<220> FEATURE:
<223> OTHER INFORMATION: sHuPH20 precursor 1-478

<400> SEQUENCE: 42

Met Gly Val Leu Lys Phe Lys His Ile Phe Phe Arg Ser Phe Val Lys
1               5                   10                  15

Ser Ser Gly Val Ser Gln Ile Val Phe Thr Phe Leu Leu Ile Pro Cys
            20                  25                  30

Cys Leu Thr Leu Asn Phe Arg Ala Pro Pro Val Ile Pro Asn Val Pro
        35                  40                  45

Phe Leu Trp Ala Trp Asn Ala Pro Ser Glu Phe Cys Leu Gly Lys Phe
    50                  55                  60

Asp Glu Pro Leu Asp Met Ser Leu Phe Ser Phe Ile Gly Ser Pro Arg
65                  70                  75                  80

Ile Asn Ala Thr Gly Gln Gly Val Thr Ile Phe Tyr Val Asp Arg Leu
                85                  90                  95

Gly Tyr Tyr Pro Tyr Ile Asp Ser Ile Thr Gly Val Thr Val Asn Gly
```

```
            100                 105                 110

Gly Ile Pro Gln Lys Ile Ser Leu Gln Asp His Leu Asp Lys Ala Lys
        115                 120                 125

Lys Asp Ile Thr Phe Tyr Met Pro Val Asp Asn Leu Gly Met Ala Val
    130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
        195                 200                 205

Leu Leu Arg Pro Asn His Leu Trp Gly Tyr Tyr Leu Phe Pro Asp Cys
    210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
            260                 265                 270

Ala Ala Thr Leu Tyr Val Arg Asn Arg Val Arg Glu Ala Ile Arg Val
        275                 280                 285

Ser Lys Ile Pro Asp Ala Lys Ser Pro Leu Pro Val Phe Ala Tyr Thr
    290                 295                 300

Arg Ile Val Phe Thr Asp Gln Val Leu Lys Phe Leu Ser Gln Asp Glu
305                 310                 315                 320

Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
            340                 345                 350

Leu Leu Asp Asn Tyr Met Glu Thr Ile Leu Asn Pro Tyr Ile Ile Asn
        355                 360                 365

Val Thr Leu Ala Ala Lys Met Cys Ser Gln Val Leu Cys Gln Glu Gln
    370                 375                 380

Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr
                405                 410                 415

Val Arg Gly Lys Pro Thr Leu Glu Asp Leu Glu Gln Phe Ser Glu Lys
            420                 425                 430

Phe Tyr Cys Ser Cys Tyr Ser Thr Leu Ser Cys Lys Glu Lys Ala Asp
        435                 440                 445

Val Lys Asp Thr Asp Ala Val Asp Val Cys Ile Ala Asp Gly Val Cys
    450                 455                 460

Ile Asp Ala Phe Leu Lys Pro Pro Met Glu Thr Glu Glu Pro
465                 470                 475


<210> SEQ ID NO 43
<211> LENGTH: 479
<212> TYPE: PRT
<213> ORGANISM: Homo sapiens
<220> FEATURE:
<223> OTHER INFORMATION: sHuPH20 precursor 1-479
```

<400> SEQUENCE: 43

Met Gly Val Leu Lys Phe Lys His Ile Phe Phe Arg Ser Phe Val Lys
1 5 10 15

Ser Ser Gly Val Ser Gln Ile Val Phe Thr Phe Leu Leu Ile Pro Cys
20 25 30

Cys Leu Thr Leu Asn Phe Arg Ala Pro Pro Val Ile Pro Asn Val Pro
35 40 45

Phe Leu Trp Ala Trp Asn Ala Pro Ser Glu Phe Cys Leu Gly Lys Phe
50 55 60

Asp Glu Pro Leu Asp Met Ser Leu Phe Ser Phe Ile Gly Ser Pro Arg
65 70 75 80

Ile Asn Ala Thr Gly Gln Gly Val Thr Ile Phe Tyr Val Asp Arg Leu
85 90 95

Gly Tyr Tyr Pro Tyr Ile Asp Ser Ile Thr Gly Val Thr Val Asn Gly
100 105 110

Gly Ile Pro Gln Lys Ile Ser Leu Gln Asp His Leu Asp Lys Ala Lys
115 120 125

Lys Asp Ile Thr Phe Tyr Met Pro Val Asp Asn Leu Gly Met Ala Val
130 135 140

Ile Asp Trp Glu Glu Trp Arg Pro Thr Trp Ala Arg Asn Trp Lys Pro
145 150 155 160

Lys Asp Val Tyr Lys Asn Arg Ser Ile Glu Leu Val Gln Gln Gln Asn
165 170 175

Val Gln Leu Ser Leu Thr Glu Ala Thr Glu Lys Ala Lys Gln Glu Phe
180 185 190

Glu Lys Ala Gly Lys Asp Phe Leu Val Glu Thr Ile Lys Leu Gly Lys
195 200 205

Leu Leu Arg Pro Asn His Leu Trp Gly Tyr Tyr Leu Phe Pro Asp Cys
210 215 220

Tyr Asn His His Tyr Lys Lys Pro Gly Tyr Asn Gly Ser Cys Phe Asn
225 230 235 240

Val Glu Ile Lys Arg Asn Asp Asp Leu Ser Trp Leu Trp Asn Glu Ser
245 250 255

Thr Ala Leu Tyr Pro Ser Ile Tyr Leu Asn Thr Gln Gln Ser Pro Val
260 265 270

Ala Ala Thr Leu Tyr Val Arg Asn Arg Val Arg Glu Ala Ile Arg Val
275 280 285

Ser Lys Ile Pro Asp Ala Lys Ser Pro Leu Pro Val Phe Ala Tyr Thr
290 295 300

Arg Ile Val Phe Thr Asp Gln Val Leu Lys Phe Leu Ser Gln Asp Glu
305 310 315 320

Leu Val Tyr Thr Phe Gly Glu Thr Val Ala Leu Gly Ala Ser Gly Ile
325 330 335

Val Ile Trp Gly Thr Leu Ser Ile Met Arg Ser Met Lys Ser Cys Leu
340 345 350

Leu Leu Asp Asn Tyr Met Glu Thr Ile Leu Asn Pro Tyr Ile Ile Asn
355 360 365

Val Thr Leu Ala Ala Lys Met Cys Ser Gln Val Leu Cys Gln Glu Gln
370 375 380

Gly Val Cys Ile Arg Lys Asn Trp Asn Ser Ser Asp Tyr Leu His Leu
385 390 395 400

Asn Pro Asp Asn Phe Ala Ile Gln Leu Glu Lys Gly Gly Lys Phe Thr
405 410 415

```
Val Arg Gly Lys Pro Thr Leu Glu Asp Leu Glu Gln Phe Ser Glu Lys
            420                 425                 430

Phe Tyr Cys Ser Cys Tyr Ser Thr Leu Ser Cys Lys Glu Lys Ala Asp
        435                 440                 445

Val Lys Asp Thr Asp Ala Val Asp Val Cys Ile Ala Asp Gly Val Cys
    450                 455                 460

Ile Asp Ala Phe Leu Lys Pro Pro Met Glu Thr Glu Glu Pro Gln
465                 470                 475


<210> SEQ ID NO 44
<211> LENGTH: 480
<212> TYPE: PRT
<213> ORGANISM: Homo sapiens
<220> FEATURE:
<223> OTHER INFORMATION: sHuPH20 precursor 1-480

<400> SEQUENCE: 44

Met Gly Val Leu Lys Phe Lys His Ile Phe Phe Arg Ser Phe Val Lys
1               5                   10                  15

Ser Ser Gly Val Ser Gln Ile Val Phe Thr Phe Leu Leu Ile Pro Cys
            20                  25                  30

Cys Leu Thr Leu Asn Phe Arg Ala Pro Pro Val Ile Pro Asn Val Pro
        35                  40                  45

Phe Leu Trp Ala Trp Asn Ala Pro Ser Glu Phe Cys Leu Gly Lys Phe
    50                  55                  60

Asp Glu Pro Leu Asp Met Ser Leu Phe Ser Phe Ile Gly Ser Pro Arg
65                  70                  75                  80

Ile Asn Ala Thr Gly Gln Gly Val Thr Ile Phe Tyr Val Asp Arg Leu
                85                  90                  95

Gly Tyr Tyr Pro Tyr Ile Asp Ser Ile Thr Gly Val Thr Val Asn Gly
            100                 105                 110

Gly Ile Pro Gln Lys Ile Ser Leu Gln Asp His Leu Asp Lys Ala Lys
        115                 120                 125

Lys Asp Ile Thr Phe Tyr Met Pro Val Asp Asn Leu Gly Met Ala Val
    130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
        195                 200                 205

Leu Leu Arg Pro Asn His Leu Trp Gly Tyr Tyr Leu Phe Pro Asp Cys
    210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
            260                 265                 270

Ala Ala Thr Leu Tyr Val Arg Asn Arg Val Arg Glu Ala Ile Arg Val
        275                 280                 285

Ser Lys Ile Pro Asp Ala Lys Ser Pro Leu Pro Val Phe Ala Tyr Thr
    290                 295                 300
```

```
Arg Ile Val Phe Thr Asp Gln Val Leu Lys Phe Leu Ser Gln Asp Glu
305                 310                 315                 320

Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
            340                 345                 350

Leu Leu Asp Asn Tyr Met Glu Thr Ile Leu Asn Pro Tyr Ile Ile Asn
        355                 360                 365

Val Thr Leu Ala Ala Lys Met Cys Ser Gln Val Leu Cys Gln Glu Gln
    370                 375                 380

Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr
                405                 410                 415

Val Arg Gly Lys Pro Thr Leu Glu Asp Leu Glu Gln Phe Ser Glu Lys
            420                 425                 430

Phe Tyr Cys Ser Cys Tyr Ser Thr Leu Ser Cys Lys Glu Lys Ala Asp
        435                 440                 445

Val Lys Asp Thr Asp Ala Val Asp Val Cys Ile Ala Asp Gly Val Cys
    450                 455                 460

Ile Asp Ala Phe Leu Lys Pro Pro Met Glu Thr Glu Glu Pro Gln Ile
465                 470                 475                 480


<210> SEQ ID NO 45
<211> LENGTH: 481
<212> TYPE: PRT
<213> ORGANISM: Homo sapiens
<220> FEATURE:
<223> OTHER INFORMATION: sHuPH20 precursor 1-481

<400> SEQUENCE: 45

Met Gly Val Leu Lys Phe Lys His Ile Phe Phe Arg Ser Phe Val Lys
1               5                   10                  15

Ser Ser Gly Val Ser Gln Ile Val Phe Thr Phe Leu Leu Ile Pro Cys
            20                  25                  30

Cys Leu Thr Leu Asn Phe Arg Ala Pro Pro Val Ile Pro Asn Val Pro
        35                  40                  45

Phe Leu Trp Ala Trp Asn Ala Pro Ser Glu Phe Cys Leu Gly Lys Phe
    50                  55                  60

Asp Glu Pro Leu Asp Met Ser Leu Phe Ser Phe Ile Gly Ser Pro Arg
65                  70                  75                  80

Ile Asn Ala Thr Gly Gln Gly Val Thr Ile Phe Tyr Val Asp Arg Leu
                85                  90                  95

Gly Tyr Tyr Pro Tyr Ile Asp Ser Ile Thr Gly Val Thr Val Asn Gly
            100                 105                 110

Gly Ile Pro Gln Lys Ile Ser Leu Gln Asp His Leu Asp Lys Ala Lys
        115                 120                 125

Lys Asp Ile Thr Phe Tyr Met Pro Val Asp Asn Leu Gly Met Ala Val
    130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190
```

```
Glu Lys Ala Gly Lys Asp Phe Leu Val Glu Thr Ile Lys Leu Gly Lys
        195                 200                 205

Leu Leu Arg Pro Asn His Leu Trp Gly Tyr Tyr Leu Phe Pro Asp Cys
    210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
            260                 265                 270

Ala Ala Thr Leu Tyr Val Arg Asn Arg Val Arg Glu Ala Ile Arg Val
        275                 280                 285

Ser Lys Ile Pro Asp Ala Lys Ser Pro Leu Pro Val Phe Ala Tyr Thr
    290                 295                 300

Arg Ile Val Phe Thr Asp Gln Val Leu Lys Phe Leu Ser Gln Asp Glu
305                 310                 315                 320

Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
            340                 345                 350

Leu Leu Asp Asn Tyr Met Glu Thr Ile Leu Asn Pro Tyr Ile Ile Asn
        355                 360                 365

Val Thr Leu Ala Ala Lys Met Cys Ser Gln Val Leu Cys Gln Glu Gln
    370                 375                 380

Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr
                405                 410                 415

Val Arg Gly Lys Pro Thr Leu Glu Asp Leu Glu Gln Phe Ser Glu Lys
            420                 425                 430

Phe Tyr Cys Ser Cys Tyr Ser Thr Leu Ser Cys Lys Glu Lys Ala Asp
        435                 440                 445

Val Lys Asp Thr Asp Ala Val Asp Val Cys Ile Ala Asp Gly Val Cys
    450                 455                 460

Ile Asp Ala Phe Leu Lys Pro Pro Met Glu Thr Glu Glu Pro Gln Ile
465                 470                 475                 480

Phe


<210> SEQ ID NO 46
<211> LENGTH: 483
<212> TYPE: PRT
<213> ORGANISM: Homo sapiens
<220> FEATURE:
<223> OTHER INFORMATION: sHuPH20 precursor 1-483

<400> SEQUENCE: 46

Met Gly Val Leu Lys Phe Lys His Ile Phe Phe Arg Ser Phe Val Lys
1               5                   10                  15

Ser Ser Gly Val Ser Gln Ile Val Phe Thr Phe Leu Leu Ile Pro Cys
            20                  25                  30

Cys Leu Thr Leu Asn Phe Arg Ala Pro Pro Val Ile Pro Asn Val Pro
        35                  40                  45

Phe Leu Trp Ala Trp Asn Ala Pro Ser Glu Phe Cys Leu Gly Lys Phe
    50                  55                  60
```

```
Asp Glu Pro Leu Asp Met Ser Leu Phe Ser Phe Ile Gly Ser Pro Arg
65                  70                  75                  80

Ile Asn Ala Thr Gly Gln Gly Val Thr Ile Phe Tyr Val Asp Arg Leu
                85                  90                  95

Gly Tyr Tyr Pro Tyr Ile Asp Ser Ile Thr Gly Val Thr Val Asn Gly
            100                 105                 110

Gly Ile Pro Gln Lys Ile Ser Leu Gln Asp His Leu Asp Lys Ala Lys
        115                 120                 125

Lys Asp Ile Thr Phe Tyr Met Pro Val Asp Asn Leu Gly Met Ala Val
    130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
        195                 200                 205

Leu Leu Arg Pro Asn His Leu Trp Gly Tyr Tyr Leu Phe Pro Asp Cys
    210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
            260                 265                 270

Ala Ala Thr Leu Tyr Val Arg Asn Arg Val Arg Glu Ala Ile Arg Val
        275                 280                 285

Ser Lys Ile Pro Asp Ala Lys Ser Pro Leu Pro Val Phe Ala Tyr Thr
    290                 295                 300

Arg Ile Val Phe Thr Asp Gln Val Leu Lys Phe Leu Ser Gln Asp Glu
305                 310                 315                 320

Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
            340                 345                 350

Leu Leu Asp Asn Tyr Met Glu Thr Ile Leu Asn Pro Tyr Ile Ile Asn
        355                 360                 365

Val Thr Leu Ala Ala Lys Met Cys Ser Gln Val Leu Cys Gln Glu Gln
    370                 375                 380

Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr
                405                 410                 415

Val Arg Gly Lys Pro Thr Leu Glu Asp Leu Glu Gln Phe Ser Glu Lys
            420                 425                 430

Phe Tyr Cys Ser Cys Tyr Ser Thr Leu Ser Cys Lys Glu Lys Ala Asp
        435                 440                 445

Val Lys Asp Thr Asp Ala Val Asp Val Cys Ile Ala Asp Gly Val Cys
    450                 455                 460

Ile Asp Ala Phe Leu Lys Pro Pro Met Glu Thr Glu Glu Pro Gln Ile
465                 470                 475                 480

Phe Tyr Asn
```

<210> SEQ ID NO 47
<211> LENGTH: 432
<212> TYPE: PRT
<213> ORGANISM: Homo sapiens
<220> FEATURE:
<223> OTHER INFORMATION: sHuPH20 mature 36-467

<400> SEQUENCE: 47

Leu Asn Phe Arg Ala Pro Pro Val Ile Pro Asn Val Pro Phe Leu Trp
1 5 10 15

Ala Trp Asn Ala Pro Ser Glu Phe Cys Leu Gly Lys Phe Asp Glu Pro
20 25 30

Leu Asp Met Ser Leu Phe Ser Phe Ile Gly Ser Pro Arg Ile Asn Ala
35 40 45

Thr Gly Gln Gly Val Thr Ile Phe Tyr Val Asp Arg Leu Gly Tyr Tyr
50 55 60

Pro Tyr Ile Asp Ser Ile Thr Gly Val Thr Val Asn Gly Gly Ile Pro
65 70 75 80

Gln Lys Ile Ser Leu Gln Asp His Leu Asp Lys Ala Lys Lys Asp Ile
85 90 95

Thr Phe Tyr Met Pro Val Asp Asn Leu Gly Met Ala Val Ile Asp Trp
100 105 110

Glu Glu Trp Arg Pro Thr Trp Ala Arg Asn Trp Lys Pro Lys Asp Val
115 120 125

Tyr Lys Asn Arg Ser Ile Glu Leu Val Gln Gln Gln Asn Val Gln Leu
130 135 140

Ser Leu Thr Glu Ala Thr Glu Lys Ala Lys Gln Glu Phe Glu Lys Ala
145 150 155 160

Gly Lys Asp Phe Leu Val Glu Thr Ile Lys Leu Gly Lys Leu Leu Arg
165 170 175

Pro Asn His Leu Trp Gly Tyr Tyr Leu Phe Pro Asp Cys Tyr Asn His
180 185 190

His Tyr Lys Lys Pro Gly Tyr Asn Gly Ser Cys Phe Asn Val Glu Ile
195 200 205

Lys Arg Asn Asp Asp Leu Ser Trp Leu Trp Asn Glu Ser Thr Ala Leu
210 215 220

Tyr Pro Ser Ile Tyr Leu Asn Thr Gln Gln Ser Pro Val Ala Ala Thr
225 230 235 240

Leu Tyr Val Arg Asn Arg Val Arg Glu Ala Ile Arg Val Ser Lys Ile
245 250 255

Pro Asp Ala Lys Ser Pro Leu Pro Val Phe Ala Tyr Thr Arg Ile Val
260 265 270

Phe Thr Asp Gln Val Leu Lys Phe Leu Ser Gln Asp Glu Leu Val Tyr
275 280 285

Thr Phe Gly Glu Thr Val Ala Leu Gly Ala Ser Gly Ile Val Ile Trp
290 295 300

Gly Thr Leu Ser Ile Met Arg Ser Met Lys Ser Cys Leu Leu Leu Asp
305 310 315 320

Asn Tyr Met Glu Thr Ile Leu Asn Pro Tyr Ile Ile Asn Val Thr Leu
325 330 335

Ala Ala Lys Met Cys Ser Gln Val Leu Cys Gln Glu Gln Gly Val Cys
340 345 350

Ile Arg Lys Asn Trp Asn Ser Ser Asp Tyr Leu His Leu Asn Pro Asp
355 360 365

```
Asn Phe Ala Ile Gln Leu Glu Lys Gly Gly Lys Phe Thr Val Arg Gly
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430


<210> SEQ ID NO 48
<211> LENGTH: 448
<212> TYPE: PRT
<213> ORGANISM: Homo sapiens
<220> FEATURE:
<223> OTHER INFORMATION: sHuPH20 mature 36-483

<400> SEQUENCE: 48

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Gln Asn Val Gln Leu
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300
```

```
Gly Thr Leu Ser Ile Met Arg Ser Met Lys Ser Cys Leu Leu Leu Asp
305                 310                 315                 320

Asn Tyr Met Glu Thr Ile Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu Pro Gln Ile Phe Tyr Asn
        435                 440                 445


<210> SEQ ID NO 49
<211> LENGTH: 1446
<212> TYPE: DNA
<213> ORGANISM: Homo sapiens
<220> FEATURE:
<223> OTHER INFORMATION: DNA encoding soluble rHuPH20 "precursor"

<400> SEQUENCE: 49

atgggagtgc taaaattcaa gcacatcttt ttcagaagct ttgttaaatc aagtggagta     60

tcccagatag ttttcacctt ccttctgatt ccatgttgct tgactctgaa tttcagagca    120

cctcctgtta ttccaaatgt gcctttcctc tgggcctgga atgccccaag tgaattttgt    180

cttggaaaat ttgatgagcc actagatatg agcctcttct ctttcatagg aagcccccga    240

ataaacgcca ccgggcaagg tgttacaata ttttatgttg atagacttgg ctactatcct    300

tacatagatt caatcacagg agtaactgtg aatggaggaa tcccccagaa gatttcctta    360

caagaccatc tggacaaagc taagaaagac attacatttt atatgccagt agacaatttg    420

ggaatggctg ttattgactg ggaagaatgg agacccactt gggcaagaaa ctggaaacct    480

aaagatgttt acaagaatag gtctattgaa ttggttcagc aacaaaatgt acaacttagt    540

ctcacagagg ccactgagaa agcaaaacaa gaatttgaaa aggcagggaa ggatttcctg    600

gtagagacta taaaattggg aaaattactt cggccaaatc acttgtgggg ttattatctt    660

tttccggatt gttacaacca tcactataag aaacccggtt acaatggaag ttgcttcaat    720

gtagaaataa aaagaaatga tgatctcagc tggttgtgga atgaaagcac tgctctttac    780

ccatccattt atttgaacac tcagcagtct cctgtagctg ctacactcta tgtgcgcaat    840

cgagttcggg aagccatcag agtttccaaa atacctgatg caaaaagtcc acttccggtt    900

tttgcatata cccgcatagt ttttactgat caagttttga aattcctttc tcaagatgaa    960

cttgtgtata catttggcga aactgttgct ctgggtgctt ctggaattgt aatatgggga   1020

accctcagta taatgcgaag tatgaaatct tgcttgctcc tagacaatta catggagact   1080

atactgaatc cttacataat caacgtcaca ctagcagcca aaatgtgtag ccaagtgctt   1140

tgccaggagc aaggagtgtg tataaggaaa aactggaatt caagtgacta tcttcacctc   1200

aacccagata attttgctat tcaacttgag aaaggtggaa agttcacagt acgtggaaaa   1260
```

```
ccgacacttg aagacctgga gcaattttct gaaaaatttt attgcagctg ttatagcacc   1320

ttgagttgta aggagaaagc tgatgtaaaa gacactgatg ctgttgatgt gtgtattgct   1380

gatggtgtct gtatagatgc ttttctaaaa cctcccatgg agacagaaga acctcaaatt   1440

ttctac                                                              1446


<210> SEQ ID NO 50
<211> LENGTH: 509
<212> TYPE: PRT
<213> ORGANISM: Homo sapiens
<220> FEATURE:
<223> OTHER INFORMATION: PH20 variant P48A

<400> SEQUENCE: 50

Met Gly Val Leu Lys Phe Lys His Ile Phe Phe Arg Ser Phe Val Lys
1               5                   10                  15

Ser Ser Gly Val Ser Gln Ile Val Phe Thr Phe Leu Leu Ile Pro Cys
            20                  25                  30

Cys Leu Thr Leu Asn Phe Arg Ala Pro Pro Val Ile Pro Asn Val Ala
        35                  40                  45

Phe Leu Trp Ala Trp Asn Ala Pro Ser Glu Phe Cys Leu Gly Lys Phe
    50                  55                  60

Asp Glu Pro Leu Asp Met Ser Leu Phe Ser Phe Ile Gly Ser Pro Arg
65                  70                  75                  80

Ile Asn Ala Thr Gly Gln Gly Val Thr Ile Phe Tyr Val Asp Arg Leu
                85                  90                  95

Gly Tyr Tyr Pro Tyr Ile Asp Ser Ile Thr Gly Val Thr Val Asn Gly
            100                 105                 110

Gly Ile Pro Gln Lys Ile Ser Leu Gln Asp His Leu Asp Lys Ala Lys
        115                 120                 125

Lys Asp Ile Thr Phe Tyr Met Pro Val Asp Asn Leu Gly Met Ala Val
    130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
        195                 200                 205

Leu Leu Arg Pro Asn His Leu Trp Gly Tyr Tyr Leu Phe Pro Asp Cys
    210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
            260                 265                 270

Ala Ala Thr Leu Tyr Val Arg Asn Arg Val Arg Glu Ala Ile Arg Val
        275                 280                 285

Ser Lys Ile Pro Asp Ala Lys Ser Pro Leu Pro Val Phe Ala Tyr Thr
    290                 295                 300

Arg Ile Val Phe Thr Asp Gln Val Leu Lys Phe Leu Ser Gln Asp Glu
305                 310                 315                 320
```

```
Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
            340                 345                 350

Leu Leu Asp Asn Tyr Met Glu Thr Ile Leu Asn Pro Tyr Ile Ile Asn
        355                 360                 365

Val Thr Leu Ala Ala Lys Met Cys Ser Gln Val Leu Cys Gln Glu Gln
    370                 375                 380

Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr
                405                 410                 415

Val Arg Gly Lys Pro Thr Leu Glu Asp Leu Glu Gln Phe Ser Glu Lys
            420                 425                 430

Phe Tyr Cys Ser Cys Tyr Ser Thr Leu Ser Cys Lys Glu Lys Ala Asp
        435                 440                 445

Val Lys Asp Thr Asp Ala Val Asp Val Cys Ile Ala Asp Gly Val Cys
    450                 455                 460

Ile Asp Ala Phe Leu Lys Pro Pro Met Glu Thr Glu Glu Pro Gln Ile
465                 470                 475                 480

Phe Tyr Asn Ala Ser Pro Ser Thr Leu Ser Ala Thr Met Phe Ile Val
                485                 490                 495

Ser Ile Leu Phe Leu Ile Ile Ser Ser Val Ala Ser Leu
            500                 505


<210> SEQ ID NO 51
<211> LENGTH: 509
<212> TYPE: PRT
<213> ORGANISM: Homo sapiens
<220> FEATURE:
<223> OTHER INFORMATION: precursor PH20 variant L499W

<400> SEQUENCE: 51

Met Gly Val Leu Lys Phe Lys His Ile Phe Phe Arg Ser Phe Val Lys
1               5                   10                  15

Ser Ser Gly Val Ser Gln Ile Val Phe Thr Phe Leu Leu Ile Pro Cys
            20                  25                  30

Cys Leu Thr Leu Asn Phe Arg Ala Pro Pro Val Ile Pro Asn Val Pro
        35                  40                  45

Phe Leu Trp Ala Trp Asn Ala Pro Ser Glu Phe Cys Leu Gly Lys Phe
    50                  55                  60

Asp Glu Pro Leu Asp Met Ser Leu Phe Ser Phe Ile Gly Ser Pro Arg
65                  70                  75                  80

Ile Asn Ala Thr Gly Gln Gly Val Thr Ile Phe Tyr Val Asp Arg Leu
                85                  90                  95

Gly Tyr Tyr Pro Tyr Ile Asp Ser Ile Thr Gly Val Thr Val Asn Gly
            100                 105                 110

Gly Ile Pro Gln Lys Ile Ser Leu Gln Asp His Leu Asp Lys Ala Lys
        115                 120                 125

Lys Asp Ile Thr Phe Tyr Met Pro Val Asp Asn Leu Gly Met Ala Val
    130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175
```

```
Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
        195                 200                 205

Leu Leu Arg Pro Asn His Leu Trp Gly Tyr Tyr Leu Phe Pro Asp Cys
    210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
            260                 265                 270

Ala Ala Thr Leu Tyr Val Arg Asn Arg Val Arg Glu Ala Ile Arg Val
        275                 280                 285

Ser Lys Ile Pro Asp Ala Lys Ser Pro Leu Pro Val Phe Ala Tyr Thr
    290                 295                 300

Arg Ile Val Phe Thr Asp Gln Val Leu Lys Phe Leu Ser Gln Asp Glu
305                 310                 315                 320

Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
            340                 345                 350

Leu Leu Asp Asn Tyr Met Glu Thr Ile Leu Asn Pro Tyr Ile Ile Asn
        355                 360                 365

Val Thr Leu Ala Ala Lys Met Cys Ser Gln Val Leu Cys Gln Glu Gln
    370                 375                 380

Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr
                405                 410                 415

Val Arg Gly Lys Pro Thr Leu Glu Asp Leu Glu Gln Phe Ser Glu Lys
            420                 425                 430

Phe Tyr Cys Ser Cys Tyr Ser Thr Leu Ser Cys Lys Glu Lys Ala Asp
        435                 440                 445

Val Lys Asp Thr Asp Ala Val Asp Val Cys Ile Ala Asp Gly Val Cys
    450                 455                 460

Ile Asp Ala Phe Leu Lys Pro Pro Met Glu Thr Glu Glu Pro Gln Ile
465                 470                 475                 480

Phe Tyr Asn Ala Ser Pro Ser Thr Leu Ser Ala Thr Met Phe Ile Val
                485                 490                 495

Ser Ile Trp Phe Leu Ile Ile Ser Ser Val Ala Ser Leu
            500                 505


<210> SEQ ID NO 52
<211> LENGTH: 6630
<212> TYPE: DNA
<213> ORGANISM: Artificial Sequence
<220> FEATURE:
<223> OTHER INFORMATION: HZ24 vector

<400> SEQUENCE: 52

tcaatattgg ccattagcca tattattcat tggttatata gcataaatca atattggcta      60

ttggccattg catacgttgt atctatatca taatatgtac atttatattg gctcatgtcc     120

aatatgaccg ccatgttggc attgattatt gactagttat taatagtaat caattacggg     180
```

-continued

```
gtcattagtt catagcccat atatggagtt ccgcgttaca taacttacgg taaatggccc    240
gcctggctga ccgcccaacg acccccgccc attgacgtca ataatgacgt atgttcccat    300
agtaacgcca atagggactt tccattgacg tcaatgggtg gagtatttac ggtaaactgc    360
ccacttggca gtacatcaag tgtatcatat gccaagtccg ccccctattg acgtcaatga    420
cggtaaatgg cccgcctggc attatgccca gtacatgacc ttacgggact ttcctacttg    480
gcagtacatc tacgtattag tcatcgctat taccatggtg atgcggtttt ggcagtacac    540
caatgggcgt ggatagcggt ttgactcacg gggatttcca agtctccacc ccattgacgt    600
caatgggagt ttgttttggc accaaaatca acgggacttt ccaaaatgtc gtaataaccc    660
cgccccgttg acgcaaatgg gcggtaggcg tgtacggtgg gaggtctata taagcagagc    720
tcgtttagtg aaccgtcaga tcactagaag ctttattgcg gtagtttatc acagttaaat    780
tgctaacgca gtcagtgctt ctgacacaac agtctcgaac ttaagctgca gaagttggtc    840
gtgaggcact gggcaggtaa gtatcaaggt tacaagacag gtttaaggag accaatagaa    900
actgggcttg tcgagacaga gaagactctt gcgtttctga taggcaccta ttggtcttac    960
tgacatccac tttgcctttc tctccacagg tgtccactcc cagttcaatt acagctctta   1020
aggctagagt acttaatacg actcactata ggctagcatg ggagtgctaa aattcaagca   1080
catctttttc agaagctttg ttaaatcaag tggagtatcc cagatagttt tcaccttcct   1140
tctgattcca tgttgcttga ctctgaattt cagagcacct cctgttattc caaatgtgcc   1200
tttcctctgg gcctggaatg ccccaagtga attttgtctt ggaaaatttg atgagccact   1260
agatatgagc ctcttctctt tcataggaag cccccgaata aacgccaccg ggcaaggtgt   1320
tacaatattt tatgttgata gacttggcta ctatccttac atagattcaa tcacaggagt   1380
aactgtgaat ggaggaatcc cccagaagat ttccttacaa gaccatctgg acaaagctaa   1440
gaaagacatt acattttata tgccagtaga caatttggga atggctgtta ttgactggga   1500
agaatggaga cccacttggg caagaaactg gaaacctaaa gatgtttaca agaataggtc   1560
tattgaattg gttcagcaac aaaatgtaca acttagtctc acagaggcca ctgagaaagc   1620
aaaacaagaa tttgaaaagg cagggaagga tttcctggta gagactataa aattgggaaa   1680
attacttcgg ccaaatcact tgtggggtta ttatcttttt ccggattgtt acaaccatca   1740
ctataagaaa cccggttaca atggaagttg cttcaatgta gaaataaaaa gaaatgatga   1800
tctcagctgg ttgtggaatg aaagcactgc tctttaccca tccatttatt tgaacactca   1860
gcagtctcct gtagctgcta cactctatgt gcgcaatcga gttcgggaag ccatcagagt   1920
ttccaaaata cctgatgcaa aaagtccact tccggttttt gcatataccc gcatagtttt   1980
tactgatcaa gttttgaaat tcctttctca agatgaactt gtgtatacat ttggcgaaac   2040
tgttgctctg ggtgcttctg gaattgtaat atggggaacc ctcagtataa tgcgaagtat   2100
gaaatcttgc ttgctcctag acaattacat ggagactata ctgaatcctt acataatcaa   2160
cgtcacacta gcagccaaaa tgtgtagcca agtgctttgc caggagcaag gagtgtgtat   2220
aaggaaaaac tggaattcaa gtgactatct tcacctcaac ccagataatt ttgctattca   2280
acttgagaaa ggtggaaagt tcacagtacg tggaaaaccg acacttgaag acctggagca   2340
attttctgaa aaattttatt gcagctgtta tagcaccttg agttgtaagg agaaagctga   2400
tgtaaaagac actgatgctg ttgatgtgtg tattgctgat ggtgtctgta tagatgcttt   2460
tctaaaacct cccatggaga cagaagaacc tcaaattttc tactgaggat ccatagctaa   2520
cgcccctctc cctcccccc ccctaacgtt actggccgaa gccgcttgga ataaggccgg   2580
```

tgtgcgtttg tctatatgtt attttccacc atattgccgt cttttggcaa tgtgagggcc 2640
cggaaacctg gccctgtctt cttgacgagc attcctaggg gtctttcccc tctcgccaaa 2700
ggaatgcaag gtctgttgaa tgtcgtgaag gaagcagttc ctctggaagc ttcttgaaga 2760
caaacaacgt ctgtagcgac cctttgcagg cagcggaacc ccccacctgg cgacaggtgc 2820
ctctgcggcc aaaagccacg tgtataagat acacctgcaa aggcggcaca accccagtgc 2880
cacgttgtga gttggatagt tgtggaaaga gtcaaatggc tctcctcaag cgtattcaac 2940
aaggggctga aggatgccca gaaggtaccc cattgtatgg gatctgatct ggggcctcgg 3000
tgcacatgct ttacatgtgt ttagtcgagg ttaaaaaaac gtctaggccc cccgaaccac 3060
ggggacgtgg ttttcctttg aaaaacacga tgataagctt gccacaaccc acagcggccg 3120
ctgccatcat ggttcgacca ttgaactgca tcgtcgccgt gtcccaaaat atggggattg 3180
gcaagaacgg agacctaccc tggcctccgc tcaggaacga gttcaagtac ttccaaagaa 3240
tgaccacaac ctcttcagtg gaaggtaaac agaatctggt gattatgggt aggaaaacct 3300
ggttctccat tcctgagaag aatcgacctt taaaggacag aattaatata gttctcagta 3360
gagaactcaa agaaccacca cgaggagctc attttcttgc caaaagtttg gatgatgcct 3420
taagacttat tgaacaaccg gaattggcaa gtaaagtaga catggtttgg atagtcggag 3480
gcagttctgt ttaccaggaa gccatgaatc aaccaggcca cctcagactc tttgtgacaa 3540
ggatcatgca ggaatttgaa agtgacacgt ttttcccaga aattgatttg gggaaatata 3600
aacttctccc agaataccca ggcgtcctct ctgaggtcca ggaggaaaaa ggcatcaagt 3660
ataagtttga agtctacgag aagaaagact aaacgcgtgg tacctctaga gtcgacccgg 3720
gcggccgctt cgagcagaca tgataagata cattgatgag tttggacaaa ccacaactag 3780
aatgcagtga aaaaaatgct ttatttgtga aatttgtgat gctattgctt tatttgtaac 3840
cattataagc tgcaataaac aagttaacaa caacaattgc attcatttta tgtttcaggt 3900
tcagggggag atgtgggagg ttttttaaag caagtaaaac ctctacaaat gtggtaaaat 3960
cgataaggat ccgggctggc gtaatagcga agaggcccgc accgatcgcc cttcccaaca 4020
gttgcgcagc ctgaatggcg aatggacgcg ccctgtagcg gcgcattaag cgcggcgggt 4080
gtggtggtta cgcgcagcgt gaccgctaca cttgccagcg ccctagcgcc cgctcctttc 4140
gctttcttcc cttcctttct cgccacgttc gccggctttc cccgtcaagc tctaaatcgg 4200
gggctccctt tagggttccg atttagtgct ttacggcacc tcgaccccaa aaaacttgat 4260
tagggtgatg gttcacgtag tgggccatcg ccctgataga cggtttttcg ccctttgacg 4320
ttggagtcca cgttctttaa tagtggactc ttgttccaaa ctggaacaac actcaaccct 4380
atctcggtct attcttttga tttataaggg attttgccga tttcggccta ttggttaaaa 4440
aatgagctga tttaacaaaa atttaacgcg aattttaaca aaatattaac gcttacaatt 4500
tcctgatgcg gtattttctc cttacgcatc tgtgcggtat ttcacaccgc atatggtgca 4560
ctctcagtac aatctgctct gatgccgcat agttaagcca gccccgacac ccgccaacac 4620
ccgctgacgc gccctgacgg gcttgtctgc tcccggcatc cgcttacaga caagctgtga 4680
ccgtctccgg gagctgcatg tgtcagaggt tttcaccgtc atcaccgaaa cgcgcgagac 4740
gaaagggcct cgtgatacgc ctatttttat aggttaatgt catgataata atggtttctt 4800
agacgtcagg tggcactttt cggggaaatg tgcgcggaac ccctatttgt ttatttttct 4860
aaatacattc aaatatgtat ccgctcatga gacaataacc ctgataaatg cttcaataat 4920

```
attgaaaaag gaagagtatg agtattcaac atttccgtgt cgcccttatt cccttttttg   4980

cggcattttg ccttcctgtt tttgctcacc cagaaacgct ggtgaaagta aaagatgctg   5040

aagatcagtt gggtgcacga gtgggttaca tcgaactgga tctcaacagc ggtaagatcc   5100

ttgagagttt tcgccccgaa gaacgttttc caatgatgag cacttttaaa gttctgctat   5160

gtggcgcggt attatcccgt attgacgccg ggcaagagca actcggtcgc cgcatacact   5220

attctcagaa tgacttggtt gagtactcac cagtcacaga aaagcatctt acggatggca   5280

tgacagtaag agaattatgc agtgctgcca taaccatgag tgataacact gcggccaact   5340

tacttctgac aacgatcgga ggaccgaagg agctaaccgc ttttttgcac aacatggggg   5400

atcatgtaac tcgccttgat cgttgggaac cggagctgaa tgaagccata ccaaacgacg   5460

agcgtgacac cacgatgcct gtagcaatgg caacaacgtt gcgcaaacta ttaactggcg   5520

aactacttac tctagcttcc cggcaacaat taatagactg gatggaggcg gataaagttg   5580

caggaccact tctgcgctcg gcccttccgg ctggctggtt tattgctgat aaatctggag   5640

ccggtgagcg tgggtctcgc ggtatcattg cagcactggg gccagatggt aagccctccc   5700

gtatcgtagt tatctacacg acggggagtc aggcaactat ggatgaacga aatagacaga   5760

tcgctgagat aggtgcctca ctgattaagc attggtaact gtcagaccaa gtttactcat   5820

atatacttta gattgattta aaacttcatt tttaatttaa aaggatctag gtgaagatcc   5880

tttttgataa tctcatgacc aaaatccctt aacgtgagtt ttcgttccac tgagcgtcag   5940

accccgtaga aaagatcaaa ggatcttctt gagatccttt ttttctgcgc gtaatctgct   6000

gcttgcaaac aaaaaaacca ccgctaccag cggtggtttg tttgccggat caagagctac   6060

caactctttt tccgaaggta actggcttca gcagagcgca gataccaaat actgttcttc   6120

tagtgtagcc gtagttaggc caccacttca agaactctgt agcaccgcct acatacctcg   6180

ctctgctaat cctgttacca gtggctgctg ccagtggcga taagtcgtgt cttaccgggt   6240

tggactcaag acgatagtta ccggataagg cgcagcggtc gggctgaacg gggggttcgt   6300

gcacacagcc cagcttggag cgaacgacct acaccgaact gagataccta cagcgtgagc   6360

tatgagaaag cgccacgctt cccgaaggga gaaaggcgga caggtatccg gtaagcggca   6420

gggtcggaac aggagagcgc acgagggagc ttccaggggg aaacgcctgg tatctttata   6480

gtcctgtcgg gtttcgccac ctctgacttg agcgtcgatt tttgtgatgc tcgtcagggg   6540

ggcggagcct atggaaaaac gccagcaacg cggccttttt acggttcctg gccttttgct   6600

ggccttttgc tcacatggct cgacagatct                                    6630
```

```
<210> SEQ ID NO 53
<211> LENGTH: 186
<212> TYPE: PRT
<213> ORGANISM: Mus musculus
<220> FEATURE:
<223> OTHER INFORMATION: dihydrofolate reductase

<400> SEQUENCE: 53

Val Arg Pro Leu Asn Cys Ile Val Ala Val Ser Gln Asn Met Gly Ile
1               5                   10                  15

Gly Lys Asn Gly Asp Leu Pro Trp Pro Pro Leu Arg Asn Glu Phe Lys
            20                  25                  30

Tyr Phe Gln Arg Met Thr Thr Thr Ser Ser Val Glu Gly Lys Gln Asn
        35                  40                  45

Leu Val Ile Met Gly Arg Lys Thr Trp Phe Ser Ile Pro Glu Lys Asn
    50                  55                  60
```

```
Arg Pro Leu Lys Asp Arg Ile Asn Ile Val Leu Ser Arg Glu Leu Lys
65                  70                  75                  80

Glu Pro Pro Arg Gly Ala His Phe Leu Ala Lys Ser Leu Asp Asp Ala
                85                  90                  95

Leu Arg Leu Ile Glu Gln Pro Glu Leu Ala Ser Lys Val Asp Met Val
            100                 105                 110

Trp Ile Val Gly Gly Ser Ser Val Tyr Gln Glu Ala Met Asn Gln Pro
        115                 120                 125

Gly His Leu Arg Leu Phe Val Thr Arg Ile Met Gln Glu Phe Glu Ser
    130                 135                 140

Asp Thr Phe Phe Pro Glu Ile Asp Leu Gly Lys Tyr Lys Leu Leu Pro
145                 150                 155                 160

Glu Tyr Pro Gly Val Leu Ser Glu Val Gln Glu Glu Lys Gly Ile Lys
                165                 170                 175

Tyr Lys Phe Glu Val Tyr Glu Lys Lys Asp
            180                 185


<210> SEQ ID NO 54
<211> LENGTH: 6
<212> TYPE: PRT
<213> ORGANISM: Artificial Sequence
<220> FEATURE:
<223> OTHER INFORMATION: His tag

<400> SEQUENCE: 54

His His His His His His
1               5


<210> SEQ ID NO 55
<211> LENGTH: 8
<212> TYPE: PRT
<213> ORGANISM: Artificial Sequence
<220> FEATURE:
<223> OTHER INFORMATION: Flag tag

<400> SEQUENCE: 55

Asp Tyr Lys Asp Asp Asp Asp Lys
1               5


<210> SEQ ID NO 56
<211> LENGTH: 1449
<212> TYPE: DNA
<213> ORGANISM: Homo sapiens
<220> FEATURE:
<223> OTHER INFORMATION: Gen2 mRNA sequence

<400> SEQUENCE: 56

atgggagtgc taaaattcaa gcacatcttt ttcagaagct ttgttaaatc aagtggagta     60

tcccagatag ttttcacctt ccttctgatt ccatgttgct tgactctgaa tttcagagca    120

cctcctgtta ttccaaatgt gcctttcctc tgggcctgga atgccccaag tgaattttgt    180

cttggaaaat ttgatgagcc actagatatg agcctcttct ctttcatagg aagcccccga    240

ataaacgcca ccgggcaagg tgttacaata ttttatgttg atagacttgg ctactatcct    300

tacatagatt caatcacagg agtaactgtg aatggaggaa tcccccagaa gatttcctta    360

caagaccatc tggacaaagc taagaaagac attacatttt atatgccagt agacaatttg    420

ggaatggctg ttattgactg ggaagaatgg agacccactt gggcaagaaa ctggaaacct    480

aaagatgttt acaagaatag gtctattgaa ttggttcagc aacaaaatgt acaacttagt    540
```

-continued

```
ctcacagagg ccactgagaa agcaaaacaa gaatttgaaa aggcagggaa ggatttcctg    600
gtagagacta taaaattggg aaaattactt cggccaaatc acttgtgggg ttattatctt    660
tttccggatt gttacaacca tcactataag aaacccggtt acaatggaag ttgcttcaat    720
gtagaaataa aaagaaatga tgatctcagc tggttgtgga atgaaagcac tgctctttac    780
ccatccattt atttgaacac tcagcagtct cctgtagctg ctacactcta tgtgcgcaat    840
cgagttcggg aagccatcag agtttccaaa atacctgatg caaaaagtcc acttccggtt    900
tttgcatata cccgcatagt ttttactgat caagttttga aattcctttc tcaagatgaa    960
cttgtgtata catttggcga aactgttgct ctgggtgctt ctggaattgt aatatgggga   1020
accctcagta taatgcgaag tatgaaatct tgcttgctcc tagacaatta catggagact   1080
atactgaatc cttacataat caacgtcaca ctagcagcca aaatgtgtag tcaagtgctt   1140
tgccaggagc aaggagtgtg tataaggaaa aactggaatt caagtgacta tcttcacctc   1200
aacccagata attttgctat tcaacttgag aaaggtggaa agttcacagt acgtggaaaa   1260
ccgacacttg aagacctgga gcaattttct gaaaaatttt attgcagctg ttatagcacc   1320
ttgagttgta aggagaaagc tgatgtaaaa gacactgatg ctgttgatgt gtgtattgct   1380
gatggtgtct gtatagatgc ttttctaaaa cctcccatgg agacagaaga acctcaaatt   1440
ttctactga                                                           1449
```

The invention claimed is:

1. A method for treating an IG-treatable disease or condition in a subject, comprising subcutaneously administering to the subject no more than once monthly a soluble hyaluronidase and an immune globulin (IG) composition for treating the disease or condition, wherein:

the IG is from human plasma;

the IG and hyaluronidase are administered separately;

the hyaluronidase is administered prior to administration of the IG;

the IG composition has a protein concentration that is 5 to 25% w/v IG;

the IG is administered at a dosage of 100 mg per kg body weight (100 mg/kg BW) to 2 g/kg BW; and the hyaluronidase is administered at a ratio of Units hyaluronidase per gram of IG that is *in* the range of about 10 to 500 Units hyaluronidase per gram of the IG, whereby the dose of IG administered is a full monthly dose.

2. The method of claim 1, wherein the soluble hyaluronidase is an ovine PH20, bovine PH20 or a soluble human PH20, wherein the soluble human PH20 is a C-terminally truncated PH20 that lacks all or a portion of the glycosylphosphatidylinositol (GPI) anchor attachment sequence.

3. The method of claim 1, wherein the soluble hyaluronidase is selected from among a polypeptide having a sequence of amino acids set forth in any of SEQ ID NOS:4-9.

4. The method of claim 1, wherein:

the IG is administered in a volume of 50 mL to 700 mL; and the hyaluronidase is administered in a volume of less than 50 mL.

5. The method of claim 1, wherein the IG *composition* is administered as a liquid solution in a volume of 50 mL to 700 mL.

6. The method of claim 1, wherein the pH of the IG [preparation] *composition* is at or about 4.8 to 5.0.

7. The method of claim 1, wherein the pH of the IG [preparation] *composition* is at or about 4.6 to 5.1.

8. The method of claim 1, wherein the pH of the IG [preparation] *composition* is at or about 4.2 to 5.4.

9. The method of claim 1, wherein 20-30 grams (g) IG is administered.

10. The method of claim 1, wherein about or 5 grams (g), 10 g, 15 g, 20 g, 21 g, 22 g, 23 g, 24 g, 25 g, 26 g, 27 g, 28 g, 29 g, 30 g, 31 g, 32 g, 33 g, 34 g, 35 g, 36 g, 37 g, 38 g, 39 g or 40 g of IG is administered.

11. The method of claim 1, wherein at least 5 grams (g) of IG is administered.

12. The method of claim 1, wherein the IG is administered at a dosage of at least 200 mg/kg BW, 300 mg/kg BW, 400 mg/kg BW, 500 mg/kg BW or 600 mg/kg BW.

13. The method of claim 1, wherein the IG is administered at 600 mg/kg body weight (BW) and the soluble hyaluronidase is administered at a ratio of 50 units hyaluronidase/gram of IG.

14. The method of claim 1, wherein the hyaluronidase is administered in a volume of less than 50 mL.

15. The method of claim 1, wherein the hyaluronidase is administered in a volume of 5-30 mL.

16. The method of claim 1, wherein bioavailability of the subcutaneously administered IG is at least about 90% of the bioavailability of the same dosage administered via IV administration.

17. The method of claim 1, wherein the soluble hyaluronidase is a PH20,or a truncated form thereof.

18. The method of claim 17, wherein the PH20 is selected from an ovine, bovine or truncated human PH20.

19. The method of claim 18, wherein the PH20 is a truncated human PH20 selected from among a polypeptide having a sequence of amino acids set forth in any of SEQ ID NOS:4-9, or a variant thereof that has at least 95% sequence identity with any of SEQ ID NOS:4-9, is soluble and exhibits hyaluronidase activity.

20. The method of claim 18, wherein the truncated human PH20 is selected from among a polypeptide having a sequence of amino acids set forth in any of SEQ ID NOS:4-9.

21. The method of claim 1, wherein the soluble hyaluronidase is designated rHuPH20.

[22. The method of claim 1, wherein the IG is purified from human plasma.]

23. The method of claim [22] *1*, wherein the IG [purified] from human plasma is purified by alcohol fractionation.

24. The method of claim 23, wherein the IG is further purified by any one or more of a chemical modification, so incubation at pH 4.0 with or without pepsin, polyethylene glycol (PEG) precipitation, ion-exchange chromatography, enzymatic cleavage, solvent detergent treatment, diafiltration or ultrafiltration.

25. The method of claim 1, wherein the IG *composition* contains IgG, IgA and IgM.

26. The method of claim 25, wherein the IG *composition* contains greater than 95% IgG.

27. The method of claim 26, wherein the IgG is monomeric.

28. The method of claim 1, wherein the IG *composition* further contains protein-stabilizing excipients.

29. The method of claim 28, wherein the protein-stabilizing excipient is selected from among one or more of glycine, maltose, a polyol, human serum albumin, mannitol, and non-ionic detergent.

30. The method of claim 1, wherein the pH of the IG [preparation] *composition* is at or about 4.2 to 5.4, 4.6 to 5.1 or 4.8 to 5.0.

31. The method of claim 30, wherein the IG *composition* has a protein concentration that is or is about 5 to 15% w/v, 6 to 15% w/v, or 8 to 12% w/v of IG composition.

32. The method of claim 30, wherein the IG has a protein concentration that is or is about 5 to 15% w/v of IG composition.

33. The method of claim 31, wherein the protein concentration is 10% w/v.

34. The method of claim 1, where the IG *composition* is administered as a liquid solution and the volume of liquid is or is about to 100 ml, 150 ml, 200 ml, 300 ml, 400 ml, 500 ml, 600 ml or 700 ml.

35. The method of claim 1, wherein the IG *composition* is infused at a rate of 10 ml/hr to 300 ml/hr.

36. The method of claim 35, wherein the rate is selected is from among at or about 10 ml/hr, 20 ml/hr, 30 ml/hr, 40 ml/hr, 50 ml/hr, 60 ml/hr, 70 ml/hr, 80 ml/hr, 90 ml/hr, 100 ml/hr, 150 ml/hr, 200 ml/hr, 250 ml/hr and 300 ml/hr.

37. The method of claim 35, wherein the rate is controlled by a pump.

38. The method of claim 35, wherein the rate is controlled by gravity.

39. The method of claim 1, wherein the hyaluronidase is administered 0.5 minutes, 1 minute, 2 minutes, 3 minutes, 4 minutes, 5 minutes, 6 minutes, 7 minutes, 8 minutes, 9 minutes, 10 minutes, 20 minutes or 30 minutes prior to administration of IG.

40. The method of claim 1, wherein the hyaluronidase is administered at a ratio (units hyaluronidase/grams of IG) at or about 10 U/gram (g), 20 U/g, 30 U/g, 35 U/g, 40 U/g, 50 U/g, 60 U/g, 70 U/g, 80 U/g, 90 U/g, 100 U/g, 150 U/g, or 300 U/g.

41. The method of claim 40, wherein the hyaluronidase is administered at a ratio of or about 50 U/gram IG.

42. The method of claim 1, wherein the hyaluronidase that is administered is at or about 10 Units to 500,000 Units, 100 Units to 100,000 Units, 500 Units to 50,000 Units, 1000 Units to 10,000 Units, 5000 Units to 7500 Units, 5000 Units to 50,000 Units, or 1,000 Units to 10,000 Units.

43. The method of claim 1, wherein the IG-treatable disease or condition is selected from among immunodeficiency; acquired hypogammaglobulinemia secondary to hematological malignancies; Kawasaki's disease; chronic inflammatory demyelinating polyneuropathy (CIDP); Guillain-Barre Syndrome; Idiopathic thrombocytopenic purpura; inflammatory myopathies; Lambert-Eaton myasthenic syndrome; multifocal motor neuropathy; Myasthenia Gravis; Moersch-Woltmann syndrome; secondary hypogammaglobulinaemia specific antibody deficiency; Acute disseminated encephalomyelitis; ANCA-positive systemic necrotizing vasculitis; Autoimmune haemolytic anaemia; Bullous pemphigoid; Cicatricial pemphigoid; Evans syndrome; Foeto-maternal/neonatal alloimmune thrombocytopenia (FMAIT/NAIT); Haemophagocytic syndrome; high-risk allogeneic haemopoietic stem cell transplantation; IgM paraproteinaemic neuropathy; kidney transplantation; multiple sclerosis; Opsoclonus myoclonus ataxia; Pemphigus foliaceus; Pemphigus vulgaris; Post-transfusion purpura; Toxic epidermal necrolysis/Steven Johnson syndrome (TEN/SJS); Toxic shock syndrome; Alzheimer's Disease; Systemic lupus erythematosus; multiple myeloma; sepsis; B cell tumors; trauma; and a bacterial, viral or fungal infection.

44. The method of claim 43, wherein the IG-treatable disease or condition is an immunodeficiency and the immunodeficiency is selected from among common variable immunodeficiency (CVID), congenital agammaglobulinemia, Wiskott-Aldrich syndrome, severe combined immunodeficiency (SCID), primary hypogammaglobulinemia, primary immunodeficiency diseases with antibody deficiency, X-linked agammaglobulinemia (XLA), hypogammaglobulinemia of infancy, and paraneoplastic cerebellar degeneration with no antibodies.

45. The method of claim 43, wherein the IG-treatable disease or condition is acquired hypogammaglobulinemia secondary to hematological malignancies and the hematological malignancy is selected from among chronic lymphocytic leukemia (CLL), multiple myeloma (MM) and non-Hodgkin's lymphoma (NHL).

46. The method of claim 43, wherein the IG-treatable disease or condition is an inflammatory myopathy and the inflammatory myopathy is selected from among polymyositis, dermatomyositis and inclusion body myositis.

47. The method of claim 43, wherein the IG-treatable disease or condition is a bacteria, viral or fungal condition and the bacterial viral or fungal condition is selected from among Haemophilus influenzae type B, Pseudomonas aeruginosa types A and B, Staphylococcus aureus, Group B Streptococcus, Streptococcus pneumoniae types 1, 3, 4, 6, 7, 8, 9, 12, 14, 18, 19, and 23, Adenovirus types 2 and 5, Cytomegalovirus, Epstein Barr virus VCA, Hepatitis A virus, Hepatitis B virus, Herpes simplex virus-1, Herpes simplex virus-2, Influenza A, Measles, Parainfluenza types 1, 2 and 3, Polio, Varicella zoster virus, Aspergillus and Candida albicans.

*48. The method of claim 1, wherein the IG composition has a protein concentration of from about 8 to about 12% w/v of IG.*

*49. The method of claim 1, wherein the IG composition has a protein concentration of from about 15 to about 25% w/v of IG.*

*50. The method of claim 1, wherein the IG composition has a protein concentration of from about 20 to about 25% w/v of IG.*

51. The method of claim 1, wherein the soluble hyaluronidase comprises an amino acid sequence that is at least about 95% identical to SEQ ID NO:9.

52. The method of claim 1, wherein the soluble hyaluronidase comprises the amino acid sequence of SEQ ID NO:9.

53. The method of claim 1, wherein the IG is administered at from about 300 mg/kg BW to about 600 mg/kg BW.

54. The method of claim 1, wherein the IG-treatable disease or condition is a primary immunodeficiency.

55. The method of claim 1, wherein the IG-treatable disease or condition is chronic inflammatory demyelinating polyneuropathy.

56. A method for treating an immune globulin (IG)-treatable disease or condition in a subject, comprising:

subcutaneously administering a hyaluronidase composition comprising a soluble hyaluronidase at one or more sites on the subject;

after administering the hyaluronidase composition, subcutaneously administering an IG composition comprising IG for treating the disease or condition at the one or more sites on the subject, wherein:

the IG is from human plasma, the IG composition has a protein concentration of from about 5 to about 25% w/v IG, the subject is administered an IG dosage of from about 100 mg per kg body weight (mg/kg BW) to about 2 g/kg BW, and the subject is administered a soluble hyaluronidase dosage at a ratio of from about 10 to about 500 Units hyaluronidase per gram of the administered IG;

wherein the hyaluronidase composition and the IG composition are subcutaneously administered to the subject no more frequently than once every three weeks.

57. The method of claim 56, wherein the IG-treatable disease or condition is selected from among immunodeficiency; acquired hypogammaglobulinemia secondary to hematological malignancies; Kawasaki's disease; chronic inflammatory demyelinating polyneuropathy (CIDP); Guillain-Barre Syndrome; Idiopathic thrombocytopenic purpura; inflammatory myopathies; Lambert-Eaton myasthenic syndrome; multifocal motor neuropathy; Myasthenia Gravis; Moersch-Woltmann syndrome; secondary hypogammaglobulinaemia specific antibody deficiency; Acute disseminated encephalomyelitis; ANCA-positive systemic necrotizing vasculitis; Autoimmune haemolytic anaemia; Bullous pemphigoid; Cicatricial pemphigoid; Evans syndrome; Foeto-maternal/neonatal alloimmune thrombocytopenia (FMAIT/NAIT); Haemophagocytic syndrome; high-risk allogeneic haemopoietic stem cell transplantation; IgM paraproteinaemic neuropathy; kidney transplantation; multiple sclerosis; Opsoclonus myoclonus ataxia; Pemphigus foliaceus; Pemphigus vulgaris; Post-transfusion purpura; Toxic epidermal necrolysis/Steven Johnson syndrome (TEN/SJS); Toxic shock syndrome; Alzheimer's Disease; Systemic lupus erythematosus; multiple myeloma; sepsis; B cell tumors; trauma; and a bacterial, viral or fungal infection.

58. The method of claim 56, wherein the IG-treatable disease or condition is a primary immunodeficiency.

59. The method of claim 56, wherein the IG-treatable disease or condition is chronic inflammatory demyelinating polyneuropathy.

60. The method of claim 56, wherein the hyaluronidase composition administered to the subject has a volume of less than about 50 mL.

61. The method of claim 56, wherein the soluble hyaluronidase is a soluble human PH2O that is C-terminally truncated and lacks all or a portion of the glycosylphosphatidylinositol (GPI) anchor attachment sequence.

62. The method of claim 56, wherein the soluble hyaluronidase has an amino acid sequence that is at least about 95% identical to SEQ ID NO:9.

63. The method of claim 56, wherein the soluble hyaluronidase has an amino acid sequence of SEQ ID NO:9.

64. The method of claim 56, wherein the subject is administered a soluble hyaluronidase dosage at a ratio of from about 50 to about 100 Units hyaluronidase per gram of the administered IG.

65. The method of claim 56, wherein the pH of the IG composition is about 4.6 to about 5.1.

66. The method of claim 56, wherein the protein content of the IG composition comprises at least about 95% IgG.

67. The method of claim 56, wherein the IG composition further comprises an amino acid.

68. The method of claim 56, wherein the IG composition has a protein concentration of from about 5% to about 15%.

69. The method of claim 56, wherein the IG composition has a protein concentration of from about 15 to about 25% w/v of IG.

70. The method of claim 56, wherein the IG composition has a protein concentration of about 10% w/v of IG.

71. The method of claim 56, wherein the IG composition has a protein concentration of from about 20 to about 25% w/v of IG.

72. The method of claim 56, wherein the IG composition is administered to the subject at an infusion rate of from about 10 mL/hr to about 300 mL/hr.

73. The method of claim 56, wherein the IG composition is administered to the subject at an infusion rate of from about 120 mL/hr to about 300 mL/hr.

74. The method of claim 56, wherein the IG composition is administered to the subject at an infusion rate of at least about 200 mL/hr.

75. The method of claim 56, wherein the IG composition is started within about 20 minutes of completion of administration of the hyaluronidase composition.

76. The method of claim 56, wherein the IG composition is started within about 10 minutes of completion of administration of the hyaluronidase composition.

77. The method of claim 56, wherein the subject is administered an IG dosage of from about 300 mg/kg BW to about 600 mg/kg BW.

78. The method of claim 56, wherein the bioavailability of the subcutaneously administered IG is at least about 80% of the bioavailability of the same dosage of IG administered via intravenous (IV) administration.

79. The method of claim 56, wherein the soluble hyaluronidase is selected from among a polypeptide having a sequence of amino acids set forth in any of SEQ ID NOS:4-9.

* * * * *